(12) United States Patent
Chang et al.

(10) Patent No.: US 10,954,567 B2
(45) Date of Patent: Mar. 23, 2021

(54) MUTATIONS ASSOCIATED WITH RESISTANCE TO INHIBITORS OF BRUTON'S TYROSINE KINASE (BTK)

(71) Applicant: Pharmacyclics LLC, Sunnyvale, CA (US)

(72) Inventors: Betty Chang, Cupertino, CA (US); Joseph J. Buggy, Mountain View, CA (US); Susanne M. Steggerda, San Francisco, CA (US)

(73) Assignees: Pharmacyclics LLC, Sunnyvale, CA (US); Cornell University, Ithaca, NY (US)

( * ) Notice: Subject to any disclaimer, the term of this patent is extended or adjusted under 35 U.S.C. 154(b) by 1 day.

(21) Appl. No.: 14/417,097

(22) PCT Filed: Jul. 23, 2013

(86) PCT No.: PCT/US2013/051741
§ 371 (c)(1),
(2) Date: Jan. 23, 2015

(87) PCT Pub. No.: WO2014/018567
PCT Pub. Date: Jan. 30, 2014

(65) Prior Publication Data
US 2015/0184249 A1 Jul. 2, 2015

Related U.S. Application Data

(60) Provisional application No. 61/675,303, filed on Jul. 24, 2012.

(51) Int. Cl.
| | |
|---|---|
| *C12Q 1/68* | (2018.01) |
| *C12Q 1/6886* | (2018.01) |
| *A61K 31/505* | (2006.01) |
| *A61K 31/506* | (2006.01) |
| *A61K 31/519* | (2006.01) |
| *A61K 31/52* | (2006.01) |
| *A61K 45/06* | (2006.01) |
| *C07K 14/00* | (2006.01) |
| *C12N 9/12* | (2006.01) |
| *C12N 9/16* | (2006.01) |
| *G01N 33/50* | (2006.01) |

(52) U.S. Cl.
CPC .......... *C12Q 1/6886* (2013.01); *A61K 31/505* (2013.01); *A61K 31/506* (2013.01); *A61K 31/519* (2013.01); *A61K 31/52* (2013.01); *A61K 45/06* (2013.01); *C07K 14/00* (2013.01); *C12N 9/12* (2013.01); *C12N 9/16* (2013.01); *G01N 33/5041* (2013.01); *C12Q 2600/106* (2013.01); *C12Q 2600/156* (2013.01); *C12Q 2600/16* (2013.01); *C12Y 207/10002* (2013.01); *C12Y 301/04011* (2013.01)

(58) Field of Classification Search
None
See application file for complete search history.

(56) References Cited

U.S. PATENT DOCUMENTS

| | | |
|---|---|---|
| 3,547,119 A | 12/1970 | Farb |
| 4,311,137 A | 1/1982 | Gerard |
| 4,360,019 A | 11/1982 | Portner et al. |
| 4,487,603 A | 12/1984 | Harris |
| 4,531,937 A | 7/1985 | Yates |
| 4,683,202 A | 7/1987 | Mullis |
| 4,692,147 A | 9/1987 | Duggan |
| 4,725,852 A | 2/1988 | Gamblin et al. |
| 4,755,173 A | 7/1988 | Konopka et al. |
| 4,843,155 A | 6/1989 | Chomczynski |
| 5,033,252 A | 7/1991 | Carter |
| 5,052,558 A | 10/1991 | Carter |
| 5,323,907 A | 6/1994 | Kalvelage |
| 5,384,261 A | 1/1995 | Winkler et al. |
| 5,397,787 A | 3/1995 | Buzzetti et al. |
| 5,445,934 A | 8/1995 | Fodor et al. |

(Continued)

FOREIGN PATENT DOCUMENTS

| | | |
|---|---|---|
| CA | 2663116 A1 | 4/2008 |
| CA | 2847852 A1 | 4/2008 |

(Continued)

OTHER PUBLICATIONS

Dores, G et al; British Journal of Haematology; vol. 139, pp. 809-819; 2007.*

(Continued)

*Primary Examiner* — Jehanne S Sitton
(74) *Attorney, Agent, or Firm* — Foley Hoag LLP

(57) ABSTRACT

Described herein are mutations that confer resistance to treatment with a BTK inhibitor. Described herein are modified BTK polypeptides that exhibit decreased inhibition (i.e. are resistant) to a covalent and/or irreversible BTK inhibitor. Also described herein modifications of PLCy2 and CARD 11 polypeptides that confer resistance to treatment with a BTK inhibitor. Described herein are diagnostic methods for detecting the modified polypeptides and nucleic acids encoding the modified polypeptides and applications of the methods thereof. Described herein are compositions, combinations, and kits containing the modified polypeptides and methods of using the modified polypeptides. Also described herein are methods of using modified BTK polypeptides as screening agents for the identification and design of second-generation BTK inhibitors.

23 Claims, 7 Drawing Sheets
Specification includes a Sequence Listing.

(56) References Cited

U.S. PATENT DOCUMENTS

| | | |
|---|---|---|
| 5,530,012 A | 6/1996 | Mattson et al. |
| 5,593,997 A | 1/1997 | Dow et al. |
| 5,643,207 A | 7/1997 | Rise |
| 5,677,195 A | 10/1997 | Winkler et al. |
| 5,708,153 A | 1/1998 | Dower et al. |
| 5,744,305 A | 4/1998 | Fodor et al. |
| 5,770,358 A | 6/1998 | Dower et al. |
| 5,770,722 A | 6/1998 | Lockhart et al. |
| 5,789,162 A | 8/1998 | Dower et al. |
| 5,800,992 A | 9/1998 | Fodor et al. |
| 5,807,876 A | 9/1998 | Armistead et al. |
| 5,820,589 A | 10/1998 | Torgerson et al. |
| 5,854,033 A | 12/1998 | Lizardi |
| 5,856,174 A | 1/1999 | Lipshutz et al. |
| 5,874,219 A | 2/1999 | Rava et al. |
| 5,922,591 A | 7/1999 | Anderson et al. |
| 6,001,839 A | 12/1999 | Calderwood et al. |
| 6,017,328 A | 1/2000 | Fischell et al. |
| 6,020,135 A | 2/2000 | Levine et al. |
| 6,033,860 A | 3/2000 | Lockhart et al. |
| 6,040,138 A | 3/2000 | Lockhart et al. |
| 6,040,193 A | 3/2000 | Winkler et al. |
| 6,054,472 A | 4/2000 | Armistead et al. |
| 6,160,010 A | 12/2000 | Uckun et al. |
| 6,190,937 B1 | 2/2001 | Nakagawa et al. |
| 6,198,966 B1 | 3/2001 | Heruth |
| 6,221,900 B1 | 4/2001 | Uckun et al. |
| 6,303,652 B1 | 10/2001 | Uckun et al. |
| 6,306,897 B1 | 10/2001 | Uckun et al. |
| 6,326,469 B1 | 12/2001 | Ullrich et al. |
| 6,342,247 B1 | 1/2002 | Ku et al. |
| 6,344,316 B1 | 2/2002 | Lockhart et al. |
| 6,344,465 B1 | 2/2002 | Armistead et al. |
| 6,498,178 B2 | 12/2002 | Stamos et al. |
| 6,506,769 B2 | 1/2003 | Snow et al. |
| 6,660,744 B1 | 12/2003 | Hirst et al. |
| 6,753,348 B2 | 6/2004 | Uckun et al. |
| 6,756,289 B1 | 6/2004 | Nakagawa et al. |
| 6,770,639 B2 | 8/2004 | Snow et al. |
| 6,824,768 B2 | 11/2004 | Stalgis et al. |
| 6,893,638 B2 | 5/2005 | Anderson et al. |
| 6,921,763 B2 | 7/2005 | Hirst et al. |
| 7,083,784 B2 | 8/2006 | Dall'Acqua et al. |
| 7,138,420 B2 | 11/2006 | Bentzien et al. |
| 7,332,497 B2 | 2/2008 | Hirst et al. |
| 7,514,444 B2 | 4/2009 | Honigberg et al. |
| 7,547,689 B2 | 6/2009 | Sessler et al. |
| 7,718,662 B1 | 5/2010 | Chen et al. |
| 7,732,454 B2 | 6/2010 | Honigberg et al. |
| 7,741,330 B1 | 6/2010 | Chen et al. |
| 7,825,118 B2 | 11/2010 | Honigberg et al. |
| 7,960,396 B2 | 6/2011 | Honigberg et al. |
| 8,008,309 B2 | 8/2011 | Honigberg et al. |
| 8,058,249 B2 | 11/2011 | Krieg et al. |
| 8,088,781 B2 | 1/2012 | Honigberg et al. |
| 8,158,786 B2 | 4/2012 | Honigberg et al. |
| 8,232,280 B2 | 7/2012 | Honigberg et al. |
| 8,236,812 B2 | 8/2012 | Honigberg et al. |
| 8,306,897 B2 | 11/2012 | Yolles |
| 8,377,946 B1 | 2/2013 | Chen et al. |
| 8,399,470 B2 | 3/2013 | Honigberg et al. |
| 8,426,428 B2 | 4/2013 | Miller |
| 8,476,277 B2 | 7/2013 | Tafesse |
| 8,476,284 B2 | 7/2013 | Honigberg et al. |
| 8,497,277 B2 | 7/2013 | Honigberg et al. |
| 8,501,724 B1 | 8/2013 | Chen et al. |
| 8,501,751 B2 | 8/2013 | Honigberg et al. |
| 8,552,010 B2 | 10/2013 | Honigberg et al. |
| 8,557,803 B2 | 10/2013 | Yamamoto et al. |
| 8,563,563 B2 | 10/2013 | Honigberg et al. |
| 8,568,653 B2 | 10/2013 | Thillen et al. |
| 8,633,311 B2 | 1/2014 | Bommer et al. |
| 8,642,604 B2 | 2/2014 | Knight et al. |
| 8,658,653 B2 | 2/2014 | Honigberg et al. |
| 8,691,546 B2 | 4/2014 | Honigberg et al. |
| 8,697,711 B2 | 4/2014 | Honigberg et al. |
| 8,703,780 B2 | 4/2014 | Honigberg et al. |
| 8,735,403 B2 | 5/2014 | Honigberg et al. |
| 8,735,404 B2 | 5/2014 | Honigberg et al. |
| 8,741,908 B2 | 6/2014 | Honigberg et al. |
| 8,748,438 B2 | 6/2014 | Honigberg et al. |
| 8,748,439 B2 | 6/2014 | Honigberg et al. |
| 8,754,090 B2 | 6/2014 | Buggy et al. |
| 8,754,091 B2 | 6/2014 | Honigberg et al. |
| 8,759,516 B2 | 6/2014 | Honigberg et al. |
| 8,809,273 B2 | 8/2014 | Honigberg et al. |
| 8,877,202 B2 | 11/2014 | Govindan et al. |
| 8,883,435 B2 | 11/2014 | Honigberg et al. |
| 8,883,803 B2 | 11/2014 | Honigberg et al. |
| 8,940,750 B2 | 1/2015 | Honigberg et al. |
| 8,952,015 B2 | 2/2015 | Honigberg et al. |
| 8,957,079 B2 | 2/2015 | Honigberg et al. |
| 8,975,266 B2 | 3/2015 | Honigberg et al. |
| 8,987,233 B2 | 3/2015 | Pan et al. |
| 8,999,999 B2 | 4/2015 | Buggy et al. |
| 9,012,463 B2 | 4/2015 | Chen et al. |
| 9,079,908 B2 | 7/2015 | Honigberg et al. |
| 9,107,924 B2 | 8/2015 | Buggy et al. |
| 9,117,924 B2 | 8/2015 | Kitagawa et al. |
| 9,125,889 B2 | 9/2015 | Buggy et al. |
| 9,127,012 B2 | 9/2015 | Honigberg et al. |
| 9,133,198 B2 | 9/2015 | Honigberg et al. |
| 9,133,201 B2 | 9/2015 | Honigberg et al. |
| 9,133,202 B2 | 9/2015 | Honigberg et al. |
| 9,139,591 B2 | 9/2015 | Honigberg et al. |
| 9,181,257 B2 | 11/2015 | Honigberg et al. |
| 9,181,263 B2 | 11/2015 | Honigberg et al. |
| 9,193,735 B2 | 11/2015 | Honigberg et al. |
| 9,206,189 B2 | 12/2015 | Honigberg et al. |
| 9,212,185 B2 | 12/2015 | Honigberg et al. |
| 9,266,893 B2 | 2/2016 | Honigberg et al. |
| 9,273,051 B2 | 3/2016 | Chen et al. |
| 9,278,100 B2 | 3/2016 | Honigberg et al. |
| 9,296,753 B2 | 3/2016 | Smyth et al. |
| 9,409,911 B2 | 8/2016 | Honigberg et al. |
| 9,415,050 B2 | 8/2016 | Chen et al. |
| 9,540,382 B2 | 1/2017 | Purro et al. |
| 9,540,385 B2 | 1/2017 | Chen et al. |
| 9,545,407 B2 | 1/2017 | Shu et al. |
| 9,556,182 B2 | 1/2017 | Honigberg et al. |
| 9,655,857 B2 | 5/2017 | Chong et al. |
| 9,670,205 B2 | 6/2017 | Aktoudianakis et al. |
| 9,713,617 B2 | 7/2017 | Purro et al. |
| 9,717,731 B2 | 8/2017 | Buggy et al. |
| 9,730,938 B2 | 8/2017 | Kuo et al. |
| 9,795,604 B2 | 10/2017 | Byrd et al. |
| 9,801,881 B2 | 10/2017 | Buggy et al. |
| 9,801,883 B2 | 10/2017 | Buggy et al. |
| 9,814,721 B2 | 11/2017 | Buggy et al. |
| 9,885,086 B2 | 2/2018 | Byrd et al. |
| 10,004,745 B2 | 6/2018 | Honigberg et al. |
| 10,004,746 B2 | 6/2018 | Honigberg et al. |
| 10,010,507 B1 | 7/2018 | Honigberg et al. |
| 10,016,435 B2 | 7/2018 | Honigberg et al. |
| 10,213,386 B2 | 2/2019 | Chong et al. |
| 10,478,439 B2 | 11/2019 | Honigberg et al. |
| 10,653,696 B2 | 5/2020 | Buggy et al. |
| 2001/0041423 A1 | 11/2001 | Nishida et al. |
| 2002/0004584 A1 | 1/2002 | Laughlin |
| 2002/0016460 A1 | 2/2002 | Snow et al. |
| 2002/0086138 A1 | 7/2002 | Iijima |
| 2002/0127203 A1 | 9/2002 | Albrecht |
| 2002/0155505 A1 | 10/2002 | Wells et al. |
| 2003/0013118 A1 | 1/2003 | Edge et al. |
| 2003/0013125 A1 | 1/2003 | Braisted et al. |
| 2003/0035833 A1 | 2/2003 | He |
| 2003/0040461 A1 | 2/2003 | McAtee |
| 2003/0103938 A1 | 6/2003 | Jinquan et al. |
| 2003/0118078 A1 | 6/2003 | Carlson et al. |
| 2003/0125235 A1 | 7/2003 | Foxwell |
| 2003/0175761 A1 | 9/2003 | Sabath et al. |
| 2004/0002280 A1 | 1/2004 | Abe et al. |
| 2004/0006083 A1 | 1/2004 | Hirst et al. |
| 2004/0136954 A1 | 7/2004 | Grusby et al. |

(56) References Cited

U.S. PATENT DOCUMENTS

| | | |
|---|---|---|
| 2004/0226602 A1 | 11/2004 | Durr et al. |
| 2004/0241651 A1 | 12/2004 | Olek et al. |
| 2005/0008640 A1 | 1/2005 | Waegell et al. |
| 2005/0064464 A1 | 3/2005 | Punnonen et al. |
| 2005/0084905 A1 | 4/2005 | Prescott et al. |
| 2005/0090499 A1 | 4/2005 | Currie et al. |
| 2005/0101604 A1 | 5/2005 | Currie et al. |
| 2005/0152983 A1 | 7/2005 | Ashraf et al. |
| 2005/0153990 A1 | 7/2005 | Watkins |
| 2005/0196851 A1 | 9/2005 | Uckun |
| 2005/0209255 A1 | 9/2005 | Jimenez et al. |
| 2006/0079494 A1 | 4/2006 | Santi et al. |
| 2006/0167090 A1 | 7/2006 | Uckun et al. |
| 2006/0178367 A1 | 8/2006 | Currie et al. |
| 2006/0211112 A1 | 9/2006 | Harris et al. |
| 2006/0292181 A1 | 12/2006 | Brayden |
| 2007/0032457 A1 | 2/2007 | Blatt |
| 2007/0065449 A1 | 3/2007 | Verschraegen |
| 2007/0105136 A1 | 5/2007 | Staudt et al. |
| 2007/0122417 A1 | 5/2007 | Holt et al. |
| 2007/0281907 A1 | 12/2007 | Watkins |
| 2007/0293499 A1 | 12/2007 | Flynn et al. |
| 2008/0076921 A1 | 3/2008 | Honigberg et al. |
| 2008/0108636 A1 | 5/2008 | Honigberg et al. |
| 2008/0139582 A1 | 6/2008 | Honigberg et al. |
| 2008/0146555 A1 | 6/2008 | Caligiuri et al. |
| 2008/0153877 A1 | 6/2008 | Adimoolam et al. |
| 2008/0214501 A1 | 9/2008 | Pan et al. |
| 2009/0010911 A1 | 1/2009 | Andreotti et al. |
| 2009/0039734 A1 | 2/2009 | Takahashi et al. |
| 2009/0047353 A1 | 2/2009 | O'Hagan |
| 2009/0074787 A1 | 3/2009 | Gomez-Navarro et al. |
| 2009/0098137 A1 | 4/2009 | Burke et al. |
| 2009/0105209 A1 | 4/2009 | Dewdney et al. |
| 2009/0149389 A1 | 6/2009 | Panitch et al. |
| 2009/0181987 A1 | 7/2009 | Honigberg et al. |
| 2009/0186898 A1 | 7/2009 | Dewdney et al. |
| 2009/0197853 A1 | 8/2009 | Magda |
| 2009/0297551 A1 | 12/2009 | Sattentau et al. |
| 2009/0317836 A1 | 12/2009 | Kuhn et al. |
| 2010/0004270 A1 | 1/2010 | Honigberg et al. |
| 2010/0016296 A1 | 1/2010 | Singh et al. |
| 2010/0022561 A1 | 1/2010 | Honigberg et al. |
| 2010/0041677 A1 | 2/2010 | Honigberg et al. |
| 2010/0069458 A1 | 3/2010 | Atadja et al. |
| 2010/0087482 A1 | 4/2010 | Haber et al. |
| 2010/0143301 A1 | 6/2010 | Desai et al. |
| 2010/0158866 A1 | 6/2010 | Zhu |
| 2010/0185419 A1 | 7/2010 | Singh et al. |
| 2010/0189711 A1 | 7/2010 | Dranoff et al. |
| 2010/0222325 A1 | 9/2010 | Berthel et al. |
| 2010/0254905 A1 | 10/2010 | Honigberg et al. |
| 2010/0266589 A1 | 10/2010 | Hedrick et al. |
| 2010/0324050 A1 | 12/2010 | Honigberg et al. |
| 2011/0039868 A1 | 2/2011 | Honigberg et al. |
| 2011/0059854 A1 | 3/2011 | Gordon et al. |
| 2011/0086866 A1 | 4/2011 | Chen et al. |
| 2011/0124628 A1 | 5/2011 | Bruncko et al. |
| 2011/0125628 A1 | 5/2011 | Marchegiani |
| 2011/0152240 A1 | 6/2011 | Haddach et al. |
| 2011/0177011 A1 | 7/2011 | Currie et al. |
| 2011/0209230 A1 | 8/2011 | Korman et al. |
| 2011/0224235 A1 | 9/2011 | Honigberg et al. |
| 2011/0244465 A1 | 10/2011 | Harvey et al. |
| 2011/0281322 A1 | 11/2011 | Honigberg et al. |
| 2011/0281850 A1 | 11/2011 | Flynn et al. |
| 2011/0288032 A1 | 11/2011 | Ganji |
| 2011/0306599 A1 | 12/2011 | Inoue et al. |
| 2012/0039850 A1 | 2/2012 | McNair et al. |
| 2012/0065201 A1 | 3/2012 | Honigberg et al. |
| 2012/0071497 A1 | 3/2012 | Buggy et al. |
| 2012/0087915 A1 | 4/2012 | Buggy et al. |
| 2012/0088912 A1 | 4/2012 | Honigberg et al. |
| 2012/0095026 A1 | 4/2012 | Honigberg et al. |
| 2012/0100138 A1 | 4/2012 | Buggy et al. |
| 2012/0101113 A1 | 4/2012 | Honigberg et al. |
| 2012/0101114 A1 | 4/2012 | Honigberg et al. |
| 2012/0108547 A1 | 5/2012 | Jankowski et al. |
| 2012/0108612 A1 | 5/2012 | Honigberg et al. |
| 2012/0115889 A1 | 5/2012 | Honigberg et al. |
| 2012/0122894 A1 | 5/2012 | Honigberg et al. |
| 2012/0129821 A1 | 5/2012 | Honigberg et al. |
| 2012/0129853 A1 | 5/2012 | Elmore et al. |
| 2012/0129873 A1 | 5/2012 | Honigberg et al. |
| 2012/0135944 A1 | 5/2012 | Honigberg et al. |
| 2012/0165328 A1 | 6/2012 | Honigberg et al. |
| 2012/0178753 A1 | 7/2012 | Honigberg et al. |
| 2012/0183535 A1 | 7/2012 | Buggy et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0214826 A1 | 8/2012 | Honigberg et al. |
| 2012/0219522 A1 | 8/2012 | Xi |
| 2012/0252821 A1 | 10/2012 | Honigberg et al. |
| 2012/0252822 A1 | 10/2012 | Honigberg et al. |
| 2012/0277225 A1 | 11/2012 | Honigberg et al. |
| 2012/0277254 A1 | 11/2012 | Honigberg et al. |
| 2012/0277255 A1 | 11/2012 | Honigberg et al. |
| 2012/0283276 A1 | 11/2012 | Honigberg et al. |
| 2012/0283277 A1 | 11/2012 | Honigberg et al. |
| 2012/0296089 A1 | 11/2012 | Honigberg et al. |
| 2012/0329130 A1 | 12/2012 | Honigberg et al. |
| 2013/0005745 A1 | 1/2013 | Honigberg et al. |
| 2013/0005746 A1 | 1/2013 | Honigberg et al. |
| 2013/0012525 A1 | 1/2013 | Honigberg et al. |
| 2013/0018060 A1 | 1/2013 | Honigberg et al. |
| 2013/0029984 A1 | 1/2013 | Castro et al. |
| 2013/0035334 A1 | 2/2013 | Honigberg et al. |
| 2013/0041013 A1 | 2/2013 | Lavitrano et al. |
| 2013/0041014 A1 | 2/2013 | Lavitrano et al. |
| 2013/0079327 A1 | 3/2013 | Yamamoto et al. |
| 2013/0172314 A1 | 7/2013 | Chen et al. |
| 2013/0184223 A1 | 7/2013 | Land et al. |
| 2013/0184342 A1 | 7/2013 | Mills et al. |
| 2013/0195852 A1 | 8/2013 | Buggy et al. |
| 2013/0202611 A1 | 8/2013 | Buggy et al. |
| 2013/0217880 A1 | 8/2013 | Yamamoto et al. |
| 2013/0231328 A1 | 9/2013 | Harriman et al. |
| 2013/0273030 A1 | 10/2013 | Buggy et al. |
| 2013/0310402 A1 | 11/2013 | Buggy et al. |
| 2013/0338172 A1 | 12/2013 | Smyth et al. |
| 2014/0016306 A1 | 1/2014 | de Blois |
| 2014/0018414 A1 | 1/2014 | Brosnan |
| 2014/0039186 A1 | 2/2014 | Honigberg et al. |
| 2014/0057907 A1 | 2/2014 | Honigberg et al. |
| 2014/0079690 A1 | 3/2014 | Buggy et al. |
| 2014/0080844 A1 | 3/2014 | Chen et al. |
| 2014/0128413 A1 | 5/2014 | Honigberg et al. |
| 2014/0128414 A1 | 5/2014 | Honigberg et al. |
| 2014/0134265 A1 | 5/2014 | Buggy et al. |
| 2014/0135347 A1 | 5/2014 | Honigberg et al. |
| 2014/0142123 A1 | 5/2014 | Honigberg et al. |
| 2014/0163027 A1 | 6/2014 | Verner et al. |
| 2014/0163046 A1 | 6/2014 | Honigberg et al. |
| 2014/0171453 A1 | 6/2014 | Honigberg et al. |
| 2014/0187564 A1 | 7/2014 | Honigberg et al. |
| 2014/0187565 A1 | 7/2014 | Honigberg et al. |
| 2014/0194417 A1 | 7/2014 | Greenwood et al. |
| 2014/0194446 A1 | 7/2014 | Buggy et al. |
| 2014/0206681 A1 | 7/2014 | Kim et al. |
| 2014/0212485 A1 | 7/2014 | Honigberg et al. |
| 2014/0243355 A1 | 8/2014 | Honigberg et al. |
| 2014/0249215 A1 | 9/2014 | Pimont-Garro et al. |
| 2014/0275125 A1 | 9/2014 | Honigberg et al. |
| 2014/0303191 A1 | 10/2014 | Buggy et al. |
| 2014/0336203 A1 | 11/2014 | Smyth et al. |
| 2014/0336206 A1 | 11/2014 | Honigberg et al. |
| 2014/0371241 A1 | 12/2014 | Buggy et al. |
| 2014/0377258 A1 | 12/2014 | Stern et al. |
| 2014/0378446 A1 | 12/2014 | Chen et al. |
| 2015/0018336 A1 | 1/2015 | Chen et al. |
| 2015/0031710 A1 | 1/2015 | Buggy et al. |
| 2015/0031711 A1 | 1/2015 | Buggy et al. |
| 2015/0038518 A1 | 2/2015 | Balasubramanian |

(56) References Cited

U.S. PATENT DOCUMENTS

| | | |
|---|---|---|
| 2015/0044217 A1 | 2/2015 | Chen et al. |
| 2015/0072988 A1 | 3/2015 | Carducci et al. |
| 2015/0105409 A1 | 4/2015 | Quayle et al. |
| 2015/0118222 A1 | 4/2015 | Levy et al. |
| 2015/0133661 A1 | 5/2015 | Honigberg et al. |
| 2015/0140036 A1 | 5/2015 | Mannick et al. |
| 2015/0140085 A1 | 5/2015 | Goldstein |
| 2015/0152115 A1 | 6/2015 | Honigberg et al. |
| 2015/0158871 A1 | 6/2015 | Purro et al. |
| 2015/0184249 A1 | 7/2015 | Chang et al. |
| 2015/0210769 A1 | 7/2015 | Freeman et al. |
| 2015/0238490 A1 | 8/2015 | Burger |
| 2015/0239897 A1 | 8/2015 | Chen et al. |
| 2015/0265618 A1 | 9/2015 | Honigberg et al. |
| 2015/0267261 A1 | 9/2015 | Byrd et al. |
| 2015/0306103 A1 | 10/2015 | Honigberg et al. |
| 2015/0306106 A1 | 10/2015 | Honigberg et al. |
| 2015/0307500 A1 | 10/2015 | Honigberg et al. |
| 2015/0361504 A1 | 12/2015 | Byrd et al. |
| 2016/0000792 A1 | 1/2016 | Buggy et al. |
| 2016/0009714 A1 | 1/2016 | Sun et al. |
| 2016/0022683 A1 | 1/2016 | Fardis et al. |
| 2016/0022684 A1 | 1/2016 | Kuo et al. |
| 2016/0032404 A1 | 2/2016 | Schweighofer et al. |
| 2016/0101128 A1 | 4/2016 | Wang et al. |
| 2016/0108045 A1 | 4/2016 | Andres et al. |
| 2016/0108123 A1 | 4/2016 | Freeman et al. |
| 2016/0159905 A1 | 6/2016 | Abdiche et al. |
| 2016/0175312 A1 | 6/2016 | Buggy et al. |
| 2016/0243033 A1 | 8/2016 | Buggy et al. |
| 2016/0287592 A1 | 10/2016 | Chang et al. |
| 2016/0324859 A1 | 11/2016 | Buggy et al. |
| 2017/0007611 A1 | 1/2017 | Honigberg et al. |
| 2017/0035762 A1 | 2/2017 | Buggy et al. |
| 2017/0071962 A1 | 3/2017 | Lannutti et al. |
| 2017/0209462 A1 | 7/2017 | Bilotti et al. |
| 2017/0209574 A1 | 7/2017 | Cao et al. |
| 2017/0266186 A1 | 9/2017 | Buggy et al. |
| 2017/0354655 A1 | 12/2017 | Beaupre et al. |
| 2017/0360796 A1 | 12/2017 | Jaglowski |
| 2017/0362246 A1 | 12/2017 | Buggy et al. |
| 2018/0015091 A1 | 1/2018 | Buggy et al. |
| 2018/0036313 A1 | 2/2018 | Buggy et al. |
| 2018/0071293 A1 | 3/2018 | Buggy et al. |
| 2018/0071295 A1 | 3/2018 | Kuo et al. |
| 2018/0085372 A1 | 3/2018 | Honigberg et al. |
| 2018/0256581 A1 | 9/2018 | Buggy et al. |
| 2020/0055859 A1 | 2/2020 | Buggy et al. |
| 2020/0108072 A1 | 4/2020 | Honigberg et al. |
| 2020/0147084 A1 | 5/2020 | Buggy et al. |
| 2020/0163968 A1 | 5/2020 | Buggy et al. |

FOREIGN PATENT DOCUMENTS

| | | |
|---|---|---|
| CA | 2681756 A1 | 10/2008 |
| CA | 2874756 A1 | 10/2008 |
| CA | 2991994 A1 | 12/2013 |
| CN | 101610676 A | 12/2009 |
| CN | 101626758 A | 1/2010 |
| CN | 103923084 A | 7/2014 |
| CN | 106336413 A | 1/2017 |
| CN | 106474143 A | 3/2017 |
| EP | 1038392 A1 | 9/2000 |
| EP | 1046399 | 10/2000 |
| EP | 1091440 A1 | 4/2001 |
| EP | 1132393 | 9/2001 |
| EP | 1225034 A1 | 7/2002 |
| EP | 1473039 A1 | 11/2004 |
| EP | 1240899 | 8/2010 |
| EP | 2220116 | 8/2010 |
| JP | H01167840 A | 7/1989 |
| JP | 2003509428 A | 3/2003 |
| JP | 2004/518615 A | 6/2004 |
| JP | 2005/089352 A | 4/2005 |
| JP | 2007520559 A | 7/2007 |
| JP | 2010526768 A | 8/2010 |
| JP | 2011/508749 A | 3/2011 |
| JP | 4934197 B2 | 5/2012 |
| JP | 2013/506680 A | 2/2013 |
| JP | 2013507448 A | 3/2013 |
| JP | 2013/529207 A | 7/2013 |
| JP | 5717109 B2 | 5/2015 |
| JP | 5841998 B2 | 1/2016 |
| KR | 2011/0099027 A | 9/2011 |
| WO | WO-1994/014436 A1 | 7/1994 |
| WO | WO-9728161 A1 | 8/1997 |
| WO | WO-1997/040028 A1 | 10/1997 |
| WO | WO-1997/049706 A1 | 12/1997 |
| WO | WO-1998/040381 A1 | 9/1998 |
| WO | WO-1998/041525 A1 | 9/1998 |
| WO | WO-9954286 A2 | 10/1999 |
| WO | WO-1999/63599 A1 | 12/1999 |
| WO | WO-2000/000823 | 1/2000 |
| WO | WO-2000/056331 A1 | 9/2000 |
| WO | WO-2000/056737 | 9/2000 |
| WO | WO-0056737 A2 | 9/2000 |
| WO | WO-0119829 A2 | 3/2001 |
| WO | WO-2001/025238 | 4/2001 |
| WO | WO-0125238 A2 | 4/2001 |
| WO | WO-0129058 A1 | 4/2001 |
| WO | WO-0141754 A2 | 6/2001 |
| WO | WO-0144258 A1 | 6/2001 |
| WO | WO-0119829 A3 | 9/2001 |
| WO | WO-2002/038797 | 5/2002 |
| WO | WO-0238797 A2 | 5/2002 |
| WO | WO-02076986 A1 | 10/2002 |
| WO | WO-02078731 A1 | 10/2002 |
| WO | WO-02080926 A1 | 10/2002 |
| WO | WO-2003/004053 | 1/2003 |
| WO | WO-03000187 A2 | 1/2003 |
| WO | WO-2003/013540 | 2/2003 |
| WO | WO-2003/046200 | 6/2003 |
| WO | WO-2003/097645 | 11/2003 |
| WO | WO-2004/060319 A2 | 7/2004 |
| WO | WO-2004/074290 A1 | 9/2004 |
| WO | WO-2004096253 A1 | 11/2004 |
| WO | WO-2004100868 A2 | 11/2004 |
| WO | WO-2005/000197 A2 | 1/2005 |
| WO | WO-2005005429 A1 | 1/2005 |
| WO | WO-2005014599 A1 | 2/2005 |
| WO | WO-2005/037836 A2 | 4/2005 |
| WO | WO-2005/037843 A1 | 4/2005 |
| WO | WO-2005/060956 A1 | 7/2005 |
| WO | WO-2004100868 A3 | 7/2005 |
| WO | WO-2005/074603 A2 | 8/2005 |
| WO | WO-2006/002871 A1 | 1/2006 |
| WO | WO-2006/012422 A1 | 2/2006 |
| WO | WO-2006/036527 A1 | 4/2006 |
| WO | WO-2006/036788 A2 | 4/2006 |
| WO | WO-2006/036941 A2 | 4/2006 |
| WO | WO-2006039644 A2 | 4/2006 |
| WO | WO-2006050946 A2 | 5/2006 |
| WO | WO-2006/053121 A2 | 5/2006 |
| WO | WO-2006/071017 A1 | 7/2006 |
| WO | WO-2006/099075 A2 | 9/2006 |
| WO | WO-2006/124462 A2 | 11/2006 |
| WO | WO-2007/002325 A1 | 1/2007 |
| WO | WO-2007/058832 A2 | 5/2007 |
| WO | WO-2007/087068 A2 | 8/2007 |
| WO | WO-2007/116025 A2 | 10/2007 |
| WO | WO-2007136790 A2 | 11/2007 |
| WO | WO-2008039218 A2 | 4/2008 |
| WO | WO-2008/063727 A2 | 5/2008 |
| WO | WO-2008054827 A2 | 5/2008 |
| WO | WO-2008069881 A2 | 6/2008 |
| WO | WO-2008/108636 A1 | 9/2008 |
| WO | WO-2008/121742 A2 | 10/2008 |
| WO | WO-2008/124138 A1 | 10/2008 |
| WO | WO-2008127659 A2 | 10/2008 |
| WO | WO-2008/138578 A2 | 11/2008 |
| WO | WO-2009/021137 A2 | 2/2009 |
| WO | WO-2009/051822 A1 | 4/2009 |
| WO | WO-2009/089399 A2 | 7/2009 |
| WO | WO-2009/118142 A1 | 10/2009 |

(56) References Cited

FOREIGN PATENT DOCUMENTS

| | | |
|---|---|---|
| WO | WO-2009/118523 A1 | 10/2009 |
| WO | WO-2009/140853 A1 | 11/2009 |
| WO | WO-2009/149179 A2 | 12/2009 |
| WO | WO-2009/1585871 A1 | 12/2009 |
| WO | WO-2010/009342 A2 | 1/2010 |
| WO | WO-2010/009342 A3 | 1/2010 |
| WO | WO-2010/034670 A2 | 4/2010 |
| WO | WO-2010057048 A1 | 5/2010 |
| WO | WO-2010/065824 A2 | 6/2010 |
| WO | WO-2010/065898 A2 | 6/2010 |
| WO | WO-2010/069809 A1 | 6/2010 |
| WO | WO-2010/077634 A1 | 7/2010 |
| WO | WO-2010/093843 A2 | 8/2010 |
| WO | WO-2010/126960 A1 | 11/2010 |
| WO | WO-2011/034907 A2 | 3/2011 |
| WO | WO-2011/041462 A2 | 4/2011 |
| WO | WO-2011/046771 | 4/2011 |
| WO | WO-2011046964 A2 | 4/2011 |
| WO | WO-2011/068560 A1 | 6/2011 |
| WO | WO-2011/133609 A2 | 10/2011 |
| WO | WO-2011/145035 A1 | 11/2011 |
| WO | WO-2011/152351 A1 | 12/2011 |
| WO | WO-2011/153514 A2 | 12/2011 |
| WO | WO-2011/160206 A1 | 12/2011 |
| WO | WO-2011/162515 A2 | 12/2011 |
| WO | WO-2012/001090 A1 | 1/2012 |
| WO | WO-2012/021444 A1 | 2/2012 |
| WO | WO-2012/158764 A1 | 11/2012 |
| WO | WO-2013/010868 A1 | 1/2013 |
| WO | WO-2013/036994 A1 | 3/2013 |
| WO | WO-2013/059738 A2 | 4/2013 |
| WO | WO-2013/085893 A1 | 6/2013 |
| WO | WO-2013/160645 A1 | 10/2013 |
| WO | WO-2013/184572 A1 | 12/2013 |
| WO | WO-2014/004707 A1 | 1/2014 |
| WO | WO-2014004376 A2 | 1/2014 |
| WO | WO-2014018567 A1 | 1/2014 |
| WO | WO-2014/039855 A1 | 3/2014 |
| WO | WO-2014/071205 A1 | 5/2014 |
| WO | WO-2014/071231 A1 | 5/2014 |
| WO | WO-2014/135669 A1 | 9/2014 |
| WO | WO-2014/168975 A1 | 10/2014 |
| WO | WO-2014/194254 A1 | 12/2014 |
| WO | WO-2014/195888 A1 | 12/2014 |
| WO | WO-2015/013579 A1 | 1/2015 |
| WO | WO-2015018522 A1 | 2/2015 |
| WO | WO-2015/048689 A1 | 4/2015 |
| WO | WO-2015/061751 A1 | 4/2015 |
| WO | WO-2015/061752 A1 | 4/2015 |
| WO | WO-2015/084892 A1 | 6/2015 |
| WO | WO-2015/127234 A1 | 8/2015 |
| WO | WO-2015/127261 A1 | 8/2015 |
| WO | WO-2015/143400 A1 | 9/2015 |
| WO | WO-2015/149105 A1 | 10/2015 |
| WO | WO-2015/181747 A1 | 12/2015 |
| WO | WO-2015/192081 A1 | 12/2015 |
| WO | WO-2016/014859 A1 | 1/2016 |
| WO | WO-2016/019341 A1 | 2/2016 |
| WO | WO-2016/022853 A1 | 2/2016 |
| WO | WO-2016/024227 A1 | 2/2016 |
| WO | WO-2016/044774 A1 | 3/2016 |
| WO | WO-2016/54555 A2 | 4/2016 |
| WO | WO-2016/054627 A1 | 4/2016 |
| WO | WO-2016/081460 A1 | 5/2016 |
| WO | WO-2016/106381 A1 | 6/2016 |
| WO | WO-2016/123504 A1 | 8/2016 |
| WO | WO-2016/141092 A1 | 9/2016 |
| WO | WO-2016/161347 A1 | 10/2016 |
| WO | WO-2017/011314 A1 | 1/2017 |
| WO | WO-2017/040617 A1 | 3/2017 |
| WO | WO-2017/087947 A2 | 5/2017 |

OTHER PUBLICATIONS

Burger J.A., "The Bruton's Tyrosine Kinase Inhibitor, PCI-32765, Is Well Tolerated and Demonstrates Promising Clinical Activity in Chronic Lymphocytic Leukemia (CLL) and Small Lymphocytic Lymphoma (SLL): An Update on Ongoing Phase 1 Studies," Blood, Nov. 19, 2010, vol. 116 (21), p. 57.

Chang et al., "Use of tumor genomic profiling to reveal mechanisms of resistance to the BTK inhibitor ibrutinib in chronic lymphocytic leukemia (CLL)," Journal of Clinical Oncology, 2013, vol. 31, No. 15, May 20 Suppl,. Abstract No. 7014.

Woyach et al. Resistance mechanisms for the Bruton's tyrosine kinase inhibitor ibrutinib. N Engl J Med 370(24):2286-2294 (2014).

Honigberg et al. The Bruton tyrosine kinase inhibitor PCI-32765 blocks B-cell activation and is efficacious in models of autoimmune disease and B-cell malignancy. PNAS USA 107:13075-13080 (2010).

Advani et al. The BTK inhibitor PCI-32765 is highly active and well tolerated in patients (PTS) with relapsed/refractory B cell malignancies: final results from a phase I study, Ann. Oncol. 22(suppl 4): abstract 153 (2011).

Arnold et al. Pyrrolo[2,3-d]pyrimidines Containing an Extended 5-Substituent as Potent and Selective Inhibitors of Ick 1. Bioorg. Med. Chem. Ltrs. 10:2167-2170 (2000).

Banker et al. Modern Pharmaceutics, 3ed., Marcel Dekker, New York 1996, p. 596.

Browning. B cells move to centre stage: novel opportunities for autoimmune disease treatment. Nature Reviews/Drug Discovery 5:564-576 (Jul. 2006).

Burchat et al. Pyrazolo[3,4-d]pyrimidines Containing an Extended 3-Substituent as Potent Inhibitors of Lck—a Selectivity Insight. Bioorg. Med. Chem. Ltrs. 12:1687-1690 (2002).

Byrd et al. Entering the era of targeted therapy for chronic lymphocytic leukemia: impact on the practicing clinician. J. Clinical Oncology (Jul. 21, 2014) (pii: JCO.2014.55.8262).

Chang et al. The Bruton tyrosine kinase inhibitor PCI-32765 ameliorates autoimmune arthritis by inhibition of multiple effector cells. Arthritis Research & Therapy, 13:R115 (2011).

Cohen et al. Structural Bioinformatics-Based Design of Selective, Irreversible Kinase Inhibitors. Science 308:1318-1321 (May 27, 2005).

Co-pending U.S. Appl. No. 14/613,309, filed Feb. 3, 2015.

Czuczman et al. Rituximab in combination with fludarabine chemotherapy in low-grade or follicular lymphoma. J. Clin. Oncol. 23(4):694-704 (Feb. 1, 2005).

Desiderio. Role of Btk in B cell development and signaling. Curr. Op. in Immunology 1997, 9:534-540.

Dorwald. A. Side Reactions in Organic Synthesis, Wiley:VCH, Weinheim p. IX of Preface, Wiley-VCH Verlag GmbH & Co. KGaA (2005).

Fabian et al. A small molecule-kinase interaction map for clinical kinase inhibitors. Nature Biotechnology, 23(3): 329-336 (2005).

Fisher et al. Prolonged disease-free survival in Hodgkin's disease with MOPP reinduction after first relapse. Ann. Intern. Med., 90(5):761-763 (1979).

Fowler et al. The Bruton's tyrosine kinase inhibitor ibrutinib (PCI-32765) is active and tolerated in relapsed follicular lymphoma. 54th American Society of Hematology Annual Meeting and Exposition, Atlanta, GA, Abstract 156 (Dec. 8-11, 2012).

Fruman. Xid-like Phenotypes: A B Cell Signalosome Takes Shape. Immunity 13:1-3 (Jul. 2000).

Ghia. Ibrutinib: better combined with other drugs? Lancet 15:1043-1044 (2014).

Gold. To make antibodies or not:signaling by the B-cell antigen receptor. Trends in Pharmacological Sciences, 23(7):316-324 (Jul. 2002).

Hantschel et al. Systematic profiling and novel targets of the Bcr-Abl kinase inhibitors imatinib, nilotinib and dasatinib. Blood 110(11, Part 2):207B (2007) & 49th Annual Meeting of the American-Society-Of-Hematology; Atlanta, Ga, USA; Dec. 8-11, 2007.

Hantschel et al. The Btk Tyrosine Kinase is a Major Target of the Bcr-Abl Inhibitor Dasatinib. PNAS 104(33):13283-13288 (2007).

Hata et al. Bruton's tyrosine kinase-mediated Interleukin-2 gene activation in mast cells. J. Biol. Chem. 273(18): 10979-10987 (1998).

(56) References Cited

OTHER PUBLICATIONS

Herman et al. Bruton tyrosine kinase represents a promising therapeutic target for treatment of chronic lymphocytic leukemia and is effectively targeted by PCI-32765. Blood (Epub Mar. 21, 2011), 117(23):6287-6296 (Jun. 2011).
Hiddeman et al. Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German Low-Grade Lymphoma Study Group. Blood (Epub Aug. 25, 2005) 106(12):3725-3732 (Dec. 2005).
Horwood et al. Bruton's Tyrosin Kinase Is Required for Lipopolysaccharide-induced Tumor Necrosis Factor α Production. J. Exp. Med. 197(12):1603-1611 (Jun. 2003).
http://www.uspto.gov/web/offices/pac/dapp/1pecba.htm#7, last accessed Feb. 16, 2011.
Iwaki et al. Btk Plays a Crucial Role in the Amplification of FceRI-mediated Mast Cell Activation by Kit. J. Biol. Chem. 280(48):40261-40270 (Dec. 2, 2005).
Jefferies et al. Bruton's Tyrosine Kinase Is a Toll/Interleukin-1 Receptor Domain-binding Protein That Participates in Nuclear Factor κB Activation by Toll-like Receptor 4. J. Biol. Chem. 278:26258-26264 (2003).
Kawakami et al. Terreic acid, a quinone epoxide inhibitor of Bruton's tyrosine kinase. PNAS USA 96:2227-2232 (1999).
Kuppers. Mechanisms of B-cell lymphoma pathogenesis. Nature Reviews/Cancer 5:251-262 (2005).
Kurosaki. Functional dissection of BCR signaling pathways. Curr. Op. Imm. 12:276-281 (2000).
Kushner et al. Pharmacological uses and perspective of heavy water and deuterated compounds. Canadian Journal of Physiology and Pharmacology 77(2):79-88 (1999).
Liu et al. Structural Basis for selective inhibition of Src family kinases by PPI. Chemistry and Biology 6:671-678, in particular table 1, p. 671 (1999).
Luskova et al. Modulation of the Fce Receptor I Signaling by Tyrosin Kinase Inhibitors: Search for Therapeutic Targets of Inflammatory and Allergy Diseases. Curr. Pharmaceutical Design 10:1727-1737 (2004).
Mahajan et al. Rational Design and Synthesis of a Novel Antileukemic Agent Targeting Bruton's Tyrosine Kinase (BTK), LFM-A13 [α-Cyano-β-Methyl-N-(2,5-Dibromophenyl)Propenamide]. J. of Biol. Chem. 274(14):9587-9599 (1999).
Mangla et al. Pleiotropic consequences of Bruton tyrosin kinase deficiency in myeloid lineages lead to poor inflammatory responses. Blood 104(4):1191-1197 (2004).
Merged Markush Service Search, Jun. 27, 2005.
Niiro et al. Regulation of B-Cell Fate by Antigen-Receptor Signals. Nature Reviews 2:945-956 (2002).
Nisitani et al. In situ detection of activated Bruton's tyrosine kinase in the Ig signaling complex by phosphopeptide-specific monoclonal antibodies. PNAS USA 96:2221-2226 (1999).
Oligino et al. Targeting B cells for the treatment of rheumatoid arthritis. Arthritis Res. Ther., 5(Suppl.4):S7-S11 (2002).
Pan et al. Discovery of Selective Irreversible Inhibitors for Bruton's Tyrosine Kinase, ChemMedChem. 2:58-61 (2007).
PCT/US2006/49626 International Preliminary Report on Patentability Search Report dated Mar. 24, 2009.
PCT/US2006/49626 International Search Report dated Apr. 9, 2008.
PCT/US2013/051741 International Preliminary Report on Patentability dated Jan. 27, 2015.
PCT/US2013/051741 International Search Report and Written Opinion dated Jan. 7, 2014.
Peterson et al. Prolonged single-agent versus combination chemotherapy in indolent follicular lymphomas: a study of the cancer and leukemia group. Br. J. Clin. Oncol., 21(1):5-15 (Jan. 1, 2003).
Ponader et al. The Bruton tyrosine kinase inhibitor PCI-32765 thwarts chronic lymphocytic leukemia cell survival and tissue homing in vitro and in vivo. Blood (Epub Dec. 16, 2011), 119(5):1182-1189 (Feb. 2012).
Quek et al. A role for Bruton's tyrosine kinase (Btk) in platelet activation by collagen. Curr. Biol. 8(20) :1137-1140 (1998).
Sada et al. Protein-Tyrosine Kinases and Adaptor Proteins in FceRI-Mediated Signaling in Mast Cells. Curr. Mol. Med. 3(1):85-94 (2003).
Schaeffer et al. Tec family kinases in lymphocyte signaling and function. Curr. Op. Imm. 12:282-288 (2000).
Science IP CAS Search, Mar. 16, 2006.
Science IP CAS Search, Sep. 5, 2006.
Shaffer et al. Lymphoid malignancies: the dark side of B-cell differentiation. Nature Reviews/Immunology 2:920-932 (2002).
Shah et al. Ibrutinib for the treatment of mantle cell lymphoma. Expert Rev. Hematol. 7(5):521-531 (2014) (Epub Aug. 27, 2014).
Smaill et al. Tyrosine Kinase Inhibitors. 15. 4-(Phenylamino)quinazoline and 4-(Phenylamino)prido[d]pyrimidine Acrylamides as Irreversible Inhibitors of the ATP Binding Site of the Epidermal Growth Factor Receptor. J. Med. Chem. 42(10):1803-1815 (1999).
Smith et al. The Tec family of cytoplasmic tyrosine kinases: mammalian Btk, Bmx, Itk, Tec, Txk and homologs in other species. BioEssays 23:436-446 (2001).
Smolen et al. Therapeutic Strategies for Rheumatoid Arthritis. Nature Reviews 2:473-488 (2003).
Tinmouth et al. Fludarabine in alkylator-resistant follicular non-Hodgkin's lymphoma. Leuk. Lymphoma 41(1-2):137-145 (2001).
Uckun et al. Bruton's tyrosine kinase as a molecular target in treatment of leukemias and lymphomas as well as inflammatory disorders and autoimmunity. Expert Opinion Ther. Patents 20(11):4157-1470 (2010).
Uckun et al. Bruton's Tyrosine Kinase (BTK) as a Dual-Function Regulator of Apoptosis. Biochem. Pharmacology 56:683-691 (1998).
Uckun et al. BTK as a Mediator of Radiation-Induced Apoptosis in DT-40 Lymphoma B Cells. Science 273(5278):1096-1100 (1996).
Uckun et al. In Vivo Pharmacokinetic Features, Toxicity Profile, and Chemosensitizing Activity of α-Cyano-β-hydroxy-β-methyl-N-(2,5-dibromophenyl)propenamide (LFM-A13), a Novel Antileukemic Agent Targeting Bruton's Tyrosine Kinase. Clin. Cancer Res. 8:1224-1233 (2002).
Uckun et al. The Anti-leukemic Bruton's Tyrosin Kinase Inhibitor α-cyano-β-hydroxy-β-mehyl-N-(2,5-dibromophenyl)Propenamide (LFM-A13)Prevents Fatal Thromboembolism. Leuk. Lymphoma 44(9):1569-1577 (2003).
U.S. Appl. No. 14/079,508 Office Action dated Dec. 15, 2014.
U.S. Appl. No. 11/617,645 Final Office Action dated Oct. 16, 2008.
U.S. Appl. No. 11/617,645 Notice of Allowance dated Feb. 9, 2009.
U.S. Appl. No. 11/617,645 Office Action dated Jan. 24, 2008.
U.S. Appl. No. 11/617,645 Office Action dated May 13, 2008.
U.S. Appl. No. 11/692,870 Final Office Action dated Aug. 19, 2009.
U.S. Appl. No. 11/692,870 Office Action dated Jan. 26, 2009.
U.S. Appl. No. 12/356,498 Final Office Action dated Jul. 8, 2011.
U.S. Appl. No. 12/356,498 Office Action dated Apr. 14, 2011.
U.S. Appl. No. 12/499,002 Final Office Action dated Dec. 14, 2012.
U.S. Appl. No. 12/499,002 Final Office Action dated Oct. 25, 2011.
U.S. Appl. No. 12/499,002 Office Action dated Mar. 3, 2011.
U.S. Appl. No. 12/499,002 Office Action dated Jun. 5, 2012.
U.S. Appl. No. 12/499,005 Office Action dated Feb. 17, 2011.
U.S. Appl. No. 12/499,008 Office Action dated Jul. 19, 2011.
U.S. Appl. No. 12/499,008 Office Action dated Mar. 9, 2011.
U.S. Appl. No. 12/727,703 Final Office Action dated Jul. 19, 2011.
U.S. Appl. No. 12/727,703 Office Action dated Mar. 3, 2011.
U.S. Appl. No. 12/887,428 Office Action dated Apr. 20, 2011.
U.S. Appl. No. 12/907,759 Final Office Action dated Nov. 8, 2013.
U.S. Appl. No. 12/907,759 Office Action dated Aug. 13, 2013.
U.S. Appl. No. 12/907,759 Office Action dated Dec. 31, 2013.
U.S. Appl. No. 12/907,759 Office Action dated Jul. 10, 2014.
U.S. Appl. No. 13/011,258 Office Action dated Nov. 22, 2011.
U.S. Appl. No. 13/162,449 Office Action dated Feb. 9, 2012.
U.S. Appl. No. 13/249,066 Final Office Action dated May 15, 2013.
U.S. Appl. No. 13/249,066 Office Action dated Dec. 11, 2013.
U.S. Appl. No. 13/249,066 Office Action dated Nov. 27, 2012.

(56) References Cited

OTHER PUBLICATIONS

U.S. Appl. No. 13/312,606 Final Office Action dated Apr. 5, 2013.
U.S. Appl. No. 13/312,606 Office Action dated Sep. 19, 2012.
U.S. Appl. No. 13/328,718 Final Office Action dated Dec. 27, 2012.
U.S. Appl. No. 13/328,718 Office Action dated Jul. 3, 2012.
U.S. Appl. No. 13/335,719 Final Office Action dated Nov. 8, 2013.
U.S. Appl. No. 13/335,719 Office Action dated Jul. 31, 2013.
U.S. Appl. No. 13/340,409 Final Office Action dated Nov. 12, 2013.
U.S. Appl. No. 13/340,409 Office Action dated Jul. 19, 2013.
U.S. Appl. No. 13/340,556 Office Action dated Jul. 31, 2013.
U.S. Appl. No. 13/361,726 Office Action dated Jul. 18, 2013.
U.S. Appl. No. 13/361,733 Notice of Allowance dated Nov. 14, 2012.
U.S. Appl. No. 13/361,733 Office Action dated Jul. 6, 2012.
U.S. Appl. No. 13/450,158 Non-Final Office Action dated Oct. 31, 2013.
U.S. Appl. No. 13/472,292 Office Action dated Mar. 13, 2013.
U.S. Appl. No. 13/479,053 Office Action dated Sep. 6, 2013.
U.S. Appl. No. 13/526,161 Final Office Action dated May 15, 2013.
U.S. Appl. No. 13/526,161 Office Action dated Nov. 27, 2012.
U.S. Appl. No. 13/526,161 Office Action dated Aug. 1, 2013.
U.S. Appl. No. 13/526,163 Final Office Action dated May 15, 2013.
U.S. Appl. No. 13/526,163 Office Action dated Aug. 2, 2013.
U.S. Appl. No. 13/526,163 Office Action dated Nov. 28, 2012.
U.S. Appl. No. 13/542,440 Non-Final Office Action dated Oct. 31, 2013.
U.S. Appl. No. 13/542,440 Office Action dated Jan. 7, 2014.
U.S. Appl. No. 13/654,173 Office Action dated Apr. 7, 2014.
U.S. Appl. No. 13/849,399 Office Action dated Aug. 4, 2014.
U.S. Appl. No. 13/849,399 Office Action dated Jul. 23, 2014.
U.S. Appl. No. 13/890,498 Non-Final Office Action dated Mar. 6, 2015.
U.S. Appl. No. 13/890,498 Office Action dated Aug. 19, 2014.
U.S. Appl. No. 14/033,344 Non-Final Office Action dated Dec. 10, 2014.
U.S. Appl. No. 14/073,543 Office Action dated Dec. 15, 2014.
U.S. Appl. No. 14/073,594 Office Action dated Dec. 15, 2014.
U.S. Appl. No. 14/080,640 Non-Final Office Action dated Feb. 24, 2015.
U.S. Appl. No. 14/080,640 Office Action dated Dec. 31, 2014.
U.S. Appl. No. 14/080,649 Office Action dated Feb. 5, 2015.
Vassilev et al. Bruton's Tyrosine Kinase as an Inhibitor of the Fas/CD95 Death-inducing Signaling Complex. J. Biol. Chem. 274(3):1646-1656 (1999).
Vassilev et al. Therapeutic Potential of Inhibiting Bruton's Tyrosine Kinase, (BTK). Current Pharmaceutical Design 10:1757-1766 (2004).
Vippagunta et al. Crystalline Solids, Advanced Drug Delivery Reviews, 48:3-26 (2001).
Witzig et al. Lenalidomide oral monotherapy produces durable responses in relapsed or refractory indolent non-Hodgkin's lymphoma. J. Clin. Oncol. 27:5404-5409 (Epub Oct. 5, 2009).
Wolff. Burger's Medicinal Chemistry and Drug Discovery. 5th Ed. Part 1, pp. 975-977 (1995).
Yamamoto et al. The Orally Available Spleen Tyrosine Kinase Inhibitor 2-[7-(3,4-Dimethoxyphenyl)-imidazo[1,2-c]pyrimidin-5-ylamino]-nicotinamide Dihydrochloride (BAY61-3606) Blocks Antigen-Induced Airway Inflammation in Rodents. J. Pharma. And Exp. Therapeutics 306(3):1174-1181 (2003).
U.S. Appl. No. 10/805,770.
U.S. Appl. No. 11/964,285.
U.S. Appl. No. 13/073,543.
U.S. Appl. No. 13/340,409.
U.S. Appl. No. 13/606,949.
U.S. Appl. No. 13/612,143.
U.S. Appl. No. 13/654,173.
U.S. Appl. No. 13/736,812.
U.S. Appl. No. 13/747,319.
U.S. Appl. No. 13/747,322.
U.S. Appl. No. 13/849,399.
U.S. Appl. No. 13/869,700.
U.S. Appl. No. 13/890,498.
U.S. Appl. No. 13/952,531.
U.S. Appl. No. 13/965,135.
U.S. Appl. No. 14/033,344.
U.S. Appl. No. 14/069,222.
U.S. Appl. No. 14/073,543.
U.S. Appl. No. 14/073,594.
U.S. Appl. No. 14/079,508.
U.S. Appl. No. 14/080,640.
U.S. Appl. No. 14/080,649.
U.S. Appl. No. 14/152,886.
U.S. Appl. No. 14/156,247.
U.S. Appl. No. 14/188,390.
U.S. Appl. No. 14/340,483.
U.S. Appl. No. 14/417,097.
U.S. Appl. No. 14/605,854.
U.S. Appl. No. 14/605,857.
U.S. Appl. No. 14/613,313.
U.S. Appl. No. 14/664,663.
U.S. Appl. No. 14/703,750.
U.S. Appl. No. 14/793,366.
U.S. Appl. No. 14/794,685.
U.S. Appl. No. 14/855,270.
U.S. Appl. No. 14/856,217.
ACS 2015 (http://www.cancer.org/cancer/non-hodgkinlymphoma/detailedguide/non-hodgkin-lymphoma-types-of-non-hodgkinlymphoma).
Adimoolam et al. HDAC inhibitor PCI-24781 decreases RAD51 expression and inhibits homologous recombination. PNAS 104 (49):19482-19487 (2007).
Advani et al. Effect of Btk inhibitor PCI-32765 monotherapy on responses in patients with relapsed aggressive NHL: Evidence of antitumor activity from a phase I study. J. Clin. Oncol., 2010 ASCO Annual Meeting Proceedings (Post-Meeting Edition), 28(15 Supp):8012 (2010).
Advani, R.H., et al., 2013, "Bruton tyrosine kinase inhibitor Ibrutinib (PCI-32765) ha significant activity in patients with relapsed/refractory B-cell malignancies", Journal of Clinical Oncology, vol. 31, No. 1 ,pp. 88-94.
Agathocleous et al. Preliminary Results of a Phase I/II Study of Weekly or Twice Weekly Bortezomib in Combination with Rituximab, in Patients with Follicular Lymphoma, Mantle Cell Lymphoma and Waldenstrom's Macroglobulinaemia. Blood (ASH Annual Meeting Abstracts) 110:Abstract 2559 (2007).
Agency for Toxic Substances and Disease Registry, Public Health Assessment Guidance Manual, (2005).
Ahn et al. Michael acceptors as a tool for anticancer drug design. Current Pharmaceutical Design 2(3):247-262 (1996).
Almo et al., Considerations for combined immune checkpoint modulation and radiation treatment, Radiat Res, 182(2): 230-238 (2014).
American Cancer Society Melanoma Guidelines (Last Revised Feb. 1, 2016), p. 37.
Anderson. The process of structure-based drug design. Chem and Biol 10:787-797 (2003).
Anonymous: "Ibrutinib/Rituximab combination leads to high response rate among patient with CLL," The Asco Post (2013).
Anonymous: "NCT01217749 on Apr. 16, 2012: Clinical Trials.gov Archive," Apr. 16, 2012 (Apr. 16, 2012), XP055260251, Retrieved from the Internet: URL:https://clinicaltrials.gov/archive/NCT01217749/2012_04_16.
Apsel et al. Targeted Polypharmacology: Discovery of Dual Inhibitors of Tyrosine and Phosphoinositide Kinases. Nature Chem. Bio., 4(11):691-699 (2008).
Arkin et al. HER-2-directed, small-molecule antagonists. Curr Opin Investig Drugs. 2008;9(12)1 264-1276. (saved on H drive and filesite).
Asrani et al. The HER2- and heregulin β1 (HRG)-inducible TNFR superfamily member Fn14 promotes HRG-driven breast cancer cell migration, invasion, and MMP9 expression. Mol Cancer Res. Apr. 2013;11(4):393-404. doi: 10.1158/1541-7786.MCR-12-0542. Epub Feb. 1, 2013.

(56) References Cited

OTHER PUBLICATIONS

Axelrod, et al., "Combinatorial Drug Screening Identified Synergistic Co-Targeting of Bruton's Tyrosine Kinase and the Proteasome in Mantle Cell Lymphoma," Leukemia, 28(2): 407-410 (Feb. 1, 2014).
Baghdadi et al., "The impact of the TIM gene family on tumor immunity and immunosuppression," Cell Mol Immunol, 11(1): 41-48 (2014).
Balakrishnan et al. "AT-101 induces apoptosis in CLL B cells and overcomes stromal cell-mediated Mcl-1 induction and drug resistance," Blood, Oct. 3, 2008 (Oct. 3, 2008), vol. 113, No. 1, pp. 149-153.
Baselga. Targeting tyrosine kinases in cancer: the second wave. Science 312(5777):1175-1178 (2006).
Bauzon et al., "Armed therapeutic viruses—a disruptive therapy on the horizon of cancer immunotherapy," Front Immunol, 5: 74 (2014).
Bhalla et al. PCI-24781 induces caspase and reactive oxygen species-dependent apoptosis through NF-kappaB mechanisms and is synergistic with bortezomib in lymphoma cells. Clin Cancer Res 15:3354-3365 (2009).
Biospace, Dec. 8, 2009, pharmacyclics, Inc. (PCYC) announces presentation of interim results from phase I trial of its first-in-human btk inhibitor PCI-32765.
Brahmer et al., "Safety and activity of anti-PD-L1 antibody in patients with advanced cancer," N Engl J Med, 366(26): 2455-2465 (2012).
Brown et al. Phase Ib trial of AVL-292, a covalent inhibitor of Bruton's tyrosine kinase (Btk), in chronic lymphocytic leukemia (CLL) and B-non-Hodgkin lymphoma (B-NHL). J Clin. Oncol. 30(suppl):abstract 8032 (2012); [online][retrieved on Oct. 4, 2012] Retrieved from the Internet:< http://www.asco.org/ASCOv2/ Meetings/Abstracts?&vmview=abst_detail_view&confID=114 &abstractID=98841>.
Burger et al. CXCR4 antagonists: targeting the microenvironment in leukemia and other cancers, Leukemia 23:43-52 (2009).
Burger et al. High-Level Expression of the T-Cell Chemokines CCL3 and CCL4 by Chronic Lymphocytic Leukemia B Cells in Nurselike Cell Cocultures and After BCR Stimulation. Blood 113(13):3050-3058 (2008).
Burger et al. The Btk Inhibitor Ibrutinib (PCI-32765) in Combination with Rituximab Is Well Tollerated and Displays Profound Activity in High-Risk Chronic Lyphocytic Leukemia (CLL) Patients. Blood (ASH Annual Meeing Abstracts).120:Abstract 187 (2012).
Burger et al., "Ibrutinib as Initial Therapy for Patients with Chronic Lymphocytic Leukemia," New Engl J Med, 373(25): 2425-2437 (2015).
Burger. Targeting the microenvironment in chronic lymphocytic leukemia is changing the therapeutic landscape. Curr. Opin. Oncol. 24(6):643-649 (Epub Sep. 6, 2012/Nov. 2012).
Byrd et al. Targeting BTK with Ibrutinib in relapsed chronic lymphocytic leukemia, NEJM 369(1):32-42 (Jul. 4, 2013).
Byrd J.C., et al., "Three-year follow-up of treatment-naïve and previously treated patients with CLL and SLL receiving single-agent ibrutinib", Blood, Apr. 16, 2015, vol. 125 (16), pp. 2497-2506.
Callahan et al., "At the bedside: CTLA-4- and PD-1-blocking antibodies in cancer immunotherapy," J Leukoc Biol, 94(1): 41-53 (2013).
Cannon. Chapter Nineteen in Burger's Medicinal Chemistry and Drug Discovery, Fifth Edition, vol. I: Principles and Practice, Wiley-Interscience 1995, pp. 783-802.
Carmi et al. Clinical perspectives for irreversible tyrosine kinase inhibitors in cancer. Biochem. Pharmacol. (Epub Aug. 4, 2012) 84(11):1388-1399 (Dec. 2012).
Carrle et al. Current Strategies of Chemotherapy in Osteosarcoma. International Orthopaedics 30:445-451 (2006).
Celgene Corporation: "Pomalyst (pomalidomide) capsules for oral use", Feb. 1, 2013 (Feb. 1, 2013), XP002764262, Retrieved from the Internet: URL:http://www.accessdata.fda.gov/drugsatf da docs/ label/2013/204026lbl.pdf [retrieved on Nov. 15, 2016].

Ceribelli, M et al. Blockade of oncogenic IKB kinase activity in diffuse large B-celllymphom by bromodomain and extraterminal domain protein inhibitors. Proceedings of the National Academy of Sciences. Published online: Jul. 21, 2014. vol. 111. No. 31. pp. 11365-11370.
Chang et al. Egress of CD19+CD5+ cells into peripheral blood following treatment with the Bruton tyrosine kinase inhibitor inbrutinib in mantel cell lymphoma patients. Blood, 122:2412-2424 (2013).
Chang et al., "PCI-45292, a novel Btk inhibitor with optimized pharmaceutical properties, demonstrates potent activities in rodent models of arthritis," ACR/ARHP Scientific Meeting, Poster #286 (2010).
Chaturvedi et al. "Mutant IDH1 promotes leukemogenesis in vivo and can be specifically targeted in human AML," Blood, Aug. 16, 2013, (Aug. 16, 2013), vol. 122, No. 16, pp. 2877-2887.
Chavez et al. Ibrutinib: An Evidence-Based Reviews of Its Potential in the Treatment of Advanced Chronic Lymphocytic Leukemia. Core Evidence 8:37-45 (2013).
Chen et al. "Pim kinase inhibitor, SGI-1776, induces apoptosis in chronic lymphocytic leukemia cells," Blood, Sep. 4, 2009 (Sep. 4, 2009), vol. 114, No. 19, pp. 4150-4157.
Chen et al. SYK-dependent tonic B-cell receptor signaling is a rational treatment target in diffuse large B-cell lymphoma. Blood 111(4):2230-2237 (2008) [E-pub Nov. 15, 2007].
Choi et al., "Inhibitors of B-cell receptor signaling for patients with B-cell malignancies," Cancer J, 18(5):404-410 (2012).
Clinical Trial Report: NCT01105247 (NIH, USA), "Safety of PCI-32765 in Chronic Lymphocytic Leukemia."
Clinical.Trials.gov: "Study of Ibrutinib in Combination With Pomalidomide and Dexamethasone in Subjects With Relapsed I Refractory Multiple Myeloma", Nov. 9, 2016 (Nov. 9, 2016), Retrieved from the Internet: URL:https://clinicaltrials.gov/ct2/show/ NCT02548962 [retrieved on Nov. 10, 2016].
Co-pending U.S. Appl. No. 14/855,270, filed Sep. 15, 2015.
Co-pending U.S. Appl. No. 14/856,217, filed Sep. 16, 2015.
Combination treatment of the Bruton's tyrosine kinase inhibitor ibrutinib and carfilzomib in patients with relapsed or relapsed and refractory multiple myeloma: initial results from a multicenter phase 1/2b study. NCT01962792 (2015).
D'Cruz et al. Novel Bruton's tyrosine kinase inhibitors currently in development. OncoTargets and Therapy 6:161-176 (2013).
Dana-Farber Cancer Institute. A Phase II Study of Ibrutinib Plus FCR in Previously Untreated, Younger Patients With Chronic Lymphocytic Leukemia (iFCR). In: ClinicalTrials.gov [Internet]. Bethesda (MD): National Library of Medicine (US). Sep. 23, 2014 [cited Feb. 5, 2015] Available from: https://clinicaltrial.gov/ct2/ show/NCT02251548?term=NCT02251548 NLM Identifier: NCT02251548.
Dana-Farber Cancer Institute. Ibrutinib (PCI-32765) in Waldenstrom's Macroglobulinemia. In: ClinicalTrials.gov [Internet]. Bethesda (MD): National Library of Medicine (US). May 17, 2012-[cited Nov. 22, 2013]. Available from: http://clinicaltrials.gov/ct2/show/ NCT01614821 NLM Identifier: NCT01614821.
Dasmahapatra, et al., "The Bruton Tyrosine Kinase (BTK) Inhibitor PCI-32765 Synergistically Increases Proteasome Inhibitor Activity in Diffuse large-B cell lymphoma (DLBCL) and Mantle Cell lymphoma (MCL) Cells Sensitive or Resistant to Bortezomib," British Journal of Haematology, 161(1): 43-56 (Jan. 30, 2013).
Davids et al. Targeting the B Cell Receptor Pathway in Chronic Lymphocytic Leukemia. Leuk. Lymphoma (Epub May 23, 2012), 53(12):2362-2370 (Dec. 2012).
Davis et al., "Chronic active B-cell receptor signalling in diffuse large B-cell lymphoma," Nature, 463(7277):88-92 (2010).
Delgado, MD et al. Myc Roles in Hematopoiesis and Leukemia. Genes & Cancer. 2010. vol. 1. No. 6. pp. 605-616; abstract; p. 609,Jeft column, 3rd paragraph; p. 610, righ column, 2nd paragraph; p. 612, middle column, 3rd paragraph, right column, 1st paragraph.
Devos et al., "The Bruton's tyrosine kinase (BTK) inhibitor, ibrutinib (PCI-32765), has preferential activity in the activated B cell-like (ABC) subtype of relapsed/refractory (RR) DLBCL: interim phase 2 results," Haematologica 98(s1):490 (2013).

(56) References Cited

OTHER PUBLICATIONS

Dias et al. Ibrutinib: A New Frontier in the Treatment of Chronic Lymphocytic Leukemia by Bruton's Tyrosine Kinase Inhibition. Cardiovascular & Hematological Agents in Medicinal Chemistry 11:265-271 (2013).
Dixon, "Evaluation of the CASP2 docking section," Proteins, Suppl 1: 198-204 (1997).
Dorwald, F.Z., "Side Reactions in Organic Synthesis," Wiley:VCH, Weinheim p. IX of Preface, Wiley-VCH Verlag GmbH & C KGaA (2005).
Dy et al. Understanding, recognizing, and managing toxicities of targeted anticancer therapies. CA: a cancer Journal for clinicians. 63(4):249-279 (Epub May 2013).
EA200901313 Notification of Office Action dated Oct. 31, 2011.
EA201000599 Search Report dated Nov. 15, 2010.
Edwards. BTK inhibition in myeloma: targeting the seed and the soil. Blood 120(9):1757-1759 (Aug. 2012).
Elias et al. BTK Inhibitor Ibrutinib Inhibits Breast Cancer Growth by Inhibiting ErbB Kinases. Mol Cancer Ther. 2013;12:C258. (not available on pubmed).
Emens et al., "Breast cancer immunobiology driving immunotherapy: vaccines and immune checkpoint blockade," Expert Rev Anticancer Ther, 12(12): 1597-1611 (2012).
EP 06850039 Supplemental Search Report dated Feb. 9, 2010.
EP 06850386.1 Search Report and Written Opinion dated Sep. 10, 2010.
EP 08744513 Supplementary Search Report dated Mar. 11, 2010.
EP 08744513.6 Examination Report dated Jan. 16, 2013.
EP 09798770.5 Search Report and Written Opinion dated Oct. 28, 2011.
EP 10155834.4 Search Report and Written Opinion dated May 27, 2010.
EP 10823966 Supplementary European Search Report dated Oct. 17, 2011.
EP 10823966.6 Written Opinion dated Dec. 6, 2011.
EP 12151943.3 Examination Report dated Feb. 5, 2013.
EP 12151943.3 Search Report and Written Opinion dated Mar. 13, 2012.
EP 12166295.1 Search Report and Written Opinion dated Nov. 6, 2012.
EP 12166296.9 Search Report and Written Opinion dated Nov. 8, 2012.
EP 12166298.5 Search Report and Written Opinion dated Nov. 7, 2012.
EP 12166300.9 Search Report and Written Opinion dated Oct. 31, 2012.
EP 12166301.7 Search Report and Written Opinion dated Nov. 6, 2012.
EP 12166302.5 Search Report and Written Opinion dated Nov. 6, 2012.
EP 12166305.8 Examination Report dated Dec. 3, 2013.
EP 12166305.8 Search Report and Written Opinion dated Nov. 6, 2012.
EP 12166306.6 Search Report and Written Opinion dated Nov. 8, 2012.
EP 12172840.6 Search Report and Written Opinion dated Dec. 12, 2012.
EP 12172841.4 Search Report and Written Opinion dated Jan. 2, 2013.
EP 12172842.2 Extended Search Report dated May 14, 2013.
EP 12172842.2 Partial Search Report dated Jan. 24, 2013.
EP 12172843.0 Search Report and Written Opinion dated Jan. 18, 2013.
Expert Scientific Group on Phase One Clinical Trials. Final Report. Nov. 2006, pp. C1, C35-C38.
Ezell S.A., et al., "Synergistic Induction of Apoptosis by Combination of BTK and Dual mTORC1/2 Inhibitors in Diffuse Large B Cell Lymphoma," Oncotarget, 2014, vol. 5 (13), pp. 4990-5001.
Fedorak et al. A novel colon-specific steroid prodrug enhances sodium chloride absorption in rat colitis. Am. J. Physiol. 269:G210-218 (1995).
Fowler et al. The Btk Inhibitor, PCI-32765, Induces Durable Responses with Minimal Toxicity in Patients with Relapsed/Refractory B-Cell Malignancies: Results From a Phase 1 Study. Blood (ASH Annual Meeting) 116 (21), p. 425:Abstract 964 (2010).
Friedberg et al. Inhibition of Syk with fostamatinib disodium has significant clinical activity in non-Hodgkin lymphoma and chronic lymphocytic leukemia. Blood 115(13):2578-2585 (2010) [E-pub Nov. 17, 2009].
Galli et al., "Evoking durable anti-cancer responses with blocking antibodies to PD-1 and PD-L1," Transl Cancer Res, 1(4): 287-289 (2012).
Gazitt et al. Differential mobilization of CD34+ Cells and lymphoma cells in non-Hodgkin's lymphoma patients mobilized with different growth factors, J of Hematotherapy & Stem Cell Research 10:167-176 (2001).
Giuliani. Multiple myeloma bone disease: pathophysiology of osteoblast inhibition. Blood (Epub Aug. 17, 2006) 108(13):3992-3996 (2006).
Glassman et al., "The value of fluorescence in situ hybridization in the diagnosis and prognosis of chronic lymphocytic leukemia," Cancer Genet Cytogen, 158:88-91 (2005).
Goding et al., "Combination of adoptive cell transfer, anti-PD-L1 and anti-LAG-3 antibodies for the treatment of recurrent tumors," OncoImmunology 2(8): e25050 (2013).
Gordon et al. Somatic hypermutation of the B cell receptor genes B29 (Igb, CD79b) and mb1 (Iga, CD79a). PNAS 100(7):4126-4131 (2003).
Grabinski N., et al., "Ibrutinib (ImbruvicaTM) Potently Inhibits ErbB Receptor Phosphorylation and Cell Viability of Erbb2-Positive Breast Cancer Cells," Investigational New Drugs, Aug. 2014, vol. 32 (6), pp. 1096-1104.
Grosheck et al. Molecular Target Class Is Predictive of In vitro Response Profile. Cancer Res. 70:3677-3686 (2010).
Grosso et al., CTLA-4 blockade in tumor models: an overview of preclinical and translational research, Cancer Immun, 13: 5 (2013).
Gura. Systems for Identifiying New Drugs Are Often Faulty. Science 278(5340):1041-1042 (1997).
Hagemeister. Rituximab for the treatment of non-Hodgkin's lymphoma and chronic lymphocytic leukaemia. Drugs 70(3):261-272 (2010).
Herman et al. "Ibrutinib inhibits BCR and NF-KB signaling and reduces tumor proliferation in tissue-resident cells of patients with CLL," Blood. Mar. 21, 2014 (Mar. 21, 2014 ), vol. 123, pp. 3286-3295.
Hiddeman et al. Rituximab Plus Chemotherapy in Follicular and Mantle Cell Lymphomas, Seminars in Oncology 30(1)Suppl.2:16-20 (Feb. 2003).
Higuchi et al. Pro-drugs as Novel Delivery Systems, vol. 14 of the A.C.S. Symposium Series (1975).
Hochhaus et al. A selective HPLC/RIA for dexamethasone and its prodrug dexamethasone-21-sulphobenzoate sodium in biological fluids. Biomed. Chrom., 6:283-286 (1992).
Honigberg et al., Targeting Btk in Lymphoma: PCT-32765 Inhibits Tumor Growth in Mouse Lymphoma Models and a Fluorescent Analog of PCT-32765 Is an Active-Site Probe that Enables Assessment of Btk Inhibition in Vivo. Blood (Ash Annual Meeting Abstracts). 2007. 110: Abstract 1592.
Horning et al., The natural history of initially untreated low-grade non-Hodgkin's lymphomas, (1984) N. Engl. J. Med. 311:1471-1475.
Huhn et al. Rituximab therapy of patients with B-cell chronic lymphocytic leukemia. Blood 98(5):1326-1331 (Sep. 1, 2001).
Hurrell et al. The in vitro influences of epidermal growth factor and heregulin-β1 on the efficacy of trastuzumab used in Her-2 positive breast adenocarcinoma. Cancer Cell Int. Oct. 11, 2013;13(1):97. doi: 10.1186/1475-2867-13-97.
IDW00201201693 Office Action dated Apr. 20, 2015.
Inhibitory effects of the BTK inhibitor, ibrutinib, on HER2-amplified breast cancer growth, cell cycle progression, and clonogenicity—Poster.

(56) References Cited

OTHER PUBLICATIONS

International Preliminary Report on Patentability for Application No. PCT/US15/21871, dated Sep. 29, 2016, 10 pages.
International Preliminary Report on Patentability for PCT/US2013/068132 dated May 5, 2015.
Iqbal et al., on pp. 2-4 (Molecular Biology International, 2014, Article ID 852748, 9 pages.
Iriyama et al. "Clinical significance of genetic mutations of CD79B, CARD11, MYD88, and EZH2 genes in diffuse large B-cell-lymphoma patients," Dec. 10, 2011 (Dec. 10, 2011), 53rd ASH Annual Meeting, Abstract 2633, available at https://ash.confex.com/ash/2011/webprogram/Paper36650.html.
Jaffe. The 2008 WHO classification of lymphomas: implications for clinical practice and translational research. Hematology 1:523-531 (2009).
Janssen Biotech, Inc. An open label treatment use protocol for ibrutinib in subjects with relapsed or refractory mantel cell lymphoma. In: ClinicalTrials.gov [Internet]. Bethesda (MD): National Library of Medicine (US). Apr. 6, 2013-[cited Nov. 22, 2013]. Available from: http://clinicaltrials.gov/ct2/show/NCT01833039 NLM Identifier: NCT01833039.
Janssen Pharmaceutical K.K. A study to evaluate the Bruton's tyrosine kinase (Btk) inhibitor PCI-32765 in patients with recurrent mature B-cell neoplasms. In: ClinicalTrials.gov [Internet]. Bethesda (MD): National Library of Medicine (US). Oct. 9, 2012-[cited Nov. 22, 2013]. Available from: http://clinicaltrials.gov/ct2/show/NCT01704963 NLM Identifier: NCT01704963.
Janssen Pharmaceutical K.K. Study of the Bruton's Tyrosine Kinase (BTK) Inhibitor Ibrutinib in Participants With Relapsed or Refractory Mantle Cell Lymphoma. In: ClinicalTrials.gov [Internet]. Bethesda (MD): National Library of Medicine (US). Jun. 19, 2014-[cited Feb. 5, 2015] Available from: https://clinicaltrial.gov/ct2/show/NCT02169180?term=NCT02169180 NLM Identifier: NCT02169180.
Janssen Research & Development, LLC. A Study to Evaluate the Effects of Ibrutinib on Cardiac Repolarization in Healthy Participants. In: ClinicalTrials.gov [Internet]. Bethesda (MD): National Library of Medicine (US). Oct. 20, 2014 [cited Feb. 5, 2015] Available from: https://clinicaltrial.gov/ct2/show/NCT02271438?term=NCT02271438 NLM Identifier: NCT02271438.
Janssen Research & Development, LLC. Pharmacokinetic and Pharmacodynamic Study to Evaluate Safety and Efficacy of the Combination of Ibrutinib With Nivolumab in Participants With Hematologic Malignancies. In: ClinicalTrials.gov [Internet]. Bethesda (MD): National Library of Medicine (US). Dec. 30, 2014 [cited Feb. 5, 2015] Available from: https://clinicaltrial.gov/ct2/show/NCT02329847?term=NCT02329847 NLM Identifier: NCT02329847.
Janssen Research and Development, LLC. A long-term extension study of PCI-32765 (Ibrutinib). In: ClinicalTrials.gov [Internet]. Bethesda (MD): National Library of Medicine (US). Mar. 4, 2013-[cited Nov. 22, 2013]. Available from: http://clinicaltrials.gov/ct2/show/NCT01804686 NLM Identifier: NCT01804686.
Janssen Research and Development, LLC. A pharmacokinetic study in healthy participants to assess the pharmacokinetics and safety of a supratherapeutic dose of PCI-32765 (Ibrutinib) capsule and solution formulations administered with food. In: ClinicalTrials.gov [Internet]. Bethesda (MD): National Library of Medicine (US). Aug. 19, 2013-[cited Nov. 22, 2013]. Available from: http://clinicaltrials.gov/ct2/show/NCT01969266 NLM Identifier: NCT01969266.
Janssen Research and Development, LLC. A study combining Ibrutinib with rituximab, cyclophosphamide, doxorubicin, vincristine, and prednisone in patients with CD20-positive B-cell non Hodgkin lymphoma. In: ClinicalTrials.gov [Internet]. Bethesda (MD): National Library of Medicine (US). Mar. 30, 2012-[cited Nov. 22, 2013]. Available from: http://clinicaltrials.gov/ct2/show/NCT01569750 NLM Identifier: NCT01569750.
Janssen Research and Development, LLC. A study of ibrutinib in combination with bendamustine and rituximab in patients with relapsed or refractory chronic lymphocytic leukemia or small lymphocytic lymphoma. In: ClinicalTrials.gov [Internet]. Bethesda (MD): National Library of Medicine (US). May 15, 2012-[cited Nov. 22, 2013]. Available from: http://clinicaltrials.gov/ct2/show/NCT01611090 NLM Identifier: NCT01611090.
Janssen Research and Development, LLC. A study of PCI-32765 (Ibrutinib) in combination with either bendamustine and rituximab or rituximab, cyclophosphamide, doxorubicin, vincristine, and prednisone in patients with previously treated indolent non-Hodgkin lymphoma. In: ClinicalTrials.gov [Internet]. Bethesda (MD): National Library of Medicine (US). Oct. 28, 2013-[cited Nov. 22, 2013]. Available from: http://clinicaltrials.gov/ct2/show/NCT01974440 NLM Identifier: NCT01974440.
Janssen Research and Development, LLC. A study of PCI-32765 (Ibrutinib) in patients with refractory follicular lymphoma. In: ClinicalTrials.gov [Internet]. Bethesda (MD): National Library of Medicine (US). Jan. 25, 2013-[cited Nov. 22, 2013]. Available from: http://clinicaltrials.gov/ct2/show/NCT01779791 NLM Identifier: NCT01779791.
Janssen Research and Development, LLC. A study of the Bruton's tyrosine kinase inhibitor ibrutinib given in combination with bendamustine and rituximab in patients with newly diagnosed mantel cell lymphoma. In: ClinicalTrials.gov [Internet]. Bethesda (MD): National Library of Medicine (US). Jan. 24, 2013-[cited Nov. 22, 2013]. Available from: http://clinicaltrials.gov/ct2/show/NCT01776840 NLM Identifier: NCT01776840.
Janssen Research and Development, LLC. A study of the Bruton's tyrosine kinase inhibitor PCI-32765 (Ibrutinib) versus rituximab in patients with relapsed or refractory chronic lymphocytic leukemia/small lymphocytic lymphoma. In: ClinicalTrials.gov [Internet]. Bethesda (MD): National Library of Medicine (US). Oct. 25, 2013-[cited Nov. 22, 2013]. Available from: http://clinicaltrials.gov/ct2/show/NCT01973387 NLM Identifier: NCT01973387.
Janssen Research and Development, LLC. A study on the Bruton's tyrosine kinase inhibitor, PCI-32765 (Ibrutinib), in combination with rituximab, cyclophosphamide, doxorubicin, vincristine, and prednisone in patients with newly diagnosed non-germinal center B-cell subtype of diffuse large B-cell lymphoma. In: ClinicalTrials.gov [Internet]. Bethesda (MD): National Library of Medicine (US). May 14, 2013-[cited Nov. 22, 2013]. Available from: http://clinicaltrials.gov/ct2/show/NCT01855750 NLM Identifier: NCT01855750.
Janssen Research and Development, LLC. A study to assess the absolute bioavailability of Oral PCI-32765 and the effect of grapefruit juice on the bioavailability of PCI-32765 in healthy participants. In: ClinicalTrials.gov [Internet]. Bethesda (MD): National Library of Medicine (US). May 28, 2013-[cited Nov. 22, 2013]. Available from: http://clinicaltrials.gov/ct2/show/study/NCT01866033 NLM Identifier: NCT01866033.
Janssen Research and Development, LLC. A study to assess the effect of ketoconazole on the pharmacokinetics of ibrutinib in healthy participants. In: ClinicalTrials.gov [Internet]. Bethesda (MD): National Library of Medicine (US). Jun. 18, 2012-[cited Nov. 22, 2013]. Available from: http://clinicaltrials.gov/ct2/show/NCT01626651 NLM Identifier: NCT01626651.
Janssen Research and Development, LLC. A study to assess the effect of rifampin on the pharmacokinetics of PCI-32765 in healthy participants. In: ClinicalTrials.gov [Internet]. Bethesda (MD): National Library of Medicine (US). Jan. 4, 2013-[cited Nov. 22, 2013]. Available from: http://clinicaltrials.gov/ct2/show/NCT01763021 NLM Identifier: NCT01763021.
Janssen Research and Development, LLC. A study to determine the absorption, metabolism, and routes of excretion of (14C) radiolabeled ibrutinib in healthy male participants. In: ClinicalTrials.gov [Internet]. Bethesda (MD): National Library of Medicine (US). Aug. 9, 2012-[cited Nov. 22, 2013]. Available from: http://clinicaltrials.gov/ct2/show/NCT01674322 NLM Identifier: NCT01674322.
Janssen Research and Development, LLC. A study to determine the effect of food on the pharmacokinetics of PCI-32765. In: ClinicalTrials.gov [Internet]. Bethesda (MD): National Library of Medicine (US). Mar. 4, 2013-[cited Nov. 22, 2013]. Available from: http://clinicaltrials.gov/ct2/show/NCT01820936 NLM Identifier: NCT01820936.
Janssen Research and Development, LLC. A study to evaluate the efficacy and safety of ibrutinib, in patients with mantel cell lymphoma who progress after bortezomib therapy. In: ClinicalTrials.

(56) References Cited

OTHER PUBLICATIONS gov [Internet]. Bethesda (MD): National Library of Medicine (US). May 14, 2012-[cited Nov. 22, 2013]. Available from: http://clinicaltrials.gov/ct2/show/NCT01599949 NLM Identifier: NCT01599949.

Janssen Research and Development, LLC. A study to evaluate the pharmacokinetics of PCI-32765 in participants with varying degrees of hepatic impairment. In: ClinicalTrials.gov [Internet]. Bethesda (MD): National Library of Medicine (US). Jan. 9, 2013-[cited Nov. 22, 2013]. Available from: http://clinicaltrials.gov/ct2/show/NCT01767948 NLM Identifier: NCT01767948.

Janssen Research and Development, LLC. Study of ibrutinib (a Bruton's tyrosine kinase inhibitor), versus temsirolimus in patients with relapsed or refractory mantel cell lymphoma who have received at least one prior therapy. In: ClinicalTrials.gov [Internet]. Bethesda (MD): National Library of Medicine (US). Jul. 18, 2012-[cited Nov. 22, 2013]. Available from: http://clinicaltrials.gov/ct2/show/NCT01646021 NLM Identifier: NCT01646021.

Kamb. What's wrong with our cancer models? Nature Reviews Drug Discovery 4:161-165 (2005).

Keeton et al. "AZD1208, a potent and selective pan-Pim kinase inhibitor, demonstrates efficacy in preclinical models of acute myeloid leukemia," Blood, Dec. 20, 2013 (Dec. 20, 2013), vol. 123, No. 6, pp. 905-913.

Kim et al. HRG-β1-driven ErbB3 signaling induces epithelial-mesenchymal transition in breast cancer cells. BMC Cancer. Aug. 12, 2013;13:383. doi: 10.1186/1471-2407-13-383.

Ko. Everyone's Guide to Cancer Therapy: How Cancer is Diagnosed, treated and Managed Day to Day. 3 pgs. (2009).

Kola et al. Can the pharmaceutical industry reduce attrition rates? Nature Reviews Drug Discover 3:711-715 (2004).

Kono, "Current status of cancer immunotherapy," J Stem Cells Regen med, 10(1): 8-13 (2014).

Korade-Mirnics et al. Src kinase-mediated signaling in leukocytes. J. Leukoc. Bio., 68(5):603-613 (Nov. 2000).

Kozaki et al. Development of a Bruton's tyrosine kinase (Btk) inhibitor -ONO-WG-307, a potential treatment for B-cell malignancies. 53rd American Society of Hematology Annual Meeting and Exposition, San Diego, CA, Poster #857 (Dec. 10-13, 2011).

Kuglstatter et al. Insights into the conformational flexibility of Bruton's tyrosine kinase from multiple ligand complex structures. Protein Science 20(2):428-436 (2011) [E-pub Dec. 17, 2010].

Kyi et al., "Checkpoint blocking antibodies in cancer immunotherapy," FEBS Letters, 588(2): 368-376 (2013).

Larsen et al., "Prodrug forms for the sulfonamide group. II. Water-soluble amino acid derivatives of N-methylsulfonamides as possible prodrugs," Int. J. Pharmaceutics. 47:103 (1988).

Larsen et al.Prodrug forms for the sulfonamide group. I. Evaluation of N-acyl derivatives, N-sulfonylamindes, N-sulfonylsulfilimines and sulfonylureas as possible prodrug derivatives. Int. J. Pharmaceutics 37:87-95 (1987).

Le Tourneau et al. Dose Escalation Methods in Phase I Cancer Clinical Trials. J. Natl Cancer 101:708-720 (2009).

Leaf. Why Are We Losing the War on Cancer (And How to Win It). Health Admin. V. XVII, No. 1, pp. 172-183 (2005).

Lensink et al., "Docking and scoring protein complexes: CAPRI 3rd Edition," Proteins, 69(4): 704-718 (2007).

Li et al. Activation of Bruton's Tyrosine Kinase (BTK) by a Point Mutation in its Pleckstrin Homology (PH) domain. Immunity 2:451-460 (1995).

Lichtman. Battling the hematological malignancies: The 200 years' war. The Oncologist 13:126-138 (2008).

Lim et al. Asymmetric syntheses of fused bicyclic lactams. Journal of Organic chemistry 66(26):9056-9062 (2001).

Lin et al. Selective Itk inhibitors block T-cell activation and murine lung inflammation, Biochemistry 43:11056-11062 (2004).

Lopez et al. Combining PCI-24781, a Novel Histone Deacetylase Inhibitor, with Chemotherapy for the Treatment of Soft Tissue Sarcoma. Clin Cancer Res 15:1774-1775, 3472-3483 (2009).

Lossos. Molecular Pathogenesis of Diffuse Large B-Cell Lymphoma. J. Clin. Oncol. 23(26):6351-6357 (Sep. 10, 2005).

Lou et al. Bruton's tyrosine kinase inhibitors: approaches to potent and selective inhibition, preclinical and clinical evaluation for inflammatory diseases and B cell malignancies. J Med Chem. May 24, 2012;55(10):4539-50 Publication Date (Web): Mar. 6, 2012.

M.D. Anderson Cancer Center. A Phase I/II Study of Ibrutinib in Previously Treated Epidermal Growth Factor Receptor (EGFR) Mutant Non-Small Cell Lung Cancer. In: ClinicalTrials.gov [Internet]. Bethesda (MD): National Library of Medicine (US). Dec. 17, 2014 [cited Feb. 5, 2015] Available from: https://clinicaltrial.gov/ct2/show/NCT02321540?term=NCT02321540 NLM Identifier: NCT02321540.

M.D. Anderson Cancer Center. A Phase I/II Trial of PCI-32765 (BTK Inhibitor) in Combination With Carfilzomib in Relapse/Refractory Mantle Cell Lymphoma. In: ClinicalTrials.gov [Internet]. Bethesda (MD): National Library of Medicine (US). Oct. 16, 2014 [cited Feb. 5, 2015] Available from: https://clinicaltrial.gov/ct2/show/NCT02269085?term=NCT02269085 NLM Identifier: NCT02269085.

M.D. Anderson Cancer Center. Ibrutinib Post Stem Cell Transplantation (SCT) in Double-Hit B-Cell Lymphoma. In: ClinicalTrials.gov [Internet]. Bethesda (MD): National Library of Medicine (US). Oct. 21, 2014 [cited Feb. 5, 2015] Available from: https://clinicaltrial.gov/ct2/show/NCT02272686?term=NCT02272686 NLM Identifier: NCT02272686.

M.D. Anderson Cancer Center. Ibrutinib versus ibrutinib + rituximab (i vs iR) in patients with relapsed chronic lymphocytic leukemia (CLL). In: ClinicalTrials.gov [Internet]. Bethesda (MD): National Library of Medicine (US). Dec. 5, 2013-[cited Apr. 15, 2014]. Available from: http://clinicaltrials.gov/ct2/show/NCT02007044 NLM Identifier: NCT02007044.

M.D. Anderson Cancer Center. Phase 2 ibrutinib + rituximab in relapsed/refractory mantel cell lymphoma (R/R MCL). In: ClinicalTrials.gov [Internet]. Bethesda (MD): National Library of Medicine (US). Jun. 14, 2013-[cited Nov. 22, 2013]. Available from: http://clinicaltrials.gov/ct2/show/NCT01880567 NLM Identifier: NCT01880567.

M.D. Anderson Cancer Center. Phase 2 study of the combination of Bruton's tyrosine kinase inhibitor PCI-32765 and rituximab in high-risk chronic lymphocytic leukemia and small lymphocytic lymphoma patients. In: ClinicalTrials.gov [Internet]. Bethesda (MD): National Library of Medicine (US). Jan. 25, 2012-[cited Nov. 22, 2013]. Available from: http://clinicaltrials.gov/ct2/show/NCT01520519 NLM Identifier: NCT01520519.

M.D. Anderson Cancer Center. Pilot study to determine effects of the Btk inhibitor PCI-32765 on leukemia cell kinetics and trafficking, using heavy water labeling in subjects with CLL and SLL. In: ClinicalTrials.gov [Internet]. Bethesda (MD): National Library of Medicine (US). Dec. 13, 2012-[cited Nov. 22, 2013]. Available from: http://clinicaltrials.gov/ct2/show/NCT01752426 NLM Identifier: NCT01752426.

MacPartlin et al. Bruton's tyrosine kinase is not essential for Bcr-Abl-mediated transformation of lymphoid or myeloid cells. Leukemia 22:1354-1360 (2008).

Maddocks et al. Ibrutinib in B-cell lymphomas. Current Treatment Options in Oncology 15:226-237 (2014) (Epub: Feb. 1, 2014).

Mallis et al. Structural characterization of a proline-driven conformational switch within the Itk SH2 domain. Nat. Struct. Biol., 9(12):900-905 (2002).

Marcotte et al, Structures of human Bruton's tyrosine kinase in active and inactive conformations suggest a mechanism of activation for TEC family kinases., Protein Science. 2010, 19:429-439.

Marina et al. Biology and Therapeutic Advances for Pediatric Osteosarcoma. The Oncologist 9:422-441 (2004).

Martin et al. Novel therapeutic targets in mantle cell lymphoma. Expert Opin. In Therapeutic Targets 11:929-940 (2007).

Mathews, et al., "High-Throughput Combinatorial Screening Identifies Drugs that Cooperate with Ibrutinib to Kill Activated B-cell-like diffuse large B-cell lymphoma cells," Proceedings of the National Academy of Sciences, 111(6): 2349-2354 (Jan. 27, 2014).

McConathy et al. Stereochemistry in Drug Action. J Clinical Psychiatry. 5:70-73 (2003).

(56) References Cited

OTHER PUBLICATIONS

McDermott et al., PD-1 as a potential target in cancer therapy, Cancer Med, 2(5): 662-673 (2013).
McLeod et al., "A glucocorticoid prodrug facilitates normal mucosal function in rat colitis without adrenal suppression," Gastroenterol, 106:405-413 (1994).
Memorial Sloan-Kettering Cancer Center. Bruton's Tyrosine Kinase (BTK) Inhibitor, Ibrutinib, in Patients With Refractory/Recurrent Primary Central Nervous System Lymphoma (PCNSL) and Refractory/Recurrent Secondary Central Nervous System Lymphoma (SCNSL). In: ClinicalTrials.gov [Internet]. Bethesda (MD): National Library of Medicine (US). Dec. 9, 2014 [cited Feb. 5, 2015] Available from: https://clinicaltrial.gov/ct2/show/NCT02315326?term=NCT02315326 NLM Identifier: NCT02315326.
Mendel et al. In vivo antitumor activity of SU11248, a novel tyrosine kinase inhibitor targeting vascular endothelial growth factor and platelet-derived growth factor receptors: determination of a pharmacokinetic/pharmacodynamic relationship. Clin Cancer Res 9(1):327-337 (2003).
Middendorp et al. Function of Bruton's Tyrosine Kinase during B Cell Development is Partially Independent of its Catalytic Activity. J Immunol 171:5988-5996 (2003).
Middendorp et al. Tumor Suppressor Function of Bruton Tyrosine Kinase is Independent of its catalytic activity. Blood 105(1):259-261 (2005).
Monge et al., "Genetic factors and pathogenesis of waldenstrom's macroglobulinemia," Curr Oncol Rep, 15(5): 450-456 (2013).
Montero et al. Neuregulins and cancer Clin Cancer Res. Jun. 1, 2008;14(11):3237-41. doi: 10.1158/1078-0432.CCR-07-5133.
Morgan L., Leukemia, 8 (Special Issue), 2015.
Mukoyama et al., "Preparation of imidazol [1,5-a]pyrazine derivatives, pharmaceutical compositions containing them, and their uses for prevention or treatment of protein tyrosine kinase-related diseases," retrieved from STN Database Accession No. 2005:299462 Patent No. JP2005089352, Abstract (2005).
Nagel et al. "Pharmacologic inhibition of MAL T1 protease by phenothiazines as a therapeutic approach for the treatment of aggressive ABC-DLBCL," Cancer Cell, Dec. 11, 2012 ( Dec. 11, 2012), vol. 22, No. 6, pp. 825-837.
National Cancer Institute (NCI). A multicenter phase 2 study of the Bruton's tyrosine kinase inhibitor PCI-32765 for treatment of relapsed hairy cell leukemia. In: ClinicalTrials.gov [Internet]. Bethesda (MD): National Library of Medicine (US). Nov. 2, 2013-[cited Nov. 22, 2013]. Available from: http://clinicaltrials.gov/ct2/show/NCT01981512 NLM Identifier: NCT01981512.
National Cancer Institute (NCI). Ibrutinib and rituximab compared with fludarabine phosphate, cyclophosphamide, and rituximab in treating patients with untreated chronic lymphocytic leukemia or small lymphocytic lymphoma. In: ClinicalTrials.gov [Internet]. Bethesda (MD): National Library of Medicine (US). Jan. 27, 2014-[cited Apr. 15, 2014]. Available from: http://clinicaltrials.gov/ct2/show/NCT02048813 NLM Identifier: NCT02048813.
National Cancer Institute (NCI). Ibrutinib in treating patients with relapsed hairy cell leukemia. In: ClinicalTrials.gov [Internet]. Bethesda (MD): National Library of Medicine (US). Apr. 24, 2013-[cited Nov. 22, 2013]. Available from: http://clinicaltrials.gov/ct2/show/NCT01841723 NLM Identifier: NCT01841723.
National Cancer Institute (NCI). Ibrutinib in treating patients with relapsed or refractory follicular lymphoma. In: ClinicalTrials.gov [Internet]. Bethesda (MD): National Library of Medicine (US). May 6, 2013-[cited Nov. 22, 2013]. Available from: http://clinicaltrials.gov/ct2/show/NCT01849263 NLM Identifier: NCT01849263.
National Cancer Institute (NCI). Lenalidomide and ibrutinib in treating patients with relapsed or refractory B-Cell non-Hodgkin lymphoma. In: ClinicalTrials.gov [Internet]. Bethesda (MD): National Library of Medicine (US). Sep. 27, 2013-[cited Nov. 22, 2013]. Available from: http://clinicaltrials.gov/ct2/show/NCT01955499 NLM Identifier: NCT01955499.
National Cancer Institute (NCI). Rituximab and bendamustine hydrochloride, rituximab and ibrutinib, or ibrutinib alone in treating older patients with previously untreated chronic lymphocytic leukemia. In: ClinicalTrials.gov [Internet]. Bethesda (MD): National Library of Medicine (US). Jun. 24, 2013-[cited Nov. 22, 2013]. Available from: http://clinicaltrials.gov/ct2/show/NCT01886872 NLM Identifier: NCT01886872.
National Cancer Institute (NCI). Rituximab, lenalidomide, and ibrutinib in treating patients with previously untreated stage II-IV follicular lymphoma. In: ClinicalTrials.gov [Internet]. Bethesda (MD): National Library of Medicine (US). Apr. 9, 2013-[cited Nov. 22, 2013]. Available from: http://clinicaltrials.gov/ct2/show/NCT01829568 NLM Identifier: NCT01829568.
National Cancer Institute sponsored study of classifications of non-Hodgkin's lymphomas: summary and description of a working formulation for clinical usage. The Non-Hodgkin's Lymphoma Pathologic Classification Project., The Non-Hodgkin's Lymphoma Pathologic Classification Project, Cancer 49:2112-2135 (1982).
National Cancer Institute. Ibrutinib and Combination Chemotherapy in Treating Patients With Relapsed or Refractory Diffuse Large B-Cell Lymphoma. In: ClinicalTrials.gov [Internet]. Bethesda (MD): National Library of Medicine (US). Jul. 16, 2014 [cited Feb. 5, 2015] Available from: https://clinicaltrial.gov/ct2/show/NCT02219737?term=NCT02219737 NLM Identifier: NCT02219737.
National Cancer Institute. Ibrutinib and Palbociclib Isethionate in Treating Patients With Previously Treated Mantle Cell Lymphoma. In: ClinicalTrials.gov [Internet]. Bethesda (MD): National Library of Medicine (US). Jun. 9, 2014-[cited Feb. 5, 2015] Available from: https://clinicaltrial.gov/ct2/show/NCT02159755?term=NCT02159755 NLM Identifier: NCT02159755.
National Cancer Institute. Ibrutinib in Treating Patients With Relapsed or Refractory B-cell Acute Lymphoblastic Leukemia. In: ClinicalTrials.gov [Internet]. Bethesda (MD): National Library of Medicine (US). Apr. 30, 2014 [cited Feb. 5, 2015] Available from: https://clinicaltrial.gov/ct2/show/NCT02129062?term=NCT02129062 NLM Identifier: NCT02129062.
National Cancer Institute. Ibrutinib in Treating Relapsed or Refractory B-cell Non-Hodgkin Lymphoma in Patients With HIV infection. In: ClinicalTrials.gov [Internet]. Bethesda (MD): National Library of Medicine (US). Apr. 7, 2014 [ cited Feb. 5, 2015]. Available from: https://clinicaltrial.gov/ct2/show/NCT02109224?term=NCT02109224. NLM Identifier: NCT02109224.
National Cancer Institute. Lenalidomide, Ibrutinib, and Rituximab in Treating Patients With Relapsed or Refractory Chronic Lymphocytic Leukemia or Small Lymphocytic Lymphoma. In: ClinicalTrials.gov [Internet]. Bethesda (MD): National Library of Medicine (US). May 30, 2014 [cited Feb. 15, 2015] Available from: https://clinicaltrial.gov/ct2/show/NCT02160015?term=NCT02160015 NLM Identifier: NCT02160015.
National Cancer Institute. Phase 1 Study of Ibrutinib and Immuno-Chemotherapy Using Dose-Adjusted-Temozolomide, Etoposide, Doxil, Dexamethasone, Ibrutinib,Rituximab (DA-TEDDI-R) in Primary CNS Lymphoma. In: ClinicalTrials.gov [Internet]. Bethesda (MD): National Library of Medicine (US). Jul. 29, 2014 [cited Feb. 5, 2015] Available from: https://clinicaltrial.gov/ct2/show/NCT02203526?term=NCT02203526 NLM Identifier: NCT02203526.
National Center Institute (NCI). Lenalidomide and Ibrutinib in treating patients with relapsed or refractory chronic lymphocytic leukemia or small lymphocytic lymphoma. In: ClinicalTrials.gov [Internet]. Bethesda (MD): National Library of Medicine (US). Jun. 24, 2013-[cited Nov. 22, 2013]. Available from: http://clinicaltrials.gov/ct2/show/NCT01886859 NLM Identifier: NCT01886859.
National Heart, Lung, and Blood Institute (NHLBI). PCI-32765 for special cases of chronic lymphocytic leukemia or small lymphocytic lymphoma. In: ClinicalTrials.gov [Internet]. Bethesda (MD): National Library of Medicine (US). Dec. 22, 2011-[cited Nov. 22, 2013]. Available from: http://clinicaltrials.gov/ct2/show/NCT01500733 NLM Identifier: NCT01500733.
Neidle. Cancer Drug Design and Discovery. Elsevier/Academic Press. pp. 427-431 (2008).
Nogrady (1985) Medicinal Chemistry a Biochemical Approach, Oxford University Press, New York, pp. 388-394.
Northwestern University. Ibrutinib After Intensive Induction in Treating Patients With Previously Untreated Mantle Cell Lymphoma. In: ClinicalTrials.gov [Internet]. Bethesda (MD): National

(56) References Cited

OTHER PUBLICATIONS

Library of Medicine (US). Sep. 12, 2014 [cited 2-15 Feb. 5] Available from: https://clinicaltrial.gov/ct2/show/NCT02242097?term=NCT02242097 NLM Identifier: NCT02242097.
Notification of Transmittal of the International Search Report and the Written Opinion for the of the International Searching Authority, or the Declaration for Application No. PCT/US2016/049638, dated Nov. 30, 2016, 14, pages.
O'Brien et al. Combination of the Bruton's tyrosine kinase (BTK) inhibitor PCI-32765 with bendamustine (B)/rituximan® (BR) in patients (pts) with relapsed/refractory (R/R) chronic lymphocytic leukemia (CLL): Interm results of phase Ib/II study. J Clin Onc. 2012. Supp. Abstract 6515.
Ohio State University Comprehensive Cancer Center. PCI-32765 (Ibrutinib) in treating patients with relapsed or refractory chronic lymphocytic leukemia, small lymphocytic lymphoma, or B-cell prolymphocytic leukemia. In: ClinicalTrials.gov [Internet]. Bethesda (MD): National Library of Medicine (US). Apr. 23, 2012-[cited Nov. 22, 2013]. Available from: http://clinicaltrials.gov/ct2/show/NCT01589302 NLM Identifier: NCT01589302.
Ohio State University Comprehensive Cancer Center. Rituxan/Bendamustine/PCI-32765 in relapsed DLBCL, MCL, or indolent non-Hodgkin's lymphoma. In: ClinicalTrials.gov [Internet]. Bethesda (MD): National Library of Medicine (US). Nov. 1, 2011-[cited Feb. 6, 2014]. Available from: http://clinicaltrials.gov/ct2/show/NCT01479842 NLM Identifier: NCT01479842.
Ott et al., "CTLA-4 and PD-1/PD-L1 blockade: new immunotherapeutic modalities with durable clinical benefit in melanoma patients," Clin Cancer Res, 19(19): 5300-5309 (2013).
Ou. Second-generation irreversible epidermal growth factor receptor (EGFR) tyrosine kinase inhibitors (TKIs): A better mousetrap? A review of the clinical evidence. Crit Rev Onc/Hemat. 2012;83(3):407-421.
Pagel et al., "Induction of apoptosis using inhibitors of lysophosphatidic acid acyltransferase-beta and anti-CD20 monoclonal antibodies for treatment of human non-Hodgkin's lymphomas," Clin Cancer Res, 11(13):4857-4866 (2005).
Pan, Z. et al., "Discovery of Selectable Irreversible Inhibitors for Brutons Tyrosine Kinase," ChemMedChem, 1:1-5 (2006).
Paul G Richardson et al: "Pomalidomide alone or in combination with low-dose dexamethasone in relapsed and refractory multiple myeloma: a randomized phase 2 study", Mar. 20, 2014 (Mar. 20, 2014), DOI: 1 0.1182/blood-Retrieved from the Internet: URL:http://www.bloodjournal.org/content/bloodjournal/123/12/1826. fu ll. pdf retrieved on Nov. 11, 2016].
PCT/US06/49626 Search Report dated Apr. 9, 2008.
PCT/US08/058528 Search Report and Written Opinion dated Sep. 30, 2008.
PCT/US09/50897 Search Report dated Mar. 15, 2010.
PCT/US2010/52377 International Search Report and Written Opinion dated Jun. 29, 2011.
PCT/US2011/039190 International Preliminary Report on Patentability Search Report dated Dec. 4, 2012.
PCT/US2011/039190 International Search Report and Written Opinion dated Feb. 23, 2012.
PCT/US2013/043888 International Search Report and Written Opinion dated Sep. 23, 2013.
PCT/US2014/033378 International Search Report and Written Opinion dated Aug. 26, 2014.
PCT/US2015/040214 International Search Report and Written Opinion dated Dec. 21, 2015.
PCT/US2015/043300 International search report and written opinion dated Nov. 9, 2015.
PCT/US2015/044095 International search report and written opinion dated Nov. 20, 2015.
PCT/US2015/16895 International Search Report and Written Opinion dated May 22, 2015.
Perry et al., "Biological prognostic markers in diffuse large B-cell lymphoma," Cancer Control, 19(3): 214-226 (2012).

Pharmacyclics, Inc. A Multi-Center Study of Ibrutinib in Combination With Obinutuzumab Versus Chlorambucil in Combination With Obinutuzumab in Patients With Treatment naïve CLL or SLL. In: ClinicalTrials.gov [Internet]. Bethesda (MD): National Library of Medicine (US). Oct. 1, 2014 [cited Feb. 5, 2015] Available from: https://clinicaltrial.gov/ct2/show/NCT02264574?term=NCT02264574 NLM Identifier: NCT02264574.
Pharmacyclics, Inc. A multicenter phase 2 study of PCI-32765 (Ibrutinib) in patients with relapsed or refractory chronic lymphocytic leukemia (CLL) or small lymphocytic lymphoma (SLL) with 17p deletion. In: ClinicalTrials.gov [Internet]. Bethesda (MD): National Library of Medicine (US). Dec. 3, 2012-[cited Nov. 22, 2013]. Available from: http://clinicaltrials.gov/ct2/show/NCT01744691 NLM Identifier: NCT01744691.
Pharmacyclics, Inc. A multicenter, open-label, phase 3 study of the Bruton's tyrosine kinase inhibitor PCI-32765 versus chlorambucil in patients 65 years or older with treatment-naive chronic lymphocytic leukemia or small lymphocytic lymphoma (RESONATE-2). In: ClinicalTrials.gov [Internet]. Bethesda (MD): National Library of Medicine (US). Oct. 29, 2012-[cited Nov. 22, 2013]. Available from: http://clinicaltrials.gov/ct2/show/NCT01722487 NLM Identifier: NCT01722487.
Pharmacyclics, Inc. A phase 3 study of ibrutinib (PCI-32765) versus ofatumumab in patients with relapsed or refractory chronic lymphocytic leukemia (RESONATE). In: ClinicalTrials.gov [Internet]. Bethesda (MD): National Library of Medicine (US). Apr. 11, 2012-[cited Nov. 22, 2013]. Available from: http://clinicaltrials.gov/ct2/show/NCT01578707 NLM Identifier: NCT01578707.
Pharmacyclics, Inc. An open-label extension study in patients 65 years or older with chronic lymphocytic leukemia (CLL) or small lymphocytic lymphoma (SLL) who participated in study PCYC-115-CA (PCI-32765 versus chlorambucil). In: ClinicalTrials.gov [Internet]. Bethesda (MD): National Library of Medicine (US). Nov. 2, 2012-[cited Nov. 22, 2013]. Available from: http://clinicaltrials.gov/ct2/show/NCT01724346 NLM Identifier: NCT01724346.
Pharmacyclics, Inc. Efficacy and safety study of PCI-32765 combined with ofatumumab in CLL (PCYC-1109-CA). In: ClinicalTrials.gov [Internet]. Bethesda (MD): National Library of Medicine (US). Oct. 7, 2010-[cited Nov. 22, 2013]. Available from: http://clinicaltrials.gov/ct2/show/NCT01217749 NLM Identifier: NCT01217749.
Pharmacyclics, Inc. Ibrutinib and Lenalidomide With Dose Adjusted EPOCH-R in Subjects With Relapsed/Refractory Diffuse Large B-cell Lymphoma. In: ClinicalTrials.gov [Internet]. Bethesda (MD): National Library of Medicine (US). May 12, 2014 [cited Feb. 5, 2015] Available from: https://clinicaltrial.gov/ct2/show/NCT02142049?term=NCT02142049 NLM Identifier: NCT02142049.
Pharmacyclics, Inc. Ibrutinib in combination with lenalidomide, with and without rituximab in participants with relapsed or refractory diffuse large B-cell lymphoma. In: ClinicalTrials.gov [Internet]. Bethesda (MD): National Library of Medicine (US). Feb. 10, 2014-[cited Apr. 15, 2014]. Available from: http://clinicaltrials.gov/ct2/show/NCT02077166 NLM Identifier: NCT02077166.
Pharmacyclics, Inc. Ibrutinib With Rituximab in Previously Treated Adults With Waldenstrom's Macroglobulinemia. In: ClinicalTrials.gov [Internet]. Bethesda (MD): National Library of Medicine (US). Jun. 9, 2014 [cited Feb. 5, 2015] Available from: https://clinicaltrial.gov/ct2/show/NCT02165397?term=NCT02165397 NLM Identifier: NCT02165397.
Pharmacyclics, Inc. Safety and efficacy of PCI-32765 in subjects with relapsed/refractory mantel cell lymphoma (MCL). In: ClinicalTrials.gov [Internet]. Bethesda (MD): National Library of Medicine (US). Oct. 18, 2010-[cited Nov. 22, 2013]. Available from: http://clinicaltrials.gov/ct2/show/NCT01236391 NLM Identifier: NCT01236391.
Pharmacyclics, Inc. Safety and efficacy study of Bruton's tyrosine kinase inhibitor in subjects with relapsed or refractory diffuse large B-cell lymphoma. In: ClinicalTrials.gov [Internet]. Bethesda (MD): National Library of Medicine (US). Feb. 2, 2011-[cited Nov. 22, 2013]. Available from: http://clinicaltrials.gov/ct2/show/NCT01325701 NLM Identifier: NCT01325701.
Pharmacyclics, Inc. Safety and tolerability study of PCI-32765 combined with fludarabine/cyclophosphamide/rituximab (FCR) and bendamustine/rituximab (BR) in chronic lymphocytic leukemia (CLL). In: ClinicalTrials.gov [Internet]. Bethesda (MD): National

(56) References Cited

OTHER PUBLICATIONS

Library of Medicine (US). Feb. 2, 2011-[cited Nov. 22, 2013]. Available from: http://clinicaltrials.gov/ct2/show/NCT01292135 NLM Identifier: NCT01292135.
Pharmacyclics, Inc. Safety and tolerability study of PCI-32765 in B Cell lymphoma and chronic lymphocytic leukemia. In: ClinicalTrials. gov [Internet]. Bethesda (MD): National Library of Medicine (US). Apr. 19, 2010-[cited Nov. 25, 2013]. Available from: http://clinicaltrials. gov/ct2/show/NCT01109069 NLM Identifier: NCT01109069.
Pharmacyclics, Inc. Safety of PCI-32765 in chronic lymphocytic leukemia. In: ClinicalTrials.gov [Internet]. Bethesda (MD): National Library of Medicine (US). Apr. 13, 2010-[cited Nov. 22, 2013]. Available from: http://clinicaltrials.gov/ct2/show/NCT01105247 NLM Identifier: NCT01105247.
Pharmacyclics, Inc. Study of the Bruton's tyrosine kinase inhibitor in combination with carfilzomib (Kyprolis), in subjects with relapsed or relapsed and refractory multiple myeloma. In: ClinicalTrials.gov [Internet]. Bethesda (MD): National Library of Medicine (US). Sep. 27, 2013-[cited Nov. 22, 2013]. Available from: http://clinicaltrials. gov/ct2/show/NCT01962792 NLM Identifier: NCT01962792.
Pharmacyclics, Inc. Study of the Bruton's tyrosine kinase inhibitor in combination with rituximab in previously untreated subjects with follicular lymphoma. In: ClinicalTrials.gov [Internet]. Bethesda (MD): National Library of Medicine (US). Oct. 24, 2013-[cited Nov. 22, 2013]. Available from: http://clinicaltrials.gov/ct2/show/ NCT01980654 NLM Identifier: NCT01980654.
Pharmacyclics, Inc. Study of the Bruton's Tyrosine Kinase Inhibitor in Subjects With Chronic Graft Versus Host Disease. In: ClinicalTrials. gov [Internet]. Bethesda (MD): National Library of Medicine (US). Jul. 11, 2014 [cited Feb. 5, 2015] Available from: https://clinicaltrial. gov/ct2/show/NCT02195869?term=NCT02195869 NLM Identifier: NCT02195869.
Pharmacyclics, Inc. Study of the Bruton's tyrosine kinase inhibitor in subjects with relapsed or relapsed and refractory multiple myeloma. In: ClinicalTrials.gov [Internet]. Bethesda (MD): National Library of Medicine (US). Nov. 18, 2011-[cited Nov. 22, 2013]. Available from: http://clinicaltrials.gov/ct2/show/NCT01478581 NLM Identifier: NCT01478581.
Pharmacyclics, Inc. Study of the Bruton's tyrosine kinase inhibitor in subjects with relapsed/refractory marginal zone lymphoma. In: ClinicalTrials.gov [Internet]. Bethesda (MD): National Library of Medicine (US). Oct. 29, 2013-[cited Nov. 22, 2013]. Available from: http://clinicaltrials.gov/ct2/show/NCT01980628 NLM Identifier: NCT01980628.
Pharmacyclics, Inc. Study of the safety and tolerability of PCI-32765 in patients with recurrent B cell lymphoma (PCYC-04753). In: ClinicalTrials.gov [Internet]. Bethesda (MD): National Library of Medicine (US). Feb. 20, 2009-[cited Nov. 22, 2013]. Available from: http://clinicaltrials.gov/ct2/show/NCT00849654 NLM Identifier: NCT00849654.
Pharmacyclics: Pharmacyclics initiates phase 1 clinical trial of novel oral Btk inhibitor for refractory B-cell non-Hodgkin's lymphoma. The American Association of Cancer Research (AACR) 100th Annual Meeting in Denver, CO (Apr. 13, 2009).
Picci, P. et al., "Osteosarcoma (osteogenic sarcoma)," Orphanet J Rare Dis, 2(6):1-4 (2007).
Pileri et al. Mantle Cell Lymphoma. Haematologica 94(11):1488-1492 (2009).
Pollyea D.A., et al., "A Phase I Dose Escalation Study of the Btk Inhibitor PCI-32765 in Replace and Refractory B Cell Non-Hodgkin Lymphoma and Use of a Novel Fluorescent Probe Pharmacodynamic Assay," Blood, 2009, vol. 114, Abstract 3713.
Pollyea et al., "A phase I dose escalation study of the Btk inhibitor PCI-32765 in relapsed and refractory B cell non-Hodgkin lymphoma and use of a novel fluorescent probe pharmacodynamic assay," 51st ASH Annual Meeting and Exposition, Poster Abstract #3713 (2009).
Powers et al. Irreversible Inhibitors of Serine, Cysteine, and Threonine Proteases. Chem. Rev., 102(12):4639-4750 (2002).

Prakash et al. Chicken sarcoma to human cancers: a lesson in molecular therapeutics. The Ochsner Journal, 7(2):61-64 (Jan. 1, 2007).
Prenata et al., "Separation on the basis of size: Gel permeation chromatography," Protein Purification Methods: A Practical Approach, (Harris & Angal Eds.) IRL Press 1989 293-306.
PRNewsire "U.S. FDA grants regular (full) approval for IMBRUVICA for two indications," Jul. 28, 2014.
PRNewswire, "Pharmacyclics, Inc. announces presentation of interim results from phase I trial of its first-in-human Btk inhibitor PCI-32765," Dec. 7, 2009.
PRNewswire, "Update on preclinical finding and development timeline for PCI-45292," Mar. 2, 2011.
PubChem CID 134780, "Pomalidomide."
PubChem CID 24821094, "Ibrutinib."
Rabin et al. Absolute Lymphocyte Counts Refine MRD-Based Risk Stratification in Pediatric ALL. Blood (Ash Annual Meeting Abstracts) 114:Abstract 1593 (2009).
Rao et al. Inhibition of invasion, angiogenesis, tumor growth, and metastasis by adenovirus-mediated transfer of antisense uPAR and MMP-9 in non-small cell lung cancer cells. Mol Cancer Ther 4(9):1399-1408 (2005).
Rastetter et al. Rituximab: expanding role in therapy for lymphomas and autoimmune diseases. Ann. Rev. Med 55:477-503 (2004).
Raval et al., "Tumor immunology and cancer immunotherapy: summary of the 2013 SITC primer," J Immunother Cancer, 2:14 (2014).
Ritter et al. Osteosarcoma. Ann. Oncol. 21(Supplement 7):320-325 (2010).
Robak et al. A Targeted Therapy for Protein and Lipid Kinases in Chronic Lymphocytic Leukemia. Curr. Med. Chem. (Epub Jul. 24, 2012), 19(31):5294-5318 (2012).
Robak et al. Tyrosine kinase inhibitors as potential drugs for B-cell lymphoid malignancies and autoimmune disorders. Expert Opin. Investig. Drugs (Epub May 22, 2012), 21(7):921-947 (Jul. 2012).
Roberts, Jr. et al. Trends in the Risks and Benefits to Patients With Cancer Participating in Phase 1 Clinical Trials. JAMA 292(17):2130-2140 (2004).
Rohle et al. "An inhibitor of mutant IDH1 delays growth and promotes differentiation of glioma cells," Science, Apr. 4, 2013 (Apr. 4, 2013), vol. 340, No. 6132, pp. 626-630.
Rooij et al. "The Clinically active BTK inhibitor PCI-32765 targets B-cell receptor-and chemokine-controlled adhesion and migration in chronic lymphocytic leukemia," Blood, Mar. 15, 2012, vol. 119, No. 11, pp. 2590-2594.
Rosenquist et al., Prognostic markers and their clinical applicability in chronic lymphocytic leukemia: where do we stand? Leuk Lymphoma, 54(11): 2351-2361 (2013).
Rozali et al., "Programmed death ligand 2 in cancer-induced immune suppression," Clin Dev Immunol, Article ID: 656340 (2012).
Rushworth et al. BTK inhibitor ibrutinib is cytotoxic to myeloma and potently enhances bortezomib and lenalidomide activities through NF-κB. Cell Signal (Epub Sep. 11, 2012), 25(1):106-112 (Jan. 2013).
Sagiv-Barfi et al. Therapeutic anti-tumor immunity by checkpoint blockade is enhanced by ibrutinib, an inhibitor of both BTK and ITK. Proc. Natl. Acad. Sci. USA 112(9):E966-E972 (Mar. 2015).
Saulnier et al., "An efficient method for the synthesis of guanidine prodrugs," Bioorganic and Medicinal Chemistry Letters, vol. 4, p. 1985-90 (1994).
Schnute et al., "Bruton's tyrosine kinase (Btk)," Anti-Inflammatory Drug Discovery, Ed. J.I. Levin and S. Laufer, (2012), pp. 297-326.
Schwamb et al. B-cell receptor triggers drug sensitivity of primary CLL cells by controlling glucosylation of ceramides. Blood (Epub Aug. 27, 2012), 120(19):3978-3985 (Nov. 2012).
Science Daily Counting tumor cells in blood predicts treatment benefit in prostate cancer. (Jul. 7, 2008), http://www.sciencedaily.com/releases/2008/07/080706083142.htm, last accessed Jul. 23, 2013.
Science Daily, "Drug shows surprising efficacy as treatment for chronic leukemia, mantle cell lymphoma," (Jun. 19, 2013), http://www.sciencedaily.com/releases/2013/06/130619195217.htm, last accessed Jan. 15, 2016.

(56) References Cited

OTHER PUBLICATIONS

Search Report and Written Opinion for Singapore Application No. 11201401625T, dated Dec. 8, 2016, 27 pages.
SG201208724-3 Search Report and Written Opinion dated Mar. 17, 2015.
Silverman. The Organic Chemistry of Drug Design and Drug Action, Academic Press, Inc., San Diego, pp. 352-401 (1992).
Singapore Patent Application No. 201006601-7 Written Opinion dated Aug. 19, 2013.
Singh et al., "Therapeutic vaccines as a promising treatment modality against prostate cancer: rationale and recent advances," Ther Adv Vaccines, 2(5): 137-148 (2014).
Sinkula et al. Rationale for design of biologically reversible drug derivatives: prodrugs. J. Pharm. Sci., 64:181-210 (1975).
Sivina et al. CCL3 (MIP-1a) Plasma Levels and the Risk for Disease Progression in Chronic Lymphocytic Leukemia. Blood 117(5):1662-1669 (2010).
Spurrell et al., "Adaptive immunity in cancer immunology and therapeutics," Ecancermedicalscience, 2(8): 441 (2014).
Srivastava et al., "Update on benefit of immunotherapy and targeted therapy in melanoma: the changing landscape," Cancer Manag Res, 6: 279-289 (2014).
Stead et al. Concise synthesis of (+/-)-Cytisine via lithiation of N-Boc-bispidine. Organic Letters 7(20):4459-4462 (2005).
STN Registry No. 936563-96-1. Ibrutinib. Retrieved from STN Registry Jul. 27, 2015. 1 pg.
Strimbu et al. What are biomarkers? Curr Opin HIV AIDS 5(6):463-466 (2010.
Supplementary European Search Report for Application No. EP14774808, dated Oct. 24, 2016, 9 pages.
Supplementary European Search Report for Application No. EP14782886, dated Feb. 8, 2017, 16 pages.
Supplementary European Search Report for EP13850097 dated Mar 31, 2016.
Supplementary Partial European Search Report for Application No. EP14782886 dated Nov. 4, 2016, 11 pages.
Taiwan Search Report for TW104125847 dated Jun. 13, 2016.
Takahashi et at. Serum CCL3 and CCL4 Levels Function As Novel Prognostic Markers in Diffuse Large B Cell Lymphoma [online]. 54th ASH Annual Meeting and Exposition. [retrieved on Apr. 21, 2015], Abstract 2709. Retrieved from the Internet: <URL: https://ash.confex.com/ash/2012/webprogram/Paper53900.html>.
Tame, "Scoring functions: a view from the bench," J Comput Aided Mol Des, 13(2): 99-108 (1999).
TG Therapeutics, Inc. Ublituximab + ibrutinib in select B-cell malignancies. In: ClinicalTrials.gov [Internet]. Bethesda (MD): National Library of Medicine (US). Dec. 11, 2013-[cited Apr. 15, 2014]. Available from: http://clinicaltrials.gov/ct2/show/NCT02013128 NLM Identifier: NCT02013128.
The Lymphoma Academic Research Organisation. Bruton's tyrosine kinase (BTK) inhibition in B-cell lymphomas (BIBLOS). In: ClinicalTrials.gov [Internet]. Bethesda (MD): National Library of Medicine (US). Jan. 31, 2014-[cited Apr. 15, 2014]. Available from: http://clinicaltrials.gov/ct2/show/NCT02055924 NLM Identifier: NCT02055924.
THEIL. Structure-aided drug design's next generation. Nature Biotechnol 2:513-519 (2004).
Thurn et al. (Future Oncol. Feb. 2011; 7(2): 263-2830.
Toomer et al., "Autoimmunity as a double agent in tumor killing and cancer promotion," Front Immunol, 5: 116 (2014).
Tosti et al., "Anti-cytotoxic T lymphocyte antigen-4 antibodies in melanoma," Clin Cosmet Investig Dermatol, 6: 245-256 (2013).
Traxler et al., "Use of a pharmacophore model for the design of EGF-R tyrosine kinase inhibitors: 4-(phenylamino)pyrazolo[3,4-d]pyrimidines," J Med Chem, 40(22):3601-16 (1997).
Tykodi et al., "PD-1 as an emerging therapeutic target in renal cell carcinoma: current evidence," OncoTargets and Therapy, 7: 1349-1359 (2014).
University of California, San Diego. A Phase Ib/II Study of Ibrutinib in Combination With GA101—Obinutuzumab in Previously Untreated Chronic Lymphocytic Leukemia (CLL) Patients Over 65 Years of Age or With Comorbidities That Preclude the Use of Chemotherapy Based Treatment. In: ClinicalTrials.gov [Internet]. Bethesda (MD): National Library of Medicine (US). Oct. 30, 2014 [cited Feb. 5, 2015] Available from: https://clinicaltrial.gov/ct2/show/NCT02315768?term=NCT02315768 NLM Identifier: NCT02315768.
US Unpublished U.S. Appl. No. 14/340,483, filed Jul. 24, 2014.
Vanneman et al., "Combining immunotherapy and targeted therapies in cancer treatment," Nat Rev Cancer, 12(4): 237-251 (2012).
Vargas et al., "Inhibitors of BTK and ITK: state of the new drugs for cancer, autoimmunity and inflammatory diseases," Scand J Immunol, 78(2): 130-139 (2013).
Vij Ravi et al: "Ibrutinib, Single Agent or in Combination with Dexamethasone, in Patients with Relapsed or Relapsed/Refractory Multiple Myeloma (MM): Preliminary Phase 2 Results", Blood, American Society of Hematology, US, vol. 124, No. 21, Dec. 1, 2014 (Dec. 1, 2014), ISSN: 0006-4971.
Vose. Mantle cell lymphoma: 2012 update on diagnosis, risk-stratification, and clinical management. Am. J. Hematol. 87(6):604-609 (Jun. 2012).
Walker et al., "Treg and CTLA-4: two intertwining pathways to immune tolerance," J Autoimmun, 45: 49-57 (2013).
Wang et al. "Ibrutinib and rituximab are an efficacious and safe combination in relapsed mantle cell lymphoma: preliminary results from a Phase II clinical trial," Oral Abstract Session 624, 56th ASH Annual Meeting and Exposition (Dec. 6-9, 2014).
Wang et al. Targeting BTK with ibrutinib in relapsed or refractory mantel-cell lymphoma. N Engl J Med 369(6):507-516 (Aug. 8, 2013).
Wanner et al., "Mammalian Target of Rapamycin Inhibition Includes Cell Cycle Arrest in Diffuse Large B Cell Lymphoma (DLBCL) Cells and Sensitises DLBCL Cells to RituXimab," British Journal of Haematology, 2006, vol. 134, pp. 475-484.
Wilkinson et al. Selective tyrosine kinase inhibitors. Expert Opin. Emerging Drugs 5(3):287-297 (2000).
Wilson et al. "Targeting B cell receptor signaling with ibrutinib in diffuse large B cell lymphoma," Nat Med. Jul. 20, 2015 (Jul. 20, 2015), vol. 21, pp. 922-926. entire document.
Wilson et al., "The Bruton's tyrosine kinase (BTK) inhibitor, ibrutinib (PCI-32765), has preferential activity in the ABC subtype of relapsed/refractory de novo diffuse large B-cell lymphoma (DLBCL): interim results of a multicenter, open-label, phase 2 study," Blood 120:Abstract 686 (2012).
Winer et al. "PCI-32765: a novel Bruton's tyrosine kinase inhibitor for the treatment of lymphoma malignacies," Expert Opinion on Investigational Drugs, Mar. 2012, vol. 21, No. 3, pp. 355-361.
Witzens-Harig et al. Current treatment of mantle cell lymphoma: results of a national survey and consensus meeting. Ann Hematol. (Epub Aug. 29, 2012), 91(11):1765-1772 (Nov. 2012).
Witzig et al. Detection of myeloma cells in the peripheral blood by flow cytometry. Cytometry (Communications in Clinical Cytometry), 26:113-120 (1996).
Wu et al., "Immunotherapies: the blockade of inhibitory signals," Int J Biol Sci, 8(10): 1420-1430 (2012).
Yang et al. Tyrosine kinase inhibition in diffuse large B-cell lymphoma: molecular basis for antitumor activity and drug resistance of dasatinib. Leukemia 22(9):1755-1766 (2008) [E-pub Jul. 3, 2008].
Yang, et al., "Exploiting Synthetic Lethality for the Therapy of ABC Diffuse Large B Cell Lymphoma," Cancer Cell, 21(6): 723-737 (Jun. 1, 2012).
Yasuhiro et al., "ONO-WG-307, a novel, potent and selective inhibitor of Bruton's tyrosine kinase, in sustained inhibition of the Erk, Akt and PKD signaling pathways," 53rd American Society of Hematology Annual Meeting and Exposition, San Diego, CA, Poster #2021 (2011).
Zent et al. The Treatment of Recurrent/Refractory chronic Lymphocytic Leukemia/Small Lymphocytic Lymphoma (CLL) With Everolimus Results in Clinical Responses and Mobilization of CLL Cells Into the Circulation. Cancer 116(9):2201-2207 (2010).
Zhao, et al., "Combination of Ibrutinib with ABT-199, a BCL-2 Pathway Inhibitor: Effective Therapeutic Strategy in a Novel Mantle Cell Lymphoma Cell Line Model," Blood, 122(21): 645 (2013).

(56) References Cited

OTHER PUBLICATIONS

Zhu et al., "Calpain inhibitor II induces caspase-dependent apoptosis in human acute lymphoblastic leukemia and non-Hodgkin's lymphoma cells as well as some solid tumor cells," Clin Cancer Res, 6:2456-63 (2000).
Zitvogel et al., "Targeting PD-1/PD-L1 interactions for cancer immunotherapy," Oncoimmunology, 1(8):1223-1225, (2012).
Abraham, "Leukemia," Demos Medical Publishing: New York (2011).
Ansell, "Two targets for the price of one," Blood 122(15): 2529-2531 (Oct. 10, 2013).
Atsukawa et al, "Ribavirin downmodulates inducible costimulator on Cd4+ T cells and their interleukin-10 secretion to assist in hepatitis C virus clearance," J Gastoenterology and Hepatology, 27:823-831 (2012).
Badoux et al., "Patients with Relapsed CLL and 17p Deletion by FISH Have Very Poor Survival Outcomes," Blood, 114: 1248 (2009).
Balasubramanian et al., "Identification of MicroRNA Markers of Sensitivity to the Novel Bruton's Tyrosine Kinase (BTK) Inhibitor PCI-32765 in Non-Hodgkin's Lymphoma," Blood, 112(11): 3366 (2008).
Bam et al., "Role of Bruton's Tyrosine Kinase (BTK) in Growth and Metastasis of INA6 Myeloma Cells," Blood Cancer Journal, 4: 1-9 (2014).
Barany, "Genetic Disease Detection and DNA Amplification Using Cloned Thermostable Ligase," Proc. Natl. Acad. Sci. USA, 88:189-193 (1991).
Bartlett et al., "Ibrutinib Monotherapy in Relapsed/Refractory Follicular Lymphoma (FL): Preliminary Results of a Phase 2 Consortium (P2C) Trial," Blood, 124: 800 (2014).
Bernstein, "Polymorphism—A Perspective," Crystal Growth & Design, 11: 632-650 (2011).
Bhagat et al., "Abstract 2570: IMO-8400, a Selective Antagonist of TLRs 7, 8 and 9, Inhibits MYD88 L265P Mutation-driven Signaling and Cell Survival: A Potential Novel Approach for Treatment of B-cell Lymphomas Harboring MYd88 L265P Mutation," Cancer Res, 74: Abstract 2570 (2014).
Biocompare, "Th1 and Th2 Balance, Regulation, and Involvement in Disease," http://www.biocompare.com/Application-Notes/43518-Th1-And-Th1-Balance-Regulation-And-Involvement-In-Disease (Apr. 24, 2006).
Bischler et al., "A new method for the synthesis of isoquinolones," Ber, 26:1093-1908 (1893).
Blum et al., "Adult Burkitt Leukemia and Lymphoma," Blood, 104: 3009-3020 (2004).
Bohers et al., "Targetable Activating Mutations are Very Frequent in GCB and ABC Diffuse Large B-Cell Lymphoma," Genes, Chromosomes & Cancer, 53(2): 114-153 (2014).
Bowen et al., "Adaptive Immune Responses in Acute and Chronic Hepatitis C Virus Infection," Nature, 436(7053):946-852 (2005).
Brown et al., "PCI-32765, the first BTK (Bruton's Tyrosine Kinase) inhibitor in clinical trials," Curr Hematol Malig Rep, 8(1): 1-6 (2013).
Byrd et al., "Ibrutinib versus Ofatumumab in Previously Treated Chronic Lymphoid Leukemia," The New England Journal of Medicine, 371(3): 213-223 (2014).
Byrn et al., "Pharmaceutical Solids: A Strategic Approach to Regulatory Considerations," Pharmaceutical Research, 12: 945-954 (1995).
Calderwood et al., "Pyrrolo[2,3-d]pyrimidines Containing Diverse N-7 Substituents as Potent Inhibitors of Lcks," Bioorg Med Chem Lett, 12: 1683-1686 (2002).
Calpe et al., "ZAP-70 Enhances Migration of Malignant B Lymphocytes Toward CCL21 by Inducing CCR7 Expression via IgM-ERK1/2 Activation," Blood, 118(16): 4401-4410 (2011).
Campàs et al., "Bcl-2 Inhibitors Induce Apoptosis in Chronic Lymphocytic Leukemia Cells," Exp Hematol, 34(12): 1663-1669 (2006).
Celgene, "Safety and Efficacy of Pomalidomide, Bortezomib and Low Dose Dexamethasone in Subjects with Relapsed or Refractory Multiple Myeloma (OPTIMISMM)." ClinicalTrials.gov [Internet]. Bethesda (MD): National Library of Medicine (US). Nov. 28, 2012. Available from: <https://clinicaltrials.gov/ct2/show/NCT01734928>. NLM Identifier: NCT01734928.
Cerchietti et al., "Inhibition of Analplastic Lymphoma Kinase (ALK) Activity Provides a Therapeutic Approach for CLTC-ALK-positive Human Diffuse Large B Cell Lymphomas," PLoS One, 6(4): e18436 (2011).
Cervantes-Gomez et al., "Pharmacological and Protein Profiling Suggests Venetoclax (ABT-199) as Optimal Partner with Ibrutinib in Chronic Lymphocytic Leukemia," Clinical Cancer Research, 21(16): 3705-3715 (2015).
Chen et al., "Abstract 4564: Inhibitory Effects of the BTK Inhibitor, Ibrutinib, on Her2 Amplified Breast Cancer Growth, Cell Cycle Progression and Clonogenicity," Cancer Res, 74(19): Abstract 4564 (2014).
Cheson et al., "Bendamustine: Rebirth of an Old Drug," J Clin Oncol, 27: 1492-1501 (2009).
Chinese Journal of Transplantation (Electronic Version), 3(4): 323 (Nov. 2009).
Chiron et al., "Cell-Cycle Reprogramming for PI3K Inhibition Overrides a Relapse-Specific C481S BTK Mutation Revealed by Longitudinal Functional Genomics in Mantle Cell Lymphoma," Cancer Discov, 4(9): 1022-1035 (2014).
Chothia et al., "Canonical Structures for the Hypervariable Regions of Immunoglobulins," J. Mol. Biol., 196(4):901-917 (1987).
Ciric et al., "Clonal Evolution in Waldenstrom macroglobulinemia Highlights Functional Role of B-Cell Receptor," Blood, 97: 312-232 (2001).
Clark et al., "The Role of Ribavirin in Direct Acting Antiviral Drug Regimens for Chronic Hepatitis C," Liver Int, 32(01): 103-107 (2012).
Corigliano et al., "Plant Hsp90 Proteins Interact with B-Cells and Stimulate Their Proliferation," PLoS One, 6(6): e21231 (2011).
Cui et al., "MicroRNA-155 Influences B-Cell Receptor Signaling and Associates with Aggressive Disease in Chronic Lymphocytic Leukemia," Blood, 124(4): 546-554 (2014).
Cummings et al., "Critical Role for Phosphoinositide 3-Kinase Gamma in Parasite Invasion and Disease Progression of Cutaneous Leishmaniasis," PNAS USA, 109:1251-1256 (2012).
Cuneo et al., "Modern Treatment in Chronic Lymphocytic Leukemia: Impact on Survival and Efficacy in High-risk Subgroups," Cancer Med-US, 3(3): 555-564 (2014).
Dana-Farber Cancer Institute, "Study of Ibrutinib in Patients with Symptomatic, Previously Untreated Waldenstrom's Macroglobulinemia, and Impact on Tumor Genomic Evolution Using Whole Genome Sequencing," In: ClinicalTrials.gov. National Library of Medicine (US). Nov. 13, 2015. NLM Identifier: NCT02604511.
Davids et al., "The BCL-2-specific BH3-mimetic ABT-199 (GDC-0199) is active and well-tolerated in patients with relapsed non-Hodgkin lymphoma: interim results of a phase I study," Blood, 120(21): Abstract No. 304 (2012).
Deng et al., "New Strategies in the Treatment of Mantle Cell Lymphoma," Clin Cancer Res, 18(13): 3499-3508 (2012).
Dolganiuc et al., "T Cells with Regulatory Activity in Hepatitis C Virus Infection: What We Know and What We Don't," J Leukoc Biol. 84(3): 614-622 (2008).
Dubovsky et al., "Epigenetic Repolarization of T Lymphocytes from Chronic Lymphocytic Leukemia Patients Using 5-aza-2'-deoxycytidine," Leukemia Research, 35: 1193-1199 (2011).
Dubovsky et al., "Ibrutinib is an irreversible molecular inhibitor of ITK driving a Th1-selective pressure in T lymphocytes," Blood, 122(15): 2539-2549 (2013).
Dubovsky et al., "Restoring the Functional Immunogenicity of Chronic Lymphocytic Leukemia Using Epigenetic Modifiers," Leukemia Research, 35(3): 394-404 (2011).
Döhner et al., "Genomic Aberrations and Survival in Chronic Lymphocytic Leukemia," N Engl J Med, 343(26): 1910-1916 (2000).
European Search Report for Application No. EP 13166272 dated Sep. 4, 2013, 3 pages.
European Search Report for Application No. EP 15170739 dated Oct. 29, 2015, 2 pages.

(56) References Cited

OTHER PUBLICATIONS

Extended European Search Report for Application No. EP 14855030 dated Nov. 7, 2017.
Extended European Search Report for Application No. EP 15764524.3 dated Jan. 18, 2018.
Extended European Search Report for EP Application No. 15829601.2 dated Mar. 2, 2018.
Fallahi et al., "Cytokines and HCV-Related Disorders," Clinical and Developmental Immunology, 2012: Article ID 468102 (2012).
FDA Guidelines: FDA's Guidance for Industry, "Estimating the Maximum Safe Starting Dose in Initial Clinical Trials for Therapeutics in Adult Healthy Volunteers," (Jul. 2005).
Ferrajoli et al., "Prognostic Value of miR-155 in Individuals with Monoclonal B-Cell Lymphocytosis and Patients with B Chronic Lymphocytic Leukemai," Blood, 122(11): 1891-1899 (2013).
Fischer et al., "Bendamustine in Combination with Rituximab (BR) for Patients with Relapsed Chronic Lymphocytic Leukemia (CLL): A Multicenter Phase II Trials for the German CLL Study Group (GCLLSG)," Blood, 110: 3106 (2006).
Flynn et al., "Maintenance of TH1 HCV-Specific Responses in Individuals with Acute HCV who Achieve Sustained Virological Clearance After Treatment," J Gastroenterol Hepatol, 28(11): .doi: 10.1111/jgh.12265 (May 10, 2013).
Fodor et al., "The Mechanism of the Bischler☐Napieralski Reaction," Angew Chem Int Ed Engl, 11:911-920 (1972).
Fontan et al., "Targeting Lymphomas Through MALT1 Inhibition," Oncotarget, 3(12): 1493-1494 (2012).
Fonte et al., "In vitro sensitivity of CLL cells to fludarabine may be modulated by the stimulation of Toll-like receptors," Clin Cancer Res, 19: 367-379 (2013).
Fowell et al., "Impaired NFATc Translocation and Failure of Th2 Development in Itk-Deficient CD4+ T Cells," Immunity, 11:399-409 (1999).
Fritsche et al., "National Academy of Clinical Biochemistry Guidelines for the Use of Tumor Markers in Bladder Cancer," NACB: Practice Guidelines and Recommendations for Use of Tumor Markers in the Clinic Bladder Cancer (3H)1 (Oct. 30, 2013).
Fry et al., "Specific Irreversible Inactivation of the Epidermal Growth Factor Receptor and erbB2, by a New Class of Tyrosine Kinase Inhibitor," Proc Natl Acad Sci, 95: 12022-12027 (1998).
Gad et al., "Distinct Immunoregulatory Cytokine Pattern in Egyptian Patients with Occult Hepatitis C Infection and Unexplained Persistently Elevated Liver Transaminases," Asian J Transfus Sci, 6(1): 24-28 (2012).
Goggins, "Markers of Pancreatic Cancer: Working Toward Early Detection," Clin Cancer Res, 17(4) :635-637 (2011).
Gomez-Rodriguez et al., "Tec Family Kinases Itk and Rlk/Txk in T Lymphocytes Cross-Regulation of Cytokine Production and T-Cell Fates," FEBS Journal, 278(12):1980-1989 (2011).
Good et al., "Classification of non-hodgkin's Lymphoma," Hematol Oncol Clin N Am, 22: 781-805 (2008).
Grzywnowicz et al., "Programmed Death-1 and its Ligand are Novel Immunotolerant Molecules Expressed on Leukemic B Cells in Chronic Lymphocytic Leukemia," PLoS One, 7(4):e35178, pp. 1-8 (2012).
Gu et al., "Polymorph Screening: Influence of Solvent on the Rate of Solvent-Mediated Polymorphic Transformation," Journal of Pharmaceutical Sciences, 90(11): 1878-1890 (2001).
Guatelli et al., "Isothermal, in Vitro Amplification of Nucleic Acids by a Multienzyme Reaction Modeled After Retroviral Replication," Proc. Natl. Acad. Sci. USA, 87(5):1874-1878 (1990).
Guinn et al., "miR-155 expression is associated with chemoimmunotherapy outcome and is modulated by Bruton's tyrosine kinase inhibition with Ibrutinib," Leukemia, 29(5): 1210-1213 (2015).
Guo, "Molecular Characteristic of CTA056, a Novel Interleukin-2-Inducible T-Cell Kinase Inhibitor that Selectively Target Malignant T Cell and Modulate Oncomirs," Molecular Pharmacology 82:938-947 (Aug. 2012).

Gupta et al., "Elevated Serum IL-10 Levels in Diffuse Large B-cell Lymphoma: A Mechanism of Aberrant JAK2 Activation," Blood, 119(12): 2844-2853 (2012).
Gupta et al., "Inhibition of Histone Deacetylase Overcomes Rapamycin-mediated Resistance in Diffuse Large B-cell Lymphoma by Inhibiting Akt Signaling Through MTORC2," Blood, 114: 2926-2935 (2009).
Hahtola et al., "Th1 Response and Cytotoxicity Genes are Down-Regulated in Cutaneous T-Cell Lymphoma," Clin Cancer Res, 12(16): 4812-4821 (2006).
Hallek et al., "Continuing Medical Education Activity," Am J Hematol, 88(9): 803-816 (2013).
Hallek et al., "First-line treatment with fludarabine (F), cyclophosphamide (C), and Rituximab (R) (FCR) Improves Overall Survival (OS) in previously untreated patients (pts) with advanced chronic lymphocytic leukemia (CLL): Results of a Randomized Phase III Trial on behave of an International Group of Investigators and the German CLL Study Group [abstract No. 535]," Blood (ASH Annual Meeting Abstracts), 114 (2009).
Harris et al., "World Health Organization Classification of Neoplastic Diseases of the Hematopoietic and Lymphoid Tissue: Report of the Clinical Advisory Committee Hearing—Airlie house, Virginia, Nov. 1997," J Clin Oncol, 17(12): 3835-3849 (Dec. 1999).
Hauptrock et al., "Rituximab in the Treatment of non-Hodgkin's Lymphoma," Biologics: Targets & Therapy, 2(4): 619-633 (2008).
Igietseme et al., "Suppression of Endogenous IL-10 Gene Expression in Dendritic Cells Enhances Antigen Presentation for Specific Th1 Induction: Potential for Cellular Vaccine Development," J Immunol, 164: 4212-4219 (2000).
International Conference on Harmonisation of Technical Requirements for Registration of Pharmaceuticals for Human Use-Specifications: Test Procedures and Acceptance Criteria for New Drug Substances and New Drug Products: Chemistcal Substances (1999).
International Preliminary Report on Patentability for International Application No. PCT/US2008/058528 dated Sep. 29, 2009, 8 pages.
International Preliminary Report on Patentability for International Application No. PCT/US2009/50897 dated Jan. 27, 2011, 7 pages.
International Preliminary Report on Patentability for International Application No. PCT/US2012/061208 dated Feb. 25, 2013, 4 pages.
International Preliminary Report on Patentability for International Application No. PCT/US2014/024966 dated Sep. 15, 2015, 6 pages.
International Preliminary Report on Patentability for International Application No. PCT/US2014/068237 dated Jun. 16, 2016, 7 pages.
International Search Report and Written Opinion for International Application No. PCT/US2013/068132 dated Jan. 29, 2014, 11 pages.
International Search Report and Written Opinion for International Application No. PCT/US2014/024966 dated Aug. 27, 2014, 15 pages.
International Search Report and Written Opinion for International Application No. PCT/US2014/062278 dated Jan. 29, 2015, 19 pages.
International Search Report and Written Opinion for International Application No. PCT/US2014/068237 dated Feb. 27, 2015, 10 pages.
International Search Report and Written Opinion for International Application No. PCT/US2015/21871 dated Jul. 8, 2015, 11 pages.
International Search Report and Written Opinion for International Application No. PCT/US2015/35665 dated Sep. 21, 2015, 13 pages.
International Search Report and Written Opinion for International Patent Application No. PCT/US15/61091 dated Mar. 11, 2016, 13 pages.
International Search Report and Written Opinion for International Patent Application No. PCT/US16/15697 dated Apr. 22, 2016, 10 pages.
International Search Report and Written Opinion for International Patent Application No. PCT/US16/41550 dated Nov. 15, 2016, 12 pages.
International Search Report and Written Opinion for International Patent Application No. PCT/US16/63085 dated May 22, 2017, 13 pages.

(56) References Cited

OTHER PUBLICATIONS

International Search Report and Written Opinion for International Patent Application No. PCT/US2014/058132 dated Jan. 14, 2015, 14 pages.
International Search Report and Written Opinion for International Patent Application No. PCT/US2015/051034 dated Dec. 18, 2015, 18 pages.
International Search Report for International Application No. PCT/US15/41841 dated Oct. 29, 2015, 3 pages.
International Search Report for International Application No. PCT/US2015/067504 dated Mar. 4, 2016, 4 pages.
International Search Report for International Application No. PCT/US2016/025673 dated Jun. 23, 2016, 3 pages.
Jaglowski et al., "A Phase Ib/II Study Evaluating Activity and Tolerability of BTK Inhibitor PCI-32765 and Ofatumumab in Patients with Chronic Lymphocytic Leukemia/Small Lymphocytic Lymphoma (CLL/SLL) and related Diseases," J Clin Oncol, 30: Abstract 6508 (2012).
Jak et al., "CD40 Stimulation Sensitizes CLL Cells to Lysosomal Cell Death Induction by Type II Anti-CD20 mAb GA101," Blood, 118(19): 5178-5188 (2011).
Jordan et al., "Tamoxifen: A Most Unlikely Pioneering Medicine," Nature Reviews: Drug Discovery, 2: 205-213 (2003).
Kabat et al., "Sequences of Proteins of Immunological Interest," NIH Publ. No. 91-3242, 1:647-669 (1991).
Kang et al., "Dynamic Analysis of Th1/Th2 Cytokine Concentration During Antiretroviral Therapy of HIV-1/HCV Co-Infected Patients," BMC Infectious Diseases, 12:102-112 (2012).
Karanjawala et al., "New Markers of Pancreatic Cancer Identified Through Differential Gene Expression Analyses: Claudin 18 and Annexin A8," Am J. Surg. Pathol., 32(2): 188-196 (2008).
Kathawala et al., "Masitinib Antagonizes ATP-Binding Cassette Subfamily C Member 10-Mediated Paclitaxel Resistance: A Preclinical Study," Mol Cancer Ther, 13(3): 714-723 (2014).
Kathawala et al., "The Small Molecule Tyrosine Kinase Inhibitor NVP-BHG712 Antagonizes ABCC10-mediated Paclitaxel Resistance: A Preclinical and Pharmacokinetic Study," Oncotarget, 6(1): 510-521 (2014).
Kaur et al., "Inhibitors of Interleukin-2 Inducible T-Cell Kinase as Potential Therapeutic Candidates for the Treatment of Various Inflammatory Disease Conditions," Eur J Pharm Sci, 47(3): 574-578 (2012).
Kawakami et al., "Regulation of Dendritic Cell Maturation and Function by Bruton's Tyrosine Kinase via IL-10 and Stat3," Proc Natl Acad Sci USA, 103(1): 153-158 (2006).
Khan et al., "Circulating Biomarkers and their Possible Role in Pathogenesis of Chronic Hepatits B and C Viral Infections," Ind J Clin Biochem, 26(2): 161-168 (2011).
Kim et al., "CD79B and MYD88 Mutations in Diffuse Large B-Cell Lymphoma," Human Pathology, 45(3): 556-564 (2014).
Kong et al., "Opportunistic Autoimmune Disorders Potentiated by Immune-Checkpoint Inhibitors Anti-CTLA-4 and Anti-PD-1," Front Immunol, 5(206): 1-8 (2014).
Kuo et al., "Combination of Ibrutinib and ABT-199 in Diffuse Large B-Cell Lymphoma and Follicular Lymphoma," Molecular Cancer Therapeutics, 16(7): 1246-1256 (2017).
Kwoh et al., "Transcription-based amplification system and detection of amplified human immunodeficiency virus type 1 with a bead-based sandwich hybridization format," Proc. Natl. Acad. Sci. USA, 86:1173-1177 (1989).
Langhans et al., "Ribavirin Exerts Differential Effects on Function of Cd4+ Th1, Th2, and Regulator T Cell Clones in Hepatitis C," PLOS One, 7(7): e42094-42103 (2012).
Lapalombella et al., "Testrapanin CD37 Directly Mediates Transduction of Survival and Apoptotic Signals," Cancer Cell, 21: 694-708 (2012).
Lau et al., "Mechanism of Action of Ribavirin in the Combination of Treatment of Chronic HCV Infection," Hepatology, 35(5): 1002-1009 (2002).

Lemery et al., "U.S. Food and Drug Administration Approval: Ofatumumab for the Treatment of Patients with Chronic Lymphocytic Leukemia Refractory to Fludarabine and Alemtuzmab," Clinical Cancer Research, 16(17): 4331-4338 (2010).
Leonard et al., "Selective CDK4/6 Inhibition with Tumor Responses by PD0332991 in Patients with Mantle Cell Lymphoma," Blood, 119(20): 4597-4607 (2012).
Lester et al., "Interleukin 2-Inducible T Cell Kinase (ITK) Facilitates Efficient Egress of HIV-1 by Coordinating Gag Distribution and Actin Organization," Virology, 436(1): 235-243 (2013).
Liao et al., "Interleukin-2 at the Crossroads of Effector Responses, Tolerance, and Immunotherapy," Immunity, 38(1): 13-25 (2013).
Lin, "New Agents in Chronic Lymphocytic Leukemia," Curr Hematol Malig Rep, 5: 29-34 (2010).
Lizardi et al., "Exponential Amplification of Recombinant-RNA Hybridization Probes," Bio/Technology, 6:1197-1202 (1988).
Lo et al., "Itk Inhibitors: A Patent Review," Expert Opin Ther Patents, 20(4): 459-469 (2010).
Luban, "TRIM5 and the Regulation of HIV-1 Infectivity," Mol. Biol. Int., 2012: Article ID 426840, 6 pages (2012).
Maddocks et al., "Etiology of Ibrutinib Therapy Discontinuation and Outcomes in Patients With Chronic Lymphocytic Leukemia," JAMA Oncology, 1(1):80-87 (2015).
Medscape, "Ibrutinib." © Jun. 30, 2014. Available from: <https://web.archive.org/web/20140630074515/https://reference.medscape.com/drug/imbruvi>.
Medscape, "Pomalidomide." © Mar. 9, 2013. Available from: <https://web.archive.org/web/20130309203122/https://reference.medscape.com/drug/pomalyst-pomalidomide-999809>.
Mishan-Eisenberg et al., "Differential Regulation of Th1/Th2 Cytokine Respones by Placental Protein 14," The Journal of Immunology, 173(9): 5524-5530 (2004).
Mizuno et al., "Fas-induced Apoptosis in B Cells," Apoptosis, 8: 451 (2003).
Moingeon, "Strategies for Designing Vaccines Eliciting Th1 Responses in Humans," Journal of Biotechnology, 98:189-198 (2002).
Montserrat et al., "How I Treat Refractory CLL," Blood, 106: 1276-1284 (2006).
Morissette et al., "High-throughput Crystallization: Polymorphs, Salts, Co-Crystals and Solvates of Pharmaceutical Solids," Advanced Drug Delivery Review, 56: 275-300 (2004).
Morrison et al., "Small Lymphocytic Lymphoma," J Clin Oncol, 7(5): 598-606 (May 1989).
Murawski et al., "New Drugs for Aggressive B-cell and T-cell Lymphomas," The Lancet Oncology, 11(11): 1074-1085 (2010).
Myrmel et al., "The Hepatitis C Virus Enigma," APMIS, 117: 427-439 (2009).
Mössner et al., "Increasing the Efficacy of CD20 Antibody Therapy Through the Engineering of a New Type II Anti-CD20 Antibody with Enhanced Direct and Immune Effector Cell-Mediated B-cell Cytotoxicity," Blood, 115(22): 4393-4402 (2010).
Nam, "Ibrutinib Effective as First-line Therapy for Waldenstrom Macroglobulinemia," Cancer Therapy Advisor (Dec. 5, 2017).
National Cancer Institute, "Pomalidomide plus Low-Dose Dexamethasone Improves Survival for Patients with Multiple Myeloma," Lancet Oncology, pp. 1 of 3 through 3 of 3 (Sep. 3, 2013).
Nicolaou et al., "Calicheamicin θ1: A Rationally Designed Molecule with Extremely Potent and Selective DNA Cleaving Properties and Apoptosis Inducing Activity," Angewandte Chemie International Edition in English, 33:183-186 (1994).
Noy et al., "Targeting Bruton Tyrosine Kinase with Ibrutinib in Relapsed/refractory Marginal Zone Lymphoma," Blood, 129(16): 2224-2232 (2017).
Partial Supplementary European Search Report for EP Application No. 15828160.0 dated Feb. 19, 2018.
Paul ed., Fundamental Immunology, 3rd ed., p. 242 (1993).
Pharmacyclics, "Executive Summary: Bruton's Tyrosine Kinase (Btk) Inhibitor Programs for Oncology and Autoimmune Diseases," pp. 1-6 (Jan. 2010).
Pollyea et al., "A Phase I Dose Escalation Study of the BTK Inhibitor PCI-32765 in Relapsed and Refractory B Cell Non-Hodgkin Lymphoma," ASH Meeting Poster Abstracts (2009).

(56) References Cited

OTHER PUBLICATIONS

Ramsay et al., "Chronic Lymphocytic Leukaemia—The Role of the Microenvironment Pathogenesis and Therapy," Brit J Haematol, 162(1): 15-24 (2013).
Ramsay, "Immune checkpoint blockade immunotherapy to activate anti-tumour T-cell immunity," Brit J Haematol, 162(3): 313-325 (2013).
Readinger et al., "Selective Targeting of ITK Blocks Multiple Steps of HIV Replication," PNAS USA, 105(18): 6684-6689 (2008).
Rummel et al., "Bendamustine plus rituximab is effective and has a favorable toxicity profile in the treatment of mantle cell and low-grade non-Hodgkin's lymphoma," J Clinc Oncol, 23(15): 3383-3389 (2005).
Sahu et al., "ITK Inhibitors in Inflammation and Immune-Mediated Disorders," Curr Top Med Chem, 9(8): 690-703 (2009).
Scapin, "Structural Biology in Drug Design: Selective Protein Kinase Inhibitors," Drug Discovery Today, 7(11): 601-611 (2002).
Schaffer et al., "Identification of Potential Ibrutinib Combinations in Hematological Malignancies Using a Combination High-Throughput Screen," Leukemia & Lymphoma, 1-10 (2017).
Schiffner et al., "Development of Prophylactic Vaccines Against HIV-1," Retrovirology, 10: 72 (2013).
Scott et al., "Monoclonal Antibodies in Cancer Therapy," Cancer Immunity, 12: 14 (2012).
Shah et al., "Mantle Cell Lymphoma: A Clinically Heterogeneous Disease in Need of Tailored Approaches," Cancer Control, 19(3): 227-235 (2012).
Slupsky, "Does B cell receptor signaling in chronic lymphocytic leukaemia cells differ from that in other B cell types?," Scientifica (Cairo) 2014: Article ID 208928, 14 pages (2014).
Smaill et al., "Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," J Med Chem, 43: 1380-1397 (2000).
Sofian et al., "Serum Profile of T Helper 1 and T Helper 2 Cytokines in Hepatitis C Virus Infected Patients," Hepat Mon, 12(12): e6156, 4 pages (2012).
Souers et al., "ABT-199, a Potent and Selective BCL-2 Inhibitor, Achieves Antitumor Activity While Sparing Platelets," Nature Medicine, 19(2): 202-208 (2013).
Specialty Pharmacy Times, "MedCart Specialty Pharmacy: Preparing for the Next Advancements in Hepatitis C Therapy," (Dec. 18, 2012), http://www.specialtypharmacytimes.com/publications/specialty-pharmacy-times/2012/December-2012/MedCart-Specialty-Pharmacy-Preparing-for-the-Next-Advancements-in-Hepatitis-C-Therapy.
Stanford School of Medicine, "Precursor B Lymphoblastic Lymphoma," pp. 1-7 (2005).
Stilgenbauer et al., "Genomic Aberrations, VH Mutation Status and Outcome After fludarabine and cyclophosphamide (FC) or FC plus Rituximab (FCR) in the CLL8 Trial [abstract No. 781]," Blood (ASH Meeting Abstracts), 112 (2008).
Supplementary European Search Report for Application No. EP 11790524 dated Sep. 25, 2013, 1 page.
Supplementary Partial European Search Report for Application No. EP 14855030.4 dated Jul. 5, 2017, 16 pages.
Supplementary Partial European Search Report for Application No. EP15764524.3 dated Oct. 4, 2017, 14 pages.
Suzuki et al., "Skewed Th1 Responses Caused by Excessive Expression of Txk, a Member of the Tec Family of Tyrosine Kinases, in Patients with Behcet's Disease," Clinical Medicine & Research, 4(2): 147-151 (2006).
Tai et al., "Bruton's Tyrosine Kinase: Oncotarget in Myeloma," Oncotarget, 3(9): 913-914 (2012).
Takayama et al., "Mammalian and Viral IL-10 Enhance C-C Chemokine Receptor 5 but Down-Regulate C-C Chemokine Receptor 7 Expression by Myeloid Dendritic Cells: Impact on Chemotactic Responses and In Vivo Homing Ability," J Immunol, 166: 7136-7143 (2001).
Tam et al., "De Novo Deletion 17p13.1 Chronic Lymphocytic Leukemia shows Significant Clinical Heterogeneity: the M.D. Anderson and Mayo Clinic Experience," Blood, 114(5): 957-964 (Jul. 30, 2009).
Tam et al., "Long-term Results of fludarabine, cyclophosphamide, and rituximab regimen as initial therapy of chronic lymphocytic leukemia," Blood, 112: 975-980 (2008).
Teta et al., "Exercise is Medicine: Using Exercise to Manipulate TH1 and TH2 Immune Function," Townsend Letter, 312: 4 pages (2009), http://www.freelibrary.com/_/print/PrintArticle.aspx?id=202661767.
Thimme et al., "Determinants of Viral Clearance and Persistence During Acute Hepatitis C Virus Infection," J Exp Med, 194(10): 1395-1406 (2001).
TREANDA® label, revised Mar. 2008.
Trentin et al., "Homeostatic Chemokines Drive Migration of Malignant B Cells in Patients with non-Hodgkin Lymphomas," Blood, 104(2): 502-508 (2004).
Treon et al., "2767 Ibrutinib is Highly Active as First Line Therapy in Symptomatic Waldenstrom's Macroglobulinemia," ASH 59th Annual Meeting & Exposition, Atlanta, GA (Dec. 9-12, 2017).
Treon et al., "A Prospective, Multicentre, Phase II Study of the Bruton's Tyrosine Kinase Inhibitor Ibrutinib in Patients with Relapsed and Refractory Waldenstrom's Macroglobulinemia," Hematol Oncol, 31(Suppl 1): 96-150, Jun. 17, 2013, Abstract #067.
Tsai et al., "Detection of Type 2-Like T-Helper Cells in Hepatitis C Virus Infection: Implications for Hepatitis C Virus Chronicity," Hepatology, 25(2): 449-458 (1997).
Tse et al., "ABT-263: A Potent and Orally Bioavailable Bcl-2 Family Inhibitor," Cancer Res, 68: 3421-3428 (2008).
Tsimberidou et al., "Chemoimmunotherapy May Overcome the Adverse Prognostic Significance of 11q Deletion in Previously Untreated Patients with Chronic Lymphocytic Leukemia," Cancer, 115: 373-380 (Jan. 2009).
Tufman et al., "Biological Markers in Lung Cancer: A Clinician's Perspective," Cancer Biomarkers, 6(3-4): 123-135 (2010).
Uckun et al., "Structure-Based Design of Novel Anticancer Agents," Curr Cancer Drug Targets, 1:59 (2001).
Vargova et al., "MYB transcriptionally regulates the miR-155 host gene in chronic lymphocytic leukemia," Blood, 117(14): 3816-3825 (2011).
Villuendas et al., "Identification of Genes Involved in Imatinib Resistance in CML: A Gene-Expression Profiling Approach," Leukemia, 20(6): 1047-1054 (2006).
Vose et al., "Phase II Study of Rituximab in Combination with CHOP Chemotherapy in Patients with Previously Untreated, Aggressive non-Hodgkin's Lymphoma," J Clin Oncol, 19: 389-397 (2001).
Ward et al., "Isoform-Specific Phosphoinositide 3-Kinase Inhibitors as Therapeutic Agents," Current Opinion in Pharmacology, 3(4): 426-434 (2003).
Watters et al., "Cancer Pharmacogenomics: Current and Future Application," Biochimica, 1603(2): 99-111 (2003).
Wierda et al., "Chemoimmunotherapy with fludarabine, cyclophosphamide, and rituximab for relapsed and refractory chronic lymphocytic leukemia," J Clin Oncol, 23(18): 4070-4078 (Jun. 2005).
Wilson et al., "The Bruton's Tyrosine Kinase (BTK) Inhibitor, Ibrutinib (PCI-32765), has Preferential Activity in the ABC Subtype of Relapsed/Refractory De Novo Diffuse Large B-Cell Lymphoma (DLBCL): Interim Results of a Multicenter, Open-Label, Phase 2 Study," Blood, 120(21): Abstract 686 (Nov. 16, 2012).
Wohner et al., "Rituximab, cyclophosphamide, doxorubicin, vincristine, and prednisone (R-CHOP) for Treatment of Early-stage Gastic Diffuse Large B-Cell Lymphoma," Annals of Oncology, 15: 1086-1090 (Jul. 2004).
Woyach et al., "Bruton's Tyrosine Kinase (BTK) Function is Important to the Development and Expansion of Chronic Lymphocytic Leukemia (CLL)," Blood, 123(8): 1207-1213 (2014).
Woyach et al., "Outcome of patients with relapsed or refractory chronic lymphocytic leukemia treated with flavopiridol: impact of genetic features," Leukemia, 26: 1442-1444 (2012).

(56) References Cited

OTHER PUBLICATIONS

Yu et al., "Proteasome Inhibitors Block HIV-1 Replication by Affecting Both Cellular and Viral Targets," Biochem Biophys Res Commun, 385(1): 100-105 (2009).
Yue et al., "Th1 and Th2 Cytokine Profiles Induced by Hepatitis C Virus F Protein in Peripheral Blood Mononuclear Cells from Chronic Hepatitis C Patients," Immunol Lett, 152(2): 89-95 (2013).
Zabel et al., "The Novel Chemokine Receptor CXCR7 Regulates Trans-endothelial Migration of Cancer Cells," Mol Cancer, 10(73): 1-8 (2011).
Zapata et al., "Engineering Linear F(ab')$_2$ Fragments for Efficient Production in *Escherichia coli* and Enhanced Antiproliferative Activity," Protein Eng, 8(10): 1057-1062 (1995).
Zhang et al., "In vitro, In vivo and Ex vivo Characterization of Ibrutinib: A Potent Inhibitor of the Efflux Function of the Transporter MRP1," Brit J Pharmacol, 171: 5845-5857 (2014).
Zhu et al., "miR-181a/b significantly enhances drug sensitivity in chronic lymphocytic leukemia cells via targeting multiple anti-apoptosis genes," Carcinogenesis, 33(7): 1294-1301 (2012).
Zigmond et al., "Ly6C$^{hi}$ Monocytes in the Inflamed Colon Give Rise to Proinflammatory Effector Cells and Migratory Antigen-Presenting Cells," Immunity, 37:1-15 (2012).
Balasubramanian et al., "78: Mutational Analysis of Patients with Primary Resistance to Single-Agent Ibrutinib in Relapsed or Refractory Mantle Cell Lymphoma (MCL)," Blood, 124(21): Abstract 78 (2014).
Burger et al., "Safety and Activity of 1-14 Ibrutinib Plus Rituximab for Patients with High-Risk Chronic Lymphocytic Leukaemia: A Single-Arm, Phase 2 Study," The Lancet Oncology, 15(10):1090-1099 (2014).
Cheung et al., "Mutation Impact of Targeted Genes in Diffuse Large B-Cell Lymphoma Patients Treated with Ibrutinib," Blood, 126(23): 2642 (2015).
Extended European Search Report for EP Application No. 15828160.0 dated May 22, 2018.
Extended European Search Report for EP Application No. 15860051.0 dated May 18, 2018.
Extended European Search Report for EP Application No. 15874346 dated Jun. 28, 2018.
Fresquet et al., "Acquired Mutations in BCL2 Family Proteins Conferring Resistance to the BH3 Mimetic ABT-199 in Lymphoma," Blood, 123(26): 4111-4119 (2014).
Gross, "Evaluation of Otlertuzumab (TRU-016), an Anti-CD37 Adaptir™ Therapeutic in Preclinical Combination Studies with Kinase Inhibitors and a Next Generation anti-CD20 MAB in Vitro and in Animal Models of Non-Hodgkin's Lymphoma," Blood, 124(21) p. 3333 (2014).
Hematology Frontier, 20(S-1): 113-118 (2010).
Hematology, 62(1): 43-50 (2011).
Hendriks et al., "Targeting Bruton's tyrosine kinase in B cell malignancies," Nature Reviews Cancer, 14(4):219-232 (2014).
History of Medicine, 235: 570-576 (2010).
Kimby et al., "A Systematic Overview of Chemotherapy Effects in B-cell Chronic Lymphocytic Leukaemia," Acta Oncologica, 40(2-3): 224-230 (2001).
Kuo et al., "Combination of Ibrutinib and BCL-2 or SYK Inhibitors in Ibrutinib Resistant ABC-Subtype of Diffuse Large B-Cell Lymphoma," Blood, 124(21): 505 (2014).
Kuo et al., "The Role of PIM1 in the Ibrutinib-resistant ABC Subtype of Diffuse Large B-Cell Lymphoma," American Journal of Cancer Research 2016, 6(11): 2489-2501 (2016).
Lohr et al., "Discovery and Prioritization of Somatic Mutations in Diffuse Large B-Cell Lymphoma (DLBCL) by Whole-exome Sequencing," Proc Natl Acad Sci USA, 109(10): 3879-3884 (2012).
Morschhauser et al., "Phase I Study of RO5072759 (GA101) in Relapsed/Refractory Chronic Lymphotic Leukemia," Blood, 114(22):884 (2009).
Reid et al., "Removal of Normal Competition Increases Proliferation of Pre-Leukemic Cells in a Mouse Model of Pre-B Acute Lymphoblastic Leukemia," Blood, 114:1430 (2009).
Robak, "Current and Emerging Monoclonal antibody Treatments for Chronic Lymphocytic Leukemia: State of the Art," Expert Reviews, 7(6):841-857 (2014).
Sagiv-Barfi et al., "Ibrutinib enhances the antitumor immune response induced by intratumoral injection of a TLR9 ligand in syngeneic mouse lymphoma model," Blood, 125(13): 2079-2086 (2015).
Topalian et al., "Safety, Activity, and Immune Correlates of Anti-PD-1 Antibody in Cancer," N Engl J Med, 366(26):2443-2454 (2012).
Zoellner et al., "Differential Role of the B-Cell Receptor Pathway in Diffuse Large Cell B Cell Lymphoma: Temsirolimus Has Additive Effects in Combination with the BTK Inhibitor PCI-32765 and PI3K Inhibitor Cal101 but Antagonizes Bortezomib in GCB Subtype," Blood, 118:1664 (2011).
Al Katib et al., "Bryostatin 1 Down-Regulates mdr1 and Potentiates Vincristine Cytotoxicity in Diffuse Large Cell Lymphoma Xenografts," Clinical Cancer Research, 4:1305-1314 (1998).
Amaya-Chanaga et al., "A Phase Ib/II Study of Ibrutinib in Combination with Obinutuzumab—Gazyva as First—Line Treatment for Patients with Chronic Lymphocytic Leukemia > 65 Years Old or with Coexisting Conditions," Blood, 128:2048 (2016).
Brault et al., "PIM kinases are progression markers and emerging therapeutic targets in diffuse large B-cell lymphoma," Brit J Cancer 107(3):491-500 (2012).
Calvo et al., "Administration of CI-1033, an Irreversible Pan-erbB Tyrosine Kinase Inhibitor, Is Feasible on a 7-Day on, 7-Day Off Schedule," Clin Cancer Res, 7112-7120 (2004).
Cartron et al., "Obinutuzumab (GA101) in relapsed/refractory chronic lymphocytic leukemia: final data from the phase 1/2 GAUGUIN study," Blood, 124(14):2196-2202 (2014).
Cohen et al., "A competitive stapled peptide screen identifies a selective small molecule that overcomes MCL-1-dependent leukemia cell survival," Chem Bio 19(9):1175-1186 (2012).
Dasmahapatra et al., "Obatoclax interacts synergistically with the irreversible proteasome inhibitor carfilzomib in GC-and ABC-DLBCL cells in vitro and in vivo," Mol Cancer Therapeut 11(5):1122-1132 (2012).
Davids et al., "The single-Agent Bcl-2 Inhibitor ABT-199 (GDC-0199) In Patients with Relapsed/Refractory (R/R) Non-Hodgkin Lymphoma (NHL): Responses Observed in All Mantle Cell Lymphoma (MCL) Patients," Blood, 122:1789 (2013).
Extended European Search Report for EP Application No. 19174436.6 dated Jun. 27, 2019.
Extended European Search Report issued by the European Patent Office in corresponding Application No. EP 19174436.6 dated Jun. 27, 2019.
Fontain et al., "MALT1 Small Molecule Inhibitors Specifically Suppress ABC-DLBCL In Vitro and In Vivo," Cancer Cell 22(6):812-824 (2012).
Fontain et al., "Molecular pathways: targeting MALT1 paracaspase activity in lymphoma," Clin Cancer Res 19(24):6662-6668 (2013).
Gellen et al., "Epigenetic Determinants of Pathogenesis and Resistance to Proteosome Inhibition in Mantle Cell Lymphoma," Blood, 112:3373 (2008).
Honigberg et al., "Targeting Btk in Lymphoma: PCI-32765 Inhibits Tumor Growth in Mouse Lymphoma Models and a Fluorescent Analog of PCI-32765 is an Active-Site Probe that Enables Assessment of BTK Inhibition In Vivo," Blood, 110(11):1592 (2007).
Kloo et al., "Critical role of PI3K signaling for NF-KB-dependent survival in a subset of activated B-cell-like diffuse large B-cell lymphoma cells," PNAS 108(1):272-277 (2011).
Krappmann et al., "Attacking MALT1 for ABC-DLBCL therapy," Oncotarget 3(12):1489-1490 (2012).
Kritzer, "The secret of MIM: a novel, MCL-1-specific small molecule," Chem Bio 19(9):1082-1083 (2012).
Lujan et al., "Ib Phase Ib/I Study of Ibrutinib in Combination with Obinutuzumab—Gazyva As First Line Treatment for Patients with Chronic Lymphocytic Leukemia > 65 Years Old or with Coexisting Conditions," Blood, 132:1863 (2018).
Lujan et al., "Ibrutinib Reduces Obinutuzumab—Gazyva Infusion Related Reactions (IRR) in Patients with Chronic Lymphocytic Leukemia (CLL) and it is Associated with Changes on Plasma Cytokine Levels," Blood, 132:1864 (2018).

(56) References Cited

OTHER PUBLICATIONS

Owen et al., "Obinutuzumab for the treatment of lymphoproliferative disorders," Expert Opinion on Biological Therapy, 12(3):343-351 (2012).
Pitt et al., "Resistance Mechanisms to Immune-Checkpoint Blockade in Cancer: Tumor-Intrinsic and -Extrinsic Factors," Immunity Review, 44:1255-1269 (2016).
Rawstron et al., "Addition of Obinutuzumab to Ibrutinib Enhances Depletion of CLL Cells in the Peripheral Blood and Bone Marrow after 1 Month of Combination Therapy: Initial Results from the Bloodwise TAP Iciclle Extension Study," Blood, 128:2049 (2016).
Robak, "GA-101, a third-generation, humanized and glycoengineered anti-CD20 mAb for the treatment of B-cell lymphoid malignancies," Curr Opin Investig Drugs, 10(6):588-596 (2009).
San Miguel et al., "Pomalidomide plus low-dose dexamethasone versus high-dose dexamethasone alone for patients with relapsed and refractory multiple myeloma (MM-003): a randomized, open-label, phase 3 trial," Lancet Oncology, 14:1055-1066 (2013).
Seiler et al., "Advances in the management of follicular lymphoma," Co Oncology, 24(6):742-747 (2012).
Srivastava, "Immunotherapy of human cancer: lessons from mice," Nature Immunology, 5:363-366 (2000).
Young et al., "A new 'brew' of MALT1 inhibitors," Cancer Cell 22(6):706-707 (2012).
Zhang et al., "Genetic heterogeneity of diffuse large B-cell lymphoma," PNAS 110(4):1398-1403 (2013).
Boyle et al., "Enhancing Patient Adherence to Improve Outcomes with Oral Chemotherapy," US Pharm Oncology Suppl, 32(10):1-8 (2007).
CHMP assessment report: Imbruvica, European Medicines Agency (2014).
Chuda et al., "Ofatumumab: a novel anti-CD20 monoclonal antibody for the treatment of chronic lymphocytic leukemia," Current Drug Therapy, 7:281-289 (2012).
Dimopoulos et al., "Phase 3 Trial of Ibrutinib plus Rituximab in Waldenström's Macroglobulinemia," The New England Journal of Medicine, 378(25):2399-2410 (2018).
FDA Guidelines: "Q6A Specifications: Test Procedures and Acceptance Criteria for New Drug Substances and New Drug Products: Chemical Substances," (Dec. 2000).
Feldhahn et al., "Mimicry of a constitutively active pre-B cell receptor in acute lymphoblastic leukemia cells," J Exp Med, 201(11):1837-1853 (2005).
Feng et al., "The effect of PLC-γ2 inhibitors on the growth of human tumour cells," European Journal of Medicinal Chemistry, 54:463-469 (2012).
Gururajan et al., "Cutting Edge: Constitutive B Cell Receptor Signaling Is Critical for Basal Growth of B Lymphoma," J Immunol 176(12):7715-7719 (2006).
Honigberg et al., "A Clinical Trial of the Bruton's tyrosine kinase (Btk) inhibitor PCI-32765 in naturally occurring canine lymphoma," Cancer Res, AACR Ann Meeting, 69:Abstract 3740 (2009).
Hou et al., "B Cell Antigen Receptor Signaling and Internalization Are Mutually Exclusive Events," PLOS Biol 4(7):e200 (2006).
Imbruvica Prescribing Information, available at <http://www.accessdata.fda.gov/drugsatfda_docs/label/2018/205552s025lbl.pdf> (2018).
Ingersoll et al., "The impact of medication regimen factors on adherence to chronic treatment: a review of literature," J Behav Med, 31(3):213-224 (2008).
Kapoor et al., "Bortezomib Combination Therapy in Multiple Myeloma," Seminars in Hematology, 49(3):228-242 (2012).
Kauh et al., "Mantle Cell Lymphoma: Clinicopathologic Features and Treatments," Oncology Journal, 17(6):1-10 (2003).
Label, "Highlights of prescribing Information: Gazyva® (obinutuzumab) injection," Initial U.S. Approval 2013.
Maas et al., "Role of Bruton's tyrosine kinase in B cell development," Dev Immunol, 8(3-4):171-181 (2001).
Mao et al., "Crystal structure of bruton's tyrosine kinase domain suggests a novel pathway for activation and provides insights into the molecular basis of X-linked agammaglobulinemia," J Biol Chem, 276: 41435-41443 (2001).
Michallet et al., "Phase II, Multicenter Trial, Exploring "Chemo-Sparing" Strategy Associating Obinutuzumab+Ibrutinib Followed by a MRD Driven Strategy, in Previously Untreated Symptomatic Medically Fit Chronic Lymphocytic Leukemia Patients (CLL): Preliminary Results of the Induction Phase of the Icll-07 Filo study," Blood, 130(Suppl 1):497 (2017).
Mohamed et al., :Bruton's tyrosine kinase (Btk): function, regulation, and transformation with special emphasis on the PH domain, Immunol Rev, 228(1):58-73 (2009).
Quiroga et al., "B-cell antigen receptor signaling enhances chronic lymphocytic leukemia cell migration and survival: specific targeting with a novel spleen tyrosine kinase inhibitor, R406," Blood 114(5):1029-1037 (2009).
Richardson et al., "Bortezomib: Proteasome inhibition as an effective anticancer therapy," Annu Rev Med, 57:33-47 (2006).
Ruddy et al., "Patient Adherences and Persistence With Oral Anticancer Treatment," CA Cancer J Clin, 59(1):56-66 (2009).
Siddik, "Mechanisms of Action of Cancer Chemotherapeutic Agents: DNA Interactive Alkylating Agents and Antitumour Platinum-Based Drugs," The Cancer Handbook 1st Edition (2002).
Sissi et al., "Antitumor AZA-anthrapyrazoles: biophysical and biochemical studies on 8- and 9-aza regioisomers," Biochem Pharmacol, 67(4):631-642 (2004).
Thomas et al., "Mutational analysis of the IκBα gene in activated B cell-like diffuse large B-cell lymphoma," British Journal of Haematology, 126:50-54 (2004).
Uckun, "Clinical Potential of Targeting Bruton's Tyrosine," Int Revs Immunol 27:43-69 (2008).
Wang et al., "Targeting BTK with ibrutinib in relapsed or refractory mantel-cell lymphoma," N Engl J Med, Protocol, 369(6): 507-516 (Aug. 8, 2013).
Wilcoxen et al., "Synthesis of 3-Phenylpyrazolo[4,3-b]pyridines Via a Convenient Synthesis of 4-amino-3-arylpyrazoles and SAR of Corticotropin-Releasing Factor Receptor Type-1 Antagonists," Bioorganic & Medicinal Chemistry Letters 13: 3367-3370 (2003).
Zapf et al., "Covalent Inhibitors of Interleukin-2 Inducible T Cell Kinase (Itk) with Nanomolar Potency in a Whole-Blood Assay," J Med Chem 55:10047-10063 (2012).
Ashford, "Bioavailability—Physiochemical and Dosage form Factors," Pharmaceutics—The Science of Dosage Form Design, 2nd Ed. (2002).
Cheng et al., "BTK inhibition targets in vivo CLL proliferation through its effects on B-cell receptor signaling activity," Leukemia, 28: 649-657 (2014).
Cheng et al., "Functional Characterization of BTKC481S mutation that confers ibrutinib resistance: Exploration of alternative kinase inhibitors," Leukemia, 29: 895-900 (2015).
Furman et al., "Ibrutinib Resistance in Chronic Lymphocytic Leukemia," New Engl J Med., 370: 2352-2354 (2014).
Goy, "Bortezomib in patients with relapsed or refractory mantle cell lymphoma: updated time-to-event analyses of the multicenter phase 2 Pinnacle study," Annals of Oncology, 20:520-525 (2009).
Guo et al., "Heightened BTK-dependent cell proliferation in unmutated chronic lymphocytic leukemia confers increased sensitivity to ibrutinib," Oncotarget, 7: 4598-4610 (2015).
Ma et al., "Characterization of ibrutinib-sensitive and -resistant mantle lymphoma cells," British Journal of Haematology, 166: 849-861 (2014).
Moreau, "Subcutaneous versus intravenous administration of bortezomib in patients with relapsed multiple myeloma: a randomised, phase 3, non-inferiority study," Lancet Oncol, 12:431-440 (2011).
Scheerans et al., "Proposal for defining the relevance of drug accumulation derived from single dose study data for modified release dosage forms," Biopharm Drug Dispos, 36 (2015).
Wagner et al., "Blood levels of drug at the equilibrium state after multiple dosing," Nature, 207:5003 (1965).
Wang et al., "The Bruton's Tyrosine Kinase Inhibitor PCI-32765 is Highly Active as Single-Agent Therapy in Previously-Treated Mantle Cell Lymphoma (MCL): Preliminary Results of a Phase II Trial," Blood, 118(21): Abstract (2011).

(56) References Cited

OTHER PUBLICATIONS

Zhang et al., "Mechanisms of ibrutinib resistance in chronic lymphocytic leukemia and non-Hodgkin lymphoma," British Journal of Haematology, 170: 445-456 (2015).

* cited by examiner

SEQUENCE LISTING

```
<160> NUMBER OF SEQ ID NOS: 28

<210> SEQ ID NO 1
<211> LENGTH: 659
<212> TYPE: PRT
<213> ORGANISM: Homo sapiens
```

<400> SEQUENCE: 1

```
Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
        35                  40                  45

Arg Gly Ser Lys Lys Gly Ser Ile Asp Val Lys Ile Thr Cys Val
    50                  55                  60

Glu Thr Val Val Pro Glu Lys Asn Pro Pro Glu Arg Gln Ile Pro
65                  70                  75                  80

Arg Arg Gly Glu Glu Ser Ser Glu Met Glu Gln Ile Ser Ile Glu
                85                  90                  95

Arg Phe Pro Tyr Pro Phe Gln Val Val Tyr Asp Glu Gly Pro Leu Tyr
                100                 105                 110

Val Phe Ser Pro Thr Glu Glu Leu Arg Lys Arg Trp Ile His Gln Leu
            115                 120                 125

Lys Asn Val Ile Arg Tyr Asn Ser Asp Leu Val Gln Lys Tyr His Pro
130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Thr Pro
            180                 185                 190

Glu Glu Asp Gln Ile Leu Lys Lys Pro Leu Pro Glu Pro Ala Ala
        195                 200                 205

Ala Pro Val Ser Thr Ser Glu Leu Lys Lys Val Val Ala Leu Tyr Asp
210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
            260                 265                 270

Glu Asp Ser Ile Glu Met Tyr Glu Trp Tyr Ser Lys His Met Thr Arg
        275                 280                 285

Ser Gln Ala Glu Gln Leu Leu Lys Gln Glu Gly Lys Glu Gly Gly Phe
    290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

Cys Ser Thr Pro Gln Ser Gln Tyr Tyr Leu Ala Glu Lys His Leu Phe
            340                 345                 350

Ser Thr Ile Pro Glu Leu Ile Asn Tyr His Gln His Asn Ser Ala Gly
        355                 360                 365

Leu Ile Ser Arg Leu Lys Tyr Pro Val Ser Gln Gln Asn Lys Asn Ala
    370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
```

```
            405                 410                 415
Lys Tyr Gly Lys Trp Arg Gly Gln Tyr Asp Val Ala Ile Lys Met Ile
            420                 425                 430

Lys Glu Gly Ser Met Ser Glu Asp Glu Phe Ile Glu Ala Lys Val
        435                 440                 445

Met Met Asn Leu Ser His Glu Lys Leu Val Gln Leu Tyr Gly Val Cys
    450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
                485                 490                 495

Gln Leu Leu Glu Met Cys Lys Asp Val Cys Glu Ala Met Glu Tyr Leu
        500                 505                 510

Glu Ser Lys Gln Phe Leu His Arg Asp Leu Ala Ala Arg Asn Cys Leu
    515                 520                 525

Val Asn Asp Gln Gly Val Val Lys Val Ser Asp Phe Gly Leu Ser Arg
530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
                565                 570                 575

Lys Ser Asp Ile Trp Ala Phe Gly Val Leu Met Trp Glu Ile Tyr Ser
            580                 585                 590

Leu Gly Lys Met Pro Tyr Glu Arg Phe Thr Asn Ser Glu Thr Ala Glu
        595                 600                 605

His Ile Ala Gln Gly Leu Arg Leu Tyr Arg Pro His Leu Ala Ser Glu
    610                 615                 620

Lys Val Tyr Thr Ile Met Tyr Ser Cys Trp His Glu Lys Ala Asp Glu
625                 630                 635                 640

Arg Pro Thr Phe Lys Ile Leu Leu Ser Asn Ile Leu Asp Val Met Asp
                645                 650                 655

Glu Glu Ser

<210> SEQ ID NO 2
<211> LENGTH: 659
<212> TYPE: PRT
<213> ORGANISM: Homo sapiens

<400> SEQUENCE: 2

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
        35                  40                  45

Arg Gly Ser Lys Lys Gly Ser Ile Asp Val Glu Lys Ile Thr Cys Val
    50                  55                  60

Glu Thr Val Val Pro Glu Lys Asn Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
            100                 105                 110

Val Phe Ser Pro Thr Glu Glu Leu Arg Lys Arg Trp Ile His Gln Leu
```

```
                115                 120                 125
Lys Asn Val Ile Arg Tyr Asn Ser Asp Leu Val Gln Lys Tyr His Pro
130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
                180                 185                 190

Glu Glu Asp Gln Ile Leu Lys Lys Pro Leu Pro Pro Glu Pro Ala Ala
                195                 200                 205

Ala Pro Val Ser Thr Ser Glu Leu Lys Lys Val Val Ala Leu Tyr Asp
210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
                260                 265                 270

Glu Asp Ser Ile Glu Met Tyr Glu Trp Tyr Ser Lys His Met Thr Arg
                275                 280                 285

Ser Gln Ala Glu Gln Leu Leu Lys Gln Glu Gly Lys Glu Gly Gly Phe
290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

Cys Ser Thr Pro Gln Ser Gln Tyr Tyr Leu Ala Glu Lys His Leu Phe
                340                 345                 350

Ser Thr Ile Pro Glu Leu Ile Asn Tyr His Gln His Asn Ser Ala Gly
                355                 360                 365

Leu Ile Ser Arg Leu Lys Tyr Pro Val Ser Gln Gln Asn Lys Asn Ala
370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
                405                 410                 415

Lys Tyr Gly Lys Trp Arg Gly Gln Tyr Asp Val Ala Ile Lys Met Ile
                420                 425                 430

Lys Glu Gly Ser Met Ser Glu Asp Glu Phe Ile Glu Glu Ala Lys Val
                435                 440                 445

Met Met Asn Leu Ser His Glu Lys Leu Val Gln Leu Tyr Gly Val Cys
                450                 455                 460

Thr Lys Gln Arg Pro Ile Phe Ile Ile Thr Glu Tyr Met Ala Asn Gly
465                 470                 475                 480

Ser Leu Leu Asn Tyr Leu Arg Glu Met Arg His Arg Phe Gln Thr Gln
                485                 490                 495

Gln Leu Leu Glu Met Cys Lys Asp Val Cys Glu Ala Met Glu Tyr Leu
                500                 505                 510

Glu Ser Lys Gln Phe Leu His Arg Asp Leu Ala Ala Arg Asn Cys Leu
                515                 520                 525

Val Asn Asp Gln Gly Val Val Lys Val Ser Asp Phe Gly Leu Ser Arg
530                 535                 540
```

```
Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
                565                 570                 575

Lys Ser Asp Ile Trp Ala Phe Gly Val Leu Met Trp Glu Ile Tyr Ser
            580                 585                 590

Leu Gly Lys Met Pro Tyr Glu Arg Phe Thr Asn Ser Glu Thr Ala Glu
                595                 600                 605

His Ile Ala Gln Gly Leu Arg Leu Tyr Arg Pro His Leu Ala Ser Glu
        610                 615                 620

Lys Val Tyr Thr Ile Met Tyr Ser Cys Trp His Glu Lys Ala Asp Glu
625                 630                 635                 640

Arg Pro Thr Phe Lys Ile Leu Leu Ser Asn Ile Leu Asp Val Met Asp
                645                 650                 655

Glu Glu Ser

<210> SEQ ID NO 3
<211> LENGTH: 2611
<212> TYPE: DNA
<213> ORGANISM: Homo sapiens

<400> SEQUENCE: 3
aactgagtgg ctgtgaaagg gtggggtttg ctcagactgt ccttcctctc tggactgtaa      60
gaatatgtct ccagggccag tgtctgctgc gatcgagtcc caccttccaa gtcctggcat     120
ctcaatgcat ctgggaagct acctgcatta agtcaggact gagcacacag gtgaactcca     180
gaaagaagaa gctatggccg cagtgattct ggagagcatc tttctgaagc gatcccaaca     240 gaaaagaaa acatcacctc taaacttcaa gaagcgcctg tttctcttga ccgtgcacaa     300
actctcctac tatgagtatg actttgaacg tgggagaaga ggcagtaaga agggttcaat     360
agatgttgag aagatcactt gtgttgaaac agtggttcct gaaaaaaatc ctcctccaga     420
aagacagatt ccgagaagag gtgaagagtc cagtgaaatg gagcaaattt caatcattga     480
aaggttccct tatcccttcc aggttgtata tgatgaaggg cctctctacg tcttctcccc     540
aactgaagaa ctaaggaagc ggtggattca ccagctcaaa aacgtaatcc ggtacaacag     600
tgatctggtt cagaaatatc cccttgcttt ctggatcgat gggcagtatc tctgctgctc     660
tcagacagcc aaaaatgcta tgggctgcca aattttggag aacaggaatg gaagcttaaa     720
acctgggagt tctcaccgga agacaaaaaa gcctcttccc caacgcctg aggaggacca     780 gatcttgaaa aagccactac cgcctgagcc agcagcagca ccagtctcca caagtgagct     840
gaaaaaggtt gtggccccttt atgattacat gccaatgaat gcaaatgatc tacagctgcg     900
gaagggtgat gaatatttta tcttggagga aagcaactta ccatggtgga gagcacgaga     960
taaaaatggg caggaaggct acattcctag taactatgtc actgaagcag aagactccat    1020
agaaatgtat gagtggtatt ccaaacacat gactcggagt caggctgagc aactgctaaa    1080
gcaagagggg aaagaaggag gtttcattgt cagagactcc agcaaagctg gcaaatatac    1140
agtgtctgtg tttgctaaat ccacagggga ccctcaaggg gtgatacgtc attatgttgt    1200
gtgttccaca cctcagagcc agtattacct ggctgagaag cacctttca gcaccatccc    1260 tgagctcatt aactaccatc agcacaactc tgcaggactc atatccaggc tcaaatatcc    1320
agtgtctcaa caaaacaaga atgcaccttc cactgcaggc ctgggatacg gatcatggga    1380
aattgatcca aaggacctga ccttcttgaa ggagctgggg actggacaat tgggggtagt    1440
```

-continued

```
gaagtatggg aaatggagag gccagtacga cgtggccatc aagatgatca agaaggctc      1500 catgtctgaa gatgaattca ttgaagaagc caaagtcatg atgaatcttt cccatgagaa      1560
gctggtgcag ttgtatggcg tctgcaccaa gcagcgcccc atcttcatca tcactgagta      1620
catggccaat ggctgcctcc tgaactacct gagggagatg cgccaccgct tccagactca      1680
gcagctgcta gagatgtgca aggatgtctg tgaagccatg aatacctgg  agtcaaagca      1740 gttccttcac cgagacctgg cagctcgaaa ctgtttggta aacgatcaag gagttgttaa      1800
agtatctgat ttcggcctgt ccaggtatgt cctggatgat gaatacacaa gctcagtagg      1860
ctccaaattt ccagtccggt ggtccccacc ggaagtcctg atgtatagca agttcagcag      1920
caaatctgac atttgggctt ttggggtttt gatgtgggaa atttactccc tggggaagat      1980
gccatatgag agatttacta acagtgagac tgctgaacac attgcccaag cctacgtct       2040 ctacaggcct catctggctt cagagaaggt atataccatc atgtacagtt gctggcatga      2100
gaaagcagat gagcgtccca ctttcaaaat tcttctgagc aatattctag atgtcatgga      2160
tgaagaatcc tgagctcgcc aataagcttc ttggttctac ttctcttctc cacaagcccc      2220
aatttcactt tctcagagga aatcccaagc ttaggagccc tggagccttt gtgctcccac      2280
tcaatacaaa aaggcccctc tctacatctg ggaatgcacc tcttctttga ttccctggga      2340
tagtggcttc tgagcaaagg ccaagaaatt attgtgcctg aaatttcccg agagaattaa      2400
gacagactga atttgcgatg aaaatatttt ttaggaggga ggatgtaaat agccgcacaa      2460
aggggtccaa cagctctttg agtaggcatt tggtagagct tgggggtgtg tgtgtggggg      2520
tggaccgaat ttggcaagaa tgaaatggtg tcataaagat gggaggggag ggtgttttga      2580
taaaataaaa ttactagaaa gcttgaaagt c                                    2611
```

<210> SEQ ID NO 4
<211> LENGTH: 659
<212> TYPE: PRT
<213> ORGANISM: Mus musculus

<400> SEQUENCE: 4

```
Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
        35                  40                  45

Arg Gly Ser Lys Lys Gly Ser Ile Asp Val Glu Lys Ile Thr Cys Val
    50                  55                  60

Glu Thr Val Ile Pro Glu Lys Asn Pro Pro Glu Arg Gln Ile Pro
65                  70                  75                  80

Arg Arg Gly Glu Glu Ser Ser Glu Met Glu Gln Ile Ser Ile Glu
            85                  90                  95

Arg Phe Pro Tyr Pro Phe Gln Val Val Tyr Asp Glu Gly Pro Leu Tyr
        100                 105                 110

Val Phe Ser Pro Thr Glu Glu Leu Arg Lys Arg Trp Ile His Gln Leu
    115                 120                 125

Lys Asn Val Ile Arg Tyr Asn Ser Asp Leu Val Gln Lys Tyr His Pro
130                 135                 140

Cys Phe Trp Ile Asp Gly Gln Tyr Leu Cys Cys Ser Gln Thr Ala Lys
145                 150                 155                 160
```

-continued

```
Asn Ala Met Gly Cys Gln Ile Leu Glu Asn Arg Asn Gly Ser Leu Lys
            165                 170                 175
Pro Gly Ser Ser His Arg Lys Thr Lys Lys Pro Leu Pro Pro Thr Pro
        180                 185                 190
Glu Glu Asp Gln Ile Leu Lys Lys Pro Leu Pro Pro Glu Pro Thr Ala
    195                 200                 205
Ala Pro Ile Ser Thr Thr Glu Leu Lys Lys Val Val Ala Leu Tyr Asp
210                 215                 220
Tyr Met Pro Met Asn Ala Asn Asp Leu Gln Leu Arg Lys Gly Glu Glu
225                 230                 235                 240
Tyr Phe Ile Leu Glu Glu Ser Asn Leu Pro Trp Trp Arg Ala Arg Asp
                245                 250                 255
Lys Asn Gly Gln Glu Gly Tyr Ile Pro Ser Asn Tyr Ile Thr Glu Ala
            260                 265                 270
Glu Asp Ser Ile Glu Met Tyr Glu Trp Tyr Ser Lys His Met Thr Arg
        275                 280                 285
Ser Gln Ala Glu Gln Leu Leu Lys Gln Glu Gly Lys Glu Gly Gly Phe
    290                 295                 300
Ile Val Arg Asp Ser Ser Lys Ala Gly Lys Tyr Thr Val Ser Val Phe
305                 310                 315                 320
Ala Lys Ser Thr Gly Glu Pro Gln Gly Val Ile Arg His Tyr Val Val
                325                 330                 335
Cys Ser Thr Pro Gln Ser Gln Tyr Tyr Leu Ala Glu Lys His Leu Phe
            340                 345                 350
Ser Thr Ile Pro Glu Leu Ile Asn Tyr His Gln His Asn Ser Ala Gly
        355                 360                 365
Leu Ile Ser Arg Leu Lys Tyr Pro Val Ser Lys Gln Asn Lys Asn Ala
    370                 375                 380
Pro Ser Thr Ala Gly Leu Gly Tyr Gly Ser Trp Glu Ile Asp Pro Lys
385                 390                 395                 400
Asp Leu Thr Phe Leu Lys Glu Leu Gly Thr Gly Gln Phe Gly Val Val
                405                 410                 415
Lys Tyr Gly Lys Trp Arg Gly Gln Tyr Asp Val Ala Ile Lys Met Ile
            420                 425                 430
Arg Glu Gly Ser Met Ser Glu Asp Glu Phe Ile Glu Glu Ala Lys Val
        435                 440                 445
Met Met Asn Leu Ser His Glu Lys Leu Val Gln Leu Tyr Gly Val Cys
    450                 455                 460
Thr Lys Gln Arg Pro Ile Phe Ile Ile Thr Glu Tyr Met Ala Asn Gly
465                 470                 475                 480
Cys Leu Leu Asn Tyr Leu Arg Glu Met Arg His Arg Phe Gln Thr Gln
                485                 490                 495
Gln Leu Leu Glu Met Cys Lys Asp Val Cys Glu Ala Met Glu Tyr Leu
            500                 505                 510
Glu Ser Lys Gln Phe Leu His Arg Asp Leu Ala Ala Arg Asn Cys Leu
        515                 520                 525
Val Asn Asp Gln Gly Val Val Lys Val Ser Asp Phe Gly Leu Ser Arg
    530                 535                 540
Tyr Val Leu Asp Asp Glu Tyr Thr Ser Ser Val Gly Ser Lys Phe Pro
545                 550                 555                 560
Val Arg Trp Ser Pro Pro Glu Val Leu Met Tyr Ser Lys Phe Ser Ser
                565                 570                 575
Lys Ser Asp Ile Trp Ala Phe Gly Val Leu Met Trp Glu Ile Tyr Ser
```

```
                    580                 585                 590
Leu Gly Lys Met Pro Tyr Glu Arg Phe Thr Asn Ser Glu Thr Ala Glu
                595                 600                 605

His Ile Ala Gln Gly Leu Arg Leu Tyr Arg Pro His Leu Ala Ser Glu
            610                 615                 620

Arg Val Tyr Thr Ile Met Tyr Ser Cys Trp His Glu Lys Ala Asp Glu
625                 630                 635                 640

Arg Pro Ser Phe Lys Ile Leu Leu Ser Asn Ile Leu Asp Val Met Asp
                645                 650                 655

Glu Glu Ser

<210> SEQ ID NO 5
<211> LENGTH: 657
<212> TYPE: PRT
<213> ORGANISM: Gallus gallus

<400> SEQUENCE: 5

Met Ala Ser Ile Ile Leu Glu Ser Ile Phe Leu Lys Arg Ser Gln Gln
1               5                   10                  15

Lys Lys Lys Thr Ser Pro Leu Asn Phe Lys Arg Leu Phe Leu Leu
            20                  25                  30

Thr Glu Ser Lys Leu Ser Tyr Tyr Glu Tyr Asp Phe Glu Arg Gly Arg
        35                  40                  45

Arg Gly Ser Lys Lys Gly Ser Val Asp Ile Glu Lys Ile Thr Cys Val
    50                  55                  60

Glu Thr Val Val Pro Glu Asn Asn Pro Pro Glu Arg Gln Val Pro
65                  70                  75                  80

Lys Lys Gly Glu Asp Tyr Asn Met Glu Gln Ile Ser Ile Ile Glu Arg
                85                  90                  95

Phe Pro Tyr Pro Phe Gln Val Val Tyr Asp Glu Gly Pro Leu Tyr Val
            100                 105                 110

Phe Ser Pro Thr Glu Glu Leu Arg Lys Arg Trp Ile His Gln Leu Lys
        115                 120                 125

Ser Val Ile Arg Tyr Asn Ser Asp Leu Val Gln Lys Tyr His Pro Cys
    130                 135                 140

Phe Trp Ile Asp Gly Gln Tyr Leu Cys Cys Ser Gln Thr Ala Lys Asn
145                 150                 155                 160

Ala Met Gly Cys Lys Ile Leu Glu Ser Arg Asn Gly Ser Leu Lys Ala
                165                 170                 175

Gly Arg Ser His Arg Lys Thr Lys Lys Pro Leu Pro Pro Thr Pro Glu
            180                 185                 190

Glu Asp Thr Met Val Met Lys Pro Leu Pro Pro Glu Pro Ala Pro Ser
        195                 200                 205

Ala Ala Gly Glu Met Lys Lys Val Val Ala Leu Tyr Asn Tyr Val Pro
    210                 215                 220

Met Asn Val Gln Asp Leu Gln Leu Gln Lys Gly Glu Asp Tyr Leu Ile
225                 230                 235                 240

Leu Glu Glu Ser His Leu Pro Trp Trp Lys Ala Arg Asp Lys Asn Gly
                245                 250                 255

Arg Glu Gly Tyr Ile Pro Ser Asn Tyr Val Thr Ala Thr Ser Asn Ser
            260                 265                 270

Leu Glu Ile Tyr Glu Trp Tyr Ser Lys Asn Ile Thr Arg Ser Gln Ala
        275                 280                 285

Glu Gln Leu Leu Lys Gln Glu Gly Lys Glu Gly Gly Phe Ile Val Arg
```

|   |   |   |   |   | 290 |   |   |   | 295 |   |   |   | 300 |   |   |
|---|---|---|---|---|---|---|---|---|---|---|---|---|---|---|---|

Asp Ser Thr Ser Lys Thr Gly Lys Tyr Thr Val Ser Val Tyr Ala Lys
305                 310                 315                 320

Ser Ala Val Asp Pro Gln Gly Met Ile Arg His Tyr Val Val Cys Cys
            325                 330                 335

Thr Pro Gln Asn Gln Tyr Tyr Leu Ala Glu Lys His Leu Phe Asn Thr
        340                 345                 350

Ile Pro Glu Leu Ile Thr Tyr His Gln His Asn Ser Ala Gly Leu Ile
    355                 360                 365

Ser Arg Leu Lys Tyr Pro Val Ser Arg His Gln Lys Ser Ala Pro Ser
370                 375                 380

Thr Ala Gly Leu Gly Tyr Gly Ser Trp Glu Ile Asp Pro Lys Asp Leu
385                 390                 395                 400

Thr Phe Leu Lys Glu Leu Gly Thr Gly Gln Phe Gly Val Val Lys Tyr
                405                 410                 415

Gly Lys Trp Arg Gly Gln Tyr Asn Val Ala Ile Lys Met Ile Arg Glu
            420                 425                 430

Gly Ser Met Ser Glu Asp Glu Phe Ile Asp Glu Ala Lys Val Met Met
        435                 440                 445

Asn Leu Ser His Glu Lys Leu Val Gln Leu Tyr Gly Val Cys Thr Lys
    450                 455                 460

Gln Arg Pro Ile Phe Ile Ile Thr Glu Tyr Met Ala Asn Gly Cys Leu
465                 470                 475                 480

Leu Asn Phe Leu Arg Glu Thr Gln Arg Phe Gln Pro Ala Glu Leu
                485                 490                 495

Leu Glu Met Cys Lys Asp Val Cys Glu Ala Met Glu Tyr Leu Glu Ser
            500                 505                 510

Lys Gln Phe Leu His Arg Asp Leu Ala Ala Arg Asn Cys Leu Val Asn
        515                 520                 525

Asp Gln Gly Ile Val Lys Val Ser Asp Phe Gly Leu Ser Arg Tyr Val
    530                 535                 540

Leu Asp Asp Glu Tyr Thr Ser Ser Met Gly Ser Lys Phe Pro Val Arg
545                 550                 555                 560

Trp Ser Pro Pro Glu Val Leu Leu Tyr Ser Lys Phe Ser Ser Lys Ser
                565                 570                 575

Asp Val Trp Ser Phe Gly Val Leu Met Trp Glu Val Tyr Ser Leu Gly
            580                 585                 590

Lys Met Pro Tyr Glu Arg Phe Asn Asn Ser Glu Thr Thr Glu His Val
        595                 600                 605

Ile Gln Gly Leu Arg Leu Tyr Arg Pro Gln Gln Ala Ser Glu Arg Val
    610                 615                 620

Tyr Ala Ile Met Tyr Ser Cys Trp His Glu Lys Ala Glu Glu Arg Pro
625                 630                 635                 640

Thr Phe Ser Ala Leu Leu Gly Ser Ile Val Asp Ile Thr Asp Glu Glu
                645                 650                 655

Pro

<210> SEQ ID NO 6
<211> LENGTH: 660
<212> TYPE: PRT
<213> ORGANISM: Rattus norvegicus

<400> SEQUENCE: 6

Met Ala Ala Val Ile Leu Glu Ser Ile Phe Leu Lys Arg Ser Gln Gln

```
  1               5                   10                  15
Lys Lys Lys Thr Ser Pro Leu Asn Phe Lys Lys Arg Leu Phe Leu Leu
            20                  25                  30
Thr Val His Lys Leu Ser Tyr Tyr Glu Tyr Asp Phe Glu Arg Gly Gly
            35                  40                  45
Arg Gly Cys Thr Phe His Phe Leu Asp Val Glu Asn Tyr Tyr Cys Val
            50                  55                  60
Glu Asn Ile Leu Pro Pro Pro Pro Pro Pro Pro Pro Leu Ser Ser
 65                  70                  75                  80
Lys Arg Arg Gly Glu Glu Ser Ser Glu Met Glu Gln Ile Ser Ile Ile
                85                  90                  95
Glu Arg Phe Pro Tyr Pro Phe Gln Val Val Tyr Asp Glu Gly Pro Leu
               100                 105                 110
Tyr Val Phe Ser Pro Thr Glu Glu Leu Arg Lys Arg Trp Ile His Gln
               115                 120                 125
Leu Lys Asn Val Ile Arg Tyr Asn Ser Asp Leu Val Gln Lys Tyr His
           130                 135                 140
Pro Cys Phe Trp Ile Asp Gly Gln Tyr Leu Cys Cys Ser Gln Thr Ala
145                 150                 155                 160
Lys Asn Ala Met Gly Cys Gln Ile Leu Glu Asn Arg Asn Gly Ser Leu
               165                 170                 175
Lys Pro Gly Ser Ser His Arg Lys Thr Lys Lys Pro Leu Pro Pro Thr
           180                 185                 190
Pro Glu Glu Asp Gln Ile Leu Lys Lys Pro Leu Pro Pro Glu Pro Thr
       195                 200                 205
Ala Ala Pro Ile Ser Thr Ser Glu Leu Lys Lys Val Val Ala Leu Tyr
   210                 215                 220
Asp Tyr Met Pro Met Asn Ala Asn Asp Leu Gln Leu Arg Lys Gly Glu
225                 230                 235                 240
Glu Tyr Phe Ile Leu Glu Glu Ser Asn Leu Pro Trp Trp Arg Ala Arg
               245                 250                 255
Asp Lys Asn Gly Gln Glu Gly Tyr Ile Pro Ser Asn Tyr Val Thr Glu
           260                 265                 270
Ala Glu Asp Ser Ile Glu Met Tyr Glu Trp Tyr Ser Lys His Met Thr
       275                 280                 285
Arg Ser Gln Ala Glu Gln Leu Leu Lys Gln Glu Gly Lys Glu Gly Gly
       290                 295                 300
Phe Ile Val Arg Asp Ser Ser Lys Ala Gly Lys Tyr Thr Val Ser Val
305                 310                 315                 320
Phe Ala Lys Ser Thr Gly Glu Pro Gln Gly Val Ile Arg His Tyr Val
               325                 330                 335
Val Cys Ser Thr Pro Gln Ser Gln Tyr Tyr Leu Ala Glu Lys His Leu
           340                 345                 350
Phe Ser Thr Ile Pro Glu Leu Ile Asn Tyr His Gln His Asn Ser Ala
       355                 360                 365
Gly Leu Ile Ser Arg Leu Lys Tyr Pro Val Ser Lys Gln Asn Lys Asn
   370                 375                 380
Ala Pro Ser Thr Ala Gly Leu Gly Tyr Gly Ser Trp Glu Ile Asp Pro
385                 390                 395                 400
Lys Asp Leu Thr Phe Leu Lys Glu Leu Gly Thr Gly Gln Phe Gly Val
           405                 410                 415
Val Lys Tyr Gly Lys Trp Arg Gly Gln Tyr Asp Val Ala Ile Lys Met
       420                 425                 430
```

Ile Arg Glu Gly Ser Met Ser Glu Asp Glu Phe Ile Glu Glu Ala Lys
            435                 440                 445

Val Met Met Asn Leu Ser His Glu Lys Leu Val Gln Leu Tyr Gly Val
    450                 455                 460

Cys Thr Lys Gln Arg Pro Ile Phe Ile Ile Thr Glu Tyr Met Ala Asn
465                 470                 475                 480

Gly Cys Leu Leu Asn Tyr Leu Arg Glu Met Arg His Arg Phe Gln Thr
                485                 490                 495

Gln Gln Leu Leu Glu Met Cys Lys Asp Val Cys Glu Ala Met Glu Tyr
            500                 505                 510

Leu Glu Ser Lys Gln Phe Leu His Arg Asp Leu Leu Asp Arg Asp Ser
            515                 520                 525

Lys Lys Glu Asn Arg Gly Phe Val Lys Ser Arg Asp Phe Asp Ser Gly
    530                 535                 540

Arg Tyr Val Leu Asp Asp Glu Tyr Thr Ser Ser Val Gly Ser Lys Phe
545                 550                 555                 560

Pro Val Arg Trp Ser Pro Pro Glu Val Leu Met Tyr Ser Lys Phe Ser
                565                 570                 575

Ser Lys Ser Asp Ile Trp Ala Phe Gly Val Leu Met Trp Glu Ile Tyr
            580                 585                 590

Ser Leu Gly Lys Ile Pro Tyr Glu Arg Phe Thr Asn Ser Glu Thr Ala
            595                 600                 605

Glu His Ile Ala Gln Gly Leu Arg Leu Tyr Arg Pro His Leu Ala Ser
    610                 615                 620

Asp Arg Val Tyr Thr Ile Met Tyr Ser Cys Trp His Glu Lys Ala Asp
625                 630                 635                 640

Glu Arg Pro Ser Phe Lys Ile Leu Leu Ser Asn Ile Leu Asp Val Met
                645                 650                 655

Asp Glu Glu Ser
            660

<210> SEQ ID NO 7
<211> LENGTH: 1980
<212> TYPE: DNA
<213> ORGANISM: Homo sapiens

<400> SEQUENCE: 7
atggccgcag tgattctgga gagcatcttt ctgaagcgat cccaacagaa aagaaaaca      60 tcacctctaa acttcaagaa gcgcctgttt ctcttgaccg tgcacaaact ctcctactat     120
gagtatgact ttgaacgtgg gagaagaggc agtaagaagg gttcaataga tgttgagaag     180
atcacttgtg ttgaaacagt ggttcctgaa aaaaatcctc ctccagaaag acagattccg     240
agaagaggtg aagagtccag tgaaatggag caaatttcaa tcattgaaag gttccctat     300 cccttccagg ttgtatatga tgaagggcct ctctacgtct ctccccaac tgaagaacta     360 aggaagcggt ggattcacca gctcaaaaac gtaatccggt acaacagtga tctggttcag     420
aaatatcacc cttgcttctg gatcgatggg cagtatctct gctgctctca gacagccaaa     480
aatgctatgg gctgccaaat tttgagaac aggaatggaa gcttaaaacc tgggagttct     540
caccggaaga caaaaagcc tcttcccca cgcctgagg aggaccagat cttgaaaaag     600
ccactaccgc ctgagccagc agcagcacca gtctccacaa gtgagctgaa aaaggttgtg     660 gcccttatg attacatgcc aatgaatgca atgatctac agctgcggaa gggtgatgaa     720
tattttatct tggaggaaag caacttacca tggtggagag cacgagataa aaatgggcag     780

```
gaaggctaca ttcctagtaa ctatgtcact gaagcagaag actccataga aatgtatgag      840
tggtattcca aacacatgac tcggagtcag gctgagcaac tgctaaagca agaggggaaa      900
gaaggaggtt tcattgtcag agactccagc aaagctggca aatatacagt gtctgtgttt      960
gctaaatcca caggggaccc tcaaggggtg atacgtcatt atgttgtgtg ttccacacct     1020
cagagccagt attacctggc tgagaagcac cttttcagca ccatccctga gctcattaac     1080
taccatcagc acaactctgc aggactcata tccaggctca aatatccagt gtctcaacaa     1140
aacaagaatg caccttccac tgcaggcctg ggatacggat catgggaaat tgatccaaag     1200
gacctgacct tcttgaagga gctggggact ggacaatttg gggtagtgaa gtatgggaaa     1260
tggagaggcc agtacgacgt ggccatcaag atgatcaaag aaggctccat gtctgaagat     1320
gaattcattg aagaagccaa agtcatgatg aatctttccc atgagaagct ggtgcagttg     1380
tatggcgtct gcaccaagca gcgccccatc ttcatcatca ctgagtacat ggccaatggc     1440
agcctcctga actacctgag ggagatgcgc accgcttcc agactcagca gctgctagag     1500
atgtgcaagg atgtctgtga agccatggaa tacctggagt caaagcagtt ccttcaccga     1560
gacctggcag ctcgaaactg tttggtaaac gatcaaggag ttgttaaagt atctgatttc     1620
ggcctgtcca ggtatgtcct ggatgatgaa tacacaagct cagtaggctc caaatttcca     1680
gtccggtggt ccccaccgga agtcctgatg tatagcaagt tcagcagcaa atctgacatt     1740
tgggcttttg gggttttgat gtgggaaatt tactccctgg ggaagatgcc atatgagaga     1800
tttactaaca gtgagactgc tgaacacatt gcccaaggcc tacgtctcta caggcctcat     1860
ctggcttcag agaaggtata taccatcatg tacagttgtt ggcatgagaa agcagatgag     1920
cgtcccactt tcaaaattct tctgagcaat attctagatg tcatggatga agaatcctga     1980
```

<210> SEQ ID NO 8
<211> LENGTH: 1980
<212> TYPE: DNA
<213> ORGANISM: Homo sapiens

<400> SEQUENCE: 8

```
atggccgcag tgattctgga gagcatcttt ctgaagcgat cccaacagaa aaagaaaaca       60
tcacctctaa acttcaagaa gcgcctgttt ctcttgaccg tgcacaaact ctcctactat      120
gagtatgact ttgaacgtgg gagaagaggc agtaagaagg gttcaataga tgttgagaag      180
atcacttgtg ttgaaacagt ggttcctgaa aaaaatcctc ctccagaaag acagattccg      240
agaagaggtg aagagtccag tgaaatggag caaatttcaa tcattgaaag gttcccttat      300
cccttccagg ttgtatatga tgaagggcct ctctacgtct ctcccccaac tgaagaacta      360
aggaagcggg ggattcacca gctcaaaaac gtaatccggt acaacagtga tctggttcag      420
aaatatcacc cttgcttctg gatcgatggg cagtatctct gctgctctca gacagccaaa      480
aatgctatgg gctgccaaat tttgagaac aggaatggaa gcttaaaacc tgggagttct      540
caccggaaga caaaaaagcc tcttccccca acgcctgagg aggaccagat cttgaaaaag      600
ccactaccgc ctgagccagc agcagcacca gtctccacaa gtgagctgaa aaaggttgtg      660 gcccttttatg attacatgcc aatgaatgca aatgatctac agctgcggaa gggtgatgaa      720
tattttatct tggaggaaag caacttacca tggtggagag cacgagataa aaatgggcag      780
gaaggctaca ttcctagtaa ctatgtcact gaagcagaag actccataga aatgtatgag      840
tggtattcca aacacatgac tcggagtcag gctgagcaac tgctaaagca agaggggaaa      900
```

```
gaaggaggtt tcattgtcag agactccagc aaagctggca aatatacagt gtctgtgttt      960
gctaaatcca caggggaccc tcaaggggtg atacgtcatt atgttgtgtg ttccacacct     1020
cagagccagt attacctggc tgagaagcac ctttcagca  ccatccctga gctcattaac    1080
taccatcagc acaactctgc aggactcata tccaggctca aatatccagt gtctcaacaa    1140
aacaagaatg caccttccac tgcaggcctg ggatacggat catgggaaat tgatccaaag    1200
gacctgacct tcttgaagga gctggggact ggacaatttg gggtagtgaa gtatgggaaa    1260
tggagaggcc agtacgacgt ggccatcaag atgatcaaag aaggctccat gtctgaagat    1320
gaattcattg aagaagccaa agtcatgatg aatctttccc atgagaagct ggtgcagttg    1380
tatggcgtct gcaccaagca gcgccccatc ttcatcatca ctgagtacat ggccaatggc    1440
tccctcctga actacctgag ggagatgcgc accgcttcc  agactcagca gctgctagag    1500
atgtgcaagg atgtctgtga agccatggaa tacctggagt caaagcagtt ccttcaccga    1560
gacctggcag ctcgaaactg tttggtaaac gatcaaggag ttgttaaagt atctgatttc    1620
ggcctgtcca ggtatgtcct ggatgatgaa tacacaagcc agtaggctc  caaatttcca    1680 gtccggtggt ccccaccgga agtcctgatg tatagcaagt tcagcagcaa atctgacatt    1740
tgggcttttg gggttttgat gtgggaaatt tactccctgg ggaagatgcc atatgagaga    1800
tttactaaca gtgagactgc tgaacacatt gcccaaggcc tacgtctcta caggcctcat    1860
ctggcttcag agaaggtata taccatcatg tacagttgct ggcatgagaa agcagatgag    1920
cgtcccactt tcaaaattct tctgagcaat attctagatg tcatggatga agaatcctga    1980
```

```
<210> SEQ ID NO 9
<211> LENGTH: 20
<212> TYPE: DNA
<213> ORGANISM: Artificial Sequence
<220> FEATURE:
<223> OTHER INFORMATION: Primer Sequence

<400> SEQUENCE: 9
aagtgaaatt ggggcttgtg                                                   20

<210> SEQ ID NO 10
<211> LENGTH: 20
<212> TYPE: DNA
<213> ORGANISM: Artificial Sequence
<220> FEATURE:
<223> OTHER INFORMATION: Primer Sequence

<400> SEQUENCE: 10
agtcccacct tccaagtcct                                                   20

<210> SEQ ID NO 11
<211> LENGTH: 1265
<212> TYPE: PRT
<213> ORGANISM: Homo sapiens

<400> SEQUENCE: 11

Met Ser Thr Thr Val Asn Val Asp Ser Leu Ala Glu Tyr Glu Lys Ser
1               5                   10                  15

Gln Ile Lys Arg Ala Leu Glu Leu Gly Thr Val Met Thr Val Phe Ser
            20                  25                  30

Phe Arg Lys Ser Thr Pro Glu Arg Arg Thr Val Gln Val Ile Met Glu
        35                  40                  45

Thr Arg Gln Val Ala Trp Ser Lys Thr Ala Asp Lys Ile Glu Gly Phe
    50                  55                  60
```

-continued

```
Leu Asp Ile Met Glu Ile Lys Glu Ile Arg Pro Gly Lys Asn Ser Lys
 65                  70                  75                  80

Asp Phe Glu Arg Ala Lys Ala Val Arg Gln Lys Glu Asp Cys Cys Phe
                 85                  90                  95

Thr Ile Leu Tyr Gly Thr Gln Phe Val Leu Ser Thr Leu Ser Leu Ala
            100                 105                 110

Ala Asp Ser Lys Glu Asp Ala Val Asn Trp Leu Ser Gly Leu Lys Ile
            115                 120                 125

Leu His Gln Glu Ala Met Asn Ala Ser Thr Pro Thr Ile Ile Glu Ser
130                 135                 140

Trp Leu Arg Lys Gln Ile Tyr Ser Val Asp Thr Arg Arg Asn Ser
145                 150                 155                 160

Ile Ser Leu Arg Glu Leu Lys Thr Ile Leu Pro Leu Ile Asn Phe Lys
                165                 170                 175

Val Ser Ser Ala Lys Phe Leu Lys Asp Lys Phe Val Glu Ile Gly Ala
            180                 185                 190

His Lys Asp Glu Leu Ser Phe Glu Gln Phe His Leu Phe Tyr Lys Lys
            195                 200                 205

Leu Met Phe Glu Gln Gln Lys Ser Ile Leu Asp Glu Phe Lys Lys Asp
            210                 215                 220

Ser Ser Val Phe Ile Leu Gly Asn Thr Asp Arg Pro Asp Ala Ser Ala
225                 230                 235                 240

Val Tyr Leu His Asp Phe Gln Arg Phe Leu Ile His Glu Gln Gln Glu
                245                 250                 255

His Trp Ala Gln Asp Leu Asn Lys Val Arg Glu Arg Met Thr Lys Phe
            260                 265                 270

Ile Asp Asp Thr Met Arg Glu Thr Ala Glu Pro Phe Leu Phe Val Asp
            275                 280                 285

Glu Phe Leu Thr Tyr Leu Phe Ser Arg Glu Asn Ser Ile Trp Asp Glu
            290                 295                 300

Lys Tyr Asp Ala Val Asp Met Gln Asp Met Asn Asn Pro Leu Ser His
305                 310                 315                 320

Tyr Trp Ile Ser Ser His Asn Thr Tyr Leu Thr Gly Asp Gln Leu
                325                 330                 335

Arg Ser Glu Ser Ser Pro Glu Ala Tyr Ile Arg Cys Leu Arg Met Gly
            340                 345                 350

Cys Arg Cys Ile Glu Leu Asp Cys Trp Asp Gly Pro Asp Gly Lys Pro
            355                 360                 365

Val Ile Tyr His Gly Trp Thr Arg Thr Thr Lys Ile Lys Phe Asp Asp
            370                 375                 380

Val Val Gln Ala Ile Lys Asp His Ala Phe Val Thr Ser Ser Phe Pro
385                 390                 395                 400

Val Ile Leu Ser Ile Glu Glu His Cys Ser Val Glu Gln Gln Arg His
                405                 410                 415

Met Ala Lys Ala Phe Lys Glu Val Phe Gly Asp Leu Leu Leu Thr Lys
            420                 425                 430

Pro Thr Glu Ala Ser Ala Asp Gln Leu Pro Ser Pro Ser Gln Leu Arg
            435                 440                 445

Glu Lys Ile Ile Ile Lys His Lys Lys Leu Gly Pro Arg Gly Asp Val
            450                 455                 460

Asp Val Asn Met Glu Asp Lys Lys Asp Glu His Lys Gln Gln Gly Glu
465                 470                 475                 480
```

```
Leu Tyr Met Trp Asp Ser Ile Asp Gln Lys Trp Thr Arg His Tyr Cys
                485                 490                 495

Ala Ile Ala Asp Ala Lys Leu Ser Phe Ser Asp Ile Glu Gln Thr
            500                 505                 510

Met Glu Glu Val Pro Gln Asp Ile Pro Pro Thr Glu Leu His Phe
            515                 520                 525

Gly Glu Lys Trp Phe His Lys Lys Val Glu Lys Arg Thr Ser Ala Glu
            530                 535                 540

Lys Leu Leu Gln Glu Tyr Cys Met Glu Thr Gly Gly Lys Asp Gly Thr
545                 550                 555                 560

Phe Leu Val Arg Glu Ser Glu Thr Phe Pro Asn Asp Tyr Thr Leu Ser
                565                 570                 575

Phe Trp Arg Ser Gly Arg Val Gln His Cys Arg Ile Arg Ser Thr Met
                580                 585                 590

Glu Gly Gly Thr Leu Lys Tyr Tyr Leu Thr Asp Asn Leu Thr Phe Ser
                595                 600                 605

Ser Ile Tyr Ala Leu Ile Gln His Tyr Arg Glu Thr His Leu Arg Cys
                610                 615                 620

Ala Glu Phe Glu Leu Arg Leu Thr Asp Pro Val Pro Asn Pro Asn Pro
625                 630                 635                 640

His Glu Ser Lys Pro Trp Tyr Tyr Asp Ser Leu Ser Arg Gly Glu Ala
                645                 650                 655

Glu Asp Met Leu Met Arg Ile Pro Arg Asp Gly Ala Phe Leu Ile Arg
                660                 665                 670

Lys Arg Glu Gly Ser Asp Ser Tyr Ala Ile Thr Phe Arg Ala Arg Gly
                675                 680                 685

Lys Val Lys His Cys Arg Ile Asn Arg Asp Gly Arg His Phe Val Leu
                690                 695                 700

Gly Thr Ser Ala Tyr Phe Glu Ser Leu Val Glu Leu Val Ser Tyr Tyr
705                 710                 715                 720

Glu Lys His Ser Leu Tyr Arg Lys Met Arg Leu Arg Tyr Pro Val Thr
                725                 730                 735

Pro Glu Leu Leu Glu Arg Tyr Asn Met Glu Arg Asp Ile Asn Ser Leu
                740                 745                 750

Tyr Asp Val Ser Arg Met Tyr Val Asp Pro Ser Glu Ile Asn Pro Ser
                755                 760                 765

Met Pro Gln Arg Thr Val Lys Ala Leu Tyr Asp Tyr Lys Ala Lys Arg
                770                 775                 780

Ser Asp Glu Leu Ser Phe Cys Arg Gly Ala Leu Ile His Asn Val Ser
785                 790                 795                 800

Lys Glu Pro Gly Gly Trp Trp Lys Gly Asp Tyr Gly Thr Arg Ile Gln
                805                 810                 815

Gln Tyr Phe Pro Ser Asn Tyr Val Glu Asp Ile Ser Thr Ala Asp Phe
                820                 825                 830

Glu Glu Leu Glu Lys Gln Ile Ile Glu Asp Asn Pro Leu Gly Ser Leu
                835                 840                 845

Cys Arg Gly Ile Leu Asp Leu Asn Thr Tyr Asn Val Val Lys Ala Pro
850                 855                 860

Gln Gly Lys Asn Gln Lys Ser Phe Val Phe Ile Leu Glu Pro Lys Gln
865                 870                 875                 880

Gln Gly Asp Pro Pro Val Glu Phe Ala Thr Asp Arg Val Glu Glu Leu
                885                 890                 895

Phe Glu Trp Phe Gln Ser Ile Arg Glu Ile Thr Trp Lys Ile Asp Thr
```

```
                900             905             910
Lys Glu Asn Asn Met Lys Tyr Trp Glu Lys Asn Gln Ser Ile Ala Ile
        915             920             925
Glu Leu Ser Asp Leu Val Val Tyr Cys Lys Pro Thr Ser Lys Thr Lys
        930             935             940
Asp Asn Leu Glu Asn Pro Asp Phe Arg Glu Ile Arg Ser Phe Val Glu
945             950             955             960
Thr Lys Ala Asp Ser Ile Ile Arg Gln Lys Pro Val Asp Leu Leu Lys
                965             970             975
Tyr Asn Gln Lys Gly Leu Thr Arg Val Tyr Pro Lys Gly Gln Arg Val
            980             985             990
Asp Ser Ser Asn Tyr Asp Pro Phe Arg Leu Trp Leu Cys Gly Ser Gln
        995             1000            1005
Met Val Ala Leu Asn Phe Gln Thr Ala Asp Lys Tyr Met Gln Met
    1010            1015            1020
Asn His Ala Leu Phe Ser Leu Asn Gly Arg Thr Gly Tyr Val Leu
    1025            1030            1035
Gln Pro Glu Ser Met Arg Thr Glu Lys Tyr Asp Pro Met Pro Pro
    1040            1045            1050
Glu Ser Gln Arg Lys Ile Leu Met Thr Leu Thr Val Lys Val Leu
    1055            1060            1065
Gly Ala Arg His Leu Pro Lys Leu Gly Arg Ser Ile Ala Cys Pro
    1070            1075            1080
Phe Val Glu Val Glu Ile Cys Gly Ala Glu Tyr Asp Asn Asn Lys
    1085            1090            1095
Phe Lys Thr Thr Val Val Asn Asp Asn Gly Leu Ser Pro Ile Trp
    1100            1105            1110
Ala Pro Thr Gln Glu Lys Val Thr Phe Glu Ile Tyr Asp Pro Asn
    1115            1120            1125
Leu Ala Phe Leu Arg Phe Val Val Tyr Glu Glu Asp Met Phe Ser
    1130            1135            1140
Asp Pro Asn Phe Leu Ala His Ala Thr Tyr Pro Ile Lys Ala Val
    1145            1150            1155
Lys Ser Gly Phe Arg Ser Val Pro Leu Lys Asn Gly Tyr Ser Glu
    1160            1165            1170
Asp Ile Glu Leu Ala Ser Leu Leu Val Phe Cys Glu Met Arg Pro
    1175            1180            1185
Val Leu Glu Ser Glu Glu Leu Tyr Ser Ser Cys Arg Gln Leu
    1190            1195            1200
Arg Arg Arg Gln Glu Glu Leu Asn Asn Gln Leu Phe Leu Tyr Asp
    1205            1210            1215
Thr His Gln Asn Leu Arg Asn Ala Asn Arg Asp Ala Leu Val Lys
    1220            1225            1230
Glu Phe Ser Val Asn Glu Asn Gln Leu Gln Leu Tyr Gln Glu Lys
    1235            1240            1245
Cys Asn Lys Arg Leu Arg Glu Lys Arg Val Ser Asn Ser Lys Phe
    1250            1255            1260
Tyr Ser
    1265

<210> SEQ ID NO 12
<211> LENGTH: 4289
<212> TYPE: DNA
<213> ORGANISM: Homo sapiens
```

<400> SEQUENCE: 12

```
agtagcgagc gccggcggcg gagggcgtga gcggcgctga gtgacccgag tcgggacgcg      60
ggctgcgcgc gcgggacccc ggagcccaaa cccggggcag gcgggcagct gtgcccgggc     120
ggcacggcca gcttcctgat ttctcccgat tccttccttc tccctggagc ggccgacaat     180
gtccaccacg gtcaatgtag attcccttgc ggaatatgag aagagccaga tcaagagagc     240
cctggagctg gggacggtga tgactgtgtt cagcttccgc aagtccaccc cgagcggag      300
aaccgtccag gtgatcatgg agacgcggca ggtggcctgg agcaagaccg ccgacaagat     360
cgagggcttc ttggatatca tggaaataaa agaaatccgc ccaggaaga actccaaaga      420
tttcgagcga gcaaaagcag ttcgccagaa agaagactgc tgcttcacca tcctatatgg     480
cactcagttc gtcctcagca cgctcagctt ggcagtgac tctaaagagg atgcagttaa      540
ctggctctct ggcttgaaaa tcttacacca ggaagcgatg aatgcgtcca cgcccaccat     600
tatcgagagt tggctgagaa agcagatata ttctgtggat caaaccagaa gaaacagcat     660
cagtctccga gagttgaaga ccatcttgcc cctgatcaac tttaaagtga gcagtgccaa     720
gttccttaaa gataagtttg tggaaatagg agcacacaaa gatgagctca gctttgaaca     780
gttccatctc ttctataaaa aacttatgtt tgaacagcaa aaatcgattc tcgatgaatt     840
caaaaaggat tcgtccgtgt tcatcctggg gaacactgac aggccggatg cctctgctgt     900
ttacctgcat gacttccaga ggtttctcat acatgaacag caggagcatt gggctcagga     960
tctgaacaaa gtccgtgagc ggatgacaaa gttcattgat gacaccatgc gtgaaactgc    1020
tgagcctttc ttgtttgtgg atgagttcct cacgtacctg ttttcacgag aaaacagcat    1080
ctgggatgag aagtatgacg cggtggacat gcaggacatg aacaaccccc tgtctcatta    1140
ctggatctcc tcgtcacata cacgtacct tacaggtgac cagctgcgga gcgagtcgtc     1200
cccagaagct tacatccgct gcctgcgcat gggctgtcgc tgcattgaac tggactgctg    1260
ggacgggccc gatgggaagc cggtcatcta ccatggctgg acgcggacta ccaagatcaa    1320
gtttgacgac gtcgtgcagg ccatcaaaga ccacgccttt gttacctcga gcttcccagt    1380
gatcctgtcc atcgaggagc actgcagcgt ggagcaacag cgtcacatgg ccaaggcctt    1440
caaggaagta tttggcgacc tgctgttgac gaagcccacg gaggccagtg ctgaccagct    1500
gccctcgccc agccagctgc gggagaagat catcatcaag cataagaagc tgggcccccg    1560
aggcgatgtg gatgtcaaca tggaggacaa gaaggacgaa cacaagcaac aggggagct    1620
gtacatgtgg gattccattg accagaaatg gactcggcac tactgcgcca ttgccgatgc    1680
caagctgtcc ttcagtgatg acattgaaca gactatggag gaggaagtgc cccaggatat    1740
accccctaca gaactacatt ttggggagaa atggttccac aagaaggtgg agaagaggac    1800
gagtgccgag aagttgctgc aggaatactg catggagacg gggggcaagg atggcacctt    1860
cctggttcgg gagagcgaga ccttcccaa tgactacacc ctgtccttct ggcggtcagg     1920
ccgggtccag cactgccgga tccgctccac catggagggc gggaccctga atactactt     1980
gactgacaac ctcaccttca gcagcatcta tgccctcatc cagcactacc gcagacgca     2040
cctgcgctgc gccgagttcg agctgcggct cacggaccct gtgcccaacc ccaacccca     2100
cgagtccaag ccgtggtact atgacagcct gagccgcgga gaggcagagg acatgctgat    2160
gaggattccc cggacggggg ccttcctgat ccggaagcga gaggggagcg actcctatgc    2220
catcaccttc agggctaggg gcaaggtaaa gcattgtcgc atcaaccggg acggccggca    2280
```

| | |
|---|---|
| ctttgtgctg gggacctccg cctatttgga gagtctggtg gagctcgtca gttactacga | 2340 |
| gaagcattca ctctaccgaa agatgagact gcgctacccc gtgaccccg agctcctgga | 2400 |
| gcgctacaat atggaaagag atataaactc cctctacgac gtcagcagaa tgtatgtgga | 2460 |
| tcccagtgaa atcaatccgt ccatgcctca gagaaccgtg aaagtctgt atgactacaa | 2520 |
| agccaagcga agcgatgagc tgagcttctg ccgtggtgcc ctcatccaca atgtctccaa | 2580 |
| ggagcccggg ggctggtgga aaggagacta tggaaccagg atccagcagt acttcccatc | 2640 |
| caactacgtc gaggacatct caactgcaga cttcgaggag ctagaaaagc agattattga | 2700 |
| agacaatccc ttagggtctc tttgcagagg aatattggac ctcaataccct ataacgtcgt | 2760 |
| gaaagcccct cagggaaaaa accagaagtc ctttgtcttc atcctggagc ccaagcagca | 2820 |
| gggcgatcct ccgtggagt ttgccacaga caggtggag gagctctttg agtggtttca | 2880 |
| gagcatccga gagatcacct ggaagattga caccaaggag aacaacatga agtactggga | 2940 |
| gaagaaccag tccatcgcca tcgagctctc tgacctggtt gtctactgca aaccaaccag | 3000 |
| caaaaccaag gacaacttag aaaatcctga cttccgagaa atccgctcct ttgtggagac | 3060 |
| gaaggctgac agcatcatca gacagaagcc cgtcgacctc ctgaagtaca atcaaaaggg | 3120 |
| cctgacccgc gtctacccaa agggacaaag agttgactct tcaaactacg acccccttccg | 3180 |
| cctctggctg tgcggttctc agatggtggc actcaatttc cagacggcag ataagtacat | 3240 |
| gcagatgaat cacgcattgt tttctctcaa tgggcgcacg ggctacgttc tgcagcctga | 3300 |
| gagcatgagg acagagaaat atgacccgat gccacccgag tcccagagga agatcctgat | 3360 |
| gacgctgaca gtcaaggttc tcggtgctcg ccatctcccc aaacttggac gaagtattgc | 3420 |
| ctgtcccttt gtagaagtgg agatctgtgg agccgagtat gacaacaaca gttcaagac | 3480 |
| gacggttgtg aatgataatg gcctcagccc tatctgggct ccaacacagg agaaggtgac | 3540 |
| atttgaaatt tatgacccaa acctggcatt tctgcgcttt gtggtttatg aagaagatat | 3600 |
| gttcagcgat cccaactttc ttgctcatgc cacttacccc attaaagcag tcaaatcagg | 3660 |
| attcaggtcc gttcctctga gaatgggta cagcgaggac atagagctgg cttccctcct | 3720 |
| ggttttctgt gagatgcggc cagtcctgga gagcgaagag gaactttact cctcctgtcg | 3780 |
| ccagctgagg aggcggcaag aagaactgaa caaccagctc tttctgtatg acacacacca | 3840 |
| gaacttgcgc aatgccaacc gggatgccct ggttaaagag ttcagtgtta atgagaacca | 3900 |
| gctccagctg taccaggaga atgcaacaa gaggttaaga gagaagagag tcagcaacag | 3960 |
| caagttttac tcatagaagc tggggtatgt gtgtaagggt attgtgtgtg tgcgcatgtg | 4020 |
| tgtttgcatg taggagaacg tgccctattc acactctggg aagacgctaa tctgtgacat | 4080 |
| cttttcttca agcctgccat caaggacatt tcttaagacc caactggcat gagttggggt | 4140 |
| aatttcctat tattttcatc ttggacaact ttcttaactt atattcttta tagaggattc | 4200 |
| cccaaaatgt gctcctcatt tttgggcctct catgttccaa acctcattga ataaaagcaa | 4260 |
| tgaaaaccctt gaaaaaaaaa aaaaaaaaa | 4289 |

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 13
tgatgggctc caaatccctg                    20

<210> SEQ ID NO 14
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 14
gaatgatggc accagcagc                                                19

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 15
aatccctgct tgcttccaca                                               20

<210> SEQ ID NO 16
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 16
ttgatgggct cagcactgg                                                19

<210> SEQ ID NO 17
<211> LENGTH: 1265
<212> TYPE: PRT
<213> ORGANISM: Homo sapiens

<400> SEQUENCE: 17

Met Ser Thr Thr Val Asn Val Asp Ser Leu Ala Glu Tyr Glu Lys Ser
1               5                   10                  15

Gln Ile Lys Arg Ala Leu Glu Leu Gly Thr Val Met Thr Val Phe Ser
            20                  25                  30

Phe Arg Lys Ser Thr Pro Glu Arg Arg Thr Val Gln Val Ile Met Glu
        35                  40                  45

Thr Arg Gln Val Ala Trp Ser Lys Thr Ala Asp Lys Ile Glu Gly Phe
    50                  55                  60

Leu Asp Ile Met Glu Ile Lys Glu Ile Arg Pro Gly Lys Asn Ser Lys
65                  70                  75                  80

Asp Phe Glu Arg Ala Lys Ala Val Arg Gln Lys Glu Asp Cys Cys Phe
                85                  90                  95

Thr Ile Leu Tyr Gly Thr Gln Phe Val Leu Ser Thr Leu Ser Leu Ala
            100                 105                 110

Ala Asp Ser Lys Glu Asp Ala Val Asn Trp Leu Ser Gly Leu Lys Ile
        115                 120                 125

Leu His Gln Glu Ala Met Asn Ala Ser Thr Pro Thr Ile Ile Glu Ser
    130                 135                 140

Trp Leu Arg Lys Gln Ile Tyr Ser Val Asp Gln Thr Arg Arg Asn Ser
145                 150                 155                 160

Ile Ser Leu Arg Glu Leu Lys Thr Ile Leu Pro Leu Ile Asn Phe Lys
                165                 170                 175

Val Ser Ser Ala Lys Phe Leu Lys Asp Lys Phe Val Glu Ile Gly Ala

```
                    180                 185                 190
His Lys Asp Glu Leu Ser Phe Glu Gln Phe His Leu Phe Tyr Lys Lys
                195                 200                 205

Leu Met Phe Glu Gln Gln Lys Ser Ile Leu Asp Glu Phe Lys Lys Asp
            210                 215                 220

Ser Ser Val Phe Ile Leu Gly Asn Thr Asp Arg Pro Asp Ala Ser Ala
225                 230                 235                 240

Val Tyr Leu Arg Asp Phe Gln Arg Phe Leu Ile His Glu Gln Gln Glu
                245                 250                 255

His Trp Ala Gln Asp Leu Asn Lys Val Arg Glu Arg Met Thr Lys Phe
            260                 265                 270

Ile Asp Asp Thr Met Arg Glu Thr Ala Glu Pro Phe Leu Phe Val Asp
            275                 280                 285

Glu Phe Leu Thr Tyr Leu Phe Ser Arg Glu Asn Ser Ile Trp Asp Glu
            290                 295                 300

Lys Tyr Asp Ala Val Asp Met Gln Asp Met Asn Asn Pro Leu Ser His
305                 310                 315                 320

Tyr Trp Ile Ser Ser Ser His Asn Thr Tyr Leu Thr Gly Asp Gln Leu
                325                 330                 335

Arg Ser Glu Ser Ser Pro Glu Ala Tyr Ile Arg Cys Leu Arg Met Gly
            340                 345                 350

Cys Arg Cys Ile Glu Leu Asp Cys Trp Asp Gly Pro Asp Gly Lys Pro
            355                 360                 365

Val Ile Tyr His Gly Trp Thr Arg Thr Thr Lys Ile Lys Phe Asp Asp
            370                 375                 380

Val Val Gln Ala Ile Lys Asp His Ala Phe Val Thr Ser Ser Phe Pro
385                 390                 395                 400

Val Ile Leu Ser Ile Glu Glu His Cys Ser Val Glu Gln Gln Arg His
                405                 410                 415

Met Ala Lys Ala Phe Lys Glu Val Phe Gly Asp Leu Leu Leu Thr Lys
            420                 425                 430

Pro Thr Glu Ala Ser Ala Asp Gln Leu Pro Ser Pro Ser Gln Leu Arg
            435                 440                 445

Glu Lys Ile Ile Ile Lys His Lys Lys Leu Gly Pro Arg Gly Asp Val
            450                 455                 460

Asp Val Asn Met Glu Asp Lys Lys Asp Glu His Lys Gln Gln Gly Glu
465                 470                 475                 480

Leu Tyr Met Trp Asp Ser Ile Asp Gln Lys Trp Thr Arg His Tyr Cys
                485                 490                 495

Ala Ile Ala Asp Ala Lys Leu Ser Phe Ser Asp Asp Ile Glu Gln Thr
            500                 505                 510

Met Glu Glu Glu Val Pro Gln Asp Ile Pro Pro Thr Glu Leu His Phe
            515                 520                 525

Gly Glu Lys Trp Phe His Lys Lys Val Glu Lys Arg Thr Ser Ala Glu
            530                 535                 540

Lys Leu Leu Gln Glu Tyr Cys Met Glu Thr Gly Gly Lys Asp Gly Thr
545                 550                 555                 560

Phe Leu Val Arg Glu Ser Glu Thr Phe Pro Asn Asp Tyr Thr Leu Ser
                565                 570                 575

Phe Trp Arg Ser Gly Arg Val Gln His Cys Arg Ile Arg Ser Thr Met
            580                 585                 590

Glu Gly Gly Thr Leu Lys Tyr Tyr Leu Thr Asp Asn Leu Thr Phe Ser
            595                 600                 605
```

Ser Ile Tyr Ala Leu Ile Gln His Tyr Arg Glu Thr His Leu Arg Cys
610                 615                 620

Ala Glu Phe Glu Leu Arg Leu Thr Asp Pro Val Pro Asn Pro Asn Pro
625                 630                 635                 640

His Glu Ser Lys Pro Trp Tyr Tyr Asp Ser Leu Ser Arg Gly Glu Ala
                645                 650                 655

Glu Asp Met Leu Met Arg Ile Pro Trp Asp Gly Ala Phe Leu Ile Arg
            660                 665                 670

Lys Arg Glu Gly Ser Asp Ser Tyr Ala Ile Thr Phe Arg Ala Arg Gly
        675                 680                 685

Lys Val Lys His Cys Arg Ile Asn Arg Asp Gly Arg His Phe Val Leu
690                 695                 700

Gly Thr Ser Ala Tyr Phe Glu Ser Leu Val Glu Leu Ser Tyr Tyr
705                 710                 715                 720

Glu Lys His Ser Leu Tyr Arg Lys Met Arg Leu Arg Tyr Pro Val Thr
                725                 730                 735

Pro Glu Leu Leu Glu Arg Tyr Asn Met Glu Arg Asp Ile Asn Ser Leu
            740                 745                 750

Tyr Asp Val Ser Arg Met Tyr Val Asp Pro Ser Glu Ile Asn Pro Ser
        755                 760                 765

Met Pro Gln Arg Thr Val Lys Ala Leu Tyr Asp Tyr Lys Ala Lys Arg
770                 775                 780

Ser Asp Glu Leu Ser Phe Cys Arg Gly Ala Leu Ile His Asn Val Ser
785                 790                 795                 800

Lys Glu Pro Gly Gly Trp Trp Lys Gly Asp Tyr Gly Thr Arg Ile Gln
                805                 810                 815

Gln Tyr Phe Pro Ser Asn Tyr Val Glu Asp Ile Ser Thr Ala Asp Phe
            820                 825                 830

Glu Glu Leu Glu Lys Gln Ile Ile Glu Asp Asn Pro Leu Gly Ser Leu
        835                 840                 845

Cys Arg Gly Ile Leu Asp Leu Asn Thr Tyr Asn Val Val Lys Ala Pro
850                 855                 860

Gln Gly Lys Asn Gln Lys Ser Phe Val Phe Ile Leu Glu Pro Lys Gln
865                 870                 875                 880

Gln Gly Tyr Pro Pro Val Glu Phe Ala Thr Asp Arg Val Glu Glu Leu
                885                 890                 895

Phe Glu Trp Phe Gln Ser Ile Arg Glu Ile Thr Trp Lys Ile Asp Thr
            900                 905                 910

Lys Glu Asn Asn Met Lys Tyr Trp Glu Lys Asn Gln Ser Ile Ala Ile
        915                 920                 925

Glu Leu Ser Asp Leu Val Val Tyr Cys Lys Pro Thr Ser Lys Thr Lys
930                 935                 940

Asp Asn Leu Glu Asn Pro Asp Phe Arg Glu Ile Arg Ser Phe Val Glu
945                 950                 955                 960

Thr Lys Ala Asp Ser Ile Ile Arg Gln Lys Pro Val Asp Leu Leu Lys
                965                 970                 975

Tyr Asn Gln Lys Gly Leu Thr Arg Val Tyr Pro Lys Gly Gln Arg Val
            980                 985                 990

Asp Ser Ser Asn Tyr Asp Pro Phe Arg Leu Trp Leu Cys Gly Ser Gln
        995                 1000                1005

Met Val Ala Leu Asn Phe Gln Thr Ala Asp Lys Tyr Met Gln Met
    1010                1015                1020

-continued

Asn His Ala Leu Phe Ser Leu Asn Gly Arg Thr Gly Tyr Val Leu
    1025                1030                1035

Gln Pro Glu Ser Met Arg Thr Glu Lys Tyr Asp Pro Met Pro Pro
    1040                1045                1050

Glu Ser Gln Arg Lys Ile Leu Met Thr Leu Thr Val Lys Val Leu
    1055                1060                1065

Gly Ala Arg His Leu Pro Lys Leu Gly Arg Ser Ile Ala Cys Pro
    1070                1075                1080

Phe Val Glu Val Glu Ile Cys Gly Ala Glu Tyr Asp Asn Asn Lys
    1085                1090                1095

Phe Lys Thr Thr Val Val Asn Asp Asn Gly Leu Ser Pro Ile Trp
    1100                1105                1110

Ala Pro Thr Gln Glu Lys Val Thr Phe Glu Ile Tyr Asp Pro Asn
    1115                1120                1125

Leu Ala Phe Leu Arg Phe Val Val Tyr Glu Glu Asp Met Phe Ser
    1130                1135                1140

Asp Pro Asn Phe Leu Ala His Ala Thr Tyr Pro Ile Lys Ala Val
    1145                1150                1155

Lys Ser Gly Phe Arg Ser Val Pro Leu Lys Asn Gly Tyr Ser Glu
    1160                1165                1170

Asp Ile Glu Leu Ala Ser Leu Leu Val Phe Cys Glu Met Arg Pro
    1175                1180                1185

Val Leu Glu Ser Glu Glu Glu Leu Tyr Ser Ser Cys Arg Gln Leu
    1190                1195                1200

Arg Arg Arg Gln Glu Glu Leu Asn Asn Gln Leu Phe Leu Tyr Asp
    1205                1210                1215

Thr His Gln Asn Leu Arg Asn Ala Asn Arg Asp Ala Leu Val Lys
    1220                1225                1230

Glu Phe Ser Val Asn Glu Asn Gln Leu Gln Leu Tyr Gln Glu Lys
    1235                1240                1245

Cys Asn Lys Arg Leu Arg Glu Lys Arg Val Ser Asn Ser Lys Phe
    1250                1255                1260

Tyr Ser
    1265

<210> SEQ ID NO 18
<211> LENGTH: 1265
<212> TYPE: PRT
<213> ORGANISM: Homo sapiens

<400> SEQUENCE: 18

Met Ser Thr Thr Val Asn Val Asp Ser Leu Ala Glu Tyr Glu Lys Ser
1               5                   10                  15

Gln Ile Lys Arg Ala Leu Glu Leu Gly Thr Val Met Thr Val Phe Ser
                20                  25                  30

Phe Arg Lys Ser Thr Pro Glu Arg Arg Thr Val Gln Val Ile Met Glu
            35                  40                  45

Thr Arg Gln Val Ala Trp Ser Lys Thr Ala Asp Lys Ile Glu Gly Phe
        50                  55                  60

Leu Asp Ile Met Glu Ile Lys Glu Ile Arg Pro Gly Lys Asn Ser Lys
65                  70                  75                  80

Asp Phe Glu Arg Ala Lys Ala Val Arg Gln Lys Glu Asp Cys Cys Phe
                85                  90                  95

Thr Ile Leu Tyr Gly Thr Gln Phe Val Leu Ser Thr Leu Ser Leu Ala
            100                 105                 110

```
Ala Asp Ser Lys Glu Asp Ala Val Asn Trp Leu Ser Gly Leu Lys Ile
            115                 120                 125

Leu His Gln Glu Ala Met Asn Ala Ser Thr Pro Thr Ile Ile Glu Ser
        130                 135                 140

Trp Leu Arg Lys Gln Ile Tyr Ser Val Asp Gln Thr Arg Arg Asn Ser
145                 150                 155                 160

Ile Ser Leu Arg Glu Leu Lys Thr Ile Leu Pro Leu Ile Asn Phe Lys
                165                 170                 175

Val Ser Ser Ala Lys Phe Leu Lys Asp Lys Phe Val Glu Ile Gly Ala
            180                 185                 190

His Lys Asp Glu Leu Ser Phe Glu Gln Phe His Leu Phe Tyr Lys Lys
        195                 200                 205

Leu Met Phe Glu Gln Gln Lys Ser Ile Leu Asp Glu Phe Lys Lys Asp
    210                 215                 220

Ser Ser Val Phe Ile Leu Gly Asn Thr Asp Arg Pro Asp Ala Ser Ala
225                 230                 235                 240

Val Tyr Leu Arg Asp Phe Gln Arg Phe Leu Ile His Glu Gln Gln Glu
                245                 250                 255

His Trp Ala Gln Asp Leu Asn Lys Val Arg Glu Arg Met Thr Lys Phe
            260                 265                 270

Ile Asp Asp Thr Met Arg Glu Thr Ala Glu Pro Phe Leu Phe Val Asp
        275                 280                 285

Glu Phe Leu Thr Tyr Leu Phe Ser Arg Glu Asn Ser Ile Trp Asp Glu
    290                 295                 300

Lys Tyr Asp Ala Val Asp Met Gln Asp Met Asn Asn Pro Leu Ser His
305                 310                 315                 320

Tyr Trp Ile Ser Ser His Asn Thr Tyr Leu Thr Gly Asp Gln Leu
                325                 330                 335

Arg Ser Glu Ser Ser Pro Glu Ala Tyr Ile Arg Cys Leu Arg Met Gly
            340                 345                 350

Cys Arg Cys Ile Glu Leu Asp Cys Trp Asp Gly Pro Asp Gly Lys Pro
        355                 360                 365

Val Ile Tyr His Gly Trp Thr Arg Thr Lys Ile Lys Phe Asp Asp
    370                 375                 380

Val Val Gln Ala Ile Lys Asp His Ala Phe Val Thr Ser Ser Phe Pro
385                 390                 395                 400

Val Ile Leu Ser Ile Glu Glu His Cys Ser Val Glu Gln Gln Arg His
                405                 410                 415

Met Ala Lys Ala Phe Lys Glu Val Phe Gly Asp Leu Leu Leu Thr Lys
            420                 425                 430

Pro Thr Glu Ala Ser Ala Asp Gln Leu Pro Ser Pro Ser Gln Leu Arg
        435                 440                 445

Glu Lys Ile Ile Ile Lys His Lys Lys Leu Gly Pro Arg Gly Asp Val
    450                 455                 460

Asp Val Asn Met Glu Asp Lys Lys Asp Glu His Lys Gln Gln Gly Glu
465                 470                 475                 480

Leu Tyr Met Trp Asp Ser Ile Asp Gln Lys Trp Thr Arg His Tyr Cys
                485                 490                 495

Ala Ile Ala Asp Ala Lys Leu Ser Phe Ser Asp Asp Ile Glu Gln Thr
            500                 505                 510

Met Glu Glu Glu Val Pro Gln Asp Ile Pro Pro Thr Glu Leu His Phe
        515                 520                 525
```

```
Gly Glu Lys Trp Phe His Lys Lys Val Glu Lys Arg Thr Ser Ala Glu
        530                 535                 540

Lys Leu Leu Gln Glu Tyr Cys Met Glu Thr Gly Gly Lys Asp Gly Thr
545                 550                 555                 560

Phe Leu Val Arg Glu Ser Glu Thr Phe Pro Asn Asp Tyr Thr Leu Ser
                565                 570                 575

Phe Trp Arg Ser Gly Arg Val Gln His Cys Arg Ile Arg Ser Thr Met
                580                 585                 590

Glu Gly Gly Thr Leu Lys Tyr Tyr Leu Thr Asp Asn Leu Thr Phe Ser
                595                 600                 605

Ser Ile Tyr Ala Leu Ile Gln His Tyr Arg Glu Thr His Leu Arg Cys
610                 615                 620

Ala Glu Phe Glu Leu Arg Leu Thr Asp Pro Val Pro Asn Pro Asn Pro
625                 630                 635                 640

His Glu Ser Lys Pro Trp Tyr Tyr Asp Ser Leu Ser Arg Gly Glu Ala
                645                 650                 655

Glu Asp Met Leu Met Arg Ile Pro Arg Asp Gly Ala Phe Leu Ile Arg
                660                 665                 670

Lys Arg Glu Gly Ser Asp Ser Tyr Ala Ile Thr Phe Arg Ala Arg Gly
                675                 680                 685

Lys Val Lys His Cys Arg Ile Asn Arg Asp Gly Arg His Phe Val Leu
690                 695                 700

Gly Thr Phe Ala Tyr Phe Glu Ser Leu Val Glu Leu Val Ser Tyr Tyr
705                 710                 715                 720

Glu Lys His Ser Leu Tyr Arg Lys Met Arg Leu Arg Tyr Pro Val Thr
                725                 730                 735

Pro Glu Leu Leu Glu Arg Tyr Asn Met Glu Arg Asp Ile Asn Ser Leu
                740                 745                 750

Tyr Asp Val Ser Arg Met Tyr Val Asp Pro Ser Glu Ile Asn Pro Ser
                755                 760                 765

Met Pro Gln Arg Thr Val Lys Ala Leu Tyr Asp Tyr Lys Ala Lys Arg
770                 775                 780

Ser Asp Glu Leu Ser Phe Cys Arg Gly Ala Leu Ile His Asn Val Ser
785                 790                 795                 800

Lys Glu Pro Gly Gly Trp Trp Lys Gly Asp Tyr Gly Thr Arg Ile Gln
                805                 810                 815

Gln Tyr Phe Pro Ser Asn Tyr Val Glu Asp Ile Ser Thr Ala Asp Phe
                820                 825                 830

Glu Glu Leu Glu Lys Gln Ile Ile Glu Asp Asn Pro Leu Gly Ser Leu
                835                 840                 845

Cys Arg Gly Ile Leu Asp Leu Asn Thr Tyr Asn Val Val Lys Ala Pro
850                 855                 860

Gln Gly Lys Asn Gln Lys Ser Phe Val Phe Ile Leu Glu Pro Lys Gln
865                 870                 875                 880

Gln Gly Tyr Pro Pro Val Glu Phe Ala Thr Asp Arg Val Glu Glu Leu
                885                 890                 895

Phe Glu Trp Phe Gln Ser Ile Arg Glu Ile Thr Trp Lys Ile Asp Thr
                900                 905                 910

Lys Glu Asn Asn Met Lys Tyr Trp Glu Lys Asn Gln Ser Ile Ala Ile
                915                 920                 925

Glu Leu Ser Asp Leu Val Val Tyr Cys Lys Pro Thr Ser Lys Thr Lys
930                 935                 940

Asp Asn Leu Glu Asn Pro Asp Phe Arg Glu Ile Arg Ser Phe Val Glu
```

```
                945                 950                 955                 960
Thr Lys Ala Asp Ser Ile Ile Arg Gln Lys Pro Val Asp Leu Leu Lys
                    965                 970                 975
Tyr Asn Gln Lys Gly Leu Thr Arg Val Tyr Pro Lys Gly Gln Arg Val
                    980                 985                 990
Asp Ser Ser Asn Tyr Asp Pro Phe Arg Leu Trp Leu Cys Gly Ser Gln
                    995                 1000                1005
Met Val Ala Leu Asn Phe Gln Thr Ala Asp Lys Tyr Met Gln Met
    1010                1015                1020
Asn His Ala Leu Phe Ser Leu Asn Gly Arg Thr Gly Tyr Val Leu
    1025                1030                1035
Gln Pro Glu Ser Met Arg Thr Glu Lys Tyr Asp Pro Met Pro Pro
    1040                1045                1050
Glu Ser Gln Arg Lys Ile Leu Met Thr Leu Thr Val Lys Val Leu
    1055                1060                1065
Gly Ala Arg His Leu Pro Lys Leu Gly Arg Ser Ile Ala Cys Pro
    1070                1075                1080
Phe Val Glu Val Glu Ile Cys Gly Ala Glu Tyr Asp Asn Asn Lys
    1085                1090                1095
Phe Lys Thr Thr Val Val Asn Asp Asn Gly Leu Ser Pro Ile Trp
    1100                1105                1110
Ala Pro Thr Gln Glu Lys Val Thr Phe Glu Ile Tyr Asp Pro Asn
    1115                1120                1125
Leu Ala Phe Leu Arg Phe Val Val Tyr Glu Glu Asp Met Phe Ser
    1130                1135                1140
Asp Pro Asn Phe Leu Ala His Ala Thr Tyr Pro Ile Lys Ala Val
    1145                1150                1155
Lys Ser Gly Phe Arg Ser Val Pro Leu Lys Asn Gly Tyr Ser Glu
    1160                1165                1170
Asp Ile Glu Leu Ala Ser Leu Leu Val Phe Cys Glu Met Arg Pro
    1175                1180                1185
Val Leu Glu Ser Glu Glu Glu Leu Tyr Ser Ser Cys Arg Gln Leu
    1190                1195                1200
Arg Arg Arg Gln Glu Glu Leu Asn Asn Gln Leu Phe Leu Tyr Asp
    1205                1210                1215
Thr His Gln Asn Leu Arg Asn Ala Asn Arg Asp Ala Leu Val Lys
    1220                1225                1230
Glu Phe Ser Val Asn Glu Asn Gln Leu Gln Leu Tyr Gln Glu Lys
    1235                1240                1245
Cys Asn Lys Arg Leu Arg Glu Lys Arg Val Ser Asn Ser Lys Phe
    1250                1255                1260
Tyr Ser
    1265

<210> SEQ ID NO 19
<211> LENGTH: 1154
<212> TYPE: PRT
<213> ORGANISM: Homo sapiens

<400> SEQUENCE: 19

Met Pro Gly Gly Gly Pro Glu Met Asp Asp Tyr Met Glu Thr Leu Lys
1               5                   10                  15
Asp Glu Glu Asp Ala Leu Trp Glu Asn Val Glu Cys Asn Arg His Met
            20                  25                  30
```

-continued

```
Leu Ser Arg Tyr Ile Asn Pro Ala Lys Leu Thr Pro Tyr Leu Arg Gln
         35                  40                  45

Cys Lys Val Ile Asp Glu Gln Asp Glu Asp Val Leu Asn Ala Pro
 50                  55                  60

Met Leu Pro Ser Lys Ile Asn Arg Ala Gly Arg Leu Leu Asp Ile Leu
 65                  70                  75                  80

His Thr Lys Gly Gln Arg Gly Tyr Val Val Phe Leu Glu Ser Leu Glu
                 85                  90                  95

Phe Tyr Tyr Pro Glu Leu Tyr Lys Leu Val Thr Gly Lys Glu Pro Thr
                100                 105                 110

Arg Arg Phe Ser Thr Ile Val Val Glu Glu Gly His Glu Gly Leu Thr
                115                 120                 125

His Phe Leu Met Asn Glu Val Ile Lys Leu Gln Gln Gln Met Lys Ala
130                 135                 140

Lys Asp Leu Gln Arg Cys Glu Leu Leu Ala Arg Leu Arg Gln Leu Glu
145                 150                 155                 160

Asp Glu Lys Lys Gln Met Thr Leu Thr Arg Val Glu Leu Leu Thr Phe
                165                 170                 175

Gln Glu Arg Tyr Tyr Lys Met Lys Glu Glu Arg Asp Ser Tyr Asn Asp
                180                 185                 190

Glu Leu Val Lys Val Lys Asp Asp Asn Tyr Asn Leu Ala Met Arg Tyr
                195                 200                 205

Ala Gln Leu Ser Glu Glu Lys Asn Met Ala Val Met Arg Ser Arg Asp
                210                 215                 220

Leu Gln Leu Glu Ile Asp Gln Leu Lys His Arg Leu Asn Lys Met Glu
225                 230                 235                 240

Glu Glu Cys Lys Leu Glu Arg Asn Gln Ser Leu Lys Leu Lys Asn Asp
                245                 250                 255

Ile Glu Asn Arg Pro Lys Lys Glu Gln Val Leu Glu Leu Glu Arg Glu
                260                 265                 270

Asn Glu Met Leu Lys Thr Lys Asn Gln Glu Leu Gln Ser Ile Ile Gln
                275                 280                 285

Ala Gly Lys Arg Ser Leu Pro Asp Ser Asp Lys Ala Ile Leu Asp Ile
                290                 295                 300

Leu Glu His Asp Arg Lys Glu Ala Leu Glu Asp Arg Gln Glu Leu Val
305                 310                 315                 320

Asn Arg Ile Tyr Asn Leu Gln Glu Glu Ala Arg Gln Ala Glu Glu Leu
                325                 330                 335

Arg Asp Lys Tyr Leu Glu Glu Lys Glu Asp Leu Glu Leu Lys Cys Ser
                340                 345                 350

Thr Leu Gly Lys Asp Cys Glu Met Tyr Lys His Arg Met Asn Thr Val
                355                 360                 365

Met Leu Gln Leu Glu Glu Val Glu Arg Glu Arg Asp Gln Ala Phe His
370                 375                 380

Ser Arg Asp Glu Ala Gln Thr Gln Tyr Ser Gln Cys Leu Ile Glu Lys
385                 390                 395                 400

Asp Lys Tyr Arg Lys Gln Ile Arg Glu Leu Glu Glu Lys Asn Asp Glu
                405                 410                 415

Met Arg Ile Glu Met Val Arg Arg Glu Ala Cys Ile Val Asn Leu Glu
                420                 425                 430

Ser Lys Leu Arg Arg Leu Ser Lys Asp Ser Asn Asn Leu Asp Gln Ser
435                 440                 445

Leu Pro Arg Asn Leu Pro Val Thr Ile Ile Ser Gln Asp Phe Gly Asp
```

```
            450                 455                 460
Ala Ser Pro Arg Thr Asn Gly Gln Glu Ala Asp Asp Ser Ser Thr Ser
465                 470                 475                 480

Glu Glu Ser Pro Glu Asp Ser Lys Tyr Phe Leu Pro Tyr His Pro Pro
                    485                 490                 495

Gln Arg Arg Met Asn Leu Lys Gly Ile Gln Leu Gln Arg Ala Lys Ser
                500                 505                 510

Pro Ile Ser Leu Lys Arg Thr Ser Asp Phe Gln Ala Lys Gly His Glu
            515                 520                 525

Glu Glu Gly Thr Asp Ala Ser Pro Ser Cys Gly Ser Leu Pro Ile
        530                 535                 540

Thr Asn Ser Phe Thr Lys Met Gln Pro Pro Arg Ser Arg Ser Ser Ile
545                 550                 555                 560

Met Ser Ile Thr Ala Glu Pro Pro Gly Asn Asp Ser Ile Val Arg Arg
                565                 570                 575

Tyr Lys Glu Asp Ala Pro His Arg Ser Thr Val Glu Glu Asp Asn Asp
                580                 585                 590

Ser Gly Gly Phe Asp Ala Leu Asp Leu Asp Asp Ser His Glu Arg
        595                 600                 605

Tyr Ser Phe Gly Pro Ser Ser Ile His Ser Ser Ser Ser His Gln
        610                 615                 620

Ser Glu Gly Leu Asp Ala Tyr Asp Leu Glu Gln Val Asn Leu Met Phe
625                 630                 635                 640

Arg Lys Phe Ser Leu Glu Arg Pro Phe Arg Pro Ser Val Thr Ser Val
                645                 650                 655

Gly His Val Arg Gly Pro Gly Pro Ser Val Gln His Thr Thr Leu Asn
                660                 665                 670

Gly Asp Ser Leu Thr Ser Gln Leu Thr Leu Leu Gly Gly Asn Ala Arg
            675                 680                 685

Gly Ser Phe Val His Ser Val Lys Pro Gly Ser Leu Ala Glu Lys Ala
        690                 695                 700

Gly Leu Arg Glu Gly His Gln Leu Leu Leu Leu Glu Gly Cys Ile Arg
705                 710                 715                 720

Gly Glu Arg Gln Ser Val Pro Leu Asp Thr Cys Thr Lys Glu Glu Ala
                725                 730                 735

His Trp Thr Ile Gln Arg Cys Ser Gly Pro Val Thr Leu His Tyr Lys
                740                 745                 750

Val Asn His Glu Gly Tyr Arg Lys Leu Val Lys Asp Met Glu Asp Gly
                755                 760                 765

Leu Ile Thr Ser Gly Asp Ser Phe Tyr Ile Arg Leu Asn Leu Asn Ile
        770                 775                 780

Ser Ser Gln Leu Asp Ala Cys Thr Met Ser Leu Lys Cys Asp Asp Val
785                 790                 795                 800

Val His Val Arg Asp Thr Met Tyr Gln Asp Arg His Glu Trp Leu Cys
                805                 810                 815

Ala Arg Val Asp Pro Phe Thr Asp His Asp Leu Asp Met Gly Thr Ile
                820                 825                 830

Pro Ser Tyr Ser Arg Ala Gln Gln Leu Leu Leu Val Lys Leu Gln Arg
            835                 840                 845

Leu Met His Arg Gly Ser Arg Glu Glu Val Asp Gly Thr His His Thr
850                 855                 860

Leu Arg Ala Leu Arg Asn Thr Leu Gln Pro Glu Glu Ala Leu Ser Thr
865                 870                 875                 880
```

```
Ser Asp Pro Arg Val Ser Pro Arg Leu Ser Arg Ala Ser Phe Leu Phe
                885                 890                 895

Gly Gln Leu Leu Gln Phe Val Ser Arg Ser Glu Asn Lys Tyr Lys Arg
            900                 905                 910

Met Asn Ser Asn Glu Arg Val Arg Ile Ile Ser Gly Ser Pro Leu Gly
            915                 920                 925

Ser Leu Ala Arg Ser Ser Leu Asp Ala Thr Lys Leu Leu Thr Glu Lys
        930                 935                 940

Gln Glu Glu Leu Asp Pro Glu Ser Glu Leu Gly Lys Asn Leu Ser Leu
945                 950                 955                 960

Ile Pro Tyr Ser Leu Val Arg Ala Phe Tyr Cys Glu Arg Arg Pro
                965                 970                 975

Val Leu Phe Thr Pro Thr Val Leu Ala Lys Thr Leu Val Gln Arg Leu
            980                 985                 990

Leu Asn Ser Gly Gly Ala Met Glu Phe Thr Ile Cys Lys Ser Asp Ile
        995                1000                1005

Val Thr Arg Asp Glu Phe Leu Arg Arg Gln Lys Thr Glu Thr Ile
               1010                1015                1020

Ile Tyr Ser Arg Glu Lys Asn Pro Asn Ala Phe Glu Cys Ile Ala
           1025                1030                1035

Pro Ala Asn Ile Glu Ala Val Ala Ala Lys Asn Lys His Cys Leu
           1040                1045                1050

Leu Glu Ala Gly Ile Gly Cys Thr Arg Asp Leu Ile Lys Ser Asn
           1055                1060                1065

Ile Tyr Pro Ile Val Leu Phe Ile Arg Val Cys Glu Lys Asn Ile
           1070                1075                1080

Lys Arg Phe Arg Lys Leu Leu Pro Arg Pro Glu Thr Glu Glu Glu
           1085                1090                1095

Phe Leu Arg Val Cys Arg Leu Lys Glu Lys Glu Leu Glu Ala Leu
           1100                1105                1110

Pro Cys Leu Tyr Ala Thr Val Glu Pro Asp Met Trp Gly Ser Val
           1115                1120                1125

Glu Glu Leu Leu Arg Val Val Lys Asp Lys Ile Gly Glu Glu Gln
           1130                1135                1140

Arg Lys Thr Ile Trp Val Asp Glu Asp Gln Leu
           1145                1150

<210> SEQ ID NO 20
<211> LENGTH: 1155
<212> TYPE: PRT
<213> ORGANISM: Homo sapiens

<400> SEQUENCE: 20

Met Pro Gly Gly Gly Pro Glu Met Asp Asp Tyr Met Glu Thr Leu Lys
1               5                   10                  15

Asp Glu Glu Asp Ala Leu Trp Glu Asn Val Cys Asn Arg His Met
                20                  25                  30

Leu Ser Arg Tyr Ile Asn Pro Ala Lys Leu Thr Pro Tyr Leu Arg Gln
            35                  40                  45

Cys Lys Val Ile Asp Glu Gln Asp Glu Asp Glu Val Leu Asn Ala Pro
        50                  55                  60

Met Leu Pro Ser Lys Ile Asn Arg Ala Gly Arg Leu Leu Asp Ile Leu
65                  70                  75                  80

His Thr Lys Gly Gln Arg Gly Tyr Val Val Phe Leu Glu Ser Leu Glu
```

```
                     85                  90                  95
Phe Tyr Tyr Pro Glu Leu Tyr Lys Leu Val Thr Gly Lys Glu Pro Thr
                100                 105                 110

Arg Arg Phe Ser Thr Ile Val Val Glu Glu Gly His Glu Gly Leu Thr
                115                 120                 125

His Phe Leu Met Asn Glu Val Ile Lys Leu Gln Gln Gln Met Lys Ala
130                 135                 140

Lys Asp Leu Gln Arg Cys Glu Leu Leu Ala Arg Leu Arg Gln Leu Glu
145                 150                 155                 160

Asp Glu Lys Lys Gln Met Thr Leu Thr Arg Val Glu Leu Leu Thr Phe
                165                 170                 175

Gln Glu Arg Tyr Tyr Lys Met Lys Glu Glu Arg Asp Ser Tyr Asn Asp
                180                 185                 190

Glu Leu Val Lys Val Lys Asp Asp Asn Tyr Asn Leu Ala Met Arg Tyr
                195                 200                 205

Ala Gln Leu Ser Glu Glu Lys Asn Met Ala Val Met Arg Ser Arg Asp
                210                 215                 220

Leu Gln Leu Glu Ile Asp Gln Leu Leu Lys His Arg Leu Asn Lys Met
225                 230                 235                 240

Glu Glu Glu Cys Lys Leu Glu Arg Asn Gln Ser Leu Lys Leu Lys Asn
                245                 250                 255

Asp Ile Glu Asn Arg Pro Lys Lys Glu Gln Val Leu Glu Leu Glu Arg
                260                 265                 270

Glu Asn Glu Met Leu Lys Thr Lys Asn Gln Glu Leu Gln Ser Ile Ile
                275                 280                 285

Gln Ala Gly Lys Arg Ser Leu Pro Asp Ser Asp Lys Ala Ile Leu Asp
                290                 295                 300

Ile Leu Glu His Asp Arg Lys Glu Ala Leu Glu Asp Arg Gln Glu Leu
305                 310                 315                 320

Val Asn Arg Ile Tyr Asn Leu Gln Glu Glu Ala Arg Gln Ala Glu Glu
                325                 330                 335

Leu Arg Asp Lys Tyr Leu Glu Glu Lys Glu Asp Leu Glu Leu Lys Cys
                340                 345                 350

Ser Thr Leu Gly Lys Asp Cys Glu Met Tyr Lys His Arg Met Asn Thr
                355                 360                 365

Val Met Leu Gln Leu Glu Glu Val Glu Arg Glu Arg Asp Gln Ala Phe
                370                 375                 380

His Ser Arg Asp Glu Ala Gln Thr Gln Tyr Ser Gln Cys Leu Ile Glu
385                 390                 395                 400

Lys Asp Lys Tyr Arg Lys Gln Ile Arg Glu Leu Glu Glu Lys Asn Asp
                405                 410                 415

Glu Met Arg Ile Glu Met Val Arg Arg Glu Ala Cys Ile Val Asn Leu
                420                 425                 430

Glu Ser Lys Leu Arg Arg Leu Ser Lys Asp Ser Asn Asn Leu Asp Gln
                435                 440                 445

Ser Leu Pro Arg Asn Leu Pro Val Thr Ile Ile Ser Gln Asp Phe Gly
                450                 455                 460

Asp Ala Ser Pro Arg Thr Asn Gly Gln Glu Ala Asp Asp Ser Ser Thr
465                 470                 475                 480

Ser Glu Glu Ser Pro Glu Asp Ser Lys Tyr Phe Leu Pro Tyr His Pro
                485                 490                 495

Pro Gln Arg Arg Met Asn Leu Lys Gly Ile Gln Leu Gln Arg Ala Lys
                500                 505                 510
```

```
Ser Pro Ile Ser Leu Lys Arg Thr Ser Asp Phe Gln Ala Lys Gly His
        515                 520                 525

Glu Glu Glu Gly Thr Asp Ala Ser Pro Ser Ser Cys Gly Ser Leu Pro
530                 535                 540

Ile Thr Asn Ser Phe Thr Lys Met Gln Pro Pro Arg Ser Arg Ser Ser
545                 550                 555                 560

Ile Met Ser Ile Thr Ala Glu Pro Pro Gly Asn Asp Ser Ile Val Arg
                565                 570                 575

Arg Tyr Lys Glu Asp Ala Pro His Arg Ser Thr Val Glu Glu Asp Asn
                580                 585                 590

Asp Ser Gly Gly Phe Asp Ala Leu Asp Leu Asp Asp Ser His Glu
                595                 600                 605

Arg Tyr Ser Phe Gly Pro Ser Ser Ile His Ser Ser Ser Ser His
                610                 615                 620

Gln Ser Glu Gly Leu Asp Ala Tyr Asp Leu Glu Gln Val Asn Leu Met
625                 630                 635                 640

Phe Arg Lys Phe Ser Leu Glu Arg Pro Phe Arg Pro Ser Val Thr Ser
                645                 650                 655

Val Gly His Val Arg Gly Pro Gly Pro Ser Val Gln His Thr Thr Leu
                660                 665                 670

Asn Gly Asp Ser Leu Thr Ser Gln Leu Thr Leu Leu Gly Gly Asn Ala
                675                 680                 685

Arg Gly Ser Phe Val His Ser Val Lys Pro Gly Ser Leu Ala Glu Lys
                690                 695                 700

Ala Gly Leu Arg Glu Gly His Gln Leu Leu Leu Leu Glu Gly Cys Ile
705                 710                 715                 720

Arg Gly Glu Arg Gln Ser Val Pro Leu Asp Thr Cys Thr Lys Glu Glu
                725                 730                 735

Ala His Trp Thr Ile Gln Arg Cys Ser Gly Pro Val Thr Leu His Tyr
                740                 745                 750

Lys Val Asn His Glu Gly Tyr Arg Lys Leu Val Lys Asp Met Glu Asp
                755                 760                 765

Gly Leu Ile Thr Ser Gly Asp Ser Phe Tyr Ile Arg Leu Asn Leu Asn
                770                 775                 780

Ile Ser Ser Gln Leu Asp Ala Cys Thr Met Ser Leu Lys Cys Asp Asp
785                 790                 795                 800

Val Val His Val Arg Asp Thr Met Tyr Gln Asp Arg His Glu Trp Leu
                805                 810                 815

Cys Ala Arg Val Asp Pro Phe Thr Asp His Asp Leu Asp Met Gly Thr
                820                 825                 830

Ile Pro Ser Tyr Ser Arg Ala Gln Gln Leu Leu Leu Val Lys Leu Gln
                835                 840                 845

Arg Leu Met His Arg Gly Ser Arg Glu Glu Val Asp Gly Thr His His
850                 855                 860

Thr Leu Arg Ala Leu Arg Asn Thr Leu Gln Pro Glu Glu Ala Leu Ser
865                 870                 875                 880

Thr Ser Asp Pro Arg Val Ser Pro Arg Leu Ser Arg Ala Ser Phe Leu
                885                 890                 895

Phe Gly Gln Leu Leu Gln Phe Val Ser Arg Ser Glu Asn Lys Tyr Lys
                900                 905                 910

Arg Met Asn Ser Asn Glu Arg Val Arg Ile Ile Ser Gly Ser Pro Leu
                915                 920                 925
```

```
Gly Ser Leu Ala Arg Ser Ser Leu Asp Ala Thr Lys Leu Leu Thr Glu
    930                 935                 940

Lys Gln Glu Glu Leu Asp Pro Glu Ser Glu Leu Gly Lys Asn Leu Ser
945                 950                 955                 960

Leu Ile Pro Tyr Ser Leu Val Arg Ala Phe Tyr Cys Glu Arg Arg
                965                 970                 975

Pro Val Leu Phe Thr Pro Thr Val Leu Ala Lys Thr Leu Val Gln Arg
                980                 985                 990

Leu Leu Asn Ser Gly Gly Ala Met Glu Phe Thr Ile Cys Lys Ser Asp
            995                 1000                1005

Ile Val Thr Arg Asp Glu Phe Leu Arg Arg Gln Lys Thr Glu Thr
    1010                1015                1020

Ile Ile Tyr Ser Arg Glu Lys Asn Pro Asn Ala Phe Glu Cys Ile
    1025                1030                1035

Ala Pro Ala Asn Ile Glu Ala Val Ala Ala Lys Asn Lys His Cys
    1040                1045                1050

Leu Leu Glu Ala Gly Ile Gly Cys Thr Arg Asp Leu Ile Lys Ser
    1055                1060                1065

Asn Ile Tyr Pro Ile Val Leu Phe Ile Arg Val Cys Glu Lys Asn
    1070                1075                1080

Ile Lys Arg Phe Arg Lys Leu Leu Pro Arg Pro Glu Thr Glu Glu
    1085                1090                1095

Glu Phe Leu Arg Val Cys Arg Leu Lys Glu Lys Glu Leu Glu Ala
    1100                1105                1110

Leu Pro Cys Leu Tyr Ala Thr Val Glu Pro Asp Met Trp Gly Ser
    1115                1120                1125

Val Glu Glu Leu Leu Arg Val Val Lys Asp Lys Ile Gly Glu Glu
    1130                1135                1140

Gln Arg Lys Thr Ile Trp Val Asp Glu Asp Gln Leu
    1145                1150                1155

<210> SEQ ID NO 21
<211> LENGTH: 1977
<212> TYPE: DNA
<213> ORGANISM: Homo sapiens

<400> SEQUENCE: 21
atggccgcag tgattctgga gagcatcttt ctgaagcgat ccaacagaa aaagaaaaca      60 tcacctctaa acttcaagaa gcgcctgttt ctcttgaccg tgcacaaact ctcctactat    120
gagtatgact tgaacgtgg gagaagaggc agtaagaagg gttcaataga tgttgagaag    180
atcacttgtg ttgaaacagt ggttcctgaa aaaatcctc ctccagaaag acagattccg    240
agaagaggtg aagagtccag tgaaatggag caaatttcaa tcattgaaag gttcccttat    300
cccttccagg ttgtatatga tgaagggcct ctctacgtct ctccccaac tgaagaacta    360 aggaagcggt ggattcacca gctcaaaaac gtaatccggt acaacagtga tctggttcag    420
aaatatcacc cttgcttctg gatcgatggg cagtatctct gctgctctca gacagccaaa    480
aatgctatgg gctgccaaat tttggagaac aggaatggaa gcttaaaacc tgggagttct    540
caccggaaga caaaaaagcc tcttccccca acgcctgagg aggaccagat cttgaaaaag    600
ccactaccgc tgagccagc agcagcacca gtctccacaa gtgagctgaa aaaggttgtg    660 gcccttatg attacatgcc aatgaatgca aatgatctac agctgcggaa gggtgatgaa    720
tattttatct tggaggaaag caacttacca tggtggagag cacgagataa aaatgggcag    780
```

```
gaaggctaca ttcctagtaa ctatgtcact gaagcagaag actccataga aatgtatgag      840
tggtattcca acacatgac tcggagtcag gctgagcaac tgctaaagca agagggaaa       900 gaaggaggtt tcattgtcag agactccagc aaagctggca aatatacagt gtctgtgttt     960
gctaaatcca caggggaccc tcaaggggtg atacgtcatt atgttgtgtg ttccacacct    1020
cagagccagt attacctggc tgagaagcac cttttcagca ccatccctga gctcattaac    1080
taccatcagc acaactctgc aggactcata tccaggctca aatatccagt gtctcaacaa    1140
aacaagaatg caccttccac tgcaggcctg ggatacggat catgggaaat tgatccaaag    1200
gacctgacct tcttgaagga gctggggact ggacaatttg gggtagtgaa gtatgggaaa    1260
tggagaggcc agtacgacgt ggccatcaag atgatcaaag aaggctccat gtctgaagat    1320
gaattcattg aagaagccaa agtcatgatg aatctttccc atgagaagct ggtgcagttg    1380
tatgcgtctg caccaagca gcgccccatc ttcatcatca ctgagtacat ggccaatggc    1440
tgcctcctga actacctgag ggagatgcgc caccgcttcc agactcagca gctgctagag    1500
atgtgcaagg atgtctgtga agccatggaa tacctggagt caaagcagtt ccttcaccga    1560
gacctggcag ctcgaaactg tttggtaaac gatcaaggag ttgttaaagt atctgatttc    1620
ggcctgtcca ggtatgtcct ggatgatgaa tacacaagct cagtaggctc caaatttcca    1680
gtccggtggt ccccaccgga agtcctgatg tatagcaagt tcagcagcaa atctgacatt    1740
tgggcttttg gggttttgat gtgggaaatt tactccctgg ggaagatgcc atatgagaga    1800
tttactaaca gtgagactgc tgaacacatt gcccaaggcc tacgtctcta caggcctcat    1860
ctggcttcag agaaggtata taccatcatg tacagttgct ggcatgagaa agcagatgag    1920
cgtcccactt tcaaaattct tctgagcaat attctagatg tcatggatga agaatcc      1977

<210> SEQ ID NO 22
<211> LENGTH: 1977
<212> TYPE: DNA
<213> ORGANISM: Homo sapiens

<400> SEQUENCE: 22
atggccgcag tgattctgga gagcatcttt ctgaagcgat cccaacagaa aaagaaaaca      60
tcacctctaa acttcaagaa gcgcctgttt ctcttgaccg tgcacaaact ctcctactat     120
gagtatgact ttgaacgtgg gagaagaggc agtaagaagg gttcaataga tgttgagaag     180
atcacttgtg ttgaaacagt ggttcctgaa aaaaatcctc ctccagaaag acagattccg     240
agaagaggtg aagagtccag tgaaatggag caaatttcaa tcattgaaag gttcccttat     300
cccttccagg ttgtatatga tgaagggcct ctctacgtct tctccccaac tgaagaacta     360
aggaagcggt ggattcacca gctcaaaaac gtaatccggt acaacagtga tctggttcag     420
aaatatcacc cttgcttctg gatcgatggg cagtatctct gctgctctca gacagccaaa     480
aatgctatgg gctgccaaat tttggagaac aggaatggaa gcttaaaacc tgggagttct     540
caccggaaga caaaaaagcc tcttccccca acgcctgagg aggaccagat cttgaaaaag     600
ccactaccgc ctgagccagc agcagcacca gtctccacaa gtgagctgaa aaaggttgtg     660 gcccttatg attacatgcc aatgaatgca aatgatctac agctgcggaa gggtgatgaa     720
tattttatct tggaggaaag caacttacca tggtggagag cacgagataa aaatgggcag     780
gaaggctaca ttcctagtaa ctatgtcact gaagcagaag actccataga aatgtatgag     840
tggtattcca acacatgac tcggagtcag gctgagcaac tgctaaagca agagggaaa     900 gaaggaggtt tcattgtcag agactccagc aaagctggca aatatacagt gtctgtgttt     960
```

```
gctaaatcca caggggaccc tcaaggggtg atacgtcatt atgttgtgtg ttccacacct    1020
cagagccagt attacctggc tgagaagcac cttttcagca ccatccctga gctcattaac    1080
taccatcagc acaactctgc aggactcata tccaggctca aatatccagt gtctcaacaa    1140
aacaagaatg caccttccac tgcaggcctg ggatacggat catgggaaat tgatccaaag    1200
gacctgacct tcttgaagga gctggggact ggacaatttg gggtagtgaa gtatgggaaa    1260
tggagaggcc agtacgacgt ggccatcaag atgatcaaag aaggctccat gtctgaagat    1320
gaattcattg aagaagccaa agtcatgatg aatctttccc atgagaagct ggtgcagttg    1380 tatgcgtct  gcaccaagca gcgccccatc ttcatcatca ctgagtacat ggccaatggc    1440
agcctcctga actacctgag ggagatgcgc caccgcttcc agactcagca gctgctagag    1500
atgtgcaagg atgtctgtga agccatggaa tacctggagt caaagcagtt ccttcaccga    1560
gacctggcag ctcgaaactg tttggtaaac gatcaaggag ttgttaaagt atctgatttc    1620
ggcctgtcca ggtatgtcct ggatgatgaa tacacaagct cagtaggctc caaatttcca    1680
gtccggtggt ccccaccgga agtcctgatg tatagcaagt tcagcagcaa atctgacatt    1740
tgggcttttg gggttttgat gtgggaaatt tactccctgg ggaagatgcc atatgagaga    1800
tttactaaca gtgagactgc tgaacacatt gcccaaggcc tacgtctcta caggcctcat    1860
ctggcttcag agaaggtata taccatcatg tacagttgtt ggcatgagaa agcagatgag    1920
cgtcccactt tcaaaattct tctgagcaat attctagatg tcatggatga agaatcc      1977

<210> SEQ ID NO 23
<211> LENGTH: 1977
<212> TYPE: DNA
<213> ORGANISM: Homo sapiens

<400> SEQUENCE: 23
atggccgcag tgattctgga gagcatcttt ctgaagcgat cccaacagaa aaagaaaaca      60
tcacctctaa acttcaagaa gcgcctgttt ctcttgaccg tgcacaaact ctcctactat     120
gagtatgact ttgaacgtgg gagaagaggc agtaagaagg gttaatagag tgttgagaag     180
atcacttgtg ttgaaacagt ggttcctgaa aaaaatcctc ctccagaaag acagattccg     240
agaagaggtg aagagtccag tgaaatggag caaatttcaa tcattgaaag gttcccttat     300 ccttccagg ttgtatatga tgaagggcct ctctacgtct ctccccaac tgaagaacta      360 aggaagcggt ggattcacca gctcaaaaac gtaatccggt acaacagtga tctggttcag     420
aaatatcacc cttgcttctg gatcgatggg cagtatctct gctgctctca gacagccaaa     480
aatgctatgg gctgccaaat tttggagaac aggaatggaa gcttaaaacc tgggagttct     540
caccggaaga caaaaaagcc tcttccccca acgcctgagg aggaccagat cttgaaaaag     600
ccactaccgc ctgagccagc agcagcacca gtctccacaa gtgagctgaa aaaggttgtg     660 gcccttatg attacatgcc aatgaatgca aatgatctac agctgcggaa gggtgatgaa     720
tattttatct tggaggaaag caacttacca tggtggagag cacgagataa aaatgggcag     780
gaaggctaca ttcctagtaa ctatgtcact gaagcagaag actccataga aatgtatgag     840
tggtattcca aacacatgac tcggagtcag gctgagcaac tgctaaagca agaggggaaa     900
gaaggaggtt tcattgtcag agactccagc aaagctggca atatacagt gtctgtgttt     960 gctaaatcca caggggaccc tcaaggggtg atacgtcatt atgttgtgtg ttccacacct    1020
cagagccagt attacctggc tgagaagcac cttttcagca ccatccctga gctcattaac    1080
```

```
taccatcagc acaactctgc aggactcata tccaggctca aatatccagt gtctcaacaa    1140
aacaagaatg caccttccac tgcaggcctg ggatacggat catgggaaat tgatccaaag    1200
gacctgacct tcttgaagga gctggggact ggacaatttg gggtagtgaa gtatgggaaa    1260
tggagaggcc agtacgacgt ggccatcaag atgatcaaag aaggctccat gtctgaagat    1320
gaattcattg aagaagccaa agtcatgatg aatctttccc atgagaagct ggtgcagttg    1380 tatgcgtct gcaccaagca gcgcccatc ttcatcatca ctgagtacat ggccaatggc    1440
tccctcctga actacctgag ggagatgcgc accgcttcc agactcagca gctgctagag    1500
atgtgcaagg atgtctgtga agccatggaa tacctggagt caaagcagtt ccttcaccga    1560
gacctggcag ctcgaaactg tttggtaaac gatcaaggag ttgttaaagt atctgatttc    1620
ggcctgtcca ggtatgtcct ggatgatgaa tacacaagct cagtaggctc caaatttcca    1680
gtccggtggt ccccaccgga agtcctgatg tatagcaagt tcagcagcaa atctgacatt    1740
tgggcttttg gggttttgat gtgggaaatt tactccctgg ggaagatgcc atatgagaga    1800
tttactaaca gtgagactgc tgaacacatt gcccaaggcc tacgtctcta caggcctcat    1860
ctggcttcag agaaggtata taccatcatg tacagttgct ggcatgagaa agcagatgag    1920
cgtcccactt tcaaaattct tctgagcaat attctagatg tcatggatga agaatcc       1977

<210> SEQ ID NO 24
<211> LENGTH: 3462
<212> TYPE: DNA
<213> ORGANISM: Homo sapiens

<400> SEQUENCE: 24
atgccaggag gagggccaga gatggatgac tacatggaga cgctgaagga tgaagaggac      60
gccttgtggg agaatgtgga gtgtaaccgg cacatgctca gccgctatat caaccctgcc    120
aagctcacgc cctacctgcg tcagtgtaag gtcattgatg agcaggatga agatgaagtg    180
cttaatgccc ctatgctgcc atccaagatc aaccgagcag gccggctgtt ggacattcta    240
cataccaagg ggcaaagggg ctatgtggtc ttcttggaga gcctagaatt ttattaccca    300
gaactgtaca aactggtgac tgggaaagag cccactcgga gattctccac cattgtggtg    360
gaggaaggcc acgagggcct cacgcacttc ctgatgaacg aggtcatcaa gctgcagcag    420
cagatgaagg ccaaggacct gcaacgctgc gagctgctgg ccaggttgcg gcagctggag    480
gatgagaaga gcagatgac gctgacgcgc gtggagctgc taaccttcca ggagcggtac    540
tacaagatga aggaagagcg ggacagctac aatgacgagc tggtcaaggt gaaggacgac    600
aactacaact tagccatgcg ctacgcacag ctcagtgagg agaagaacat ggcggtcatg    660
aggagccgag acctccaact cgagatcgat cagctaaagc accggttgaa taagatggag    720
gaggaatgta gctggagag aaatcagtct ctaaaactga agaatgacat tgaaaatcgg    780
cccaagaagg agcaggttct ggaactggag cgggagaatg aaatgctgaa gaccaaaaac    840
caggagctgc agtccatcat ccaggccggg aagcgcagcc tgccagactc agacaaggcc    900
atcctggaca tcttggaaca cgaccgcaag gaggccctgg aggacaggca ggagctggtc    960
aacaggatct acaacctgca ggaggaggcc cgccaggcag aggagctgcg agacaagtac   1020
ctggaggaga aggaggacct ggagctcaag tgctcgaccc tgggaaagga ctgtgaaatg   1080
tacaagcacc gcatgaacac ggtcatgctg cagctggagg aggtggagcg ggagcgggac   1140
caggccttcc actcccgaga tgaagctcag acacagtact cgcagtgctt aatcgaaaag   1200
gacaagtaca ggaagcagat ccgcgagctg gaggagaaga acgacgagat gaggatcgag   1260
```

```
atggtgcggc gggaggcctg catcgtcaac ctggagagca agctgcggcg cctctccaag    1320
gacagcaaca acctggacca gagtctgccc aggaacctgc cagtaaccat catctctcag    1380
gactttgggg atgccagccc caggaccaat ggtcaagaag ctgacgattc ttccacctcg    1440
gaggagtcac ctgaagacag caagtacttc ctgccctacc atccgcccca gcgcaggatg    1500
aacctgaagg gcatccagct gcagagagcc aaatccccca tcagcctgaa gcgaacatca    1560
gattttcaag ccaaggggca cgaggaagaa ggcacggacg ccagccctag ctcctgcgga    1620
tctctgccca tcaccaactc cttcaccaag atgcagcccc ccggagccg cagcagcatc    1680 atgtcaatca ccgccgagcc cccgggaaac gactccatcg tcagacgcta caaggaggac    1740
gcgccccatc gcagcacagt cgaagaagac aatgacagcg cgggtttga cgccttagat    1800 ctggatgatg acagtcacga acgctactcc ttcggaccct cctccatcca ctcctcctcc    1860
tcctcccacc aatccgaggg cctggatgcc tacgacctgg agcaggtcaa cctcatgttc    1920
aggaagttct ctctggaaag acccttccgg ccttcggtca cctctgtggg gcacgtgcgg    1980
ggcccagggc cctcggtgca gcacacgacg ctgaatggcg acagcctcac ctcccagctc    2040
accctgctgg ggggcaacgc gcgagggagc ttcgtgcact cggtcaagcc tggctctctg    2100
gccgagaaag ccggcctccg tgagggccac cagctgctgc tgctagaagg ctgcatccga    2160
ggcgagaggc agagtgtccc gttggacaca tgcaccaaag aggaagccca ctggaccatc    2220
cagaggtgca gcggccccgt cacgctgcac tacaaggtca ccacgaagg gtaccggaag    2280 ctggtgaagg acatggagga cggcctgatc acatcggggg actcgttcta catccggctg    2340
aacctgaaca tctccagcca gctggacgcc tgcaccatgt ccctgaagtg tgacgatgtt    2400
gtgcacgtcc gtgacaccat gtaccaggac aggcacgagt ggctgtgcgc gcgggtcgac    2460
cctttcacag accatgacct ggatatgggc accataccca gctacagccg agcccagcag    2520
ctcctcctgg tgaaactgca gcgcctgatg caccgaggca gccgggagga ggtagacggc    2580
acccaccaca ccctgcgggc actccggaac accctgcagc cagaagaagc gctttcaaca    2640
agcgaccccc gggtcagccc ccgtctctcg cgagcaagct tccttttgg ccagctcctt    2700 cagttcgtca gcaggtccga gaacaagtat aagcggatga cagcaacga gcgggtccgc    2760 atcatctcgg ggagtccgct agggagcctg gccggtcct cgctggacgc caccaagctc    2820
ttgactgaga agcaggaaga gctggaccct gagagcgagc tgggcaagaa cctcagcctc    2880 atccccctaca gcctggtacg cgccttctac tgcgagcgcc gccggcccgt gctcttcaca    2940
cccaccgtgc tggccaagac gctggtgcag aggctgctca actcgggagg tgccatggag    3000
ttcaccatct gcaagtcaga tatcgtcaca agagatgagt tcctcagaag gcagaagacg    3060
gagaccatca tctactcccg agagaagaac cccaacgcgt tcgaatgcat cgcccctgcc    3120
aacattgaag ctgtggccgc caagaacaag cactgcctgc tggaggctgg gatcggctgc    3180
acaagagact tgatcaagtc caacatctac cccatcgtgc tcttcatccg ggtgtgtgag    3240
aagaacatca gaggttcag aaagctgctg ccccgacctg agacggagga ggagttcctg    3300
cgcgtgtgcc ggctgaagga gaaggagctg gaggccctgc cgtgcctgta cgccacggtg    3360
gaacctgaca tgtgggggcag cgtagaggag ctgctccgcg ttgtcaagga caagatcggc    3420
gaggagcagc gcaagaccat ctgggtggac gaggaccagc tg                      3462
```

<210> SEQ ID NO 25
<211> LENGTH: 3465
<212> TYPE: DNA

<213> ORGANISM: Homo sapiens

<400> SEQUENCE: 25

```
atgccaggag gagggccaga gatggatgac tacatggaga cgctgaagga tgaagaggac      60
gccttgtggg agaatgtgga gtgtaaccgg cacatgctca gccgctatat caaccctgcc     120
aagctcacgc cctacctgcg tcagtgtaag gtcattgatg agcaggatga agatgaagtg     180
cttaatgccc ctatgctgcc atccaagatc aaccgagcag gccggctgtt ggacattcta     240
cataccaagg ggcaaagggg ctatgtggtc ttcttggaga gcctagaatt ttattaccca     300
gaactgtaca aactggtgac tgggaaagag cccactcgga gattctccac cattgtggtg     360
gaggaaggcc acgagggcct cacgcacttc ctgatgaacg aggtcatcaa gctgcagcag     420
cagatgaagg ccaaggacct gcaacgctgc gagctgctgg ccaggttgcg gcagctggag     480
gatgagaaga agcagatgac gctgacgcgc gtggagctgc taaccttcca ggagcggtac     540
tacaagatga aggaagagcg ggacagctac aatgacgagc tggtcaaggt gaaggacgac     600
aactacaact tagccatgcg ctacgcacag ctcagtgagg agaagaacat ggcggtcatg     660
aggagccgag acctccaact cgagatcgat cagctttttaa agcaccggtt gaataagatg     720
gaggaggaat gtaagctgga gagaaatcag tctctaaaac tgaagaatga cattgaaaat     780
cggcccaaga aggagcaggt tctggaactg gagcgggaga atgaaatgct gaagaccaaa     840
aaccaggagc tgcagtccat catccaggcc gggaagcgca gcctgccaga ctcagacaag     900
gccatcctgg acatcttgga cacgaccgc aaggaggccc tggaggacag caggagctg     960
gtcaacagga tctacaacct gcaggaggag gcccgccagg cagaggagct gcgagacaag    1020
tacctggagg agaaggagga cctggagctc aagtgctcga ccctgggaaa ggactgtgaa    1080
atgtacaagc accgcatgaa cacggtcatg ctgcagctgg aggaggtgga gcgggagcgg    1140
gaccaggcct ccactcccg agatgaagct cagacacagt actcgcagtg cttaatcgaa    1200
aaggacaagt acaggaagca gatccgcgag ctggaggaga gaacgacga gatgaggatc    1260
gagatggtgc ggcgggaggc ctgcatcgtc aacctggaga gcaagctgcg gcgcctctcc    1320
aaggacagca caaacctgga ccagagtctg cccaggaacc tgccagtaac catcatctct    1380
caggactttg gggatgccag ccccaggacc aatggtcaag aagctgacga ttcttccacc    1440
tcggaggagt cacctgaaga cagcaagtac ttcctgccct accatccgcc ccagcgcagg    1500
atgaacctga agggcatcca gctgcagaga gccaaatccc ccatcagcct gaagcgaaca    1560
tcagattttc aagccaaggg gcacgaggaa gaaggcacgg acgccagccc tagctcctgc    1620
ggatctctgc ccatcaccaa ctccttcacc aagatgcagc cccccggag ccgcagcagc    1680
atcatgtcaa tcaccgccga gccccgggga acgactccca tcgtcagacg ctacaaggag    1740
gacgcgcccc atcgcagcac agtcgaagaa acaatgaca gcggcgggtt tgacgcctta    1800
gatctggatg atgacagtca cgaacgctac tccttcggac cctcctccat ccactcctcc    1860
tcctcctccc accaatccga gggcctggat gcctacgacc tggagcaggt caacctcatg    1920
ttcaggaagt tctctctgga agacccttc cggccttcgg tcacctctgt ggggcacgtg    1980
cggggcccag ggccctcggt gcagcacacg acgctgaatg cgacagcct cacctcccag    2040
ctcaccctgc tgggggcaa cgcgcgaggg agcttcgtgc actcggtcaa gcctggctct    2100
ctggccgaga agccggcct ccgtgagggc caccagctgc tgctgctaga aggctgcatc    2160
cgaggcgaga ggcagagtgt cccgttggac acatgcacca agaggaagc ccactggacc    2220
atccagaggt gcagcggccc cgtcacgctg cactacaagg tcaaccacga agggtaccgg    2280
```

| | | |
|---|---|---|
| aagctggtga aggacatgga ggacggcctg atcacatcgg gggactcgtt ctacatccgg | 2340 | |
| ctgaacctga acatctccag ccagctggac gcctgcacca tgtccctgaa gtgtgacgat | 2400 | |
| gttgtgcacg tccgtgacac catgtaccag gacaggcacg agtggctgtg cgcgcgggtc | 2460 | |
| gacccttrca cagaccatga cctggatatg ggcaccatac ccagctacag ccgagcccag | 2520 | |
| cagctcctcc tggtgaaact gcagcgcctg atgcaccgag gcagccggga ggaggtagac | 2580 | |
| ggcacccacc acaccctgcg ggcactccgg aacaccctgc agccagaaga agcgctttca | 2640 | |
| acaagcgacc cccgggtcag ccccgtctc tcgcgagcaa gcttccttt tggccagctc | 2700 | |
| cttcagttcg tcagcaggtc cgagaacaag tataagcgga tgaacagcaa cgagcgggtc | 2760 | |
| cgcatcatct cggggagtcc gctagggagc ctggcccggt cctcgctgga cgccaccaag | 2820 | |
| ctcttgactg agaagcagga agagctggac cctgagagcg agctgggcaa gaacctcagc | 2880 | |
| ctcatcccct acagcctggt acgcgccttc tactgcgagc gccgccggcc cgtgctcttc | 2940 | |
| acacccaccg tgctggccaa gacgctggtg cagaggctgc tcaactcggg aggtgccatg | 3000 | |
| gagttcacca tctgcaagtc agatatcgtc acaagagatg agttcctcag aaggcagaag | 3060 | |
| acggagacca tcatctactc ccgagagaag aaccccaacg cgttcgaatg catcgcccct | 3120 | |
| gccaacattg aagctgtggc cgccaagaac aagcactgcc tgctggaggc tgggatcggc | 3180 | |
| tgcacaagag acttgatcaa gtccaacatc tacccccatcg tgctcttcat ccgggtgtgt | 3240 | |
| gagaagaaca tcaagaggtt cagaaagctg ctgccccgac ctgagacgga ggaggagttc | 3300 | |
| ctgcgcgtgt gccggctgaa ggagaaggag ctggaggccc tgccgtgcct gtacgccacg | 3360 | |
| gtggaacctg acatgtgggg cagcgtagag gagctgctcc gcgttgtcaa ggacaagatc | 3420 | |
| ggcgaggagc agcgcaagac catctgggtg gacgaggacc agctg | 3465 | |

<210> SEQ ID NO 26
<211> LENGTH: 3795
<212> TYPE: DNA
<213> ORGANISM: Homo sapiens

<400> SEQUENCE: 26

| | | |
|---|---|---|
| atgtccacca cggtcaatgt agattccctt gcggaatatg agaagagcca gatcaagaga | 60 | |
| gccctggagc tggggacggt gatgactgtg ttcagcttcc gcaagtccac ccccgagcgg | 120 | |
| agaaccgtcc aggtgatcat ggagacgcgg caggtggcct ggagcaagac cgccgacaag | 180 | |
| atcgagggct tcttggatat catggaaata aagaaatcc gcccagggaa gaactccaaa | 240 | |
| gatttcgagc gagcaaaagc agttcgccag aagaagact gctgcttcac catcctatat | 300 | |
| ggcactcagt tcgtcctcag cacgctcagc ttggcagctg actctaaaga ggatgcagtt | 360 | |
| aactggctct ctggcttgaa aatcttacac caggaagcga tgaatgcgtc cacgccacc | 420 | |
| attatcgaga gttggctgag aaagcagata tattctgtgg atcaaaccag aagaaacagc | 480 | |
| atcagtctcc gagagttgaa gaccatcttg ccctgatca actttaaagt gagcagtgcc | 540 | |
| aagttcctta agataagtt tgtggaaata ggagcacaca agatgagct cagctttgaa | 600 | |
| cagttccatc tcttctataa aaacttatg tttgaacagc aaaaatcgat tctcgatgaa | 660 | |
| ttcaaaaagg attcgtccgt gttcatcctg gggaacactg acaggccgga tgcctctgct | 720 | |
| gtttacctgc atgacttcca gaggtttctc atacatgaac agcaggagca ttgggctcag | 780 | |
| gatctgaaca aagtccgtga gcggatgaca aagttcattg atgacaccat gcgtgaaact | 840 | |
| gctgagcctt tcttgtttgt ggatgagttc ctcacgtacc tgtttcacg agaaaacagc | 900 | |

```
atctgggatg agaagtatga cgcggtggac atgcaggaca tgaacaaccc cctgtctcat    960
tactggatct cctcgtcaca taacacgtac cttacaggtg accagctgcg gagcgagtcg   1020
tccccagaag cttacatccg ctgcctgcgc atgggctgtc gctgcattga actggactgc   1080
tgggacgggc ccgatgggaa gccggtcatc taccatggct ggacgcggac taccaagatc   1140
aagtttgacg acgtcgtgca ggccatcaaa gaccacgcct ttgttacctc gagcttccca   1200
gtgatcctgt ccatcgagga gcactgcagc gtggagcaac agcgtcacat ggccaaggcc   1260
ttcaaggaag tatttggcga cctgctgttg acgaagccca cggaggccag tgctgaccag   1320
ctgccctcgc ccagccagct gcgggagaag atcatcatca agcataagaa gctgggcccc   1380
cgaggcgatg tggatgtcaa catggaggac aagaaggacg aacacaagca acaggggag   1440
ctgtacatgt gggattccat tgaccagaaa tggactcggc actactgcgc cattgccgat   1500
gccaagctgt ccttcagtga tgacattgaa cagactatgg aggaggaagt gccccaggat   1560
ataccccta cagaactaca ttttggggag aaatggttcc acaagaaggt ggagaagagg   1620
acgagtgccg agaagttgct gcaggaatac tgcatggaga cggggggcaa ggatggcacc   1680
ttcctggttc gggagagcga gaccttcccc aatgactaca ccctgtcctt ctggcggtca   1740
ggccgggtcc agcactgccg gatccgctcc accatggagg gcgggaccct gaaatactac   1800
ttgactgaca acctcacctt cagcagcatc tatgccctca tccagcacta ccgcgagacg   1860
cacctgcgct gcgccgagtt cgagctgcgg ctcacggacc ctgtgcccaa ccccaacccc   1920
cacgagtcca gccgtggta ctatgacagc ctgagccgcg agaggcaga ggacatgctg   1980
atgaggattc ccgggacgg ggccttcctg atccggaagc gagaggggag cgactcctat   2040
gccatcacct tcagggctag gggcaaggta aagcattgtc gcatcaaccg ggacggccgg   2100
cactttgtgc tggggacctc cgcctatttt gagagtctgg tggagctcgt cagttactac   2160
gagaagcatt cactctaccg aaagatgaga ctgcgctacc ccgtgacccc cgagctcctg   2220
gagcgctaca atatggaaag agatataaac tccctctacg acgtcagcag aatgtatgtg   2280
gatcccagtg aaatcaatcc gtccatgcct cagagaaccg tgaaagctct gtatgactac   2340
aaagccaagc gaagcgatga gctgagcttc tgccgtggtg ccctcatcca caatgtctcc   2400
aaggagcccg ggggctggtg gaaaggagac tatggaacca ggatccagca gtacttccca   2460
tccaactacg tcgaggacat ctcaactgca gacttcgagg agctagaaaa gcagattatt   2520
gaagacaatc ccttagggtc tctttgcaga ggaatattgg acctcaatac ctataacgtc   2580
gtgaaagccc ctcagggaaa aaaccagaag tcctttgtct tcatcctgga gcccaagcag   2640
cagggcgatc ctccggtgga gtttgccaca gacagggtgg aggagctctt tgagtggttt   2700
cagagcatcc gagagatcac ctggaagatt gacaccaagg agaacaacat gaagtactgg   2760
gagaagaacc agtccatcgc catcgagctc tctgacctgg ttgtctactg caaaccaacc   2820
agcaaaacca aggacaactt agaaaatcct gacttccgag aaatccgctc ctttgtggag   2880
acgaaggctg acagcatcat cagacagaag cccgtcgacc tcctgaagta caatcaaaag   2940
ggcctgaccc gcgtctaccc aaagggacaa agagttgact cttcaaacta cgaccccttc   3000
cgcctctggc tgtgcggttc tcagatggtg cactcaatt tccagacggc agataagtac   3060
atgcagatga atcacgcatt gttttctctc aatgggcgca cgggctacgt tctgcagcct   3120
gagagcatga ggacagagaa atatgacccg atgccacccg agtcccgagag gaagatcctg   3180
atgacgctga cagtcaaggt tctcggtgct cgccatctcc ccaaacttgg acgaagtatt   3240
gcctgtccct ttgtagaagt ggagatctgt ggagccgagt atgacaacaa caagttcaag   3300
```

```
acgacggttg tgaatgataa tggcctcagc cctatctggg ctccaacaca ggagaaggtg    3360
acatttgaaa tttatgaccc aaacctggca tttctgcgct tgtggttta tgaagaagat    3420 atgttcagcg atcccaactt tcttgctcat gccacttacc ccattaaagc agtcaaatca    3480
ggattcaggt ccgttcctct gaagaatggg tacagcgagg acatagagct ggcttccctc    3540
ctggttttct gtgagatgcg gccagtcctg gagagcgaag aggaacttta ctcctcctgt    3600
cgccagctga ggaggcggca agaagaactg aacaaccagc tctttctgta tgacacacac    3660
cagaacttgc gcaatgccaa ccgggatgcc ctggttaaag agttcagtgt taatgagaac    3720
cagctccagc tgtaccagga gaaatgcaac aagaggttaa gagagaagag agtcagcaac    3780
agcaagtttt actca                                                    3795

<210> SEQ ID NO 27
<211> LENGTH: 3795
<212> TYPE: DNA
<213> ORGANISM: Homo sapiens

<400> SEQUENCE: 27
atgtccacca cggtcaatgt agattccctt gcggaatatg agaagagcca gatcaagaga      60
gccctggagc tggggacggt gatgactgtg ttcagcttcc gcaagtccac ccccgagcgg     120
agaaccgtcc aggtgatcat ggagacgcgg caggtggcct ggagcaagac cgccgacaag     180
atcgagggct tcttggatat catggaaata aagaaatcc gcccagggaa gaactccaaa     240
gatttcgagc gagcaaaagc agttcgccag aaagaagact gctgcttcac catcctatat     300
ggcactcagt tcgtcctcag cacgctcagc ttggcagctg actctaaaga ggatgcagtt     360
aactggctct ctggcttgaa aatcttacac caggaagcga tgaatgcgtc cacgcccacc     420
attatcgaga gttggctgag aaagcagata tattctgtgg atcaaaccag aagaaacagc     480
atcagtctcc gagagttgaa gaccatcttg cccctgatca actttaaagt gagcagtgcc     540
aagttcctta agataagtt tgtggaaata ggagcacaca agatgagct cagctttgaa     600 cagttccatc tcttctataa aaacttatg tttgaacagc aaaaatcgat tctcgatgaa     660
ttcaaaaagg attcgtccgt gttcatcctg gggaacactg acaggccgga tgcctctgct     720
gtttacctgc atgacttcca gaggtttctc atacatgaac agcaggagca ttgggctcag     780
gatctgaaca aagtccgtga gcggatgaca aagttcattg atgacaccat gcgtgaaact     840
gctgagcctt tcttgtttgt ggatgagttc ctcacgtacc tgttttcacg agaaaacagc     900
atctgggatg agaagtatga cgcggtggac atgcaggaca tgaacaaccc cctgtctcat     960
tactggatct cctcgtcaca taacacgtac cttacaggtg accagctgcg gagcgagtcg    1020
tccccagaag cttacatccg ctgcctgcgc atgggctgtc gctgcattga actggactgc    1080
tgggacgggc ccgatgggaa gccggtcatc taccatggct ggacgcggac taccaagatc    1140
aagtttgacg acgtcgtgca ggccatcaaa gaccacgcct tgttacctc gagcttccca    1200 gtgatcctgt ccatcgagga gcactgcagc gtggagcaac agcgtcacat ggccaaggcc    1260
ttcaaggaag tatttggcga cctgctgttg acgaagccca cggaggccag tgctgaccag    1320 ctgcctcgc ccagccagct gcgggagaag atcatcatca gcataagaa gctgggcccc    1380 cgaggcgatg tggatgtcaa catggaggac aagaaggacg aacacaagca acaggggag    1440 ctgtacatgt gggattccat tgaccagaaa tggactcggc actactgcgc cattgccgat    1500
gccaagctgt ccttcagtga tgacattgaa cagactatga ggaggaagt gccccaggat    1560
```

```
atacccccta cagaactaca ttttggggag aaatggttcc acaagaaggt ggagaagagg      1620
acgagtgccg agaagttgct gcaggaatac tgcatggaga cgggggggcaa ggatggcacc     1680 ttcctggttc gggagagcga gaccttcccc aatgactaca ccctgtcctt ctggcggtca      1740
ggccgggtcc agcactgccg gatccgctcc accatggagg cgggacccct gaaatactac      1800
ttgactgaca acctcacctt cagcagcatc tatgccctca tccagcacta ccgcgagacg      1860
cacctgcgct cgcgccagtt cgagctgcgg ctcacggacc ctgtgcccaa ccccaacccc      1920
cacgagtcca agccgtggta ctatgacagc ctgagccgcg agaggcaga ggacatgctg       1980 atgaggattc cctgggacgg ggccttcctg atccggaagc gagaggggag cgactcctat      2040
gccatcacct tcagggctag ggcaaggta aagcattgtc gcatcaaccg ggacggccgg       2100
cactttgtgc tggggacctc cgcctatttt gagagtctgg tggagctcgt cagttactac      2160
gagaagcatt cactctaccg aaagatgaga ctgcgctacc ccgtgacccc cgagctcctg      2220
gagcgctaca atatggaaag agatataaac tccctctacg acgtcagcag aatgtatgtg      2280
gatcccagtg aaatcaatcc gtccatgcct cagagaaccg tgaaagctct gtatgactac      2340
aaagccaagc gaagcgatga gctgagcttc tgccgtggtg ccctcatcca caatgtctcc      2400
aaggagcccg gggctggtg gaaaggagac tatggaacca ggatccagca gtacttccca      2460
tccaactacg tcgaggacat ctcaactgca gacttcgagg agctagaaaa gcagattatt      2520
gaagacaatc ccttagggtc tctttgcaga ggaatattgg acctcaatac ctataacgtc      2580
gtgaaagccc ctcagggaaa aaaccagaag tcctttgtct tcatcctgga gcccaagcag      2640
cagggcgatc ctccggtgga gtttgccaca gacagggtgg aggagctctt tgagtggttt      2700
cagagcatcc gagagatcac ctggaagatt gacaccaagg agaacaacat gaagtactgg      2760
gagaagaacc agtccatcgc catcgagctc tctgacctgg ttgtctactg caaaccaacc      2820
agcaaaacca aggacaactt agaaaatcct gacttccgag aaatccgctc ctttgtggag      2880
acgaaggctg acagcatcat cagacagaag cccgtcgacc tcctgaagta caatcaaaag      2940
ggcctgaccc gcgtctaccc aaagggacaa agagttgact cttcaaacta cgacccctt c      3000 cgcctctggc tgtgcggttc tcagatggtg gcactcaatt tccagacggc agataagtac      3060
atgcagatga atcacgcatt gttttctctc aatgggcgca cgggctacgt tctgcagcct      3120
gagagcatga ggacagagaa atatgacccg atgccaccccg agtcccagag gaagatcctg      3180
atgacgctga cagtcaaggt tctcggtgct cgccatctcc ccaaacttgg acgaagtatt      3240
gcctgtccct tgtagaagt ggagatctgt ggagccgagt atgacaacaa caagttcaag       3300
acgacggttg tgaatgataa tggcctcagc cctatctggg ctccaacaca ggagaaggtg      3360
acatttgaaa tttatgaccc aaacctggca tttctgcgct ttgtggttta tgaagaagat      3420
atgttcagcg atcccaactt tcttgctcat gccacttacc ccattaaagc agtcaaatca      3480
ggattcaggt ccgttcctct gaagaatggg tacagcgagg acatagagct ggcttccctc      3540
ctggttttct gtgagatgcg gccagtcctg gagagcgaag gaactttta ctcctcctgt       3600 cgccagctga ggaggcggca agaagaactg aacaaccagc tctttctgta tgacacacac      3660
cagaacttgc gcaatgccaa ccgggatgcc tggttaaag agttcagtgt taatgagaac       3720
cagctccagc tgtaccagga gaaatgcaac aagaggttaa gagagaagag agtcagcaac      3780
agcaagtttt actca                                                      3795

<210> SEQ ID NO 28
<211> LENGTH: 3795
```

<212> TYPE: DNA
<213> ORGANISM: Homo sapiens

<400> SEQUENCE: 28

| | | | | | |
|---|---|---|---|---|---|
| atgtccacca | cggtcaatgt | agattccctt | gcggaatatg | agaagagcca | gatcaagaga | 60 |
| gccctggagc | tggggacggt | gatgactgtg | ttcagcttcc | gcaagtccac | ccccgagcgg | 120 |
| agaaccgtcc | aggtgatcat | ggagacgcgg | caggtggcct | ggagcaagac | cgccgacaag | 180 |
| atcgagggct | tcttggatat | catggaaata | aagaaatcc | gcccagggaa | gaactccaaa | 240 |
| gatttcgagc | gagcaaaagc | agttcgccag | aaagaagact | gctgcttcac | catcctatat | 300 |
| ggcactcagt | tcgtcctcag | cacgctcagc | ttggcagctg | actctaaaga | ggatgcagtt | 360 |
| aactggctct | ctggcttgaa | atcttacac | caggaagcga | tgaatgcgtc | cacgcccacc | 420 |
| attatcgaga | gttggctgag | aaagcagata | tattctgtgg | atcaaaccag | aagaaacagc | 480 |
| atcagtctcc | gagagttgaa | gaccatcttg | cccctgatca | actttaaagt | gagcagtgcc | 540 |
| aagttcctta | agataagtt | tgtggaaata | ggagcacaca | aagatgagct | cagctttgaa | 600 |
| cagttccatc | tcttctataa | aaacttatg | tttgaacagc | aaaaatcgat | tctcgatgaa | 660 |
| ttcaaaaagg | attcgtccgt | gttcatcctg | gggaacactg | acaggccgga | tgcctctgct | 720 |
| gtttacctgc | atgacttcca | gaggtttctc | atacatgaac | agcaggagca | ttgggctcag | 780 |
| gatctgaaca | aagtccgtga | gcggatgaca | aagttcattg | atgacaccat | gcgtgaaact | 840 |
| gctgagcctt | tcttgtttgt | ggatgagttc | ctcacgtacc | tgttttcacg | agaaaacagc | 900 |
| atctgggatg | agaagtatga | gcggtggac | atgcaggaca | tgaacaaccc | cctgtctcat | 960 |
| tactggatct | cctcgtcaca | taacacgtac | cttacaggtg | accagctgcg | gagcgagtcg | 1020 |
| tccccagaag | cttacatccg | ctgcctcgc | atgggctgtc | gctgcattga | actggactgc | 1080 |
| tgggacgggc | ccgatgggaa | gccggtcatc | taccatggct | ggacgcggac | taccaagatc | 1140 |
| aagtttgacg | acgtcgtgca | ggccatcaaa | gaccacgcct | tgttacctc | gagcttccca | 1200 |
| gtgatcctgt | ccatcgagga | gcactgcagc | gtggagcaac | agcgtcacat | ggccaaggcc | 1260 |
| ttcaaggaag | tatttggcga | cctgctgttg | acgaagccca | cggaggccag | tgctgaccag | 1320 |
| ctgccctcgc | ccagccagct | gcgggagaag | atcatcatca | agcataagaa | gctgggcccc | 1380 |
| cgaggcgatg | tggatgtcaa | catggaggac | aagaaggacg | aacacaagca | acaggggag | 1440 |
| ctgtacatgt | gggattccat | tgaccagaaa | tggactcggc | actactgcgc | cattgccgat | 1500 |
| gccaagctgt | ccttcagtga | tgacattgaa | cagactatgg | aggaggaagt | gccccaggat | 1560 |
| atacccccta | cagaactaca | ttttggggag | aaatggttcc | acaagaaggt | ggagaagagg | 1620 |
| acgagtgccg | agaagttgct | gcaggaatac | tgcatggaga | cgggggcaa | ggatggcacc | 1680 |
| ttcctggttc | gggagagcga | gaccttcccc | aatgactaca | ccctgtcctt | ctggcggtca | 1740 |
| ggccgggtcc | agcactgccg | gatccgctcc | accatggagg | gcgggaccct | gaaatactac | 1800 |
| ttgactgaca | acctccacct | cagcagcatc | tatgccctca | tccagcacta | ccgcgagacg | 1860 |
| cacctgcgct | gcgccgagtt | cgagctgcgg | ctcacggacc | ctgtgcccaa | ccccaacccc | 1920 |
| cacgagtcca | agccgtggta | ctatgacagc | ctgagccgcg | gagaggcaga | ggacatgctg | 1980 |
| atgaggattc | cccgggacgg | ggccttcctg | atccggaagc | gagaggggag | cgactcctat | 2040 |
| gccatcacct | tcagggctag | gggcaaggta | aagcattgtc | gcatcaaccg | ggacggccgg | 2100 |
| cactttgtgc | tggggacctt | cgcctatttt | gagagtctgg | tggagctcgt | cagttactac | 2160 |
| gagaagcatt | cactctaccg | aaagatgaga | ctgcgctacc | ccgtgacccc | cgagctcctg | 2220 |

```
gagcgctaca atatggaaag agatataaac tccctctacg acgtcagcag aatgtatgtg    2280
gatcccagtg aaatcaatcc gtccatgcct cagagaaccg tgaaagctct gtatgactac    2340
aaagccaagc gaagcgatga gctgagcttc tgccgtggtg ccctcatcca caatgtctcc    2400
aaggagcccg ggggctggtg gaaaggagac tatggaacca ggatccagca gtacttccca    2460
tccaactacg tcgaggacat ctcaactgca gacttcgagg agctagaaaa gcagattatt    2520
gaagacaatc ccttagggtc tctttgcaga ggaatattgg acctcaatac ctataacgtc    2580
gtgaaagccc ctcagggaaa aaaccagaag tcctttgtct tcatcctgga gcccaagcag    2640
cagggcgatc ctccggtgga gtttgccaca gacagggtgg aggagctctt tgagtggttt    2700
cagagcatcc gagagatcac ctggaagatt gacaccaagg agaacaacat gaagtactgg    2760
gagaagaacc agtccatcgc catcgagctc tctgacctgg ttgtctactg caaaccaacc    2820
agcaaaacca aggacaactt agaaaatcct gacttccgag aaatccgctc ctttgtggag    2880
acgaaggctg acagcatcat cagacagaag cccgtcgacc tcctgaagta caatcaaaag    2940
ggcctgaccc gcgtctaccc aaagggacaa agagttgact cttcaaacta cgacccttc    3000 cgcctctggc tgtgcggttc tcagatggtg gcactcaatt ccagacggc agataagtac    3060 atgcagatga atcacgcatt gttttctctc aatgggcgca cgggctacgt tctgcagcct    3120
gagagcatga ggacagagaa atatgacccg atgccacccg agtcccgag gaagatcctg    3180 atgacgctga cagtcaaggt tctcggtgct cgccatctcc ccaaacttgg acgaagtatt    3240
gcctgtccct ttgtagaagt ggagatctgt ggagccgagt atgacaacaa caagttcaag    3300
acgacggttg tgaatgataa tggcctcagc cctatctggg ctccaacaca ggagaaggtg    3360
acatttgaaa tttatgaccc aaacctggca tttctgcgct ttgtggttta tgaagaagat    3420
atgttcagcg atcccaactt tcttgctcat gccacttacc ccattaaagc agtcaaatca    3480
ggattcaggt ccgttcctct gaagaatggg tacagcgagg acatagagct ggcttccctc    3540 ctggtttttct gtgagatgcg gccagtcctg gagagcgaag aggaacttta ctcctcctgt    3600
cgccagctga ggaggcggca agaagaactg aacaaccagc tctttctgta tgacacacac    3660
cagaacttgc gcaatgccaa ccgggatgcc ctggttaaag agttcagtgt taatgagaac    3720
cagctccagc tgtaccagga gaaatgcaac aagaggttaa gagagaagag agtcagcaac    3780
agcaagtttt actca                                                     3795
```

MUTATIONS ASSOCIATED WITH RESISTANCE TO INHIBITORS OF BRUTON'S TYROSINE KINASE (BTK)

CROSS-REFERENCE

This application is a U.S. National Stage entry of International Application No. PCT/US2013/051741, filed Jul. 23, 2013; which claims the benefit of priority from U.S. Provisional Application Ser. No. 61/675,303, filed Jul. 24, 2012, 61/682,688, filed Aug. 13, 2012, and 61/780,652, filed Mar. 13, 2013, all of which are incorporated by reference in their entirety.

INCORPORATION BY REFERENCE OF SEQUENCE LISTING SUBMITTED AS A TEXT FILE VIA EFS-WEB

The instant application contains a Sequence Listing, which has been submitted as a computer readable text file in ASCII format via EFS-Web and is hereby incorporated in its entirety by reference herein. The text file, created date of Aug. 5, 2015, is named 25922-865-831SEQ.TXT and is 129,640 bytes in size.

BACKGROUND OF THE INVENTION

Bruton's Tyrosine Kinase (BTK) is member of the Tec family of non-receptor tyrosine kinases that is critically important for the growth, differentiation and activation of B-cells, myeloid cells, and mast cells. The BTK gene is located at cytogenetic band Xq21.33-q22 and comprises 19 exons, spanning 37 kb, encoding the full length BTK protein. Mutations in BTK are known in humans and result in the immunological disorder X-linked agammaglobulemia.

BTK is activated by membrane localization stimulated by $PIP_3$ (phosphatidlinositol-3,4,5-triphosphate) generation and bonding to the BTK pleckstrin homology (PH) domain, and transphosphorylation of Tyr-551 by Src family kinases. Activated BTK is involved in the phosphorylation of a number of signaling molecules involved in the PLCγ, JNK and p38 MAPK pathways, leading to Ca2+ mobilization, mRNA stabilization and the induction of NF-κB and AP-1 transcription factors. BTK activity is negatively regulated by a number of proteins including inhibitor of BTK (IBTK), Sab and c-Cbl. During antigenic challenge, the classical NF-κB pathway is strongly activated by B-cell receptor signaling, via formation of a "CBM" signaling complex consisting of CARD11, MALT1, and BCL10. The CBM lies downstream of PLCγ activation of BTK. The CBM pathway is pathologically altered in several lymphoma subtypes; mutations in CARD11 have been found to constitutively activate downstream NF-κB signaling.

BTK is essential to B-cell receptor (BCR) signaling and in knockout mouse models its mutation has a B cell-specific phenotype. BTK protein and mRNA are significantly over expressed in chronic lymphocytic leukemia (CLL) compared with normal B-cells. Although BTK is not always constitutively active in CLL cells, B-cell receptor (BCR) or CD40 signaling is accompanied by effective activation of this pathway. BTK activity is involved in the disease progression of B-cell malignancies, such as Non-Hodgkin's Lymphomas, such as chronic lymphocytic leukemia (CLL), mantle cell leukemia (MCL), follicular lymphoma (FL) and diffuse large B-cell lymphoma (DLBCL), and multiple myeloma (MM).

SUMMARY OF THE INVENTION

Described herein is the identification of mutations in the B-cell receptor pathway that confer resistance of patients to treatment of patients with an inhibitor of Bruton's Tyrosine Kinase (BTK). In some embodiments, the BTK inhibitor is one that covalently and/or irreversibly binds to BTK. In some embodiments, the BTK inhibitor is one that covalently and/or irreversibly binds to Cysteine 481 of BTK. In some embodiments, the BTK inhibitor is ibrutinib. In some embodiments, the patient has a B-cell proliferative disorder. In some embodiments, the patient has a B-cell malignancy. In some embodiments, the patient has a leukemia or a lymphoma. In some embodiments, the patient has Non-Hodgkin's Lymphoma. In some embodiments, the patient has chronic lymphocytic leukemia (CLL), mantle cell leukemia (MCL), follicular lymphoma (FL), diffuse large B-cell lymphoma (DLBCL), or multiple myeloma (MM). In some embodiments, the patient has a solid tumor, such as a carcinoma or a sarcoma.

Described herein is the identification of mutations in Bruton's Tyrosine Kinase (BTK) that confer resistance of the kinase to inhibition by BTK inhibitors that covalently and/or irreversibly bind to Cysteine 481 of BTK. Described herein are isolated mutant BTK polypeptides and isolated nucleic acids encoding mutant BTK polypeptides. Identification of the mutations described herein allows for the selection of patients for BTK inhibitor therapy, monitoring patients receiving a BTK inhibitor therapy and modification of BTK inhibitor therapeutic regimens. Described herein are diagnostic methods for detecting mutant BTK polypeptides and nucleic acids encoding mutant BTK polypeptides and uses thereof of such method. Also described herein are methods for the identification of second-generation BTK inhibitors that inhibit the mutant BTK polypeptides.

Described herein, in certain embodiments are methods for determining whether a subject is or likely to become less responsive to therapy with a covalent and/or irreversible Bruton's Tyrosine Kinase (BTK) inhibitor, comprising: (a) testing a sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1; and (b) characterizing the subject as resistant or likely to become resistant to therapy with a covalent and/or irreversible BTK inhibitor if the subject has the modification. In some embodiments, the method further comprises a step of obtaining the sample from the subject.

Described herein, in certain embodiments are methods for characterizing a BTK as resistant to inhibition with a covalent and/or irreversible BTK inhibitor in a subject, comprising: (a) testing s sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1; and (b) characterizing the BTK as resistant to inhibition with a covalent and/or irreversible BTK inhibitor if the subject has the modification. In some embodiments, the method further comprises a step of obtaining the sample from the subject.

Described herein, in certain embodiments are methods for monitoring whether a subject receiving a covalent and/or irreversible BTK inhibitor for treatment of a cancer has developed or is likely to develop resistance to the therapy, comprising: (a) testing a sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1; and (b) characterizing the subject as resistant or is likely to become resistant to therapy with a covalent and/or irreversible BTK inhibitor if the subject has the modification. In some embodiments, the method further comprises discontinuing treatment with the BTK inhibitor if the subject has the modification. In some embodiments, the method further comprises continuing treatment with a BTK inhibitor if the subject does not have the modification. In some embodiments, the method further comprises administering second generation BTK inhibitor that inhibits the modified kinase if the subject has the modification. In some embodiments, the method further comprises a step of obtaining the sample from the subject. In some embodiments, the method further comprises administering an inhibitor of LYN, SYK, JAK, PI3K, PLCγ, MAPK, MEK, or NFκB if the subject has the modification. In some embodiments, the method further comprises administering a covalent inhibitor of BTK that does not bind to C481 if the subject has the modification. In some embodiments, the method further comprises administering a reversible inhibitor of BTK if the subject has the modification.

Described herein, in certain embodiments are methods for optimizing the therapy of a subject receiving a covalent and/or irreversible BTK inhibitor for treatment of a cancer, comprising: (a) testing s sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1; and (b) discontinuing treatment with the irreversible BTK inhibitor if the subject has the modification or continuing treatment with the irreversible BTK inhibitor if the subject does not have the modification. In some embodiments, the method further comprises administering second generation BTK inhibitor that inhibits the modified kinase if the subject has the modification. In some embodiments, the method further comprises a step of obtaining the sample from the subject. In some embodiments, the method further comprises administering an inhibitor of LYN, SYK, JAK, PI3K, PLCγ, MAPK, MEK, or NFκB if the subject has the modification. In some embodiments, the method further comprises administering a covalent inhibitor of BTK that does not bind to C481 if the subject has the modification. In some embodiments, the method further comprises administering a reversible inhibitor of BTK if the subject has the modification.

Described herein, in certain embodiments are methods for selecting a subject for therapy with a second generation BTK inhibitor, comprising: (a) testing the sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1; and (b) characterizing the subject as a candidate for therapy with a second generation BTK inhibitor if the subject has the modification. In some embodiments, the method further comprises administering second generation BTK inhibitor that inhibits the modified kinase if the subject has the modification. In some embodiments, the method further comprises a step of obtaining the sample from the subject.

In some embodiments, the modification comprises a substitution or a deletion of the amino acid at amino acid position 481 in the BTK polypeptide. In some embodiments, the modification is a substitution of cysteine to an amino acid selected from among leucine, isoleucine, valine, alanine, glycine, methionine, serine, threonine, phenylalanine, tryptophan, lysine, arginine, histidine, proline, tyrosine, asparagine, glutamine, aspartic acid and glutamic acid at amino acid position 481 of the BTK polypeptide. In some embodiments, the modification is a substitution of cysteine to an amino acid selected from among serine, methionine, or threonine at amino acid position 481 of the BTK polypeptide. In some embodiments, the modification is a substitution of cysteine to serine at amino acid position 481 of the BTK polypeptide. In some embodiments, the modification comprises a deletion of nucleic acid encoding amino acid position 481 of the BTK polypeptide.

In some embodiments of the methods, the nucleic acid molecule for use in the assay is RNA or DNA. In some embodiments of the methods, the nucleic acid molecule for use in the assay is genomic DNA. In some embodiments of the methods, the nucleic acid molecule for use in the assay is total RNA. In some embodiments of the methods, the nucleic acid molecule for use in the assay is mRNA. In some embodiments of the methods, the method further comprises isolating mRNA from the RNA sample.

In some embodiments of the methods, testing comprises performing polymerase chain reaction (PCR) amplification of nucleic acid encoding amino acid position 481 of the BTK polypeptide. In some embodiments, PCR amplification comprises using a pair of oligonucleotide primers that flank the region encoding amino acid position 481 of the BTK polypeptide. In some embodiments, the method comprises sequencing the amplified nucleic acid.

In some embodiments of the methods, testing comprises contacting the nucleic acid with a sequence specific nucleic acid probe, wherein the sequence specific nucleic acid probe: (a) binds to nucleic acid encoding a modified BTK that is modified at amino acid position 481; and (b) does not bind to nucleic acid encoding the wild-type BTK having cysteine at amino acid position 481. In some embodiments of the methods, testing comprises PCR amplification using the sequence specific nucleic acid probe.

In some embodiments, the sample for use in the methods contains one or more tumor cells from the subject. In some embodiments, the sample for use in the methods contains circulating tumor DNA (ctDNA).

In some embodiments of the methods, the nucleic acid used in the method is isolated from a tumor cell sample from the subject. In some embodiments, the sample is a tumor biopsy sample, a blood sample, a serum sample, a lymph sample, or a bone marrow aspirate.

In some embodiments of the methods, the BTK inhibitor is a covalent and/or irreversible BTK inhibitor that covalently binds to cysteine 481 of the wild-type BTK. In some embodiments, the BTK inhibitor is selected from among ibrutinib (PCI-32765), PCI-45292, PCI-45466, AVL-101, AVL-291, AVL-292, or ONO-WG-37. In some embodiments, the BTK inhibitor is ibrutinib.

In some embodiments of the methods, the subject has cancer. In some embodiments, the cancer is a hematologic cancer. In some embodiments, cancer is a B-cell malignancy. In some embodiments, cancer is selected from among a leukemia, a lymphoma, or a myeloma. In some embodiments, the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the subject has a solid tumor.

In some embodiments of the methods, the subject is treated with the irreversible BTK inhibitor prior to obtaining the sample. In some embodiments, the sample is obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, or 24 months following the first administration of the irreversible BTK inhibitor. In some embodiments, the sample is obtained 1, 2, 3, 4, 5, 6, 7, 8, 9, 10 times over the course of treatment with the irreversible BTK inhibitor. In some embodiments, the subject is responsive the treatment with the irreversible BTK inhibitor when it is first administered.

Described herein, in certain embodiments are methods for screening compounds that inhibit a modified BTK, comprising: (a) providing a modified BTK, wherein the modified BTK is modified at an amino acid position corresponding to amino acid position 481 of the amino acid sequence set forth in SEQ ID NO: 1; (b) contacting the modified BTK with a test compound; and (c) detecting the level of BTK activity, wherein a decrease in activity indicates that the compound inhibits the modified BTK. In some embodiments, the modification is a substitution or deletion of the amino acid at position 481 of the BTK polypeptide. In some embodiments, the modification is a substitution of cysteine to an amino acid selected from among leucine, isoleucine, valine, alanine, glycine, methionine, serine, threonine, phenylalanine, tryptophan, lysine, arginine, histidine, proline, tyrosine, asparagine, glutamine, aspartic acid and glutamic acid at amino acid position 481 of the BTK polypeptide. In some embodiments, the modification is a substitution of cysteine to an amino acid selected from among serine, methionine and threonine at amino acid position 481 of the BTK polypeptide. In some embodiments, the modification is a substitution of cysteine to serine at amino acid position 481 of the BTK polypeptide. In some embodiments, detecting the level of BTK activity is assessed by an in vitro kinase assay. In some embodiments, the substrate used in the kinase assay is PLeγ, ERK1/2, or AKT. In some embodiments, the substrate used in the kinase assay is a peptide substrate. In some embodiments, ibrutinib is employed as a negative control.

In some embodiments, the modified BTK polypeptide is purified from a host cell expressing the modified BTK polypeptide prior to contacting the BTK with the test compound. In some embodiments, the host cell stably expresses the modified BTK polypeptide. In some embodiments, the modified BTK polypeptide is purified by immunoaffinity or chromatography. In some embodiments, the cell is deficient for the expression of endogenous wild-type BTK. In some embodiments, the cell is chicken DT40 BTK−/− B cell or human BTK−/− B cell. In some embodiments, the cell is a non B-cell. In some embodiments, the cell is a mammalian non-B-cell. In some embodiments, the cell is a CHO cell or a Jurkat T cell. In some embodiments, the cell is a non-mammalian cell. In some embodiments, the cell is an insect cell, a bacterial cell, a yeast cell, or a plant cell.

Described herein, in certain embodiments, are isolated BTK polypeptides or variants thereof having BTK activity comprising a modification at an amino acid position corresponding to amino acid position 481 of the amino acid sequence set forth in SEQ ID NO: 1, wherein the modification confers resistance of the modified BTK polypeptide or variant to inhibition with a covalent and/or irreversible BTK inhibitor. In some embodiments, the modification confers resistance of a cancer cell to treatment with a covalent and/or irreversible BTK inhibitor. In some embodiments, the modification comprises substitution of the amino acid at position 481 compared to a wild type BTK set forth in SEQ ID NO: 1. In some embodiments, the substitution is C481S. In some embodiments, the modification comprises a deletion of amino acid position 481. In some embodiments, the BTK polypeptide comprises a substitution of the amino acid at position 481 compared to a wild type BTK set forth in SEQ ID NO: 1 and one or more additional amino acid substitutions. In some embodiments, the BTK polypeptide comprises the sequence of amino acids set forth in SEQ ID NO: 2 or a variant that has at least or at least about 60%, 70%, 75%, 80%, 85%, 90%, 95%, 96%, 97%, 98%, 99% or more sequence identity with the polypeptide having the sequence set forth in SEQ ID NO: 2, wherein the amino acid at position 481 is not cysteine. In some embodiments, the isolated BTK polypeptide or a variant thereof is a recombinant protein. In some embodiments, the isolated BTK polypeptide or a variant thereof is a purified protein. In some embodiments, the isolated BTK polypeptide or a variant thereof is a purified from a cell. In some embodiments, the cell is a prokaryotic cell or a eukaryotic cell. In some embodiments, the cell is a mammalian cell, a bacterial cell, a yeast cell, an insect cell, a plant cell, or an amphibian cell. In some embodiments, the cell is a primate cell. In some embodiments, the cell is a human cell. In some embodiments, the modified BTK polypeptide is a recombinant polypeptide.

Described herein, in certain embodiments, are isolated nucleic acid molecules encoding a modified BTK polypeptide provided herein. In some embodiments, the nucleic acid is a DNA or an RNA molecule. In some embodiments, the nucleic acid is a cDNA molecule. In some embodiments, the nucleic acid is a PCR amplification product. In some embodiments, the nucleic acid is a recombinant molecule. In some embodiments, the nucleic acid is a synthetic molecule. In some embodiments, the nucleic acid comprises the sequence of nucleic acids set forth in SEQ ID NO: 3, wherein the nucleic acid codon encoding amino acid at position 481 is modified, whereby the codon does not encode cysteine, or a variant that has at least or at least about 60%, 70%, 75%, 80%, 85%, 90%, 95%, 96%, 97%, 98%, 99% or more sequence identity with the polypeptide having the sequence set forth in SEQ ID NO: 3, wherein the nucleic acid codon encoding amino acid at position 481 does not encode cysteine. In some embodiments, the nucleic acid comprises the sequence of nucleic acids set forth in SEQ ID NO: 7, or a variant that has at least or at least about 60%, 70%, 75%, 80%, 85%, 90%, 95%, 96%, 97%, 98%, 99% or more sequence identity with the nucleic acid having the sequence set forth in SEQ ID NO: 7, wherein the nucleic acid codon encoding amino acid at position 481 does not encode cysteine. In some embodiments, the nucleic acid comprises the sequence of nucleic acids set forth in SEQ ID NO: 8, or a variant that has at least or at least about 60%, 70%, 75%, 80%, 85%, 90%, 95%, 96%, 97%, 98%, 99% or more sequence identity with the nucleic acid having the sequence set forth in SEQ ID NO: 8, wherein the nucleic acid codon encoding amino acid at position 481 does not encode cysteine. In some embodiments, the nucleic acid comprises the sequence of nucleic acids set forth in SEQ ID NO: 22, or a variant that has at least or at least about 60%, 70%, 75%, 80%, 85%, 90%, 95%, 96%, 97%, 98%, 99% or more sequence identity with the nucleic acid having the sequence set forth in SEQ ID NO: 22, wherein the nucleic acid codon encoding amino acid at position 481 does not encode cysteine. In some embodiments, the nucleic acid comprises the sequence of nucleic acids set forth in SEQ ID NO: 23, or a variant that has at least or at least about 60%, 70%, 75%, 80%, 85%, 90%, 95%, 96%, 97%, 98%, 99% or more sequence identity with the nucleic acid having the sequence set forth in SEQ ID NO: 23, wherein the nucleic acid codon encoding amino acid at position 481 does not encode cysteine. In some embodiments, the modified BTK polypeptide is a recombinant polypeptide.

Described herein, in certain embodiments, are vectors, comprising a nucleic acid molecule encoding a modified BTK polypeptide provided herein. In some embodiments, the vector is a viral or plasmid vector. In some embodiments, the nucleic acid is operably linked to a promoter. In some embodiments, the promoter is a constitutive or an inducible promoter. Described herein, in certain embodiments, is a host cell, comprising a nucleic acid molecule encoding a modified BTK polypeptide provided herein or a vector comprising a nucleic acid molecule encoding a modified BTK polypeptide provided herein. In some embodiments, the cell is a prokaryotic cell or a eukaryotic cell. In some embodiments, the cell is a mammalian cell, a bacterial cell, a yeast cell, an insect cell, a plant cell, or an amphibian cell. In some embodiments, the cell is a primate cell. In some embodiments, the cell is a human cell. Described herein, in certain embodiments, is a mutant BTK polypeptide expressed by the host cell.

Described herein, in certain embodiments, are kits comprising the mutant BTK polypeptide or a variant thereof having BTK activity comprising a modification at an amino acid position corresponding to amino acid position 481 of the amino acid sequence set forth in SEQ ID NO: 1. In some embodiments, the modification is a substitution of cysteine to serine at amino acid position 481 of the BTK polypeptide.

Described herein, in certain embodiments, are microchips comprising the mutant BTK polypeptide provided herein or the nucleic acid encoding a modified BTK polypeptide provided herein. In some embodiments, the modification is a substitution of cysteine to serine at amino acid position 481 of the BTK polypeptide.

Described herein, in certain embodiments, are kits comprising the isolated nucleic acid of any encoding a modified BTK polypeptide provided herein or a vector comprising such nucleic acid. In some embodiments, the modification is a substitution of cysteine to senile at amino acid position 481 of the BTK polypeptide.

Described herein, in certain embodiments, are kits comprising one or more reagents for the detection of a modified BTK polypeptide comprising a modification at amino acid position 481. In some embodiments, the kit comprises a microchip comprising a mutant BTK polypeptide having a modification that is C481S.

Described herein, in certain embodiments, are kits comprising one or more reagents for the detection of nucleic acid encoding a mutant BTK polypeptide comprising a modification at amino acid position 481. In some embodiments, the kit comprises a microchip comprising nucleic acid encoding a mutant BTK polypeptide having a modification that is C481S.

Described herein, in certain embodiments, are isolated antibodies that bind to a modified BTK polypeptide having a modification and amino acid position 481, wherein the antibody does not bind to or binds with lower affinity to a wild-type BTK polypeptide having the sequence of amino acids set forth in SEQ ID NO: 1. In some embodiments, the modification is a substitution of cysteine to serine at amino acid position 481 of the BTK polypeptide.

Described herein, in certain embodiments, are systems for detecting a modified BTK that is resistant to inhibition with a covalent and/or irreversible BTK inhibitor in a subject, comprising: (a) a sample containing a nucleic acid molecule encoding a BTK polypeptide from the subject; and (b) a microarray comprising nucleic acid encoding a mutant BTK polypeptide or a portion thereof that is modified at an amino acid position corresponding to amino acid position 481 of the amino acid sequence set forth in SEQ ID NO: 1. In some embodiments, the microarray is contained on a microchip.

Described herein, in certain embodiments, are systems for detecting a modified BTK that is resistant to inhibition with a covalent and/or irreversible BTK inhibitor in a subject, comprising: (a) a sample containing a nucleic acid molecule encoding a BTK polypeptide from the subject; and (b) a sequence specific nucleic acid probe, wherein the sequence specific nucleic acid probe: (i) binds to nucleic acid encoding a modified BTK that is modified at amino acid position 481; and (ii) does not bind to nucleic acid encoding the wild-type BTK having cysteine at amino acid position 481.

Described herein, in certain embodiments, are systems for detecting a modified BTK that is resistant to inhibition with a covalent and/or irreversible BTK inhibitor in a subject, comprising: (a) a sample containing a nucleic acid molecule encoding a BTK polypeptide from the subject; and (b) a pair oligonucleotide primers that flank the nucleic acid region encoding amino acid 481 of a BTK polypeptide.

Described herein, in certain embodiments, are methods of maintenance therapy in a patient having a hematologic cancer, comprising: (a) administering to the patient a maintenance therapy regimen comprising administering a therapeutically effective dose of a covalent and/or irreversible BTK inhibitor; and (b) monitoring the patient at predetermined intervals of time over the course of the maintenance therapy regimen to determine whether the subject has mutation in an endogenous gene encoding BTK that results in a modification at an amino acid position corresponding to amino acid position 481 of the amino acid sequence set forth in SEQ ID NO: 1. In some embodiments, monitoring comprises: (a) testing a sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1. In some embodiments, the method further comprises discontinuing the maintenance therapy regimen if the subject has the mutation. In some embodiments, the method further comprises continuing the maintenance therapy regimen if the subject does not have the mutation. In some embodiments, the method further comprises administering second generation BTK inhibitor that inhibits the modified BTK if the subject has the mutation. In some embodiments, the method further comprises administering an inhibitor of LYN, SYK, JAK, PI3K, PLCγ, MAPK, MEK, or NFκB if the subject has the modification. In some embodiments, the method further comprises administering a covalent inhibitor of BTK that does not bind to C481 if the subject has the modification. In some embodiments, the method further comprises administering a reversible inhibitor of BTK if the subject has the modification. In some embodiments, the modification in the BTK polypeptide is C481S. In some embodiments, the mutation in the nucleic acid is a mutation of guanine to cytosine at nucleic acid position corresponding to nucleic acid position 1635 in the sequence of nucleotides set forth in SEQ ID NO: 3. In some embodiments, the mutation in the nucleic acid is a mutation of thymine to adenine at nucleic acid position corresponding to nucleic acid position 1634 in the sequence of nucleotides set forth in SEQ ID NO: 3. In some embodiments, the predetermined interval of time is every month, every 2 months, every 3 months, every 4 months, every 5 months, every 6 months, every 7 months, every 8 months, every 9 months, every 10 months, every 11 months, or every year. In some embodiments, the sample contains one or more cancer cells. In some embodiments, the he sample contains ctDNA. In some embodiments, the method further comprises testing a sample from the subject prior to treatment with the irreversible BTK inhibitor. In some embodiments, the hematologic cancer is a B-cell malignancy. In some embodiments, the cancer is a leukemia, a lymphoma, or a myeloma. In some embodiments, the cancer is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic leukemia, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the subject has a solid tumor. In some embodiments, the B-cell malignancy is chronic lymphocytic leukemia (CLL). In some embodiments, the irreversible BTK inhibitor is selected from among ibrutinib, PCI-45292, PCI-45466, AVL-101, AVL-291, AVL-292, or ONO-WG-37. In some embodiments, the irreversible BTK inhibitor is ibrutinib. In some embodiments, ibrutinib is administered at a daily dosage of about 10 mg per day to about 2000 mg per day, about 50 mg per day to about 1500 mg per day, about 100 mg per day to about 1000 mg per day, about 250 mg per day to about 850 mg per day, or about 300 mg per day to about 600 mg per day. In some embodiments, ibrutinib is administered at a daily dosage of about 140 mg per day, 420 mg per day, 560 mg per day or 840 mg per day.

Described herein, in certain embodiments are methods for monitoring whether a subject receiving a BTK inhibitor for treatment of a cancer has developed or is likely to develop resistance to the therapy, comprising: (a) testing a sample containing a nucleic acid molecule encoding a PLCγ2 polypeptide from the subject to determine whether the encoded PLCγ2 polypeptide is modified at an amino acid position corresponding to amino acid position 665 or 707 of the amino acid sequence set forth in SEQ ID NO: 11; and (b) characterizing the subject as resistant or is likely to become resistant to therapy with a BTK inhibitor if the subject has the modification. In some embodiments, the method further comprises discontinuing treatment with the BTK inhibitor if the subject has the modification. In some embodiments, the method further comprises continuing treatment with a BTK inhibitor if the subject does not have the modification. In some embodiments, the method further comprises a step of obtaining the sample from the subject. In some embodiments, the method further comprises administering an inhibitor of LYN, SYK, JAK, PI3K, MAPK, MEK, or NFκB if the subject has the modification. In some embodiments, the modification comprises a R665W or S707F substitution in PLCγ2. In some embodiments, the BTK inhibitor is a covalent or irreversible inhibitor.

Described herein, in certain embodiments are methods for optimizing the therapy of a subject receiving an irreversible BTK inhibitor for treatment of a cancer, comprising: (a) testing a sample containing a nucleic acid molecule encoding a PLCγ2 polypeptide from the subject to determine whether the encoded PLCγ2 polypeptide is modified at an amino acid position corresponding to amino acid position 665 of the amino acid sequence set forth in SEQ ID NO: 11; and (b) discontinuing treatment with the irreversible BTK inhibitor if the subject has the modification or continuing treatment with the irreversible BTK inhibitor if the subject does not have the modification. In some embodiments, the method further comprises administering second generation BTK inhibitor that inhibits the modified kinase if the subject has the modification. In some embodiments, the method further comprises a step of obtaining the sample from the subject. In some embodiments, the method further comprises administering an inhibitor of LYN, SYK, JAK, PI3K, MAPK, MEK, or NFκB if the subject has the modification. In some embodiments, the modification comprises a R665W or S707F substitution in PLCγ2. In some embodiments, the BTK inhibitor is a covalent or irreversible inhibitor.

In some embodiments of the methods, the nucleic acid molecule for use in the assay is RNA or DNA. In some embodiments of the methods, the nucleic acid molecule is a cDNA In some embodiments of the methods, the nucleic acid molecule for use in the assay is genomic DNA. In some embodiments of the methods, the nucleic acid molecule for use in the assay is total RNA. In some embodiments of the methods, the nucleic acid molecule for use in the assay is mRNA. In some embodiments of the methods, the method further comprises isolating mRNA from the RNA sample.

In some embodiments of the methods, testing comprises performing polymerase chain reaction (PCR) amplification of nucleic acid encoding amino acid position 665 or 707 of the PLCγ2 polypeptide. In some embodiments, PCR amplification comprises using a pair of oligonucleotide primers that flank the region encoding amino acid position 665 or 707 of the PLCγ2 polypeptide. In some embodiments, the method comprises sequencing the amplified nucleic acid.

In some embodiments of the methods, testing comprises contacting the nucleic acid with a sequence specific nucleic acid probe, wherein the sequence specific nucleic acid probe: (a) binds to nucleic acid encoding a modified PLCγ2 that is modified at amino acid position 665; and (b) does not bind to nucleic acid encoding the wild-type PLCγ2 having Arginine at amino acid position 665 or 707. In some embodiments of the methods, testing comprises PCR amplification using the sequence specific nucleic acid probe.

In some embodiments, the sample for use in the methods contains one or more tumor cells from the subject. In some embodiments, the sample for use in the methods contains circulating tumor DNA (ctDNA).

In some embodiments of the methods, the nucleic acid used in the method is isolated from a tumor cell sample from the subject. In some embodiments, the sample is a tumor biopsy sample, a blood sample, a serum sample, a lymph sample, or a bone marrow aspirate.

In some embodiments, the BTK inhibitor is selected from among ibrutinib (PCI-32765), PCI-45292, PCI-45466, AVL-101, AVL-291, AVL-292, or ONO-WG-37. In some embodiments, the PLCγ2 inhibitor is ibrutinib.

In some embodiments of the methods, the subject has cancer. In some embodiments, the cancer is a hematologic cancer. In some embodiments, cancer is a B-cell malignancy. In some embodiments, cancer is selected from among a leukemia, a lymphoma, or a myeloma. In some embodiments, the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the subject has a solid tumor.

In some embodiments of the methods, the subject is treated with the BTK inhibitor prior to obtaining the sample. In some embodiments, the sample is obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, or 24 months following the first administration of the irreversible BTK inhibitor. In some embodiments, the sample is obtained 1, 2, 3, 4, 5, 6, 7, 8, 9, 10 times over the course of treatment with the BTK inhibitor. In some embodiments, the subject is responsive the treatment with the BTK inhibitor when it is first administered.

Described herein, in certain embodiments, is a kit comprising one or more reagents for the detection of a modified PLCγ2 polypeptide comprising a modification at amino acid position 665. In some embodiments, the kit comprises a microchip comprising a mutant PLCγ2 polypeptide having a modification that is R665W or S707F.

Described herein, in certain embodiments, is a kit comprising one or more reagents for the detection of nucleic acid encoding a mutant PLCγ2 polypeptide comprising a modification at amino acid position 665 or 707. In some embodiments, the kit comprises a microchip comprising nucleic acid encoding a mutant PLCγ2 polypeptide having a modification that is R665W or S707F.

Described herein, in certain embodiments, is a system for detecting a modified PLCγ2 that confers resistance to inhibition with an irreversible BTK inhibitor in a subject, comprising: (a) a sample containing a nucleic acid molecule encoding a PLCγ2 polypeptide from the subject; and (b) a microarray comprising nucleic acid encoding a mutant PLCγ2 polypeptide or a portion thereof that is modified at an amino acid position corresponding to amino acid position 665 or 707 of the amino acid sequence set forth in SEQ ID NO: 11. In some embodiments, the microarray is contained on a microchip.

Described herein, in certain embodiments, is a system for detecting a modified PLCγ2 that that confers resistance to inhibition with a BTK inhibitor in a subject, comprising: (a) a sample containing a nucleic acid molecule encoding a PLCγ2 polypeptide from the subject; and (b) a sequence specific nucleic acid probe, wherein the sequence specific nucleic acid probe: (i) binds to nucleic acid encoding a modified PLCγ2 that is modified at amino acid position 665 or 707; and (ii) does not bind to nucleic acid encoding the wild-type PLCγ2 having Arginine at amino acid position 665 or serine at position 707.

Described herein, in certain embodiments, is a system for detecting a modified PLCγ2 that that confers resistance to inhibition with an BTK inhibitor in a subject, comprising: (a) a sample containing a nucleic acid molecule encoding a PLCγ2 polypeptide from the subject; and (b) a pair oligonucleotide primers that flank the nucleic acid region encoding amino acid 665 or 707 of a PLCγ2 polypeptide.

Described herein, in certain embodiments, is method of maintenance therapy in a patient having a hematologic cancer, comprising: (a) administering to the patient a maintenance therapy regimen comprising administering a therapeutically effective dose of a BTK inhibitor; and (b) monitoring the patient at predetermined intervals of time over the course of the maintenance therapy regimen to determine whether the subject has mutation in an endogenous gene encoding PLCγ2 that results in a modification at an amino acid position corresponding to amino acid position 665 or 707 of the amino acid sequence set forth in SEQ ID NO: 11. In some embodiments, monitoring comprises: (a) testing a sample containing a nucleic acid molecule encoding a PLCγ2 polypeptide from the subject to determine whether the encoded PLCγ2 polypeptide is modified at an amino acid position corresponding to amino acid position 665 or 707 of the amino acid sequence set forth in SEQ ID NO: 11. In some embodiments, the method further comprises discontinuing treatment with the BTK inhibitor if the subject has the mutation. In some embodiments, the method further comprises continuing treatment with a BTK inhibitor if the subject does not have the mutation. In some embodiments, the method further comprises administering an inhibitor of LYN, SYK, JAK, PI3K, MAPK, MEK, or NFκB if the subject has the modification. In some embodiments, the modification in the PLCγ2 polypeptide is R665W or S707F. In some embodiments, the predetermined interval of time is every month, every 2 months, every 3 months, every 4 months, every 5 months, every 6 months, every 7 months, every 8

In some embodiments, the BTK inhibitor is administered at a daily dosage of about 10 mg per day to about 2000 mg per day, about 50 mg per day to about 1500 mg per day, about 100 mg per day to about 1000 mg per day, about 250 mg per day to about 850 mg per day, or about 300 mg per day to about 600 mg per day. In some embodiments, ibrutinib is administered at a daily dosage of about 140 mg per day, 420 mg per day, 560 mg per day or 840 mg per day. In some embodiments, the BTK inhibitor is a covalent and/or irreversible BTK inhibitor. In some embodiments, the BTK inhibitor is selected from among ibrutinib (PCI-32765), PCI-45292, PCI-45466, AVL-101, AVL-291, AVL-292, or ONO-WG-37. In some embodiments, the BTK inhibitor is ibrutinib.

Described herein, in certain embodiments are methods for monitoring whether a subject receiving a BTK inhibitor for treatment of a cancer has developed or is likely to develop resistance to the therapy, comprising: (a) testing a sample containing a nucleic acid molecule encoding a CARD11 polypeptide from the subject to determine whether the encoded CARD11 polypeptide is modified at an amino acid position corresponding to amino acid position 232 of the amino acid sequence set forth in SEQ ID NO: 19; and (b) characterizing the subject as resistant or is likely to become resistant to therapy with a BTK inhibitor if the subject has the modification. In some embodiments, the method further comprises discontinuing treatment with the BTK inhibitor if the subject has the modification. In some embodiments, the method further comprises continuing treatment with a BTK inhibitor if the subject does not have the modification. In some embodiments, the method further comprises a step of obtaining the sample from the subject. In some embodiments, the method further comprises administering an inhibitor of LYN, SYK, JAK, PI3K, MAPK, MEK, or NFκB if the subject has the modification. In some embodiments, the modification comprises a L232LL insertion in CARD11. In some embodiments, the BTK inhibitor is a covalent or irreversible inhibitor.

Described herein, in certain embodiments are methods for optimizing the therapy of a subject receiving an irreversible BTK inhibitor for treatment of a cancer, comprising: (a) testing a sample containing a nucleic acid molecule encoding a CARD11 polypeptide from the subject to determine whether the encoded CARD11 polypeptide is modified at an amino acid position corresponding to amino acid position 232 of the amino acid sequence set forth in SEQ ID NO: 19; and (b) discontinuing treatment with the irreversible BTK inhibitor if the subject has the modification or continuing treatment with the irreversible BTK inhibitor if the subject does not have the modification. In some embodiments, the method further comprises administering second generation BTK inhibitor that inhibits the modified kinase if the subject has the modification. In some embodiments, the method further comprises a step of obtaining the sample from the subject. In some embodiments, the method further comprises administering an inhibitor of LYN, SYK, JAK, PI3K, MAPK, MEK, or NFκB if the subject has the modification. In some embodiments, the modification comprises a L232LL insertion in CARD11. In some embodiments, the BTK inhibitor is a covalent or irreversible inhibitor.

In some embodiments of the methods, the nucleic acid molecule for use in the assay is RNA or DNA. In some embodiments of the methods, the nucleic acid molecule is a cDNA In some embodiments of the methods, the nucleic acid molecule for use in the assay is genomic DNA. In some embodiments of the methods, the nucleic acid molecule for use in the assay is total RNA. In some embodiments of the methods, the nucleic acid molecule for use in the assay is mRNA. In some embodiments of the methods, the method further comprises isolating mRNA from the RNA sample.

In some embodiments of the methods, testing comprises performing polymerase chain reaction (PCR) amplification of nucleic acid encoding amino acid position 232 of the CARD11 polypeptide. In some embodiments, PCR amplification comprises using a pair of oligonucleotide primers that flank the region encoding amino acid position 232 of the CARD11 polypeptide. In some embodiments, the method comprises sequencing the amplified nucleic acid.

In some embodiments of the methods, testing comprises contacting the nucleic acid with a sequence specific nucleic acid probe, wherein the sequence specific nucleic acid probe: (a) binds to nucleic acid encoding a modified CARD11 that is modified at amino acid position 232; and (b) does not bind to nucleic acid encoding the wild-type CARD11. In some embodiments of the methods, testing comprises PCR amplification using the sequence specific nucleic acid probe.

In some embodiments, the sample for use in the methods contains one or more tumor cells from the subject. In some embodiments, the sample for use in the methods contains circulating tumor DNA (ctDNA).

In some embodiments of the methods, the nucleic acid used in the method is isolated from a tumor cell sample from the subject. In some embodiments, the sample is a tumor biopsy sample, a blood sample, a serum sample, a lymph sample, or a bone marrow aspirate.

In some embodiments, the BTK inhibitor is selected from among ibrutinib (PCI-32765), PCI-45292, PCI-45466, AVL-101, AVL-291, AVL-292, or ONO-WG-37. In some embodiments, the CARD11 inhibitor is ibrutinib.

In some embodiments of the methods, the subject has cancer. In some embodiments, the cancer is a hematologic cancer. In some embodiments, cancer is a B-cell malignancy. In some embodiments, cancer is selected from among a leukemia, a lymphoma, or a myeloma. In some embodiments, the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the subject has a solid tumor.

In some embodiments of the methods, the subject is treated with the BTK inhibitor prior to obtaining the sample. In some embodiments, the sample is obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, or 24 months following the first administration of the irreversible BTK inhibitor. In some embodiments, the sample is obtained 1, 2, 3, 4, 5, 6, 7, 8, 9, 10 times over the course of treatment with the BTK inhibitor. In some embodiments, the subject is responsive the treatment with the BTK inhibitor when it is first administered.

Described herein, in certain embodiments, is a kit comprising one or more reagents for the detection of a modified CARD11 polypeptide comprising a modification at amino acid position 232. In some embodiments, the kit comprises a microchip comprising a mutant CARD11 polypeptide having a modification that is L232LL.

Described herein, in certain embodiments, is a kit comprising one or more reagents for the detection of nucleic acid encoding a mutant CARD11 polypeptide comprising a modification at amino acid position 232. In some embodiments, the kit comprises a microchip comprising nucleic acid encoding a mutant CARD11 polypeptide having a modification that is L232LL.

Described herein, in certain embodiments, is a system for detecting a modified CARD11 that confers resistance to inhibition with an irreversible BTK inhibitor in a subject, comprising: (a) a sample containing a nucleic acid molecule encoding a CARD11 polypeptide from the subject; and (b) a microarray comprising nucleic acid encoding a mutant CARD11 polypeptide or a portion thereof that is modified at an amino acid position corresponding to amino acid position 232 of the amino acid sequence set forth in SEQ ID NO: 19. In some embodiments, the microarray is contained on a microchip.

Described herein, in certain embodiments, is a system for detecting a modified CARD11 that that confers resistance to inhibition with a BTK inhibitor in a subject, comprising: (a) a sample containing a nucleic acid molecule encoding a CARD11 polypeptide from the subject; and (b) a sequence specific nucleic acid probe, wherein the sequence specific nucleic acid probe: (i) binds to nucleic acid encoding a modified CARD11 that is modified at amino acid position 232; and (ii) does not bind to nucleic acid encoding the wild-type CARD11.

Described herein, in certain embodiments, is a system for detecting a modified CARD11 that that confers resistance to inhibition with an BTK inhibitor in a subject, comprising: (a) a sample containing a nucleic acid molecule encoding a CARD11 polypeptide from the subject; and (b) a pair oligonucleotide primers that flank the nucleic acid region encoding amino acid 232 of a CARD11 polypeptide.

Described herein, in certain embodiments, is method of maintenance therapy in a patient having a hematologic cancer, comprising: (a) administering to the patient a maintenance therapy regimen comprising administering a therapeutically effective dose of a BTK inhibitor; and (b) monitoring the patient at predetermined intervals of time over the course of the maintenance therapy regimen to determine whether the subject has mutation in an endogenous gene encoding CARD11 that results in a modification at an amino acid position corresponding to amino acid position 232 of the amino acid sequence set forth in SEQ ID NO: 19. In some embodiments, monitoring comprises: (a) testing a sample containing a nucleic acid molecule encoding a CARD11 polypeptide from the subject to determine whether the encoded CARD11 polypeptide is modified at an amino acid position corresponding to amino acid position 232 of the amino acid sequence set forth in SEQ ID NO: 19. In some embodiments, the method further comprises discontinuing treatment with the BTK inhibitor if the subject has the mutation. In some embodiments, the method further comprises continuing treatment with a BTK inhibitor if the subject does not have the mutation. In some embodiments, the method further comprises administering an inhibitor of LYN, SYK, JAK, PI3K, MAPK, MEK, or NFκB if the subject has the modification. In some embodiments, the modification in the CARD11 polypeptide is L232LL. In some embodiments, the predetermined interval of time is every month, every 2 months, every 3 months, every 4 months, every 5 months, every 6 months, every 7 months, every 8

In some embodiments, the BTK inhibitor is administered at a daily dosage of about 10 mg per day to about 2000 mg per day, about 50 mg per day to about 1500 mg per day, about 100 mg per day to about 1000 mg per day, about 250 mg per day to about 850 mg per day, or about 300 mg per day to about 600 mg per day. In some embodiments, ibrutinib is administered at a daily dosage of about 140 mg per day, 420 mg per day, 560 mg per day or 840 mg per day. In some embodiments, the BTK inhibitor is a covalent and/or irreversible BTK inhibitor. In some embodiments, the BTK inhibitor is selected from among ibrutinib (PCI-32765), PCI-45292, PCI-45466, AVL-101, AVL-291, AVL-292, or ONO-WG-37. In some embodiments, the BTK inhibitor is ibrutinib.

BRIEF DESCRIPTION OF THE DRAWINGS

FIG. 2A-C demonstrates that the BTK mutation leads to reactivation of the BCR signaling pathway and changes in gene expression. FIG. 2A depicts immunoblots of BTK phosphorylation and downstream BCR signaling in the four serial samples. GAPDH was included as the loading control. FIG. 2B shows a graphical heat map with the expression profiles of a 27-gene BCR signature across all 4 serial samples. The RPKM-normalized expression counts were represented by colors using the color reference range shown below. FIG. 2C: RPKM-normalized expression counts were plotted for each individual gene in the cluster of the BCR signature. Differences among the four specimens were analyzed by one-way analysis of variance (ANOVA). $*P<0.05$, $***P<0.001$.

FIG. 3A: Longitudinal changes in Ki67+ CLL cells over patient clinical course. FIG. 3B: In vitro stroma-induced proliferation was eliminated by ibrutinib in Pre-Rx and Responding samples, but not in relapsed samples. Concentrations of ibrutinib were indicated on the top of the each column. Percentage of BrdU+ cells are indicated in each plot. Iso, isotype control. FIG. 3C: Effects of other kinase inhibitors on CLL proliferation. Concentrations used in the experiment were indicated. Untreated cells (+NK) served as the control. PRT060318, a SYK inhibitor; PRT062070, a SYK/JAK dual inhibitor; CAL101, a PI3Kδ inhibitor; tofacitinib, JAK inhibitor; and Dasatinib, a multi-kinase inhibitor.

DETAILED DESCRIPTION OF THE INVENTION

Certain Terminology

Figure 1:
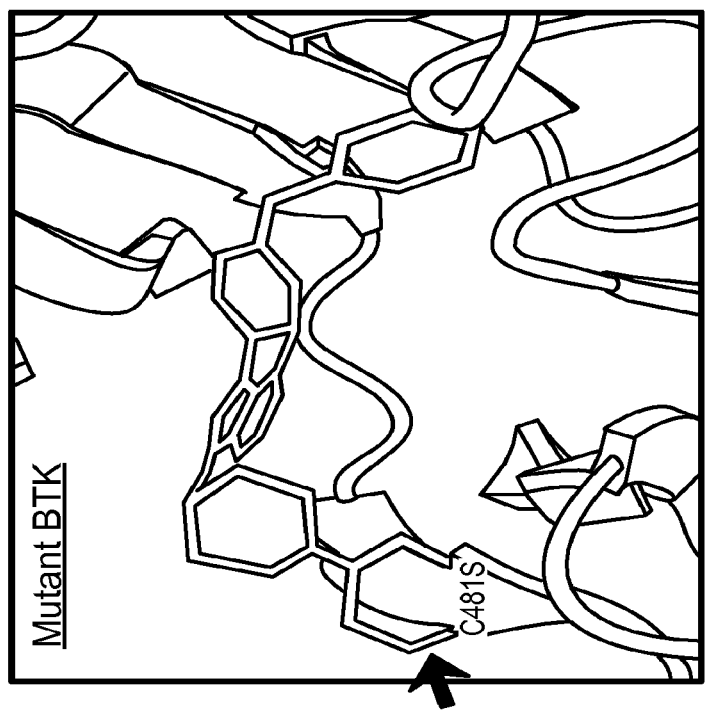
FIG. 1 depicts structural modeling of the wild-type and mutant BTK with ibrutinib. The red arrows points to the disrupted covalent bond.
Figure 1:
Figure 1:
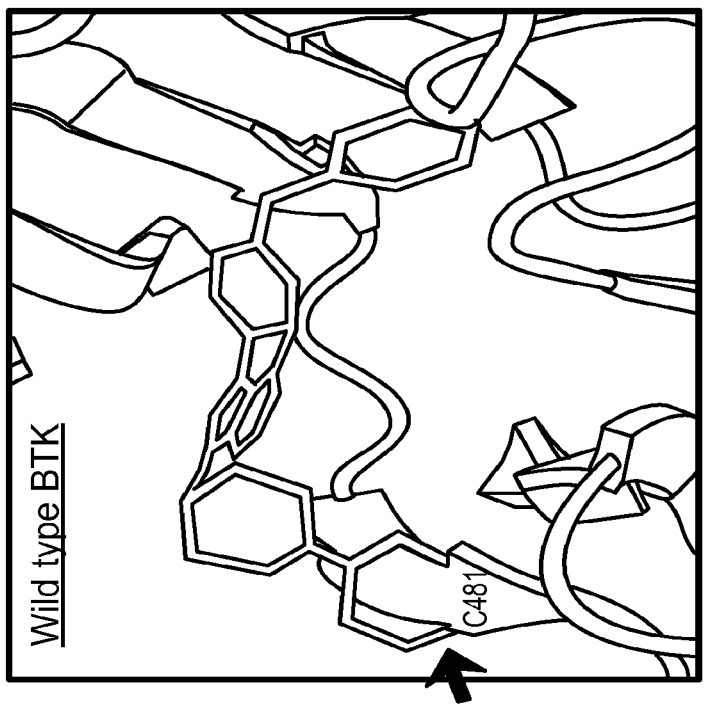

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information. Generally, the procedures for cell culture, cell infection, antibody production and molecular biology methods are methods commonly used in the art. Such standard techniques can be found, for example, in reference manual, such as, for example, Sambrook et al. (2000) and Ausubel et al. (1994).

As used herein, the singular forms "a," "an" and "the" include plural referents unless the context clearly dictates otherwise. In this application, the use of the singular includes the plural unless specifically stated otherwise. As used herein, the use of "or" means "and/or" unless stated otherwise. Furthermore, use of the term "including" as well as other forms (e.g., "include", "includes", and "included") is not limiting.

As used herein, ranges and amounts can be expressed as "about" a particular value or range. About also includes the exact amount. Hence "about 5 μg" means "about 5 μg" and also "5 μg." Generally, the term "about" includes an amount that would be expected to be within experimental error.

As used herein, a Bruton's Tyrosine Kinase (BTK) polypeptide refers to any BTK protein or polypeptide, including, but not limited to, a recombinantly produced protein, a synthetically produced protein, a native BTK protein, and a BTK protein extracted from cells or tissues. A BTK polypeptide includes related polypeptides from different species including, but not limited to animals of human and non-human origin. BTK polypeptides of non-human origin include, but are not limited to, non-human primate (e.g. chimpanzee and ape), murine (e.g., mouse and rat), canine (dog), feline (cat), leporine (rabbit), avian (bird), bovine (cow), ovine (sheep), porcine (pig), equine (horse), piscine (fish), ranine (frog) and other mammalian or non-mammalian BTK polypeptides. Exemplary BTK polypeptides include, for example, orthologs from mouse (GenBank Accession No. AAB47246), dog (GenBank Accession No. XP_549139), rat (GenBank Accession No. NP_001007799), chicken (GenBank Accession No. NP_989564), or zebra fish (GenBank Accession No. XP 698117), and fusion proteins of any of the foregoing that exhibit kinase activity towards one or more substrates of Bruton's tyrosine kinase (e.g. a peptide substrate having the amino acid sequence "AVLE-SEEELYSSARQ"). Exemplary BTK polypeptides include, but are not limited to SEQ ID NOS: 1, 2, and 4-6. A BTK polypeptide includes wild-type BTK, allelic variant isoforms, somatic mutations including those found in tumors or hematologic malignancies, synthetic molecules from nucleic acids, protein isolated from human tissue and cells, and modified forms thereof. The BTK polypeptides provided herein can be further modified by modification of the primary amino acid sequence, by deletion, addition, or substitution of one or more amino acids. A BTK polypeptide includes any BTK polypeptide or a portion thereof having BTK activity, such as kinase activity.

As used herein, a mutant BTK polypeptide, a mutant BTK protein, a modified BTK polypeptide, or a modified BTK protein or are used interchangeably herein and refer to a BTK polypeptide that is modified at one or more amino acid positions. Exemplary modifications include, but are not limited to, substitutions, deletions or additions of amino acids.

As used herein, the term "BTK inhibitor" or "BTK antagonist" refers to an agent that inhibits or reduces at least one activity of a BTK polypeptide. BTK activities include direct and indirect activities. Exemplary direct activities include, but are not limited to, association with a target molecule or phosphorylation of a target substrate (i.e. kinase activity). Exemplary indirect activities include, but are not limited to, activation or inhibition of a downstream biological event, such as for example activation of NF-κB-mediated gene transcription.

The term "irreversible inhibitor," as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor.

The term "irreversible BTK inhibitor," as used herein, refers to an inhibitor of BTK that can form a covalent bond with an amino acid residue of BTK. In one embodiment, the irreversible inhibitor of BTK can form a covalent bond with a Cysteine residue of BTK; in particular embodiments, the irreversible inhibitor can form a covalent bond with a Cysteine 481 residue (or a homolog thereof) of BTK or a cysteine residue in the homologous corresponding position of another tyrosine kinase.

As used herein, inhibition of BTK activity refers any decrease in BTK activity in the presence of an inhibitor compared to the same activity in the absence of the inhibitor.

As used herein, the phrase "confers resistance to a covalent and/or irreversible BTK inhibitor" refers to any decrease in the sensitivity of BTK to inhibition by a covalent and/or irreversible BTK inhibitor. In some embodiments provided herein, a modification of BTK at cysteine 481 confers resistance to a covalent and/or irreversible BTK inhibitor. In some embodiments, the modification prevents binding of the inhibitor to BTK. In some embodiments, the inhibitor reversibly binds to BTK. In some embodiments, the affinity of inhibitor for binding to modified BTK is decrease relative to binding to a wild-type BTK.

As used herein, the term "second-generation BTK inhibitor" refers to an agent that inhibits at least one activity of a BTK polypeptide containing an amino acid modification at cysteine 481. In some embodiments, the second-generation BTK inhibitor also inhibits the activity of a wild-type BTK polypeptide. In some embodiments, the second-generation BTK inhibitor does not inhibit the activity of a wild-type BTK polypeptide.

As used herein, the term "first-generation BTK inhibitor" refers to an agent that inhibits an activity of wild-type BTK polypeptide, but exhibits decreased inhibition towards a BTK polypeptide containing an amino acid modification at cysteine 481. In some embodiments, the first-generation BTK inhibitor is a covalent and/or irreversible BTK inhibitor.

The terms "cancer" and "cancerous" refer to or describe the physiological condition in mammals that is typically characterized by unregulated cell growth. Examples of cancer include, but are not limited to, B-cell lymphoproliferative disorders (BCLDs), such as lymphoma and leukemia, and solid tumors. By "B cell-related cancer" or "cancer of B-cell lineage" is intended any type of cancer in which the dysregulated or unregulated cell growth is associated with B cells.

By "refractory" in the context of a cancer is intended the particular cancer is resistant to, or non-responsive to, therapy with a particular therapeutic agent. A cancer can be refractory to therapy with a particular therapeutic agent either from the onset of treatment with the particular therapeutic agent (i.e., non-responsive to initial exposure to the therapeutic agent), or as a result of developing resistance to the therapeutic agent, either over the course of a first treatment period with the therapeutic agent or during a subsequent treatment period with the therapeutic agent.

As used herein, "maintenance therapy" means the ongoing use of chemotherapy or another treatment to assist in lowering the risk of recurrence (return of cancer) following a beneficial response to initial therapy, for example remission. Maintenance therapy also may be used for patients with advanced cancer (e.g. cancer that cannot be cured) to help keep it from growing and spreading further.

By "BTK-mediated signaling" it is intended any of the biological activities that are dependent on, either directly or indirection, the activity of BTK. Examples of BTK-mediated signaling are signals that lead to proliferation and survival of BTK-expressing cells, and stimulation of one or more BTK-signaling pathways within BTK-expressing cells.

A BTK "signaling pathway" or "signal transduction pathway" is intended to mean at least one biochemical reaction, or a group of biochemical reactions, that results from the activity of BTK, and which generates a signal that, when transmitted through the signal pathway, leads to activation of one or more downstream molecules in the signaling cascade. Signal transduction pathways involve a number of signal transduction molecules that lead to transmission of a signal from the cell-surface across the plasma membrane of a cell, and through one or more in a series of signal transduction molecules, through the cytoplasm of the cell, and in some instances, into the cell's nucleus. Of particular interest to the present invention are BTK signal transduction pathways which ultimately regulate (either enhance or inhibit) the activation of NF-κB via the NF-κB signaling pathway.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogs of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (e.g., phosphorothioates, phosphoroamidates). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions are achieved by generating sequences in which the third position of one or more selected (or all) codons is substituted with mixed-base and/or deoxyinosine residues (Batzer et al. (1991)*Nucleic Acid Res.* 19:5081; Ohtsuka et al. (1985) *J. Biol. Chem.* 260:2605-2608; and Cassol et al. (1992)*Mol. Cell. Probes* 6, 327-331; and Rossolini et al. (1994) *Mol. Cell. Probes* 8:91-98).

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to agents that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The terms "polypeptide", "peptide" and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, modification in reference to modification of a sequence of amino acids of a polypeptide or a sequence of nucleotides in a nucleic acid molecule and includes deletions, insertions, and replacements of amino acids and nucleotides, respectively.

To determine the percent homology of two amino acid sequences or of two nucleic acids, the sequences can be aligned for optimal comparison purposes (e.g., gaps are introduced in the sequence of a first amino acid or nucleic acid sequence for optimal alignment with a second amino or nucleic acid sequence). The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position. The percent homology between the two sequences is a function of the number of identical positions shared by the sequences (i.e., % identity=# of identical positions/total # of positions (e.g., overlapping positions)×100). In some embodiments the two sequences are the same length.

To determine percent homology between two sequences, the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877 is used. Such an algorithm is incorporated into the NBLAST and)(BLAST programs of Altschul, et al. (1990) *J. Mol. Biol.* 215:403-410. BLAST nucleotide searches are performed with the NBLAST program, score=100, wordlength=12 to obtain nucleotide sequences homologous to a nucleic acid molecules described or disclose herein. BLAST protein searches are performed with the XBLAST program, score=50, wordlength=3. To obtain gapped alignments for comparison purposes, Gapped BLAST is utilized as described in Altschul et al. (1997) *Nucleic Acids Res.* 25:3389-3402. When utilizing BLAST and Gapped BLAST programs, the default parameters of the respective programs (e.g., XBLAST and NBLAST) are used. See the website of the National Center for Biotechnology Information for further details (on the World Wide Web at ncbi.nlm.nih gov). Proteins suitable for use in the methods described herein also includes proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, e.g., 77%, 80%, 82%, 85%, 88%, 90%, 91%, 92%, 93%, 94%, 95%, 96%, 97%, 98%, 99%, or 100% identical to the amino acid sequence of any protein described herein. Such sequence-variant proteins are suitable for the methods described herein as long as the altered amino acid sequence retains sufficient biological activity to be functional in the compositions and methods described herein. Where amino acid substitutions are made, the substitutions should be conservative amino acid substitutions. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224). The BLOSUM62 table is an amino acid substitution matrix derived from about 2,000 local multiple alignments of protein sequence segments, representing highly conserved regions of more than 500 groups of related proteins (Henikoff et al (1992) *Proc. Natl. Acad. Sci. USA,* 89:10915-10919). Accordingly, the BLOSUM62 substitution frequencies are used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

As used herein, corresponding residues refers to residues that occur at aligned loci. Related or variant polypeptides are aligned by any method known to those of skill in the art. Such methods typically maximize matches, and include methods such as using manual alignments and by using the numerous alignment programs available (for example, BLASTP) and others known to those of skill in the art. By aligning the sequences of polypeptides, one skilled in the art can identify corresponding residues, using conserved and identical amino acid residues as guides. Corresponding positions also can be based on structural alignments, for example by using computer simulated alignments of protein structure. In other instances, corresponding regions can be identified.

As used herein, an allelic variant or allelic variation references to a polypeptide encoded by a gene that differs from a reference form of a gene (i.e. is encoded by an allele). Typically the reference form of the gene encodes a wildtype form and/or predominant form of a polypeptide from a population or single reference member of a species. Typically, allelic variants, which include variants between and among species typically have at least 80%, 90% or greater amino acid identity with a wildtype and/or predominant form from the same species; the degree of identity depends upon the gene and whether comparison is interspecies or intraspecies. Generally, intraspecies allelic variants have at least about 80%, 85%, 90% or 95% identity or greater with a wildtype and/or predominant form, including 96%, 97%, 98%, 99% or greater identity with a wildtype and/or predominant form of a polypeptide.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

As used herein, species variants refer to variants of the same polypeptide between and among species. Generally, interspecies variants have at least about 60%, 70%, 80%, 85%, 90%, or 95% identity or greater with a wildtype and/or predominant form from another species, including 96%, 97%, 98%, 99% or greater identity with a wildtype and/or predominant form of a polypeptide.

The term "subject" as used herein, refers to an animal which is the object of treatment, observation or experiment. By way of example only, a subject may be, but is not limited to, a mammal including, but not limited to, a human.

As used herein, the $IC_{50}$ refers to an amount, concentration or dosage of a particular test compound that achieves a 50% inhibition of a maximal response, such as inhibition of BTK, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the terms "treat," "treating" or "treatment," and other grammatical equivalents, include alleviating, abating or ameliorating one or more symptoms of a disease or condition, ameliorating, preventing or reducing the appearance, severity or frequency of one or more additional symptoms of a disease or condition, ameliorating or preventing the underlying metabolic causes of one or more symptoms of a disease or condition, inhibiting the disease or condition, such as, for example, arresting the development of the disease or condition, relieving the disease or condition, causing regression of the disease or condition, relieving a condition caused by the disease or condition, or inhibiting the symptoms of the disease or condition either prophylactically and/or therapeutically. In a non-limiting example, for prophylactic benefit, a third-generation BTK inhibitor compound disclosed herein is administered to an individual at risk of developing a particular disorder, predisposed to developing a particular disorder, or to an individual reporting one or more of the physiological symptoms of a disorder. In some embodiments, a third-generation BTK inhibitor compound disclosed herein is administered to a subject following treatment with one or more therapeutic agents. In some embodiments, a third-generation BTK inhibitor compound disclosed herein is administered to a subject in combination with treatment with one or more therapeutic agents.

As used herein, prevention or prophylaxis refers to the reduction in the risk of developing a disease or condition.

The terms "effective amount", "therapeutically effective amount" or "pharmaceutically effective amount" as used herein, refer to an amount of a BTK inhibitor compound that is sufficient to treat a disorder. In some embodiments, the result is a reduction in and/or alleviation of the signs, symptoms, or causes of a disorder, or any other desired alteration of a biological system. For example, an "effective amount" for therapeutic uses is the amount of the composition comprising a BTK inhibitor compound disclosed herein required to provide a clinically significant decrease in a disorder. An appropriate "effective" amount in any individual case is determined using any suitable technique, (e.g., a dose escalation study).

The term "pharmaceutically acceptable" as used herein, refers to a material, (e.g., a carrier or diluent), which does not abrogate the biological activity or properties of a BTK inhibitor compound described herein, and is relatively non-toxic (i.e., the material is administered to an individual without causing undesirable biological effects or interacting in a deleterious manner with any of the components of the composition in which it is contained).

As used herein, a control refers to a sample that is substantially identical to the test sample, except that it is not treated with a test parameter, or, if it is a plasma sample, it can be from a normal volunteer not affected with the condition of interest. A control also can be an internal control.

As used herein, the terms "subject", "individual" and "patient" are used interchangeably. None of the terms are to be interpreted as requiring the supervision of a medical professional (e.g., a doctor, nurse, physician's assistant, orderly, hospice worker). As used herein, the subject can be any animal, including mammals (e.g., a human or non-human animal) and non-mammals. In one embodiment of the methods and compositions provided herein, the mammal is a human.

As used herein, "contacting" refers to refers to the act of touching, making contact, or of bringing substances into immediate proximity. "Contacting" can be achieved by mixing the components in a fluid or semi-fluid mixture.

Overview: BTK Function and Drug Resistance in Cancer

Drug resistance is a problem affecting several areas of medicine including infectious diseases and cancer. During the course of cancer treatment, spontaneous random mutations occur as the cancer cell population expands by repeated divisions, some of which confer resistance and hence a survival advantage. Described herein is a mutation in BTK gene that arose during treatment of a patient with CLL with the irreversible BTK inhibitor ibrutinib. Following approximately 18 months of treatment with ibrutinib, three patients in separated studies exhibited a rise in absolute lymphocyte count (ALC) and increased lymph node size. Disease progression continued even when the ibrutinib dose was escalated from 560 mg per day to 840 mg per day in one of the patients. A blood sample was isolated from the patients, and mRNA encoding BTK was analyzed from the cells contained in the sample. It was found in two patients that a mutation in the BTK protein had emerged. In one patient, the nucleic acid encoding BTK had a missense mutation of guanine (g)-1635 to cytosine (c)-1635 resulting the substitution of the Cysteine-481 codon, TGC, to TCC (Serine). In a second patient, the nucleic acid encoding BTK had a missense mutation of thymine (t)-1634 to adenine (a)-1634 resulting the substitution of the Cysteine-481 codon, TGC, to AGC (Serine). Sample taken from the same patients early in treatment with ibrutinib did not contain these mutations. The mutation in the Cys-481 codon suggests an adaptive response by the tumor to selective pressure supplied by ibrutinib treatment.

The acquisition of a resistance mutation has been described for all major tyrosine kinase inhibitors in oncology, including imatinib (Gleevec), and the EGFR inhibitors gefitinib, and erlotinib. In advanced CML, 66% of patients relapse on imatinib, and 5% of chronic CML patients relapse within the first few years. 30-50% of these relapsed patients have acquired resistance mutations in the target kinase (ABL). Such patients go on to other therapies including dasatinib, nilotinib, etc., but many of these eventually relapse with new resistance mutations. In lung cancer, erlotinib and gefitinib have produced impressive and durable clinical results, but nearly all become ineffective within 12-18 months due to resistance. ~50% of these resistant patients have a mutation in the target kinase (EGFR) called T790M, which changes a single amino acid.

Described herein are modified BTK polypeptides that contain an amino acid substitution of cysteine at position 481 of the wild-type BTK for serine (C481S) and nucleic acids encoding the polypeptides. Also described herein are methods of producing the modified BTK nucleic acids and polypeptides described herein. Also described herein are compositions, combinations and kits containing the modified BTK nucleic acids and polypeptides described herein and reagents for detection of the modified BTK nucleic acids and polypeptides described herein. Also provided are methods of using the modified BTK polypeptides for identifying mutant BTK interacting molecules, including BTK inhibitors, including second-generation BTK inhibitors. Also described herein are modified BTK nucleic acids that are synthetic nucleic acids. Also described herein are modified BTK nucleic acids that are cDNA molecules. Also described herein are modified BTK polypeptides produced by modified BTK nucleic acids that are synthetic nucleic acids. Also described herein are modified BTK polypeptides produced by modified BTK nucleic acids that are cDNA molecules. Also described herein are modified BTK nucleic acids that do not contain BTK genomic DNA. Also described herein are modified BTK nucleic acids that are unmethylated. Also described herein are modified BTK nucleic acids that do not contain BTK intron sequences. Also described herein are modified BTK nucleic acids that comprises a sequence of nucleotides from two or more exons of the BTK genomic sequence. In some embodiments, the modified BTK nucleic acids comprise a sequence of nucleotides that encode serine at a position corresponding to position 481 of the wild-type BTK polypeptide.

As described herein, identification of a mutation at amino acid position 481 in BTK, such as for example C481S, allows for the design and screening of inhibitors effective for inhibition of a mutant BTK having one or more resistance mutations. Such inhibitors are useful in clinical and therapeutic applications. In some embodiments, the inhibitors are useful for the treatment of a cancer, such as for example, a hematologic cancer, such as a B-cell malignancy.

As described herein, in some embodiments, subjects are screened for the identification of a mutation at amino acid position 481 in BTK, such as for example C481S. In some embodiments, identification of such a mutation allows for the prescription of a cancer treatment or modification of a cancer treatment. In some embodiments, identification of such a mutation is used to stratify subjects for a particular therapy, such as for example, therapy with an inhibitor that inhibits the activity of the mutant C481S (i.e. a second-generation BTK inhibitor). In some embodiments, identification of such a mutation is used to characterize a subject as having a high risk of relapse of a BTK-mediated disease or condition, such as, for example, a hematologic cancer, such as a B-cell cancer. In some embodiments, identification of such a mutation is used to characterize a subject as lacking responsiveness to particular BTK inhibitor, such as for example a covalent and/or irreversible BTK inhibitor, such as ibrutinib.

As described herein in the example, separate mutations in downstream proteins of the BCR pathway also were identified in patients receiving therapy with a BTK inhibitor. For example, mutations in PLCγ2 and CARD11 were identified. For PLCγ2, missense mutations resulting in amino acid substitutions at R665 and S707 were found (e.g. R665W and S707F). For CARD11, an insertion of a leucine at position L232 was observed (i.e. L232LL). Such mutations are predicted to result in constitutive activity for each protein. Accordingly, provided herein are method of screening for such mutations for the selection of patients for therapy, monitoring patients receiving a BTK inhibitor therapy, and optimizing a treatment regimen, such as a maintenance therapy.

Mutant BTK Polypeptides

Provided herein are mutant BTK polypeptides. In some embodiments, the mutant BTK polypeptides are isolated mutant BTK polypeptides. In some embodiments, the isolated mutant BTK polypeptides are non-native mutant BTK polypeptides. In some embodiments, the isolated mutant BTK polypeptides are recombinant mutant BTK polypeptides. Typically, the mutant BTK polypeptides provided herein exhibit at least one BTK activity. For example, the mutant BTK polypeptides typically retain a BTK activity such as, for example, association with a target molecule or phosphorylation of a target substrate (i.e. kinase activity). In some embodiments, the mutant BTK polypeptides provided herein have decreased kinase activity relative to a wild-type BTK polypeptide. In some embodiments, the mutant BTK polypeptides provided herein have increased kinase activity relative to a wild-type BTK polypeptide. In some embodiments, the mutant BTK polypeptides provided herein have equivalent kinase activity relative to a wild-type BTK polypeptide. In some embodiments, the mutant BTK polypeptides are recombinant proteins. In some embodiments, the mutant BTK polypeptides are purified from a host cell.

In some embodiments, the mutant BTK polypeptides contain one or more amino acid substitutions that confers resistance to inhibition by a covalent and/or irreversible BTK inhibitor. In some embodiments, the irreversible BTK inhibitor inhibits the kinase activity of a wild-type BTK polypeptide. In some embodiments, the mutant BTK polypeptides contain one or more amino acid substitutions that confers resistance to inhibition by a covalent and/or irreversible BTK inhibitor that covalently binds to cysteine at amino acid position 481 of a wild-type BTK set forth in SEQ ID NO.: 1. In some embodiments, the mutant BTK polypeptides contain one or more amino acid substitutions that confers resistance to inhibition by a covalent and/or irreversible BTK inhibitor that is ibrutinib, PCI-45292, PCI-45466, AVL-101, AVL-291, AVL-292, or ONO-WG-37. In some embodiments, the mutant BTK polypeptides contain one or more amino acid substitutions that confers resistance to inhibition by a covalent and/or irreversible BTK inhibitor that is ibrutinib.

Provided herein is an isolated BTK polypeptide or a variant thereof having BTK activity comprising a modification at an amino acid position corresponding to amino acid position 481 of the amino acid sequence set forth in SEQ ID NO: 1, wherein the modification confers resistance of the modified BTK polypeptide or variant to inhibition with a covalent and/or irreversible BTK inhibitor.

In some embodiments, the modification comprises a substitution or a deletion of the amino acid at amino acid position 481 compared to a wild type BTK set forth in SEQ ID NO: 1. In some embodiments, the modification comprises substitution of the amino acid at position 481 compared to a wild type BTK set forth in SEQ ID NO: 1. In some embodiments, the modification is a substitution of cysteine to an amino acid selected from among leucine, isoleucine, valine, alanine, glycine, methionine, serine, threonine, phenylalanine, tryptophan, lysine, arginine, histidine, proline, tyrosine, asparagine, glutamine, aspartic acid and glutamic acid at amino acid position 481 of the BTK polypeptide. In some embodiments, the modification is a substitution of cysteine to an amino acid selected from among serine, methionine, or threonine at amino acid position 481 of the BTK polypeptide. In some embodiments, the modification is a substitution of cysteine to serine at amino acid position 481 of the BTK polypeptide. In some embodiments, the substitution is C481S. In some embodiments, the modification comprises a deletion of amino acid position 481 of the wild-type BTK polypeptide set forth in SEQ ID NO: 1.

In some embodiments, the mutant BTK polypeptide comprises a substitution of the amino acid at position 481 compared to a wild type BTK set forth in SEQ ID NO: 1 and one or more additional amino acid substitutions. In some embodiments, the mutant BTK polypeptide comprises the sequence of amino acids set forth in SEQ ID NO: 2 or a variant that has at least or at least about 60%, 70%, 75%, 80%, 85%, 90%, 95%, 96%, 97%, 98%, 99% or more sequence identity with the polypeptide having the sequence set forth in SEQ ID NO: 2, wherein the amino acid at position 481 is not cysteine. In some embodiments, the mutant BTK polypeptide comprises the sequence of amino acids set forth in SEQ ID NO: 2. In some embodiments the mutant BTK polypeptide comprises a polypeptide having a serine at the position corresponding to amino acid position 481 and having 65%, 70%, 75%, 80%, 85%, 90%, 95%, 96%, 97%, 98%, or 99% amino acid sequence identity to the polypeptide having the sequence set forth in SEQ ID NO: 2.

In some embodiments, the mutant BTK polypeptide comprises a modification at amino acid position 481 and a modification at one or more additional amino acid positions. In some embodiments, the mutant BTK polypeptide comprises a modification at amino acid position 481 and a modification at 1, 2, 3, 4, 5, 6, 7, 8, 9, 10, 11, 12, 13, 14, 15, 16, 17, 18, 19, 20 or more amino acid positions. In some embodiments, the mutant BTK polypeptide comprises a modification at position 481 and a modification at one additional amino acid position. In some embodiments, the mutant BTK polypeptide comprises a serine at amino acid position 481 and a modification at 1, 2, 3, 4, 5, 6, 7, 8, 9, 10, 11, 12, 13, 14, 15, 16, 17, 18, 19, 20 or more additional amino acid positions. In some embodiments, the mutant BTK polypeptide comprises a serine at position 481 and a modification at one additional amino acid position. In some embodiments, the modification at amino acid position 481 is a substitution that is C481S.

In some embodiments, the mutant BTK polypeptide comprises a portion of the mutant BTK polypeptide set forth in SEQ ID NO: 2. In some embodiments, the portion exhibits an activity of a BTK polypeptide. In some embodiments, the mutant BTK polypeptide comprises the kinase domain of a BTK polypeptide comprising the modification at amino acid position 481 of the mutant BTK polypeptide set forth in SEQ ID NO: 2.

In some embodiments, the mutant BTK polypeptide comprises a modification at position 481 and a modification selected from among BTK modifications described in, for example, Vihinen et al. (1999) *Hum. Mutat.* 13: 280-285, de Weer et al. *Hum. Mol. Genet.* (1994) 3 (1): 161-166; Perez de Diego et al. (2008) *Clin Exp Immunol.* 152(1):33-8; Kenegane et al. (2000) *Clin Exp Immunol.* 120(3): 512-517, Li et al. (1995) *Immunity* 2:451-460 and Baraldi et al. (1999) *Structure* 7:449-460. In some embodiments, the modification at amino acid position 481 is a substitution that is C481S. In some embodiments, the one or more additional modifications is selected from among substitutions at amino acid positions L11, K12, S14, K19, F25, K27, R28, R33, Y39, Y40, E41, I61, V64, R82, Q103, V113, S115, T117, Q127, C154, C155, T184, P189, P190, Y223, W251, 8288, L295, G302, R307, D308, V319, Y334, L358, Y361, H362, H364, N365, S366, L369, 1370M, R372, L408, G414, Y418, 1429, K430, E445, G462, Y476, M477, C502, C506, A508, M509, L512, L518, R520, D521, A523, R525, N526, V535, L542, R544, Y551, F559, R562, W563, E567, S578, W581, A582, F583, M587, E589, S592, G594, Y598, A607, G613, Y617, P619, A622, V626, M630, C633, R641, F644, L647, L652, V1065, and A1185. In some embodiments, the one or more additional modifications is selected from among L11P, K12R, S14F, K19E, F25S, K27R, R28H, R28C, R28P, T33P, Y3S9, Y40C, Y40N, E41K, I61N, V64F, V64D, R82K, Q103QSFSSVR, V113D, S115F, T117P, Q127H, C154S, C155G, T184P, P189A, Y223F, W251L, R288W, R288Q, L295P, G302E, R307K, R307G, R307T, D308E, V319A, Y334S, L358F, Y361C, H362Q, H364P, N365Y, S366F, L369F, 1370M, R372G, L408P, G414R, Y418H, I429N, K430E, E445D, G462D, G462V, Y476D, M477R, C502F, C502W, C506Y, C506R, A508D, M5091, M509V, L512P, L512Q, L518R, R520Q, D521G, D521H, D521N, A523E, R525G, R525P, R525Q, N526K, V535F, L542P, R544G, R544K, Y551F, F559S, R562W, R562P, W563L, E567K, S578Y, W581R, A582V, F583S, M587L, E589D, E589K, E589G, S592P, G594E, Y598C, A607D, G613D, Y617E, P619A, P619S, A622P, V626G, M630I, M630K, M630T, C633Y, R641C, F644L, F644S, L647P, L652P, V10651, and A1185V.

In some embodiments, the mutant BTK polypeptide comprises a portion of the mutant BTK polypeptide set forth in SEQ ID NO: 2. In some embodiments, the portion exhibits an activity of an BTK polypeptide. For example, in some embodiments, the portion exhibits kinase activity. In some embodiments, the mutant BTK polypeptide comprises the kinase domain of a BTK polypeptide comprising the modification at amino acid position 481 of the mutant BTK polypeptide set forth in SEQ ID NO: 2. In some embodiments, the mutant BTK polypeptide consists essentially of the kinase domain of a BTK polypeptide comprising the modification at amino acid position 481 of the mutant BTK polypeptide set forth in SEQ ID NO: 2. In some embodiments, the mutant BTK polypeptide comprises the sequence of amino acids from about amino acid position 397 to about amino acid position 652 of the mutant BTK polypeptide set forth in SEQ ID NO: 2. In some embodiments, the mutant BTK polypeptide comprises the sequence of amino acids from about amino acid position 402 to about amino acid position 652 of the mutant BTK polypeptide set forth in SEQ ID NO: 2.

In some embodiments, an BTK polypeptide is a fusion protein comprising the kinase domain of an BTK polypeptide comprising the modification at amino acid position 481 of the wild-type BTK polypeptide set forth in SEQ ID NO: 1 linked to a heterologous polypeptide. In some embodiments, the modification at amino acid position 481 is an amino acid substitution that is C481S. Methods for the generation of fusion proteins are known in the art and include standard recombinant DNA techniques. For example, in some embodiments, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In some embodiments, the fusion gene can be synthesized by conventional techniques including automated DNA synthesizers. In some embodiments, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). In some embodiments, expression vectors are commercially available that encode a fusion moiety (e.g., a GST polypeptide). A nucleic acid encoding a modified BTK polypeptide can be cloned into such an expression vector such that the fusion moiety is linked in-frame to the modified BTK polypeptide.

In some embodiments, a BTK polypeptide comprising a modification at amino acid position 481 of the wild-type BTK polypeptide set forth in SEQ ID NO: 1 linked to a peptide tag. In some embodiments, the peptide tag is an epitope tag recognized by a tag-specific antibody. In some embodiments the tag is an epitope tag, such as, but not limited to a c-myc, V-5, hemagglutinin (HA), FLAG, tag. In some embodiments the tag is an affinity tag, such as, but not limited to, biotin, strep-tag, chitin binding protein (CBP), maltose binding protein (MBP), glutathione-S-transferase (GST), or a poly(His) tag. In some embodiments, a BTK polypeptide comprising a modification at amino acid position 481 of the wild-type BTK polypeptide set forth in SEQ ID NO: 1 linked to a detectable protein or moiety, such a luminescent, chemiluminescent, bioluminescent, or fluorescent protein or moiety. In some embodiments, the fluorescent protein is a green (GFP), red (RFP), cyan (CFP), yellow (YFP), or blue (BFP) fluorescent protein. In some embodiments, a BTK polypeptide comprising a modification at amino acid position 481 of the wild-type BTK polypeptide set forth in SEQ ID NO: 1 linked to an enzyme for example, a luciferase or a beta-galactosidase.

In some embodiments, provided herein is an array comprising a mutant BTK polypeptide provided herein. In some embodiments, the mutant BTK polypeptide is bound to a microchip. In some embodiments, the mutant BTK polypeptide is bound directly to the microchip. In some embodiments, the mutant BTK polypeptide is bound indirectly to the microchip via a linker. In some embodiments, provided herein is a microchip array comprising a mutant BTK polypeptide provided herein.

Nucleic Acids Encoding Mutant BTK Polypeptides

Provided herein are nucleic acids encoding mutant BTK polypeptides. Provided herein are nucleic acids encoding any of the mutant BTK polypeptides described herein. Methods for deducing nucleic acids that encode particular polypeptides are known in the art and involve standard molecular biology techniques. Exemplary nucleic acids encoding mutant BTK polypeptides provided herein are provided. It is understood that due to the degeneracy of the genetic code multiple variants nucleic acids exist that encode the same polypeptide. Nucleic acids that encode the mutant BTK polypeptides provided herein encompass such variants. In some embodiments, the mutant BTK nucleic acids are synthetic nucleic acids. In some embodiments, the mutant BTK nucleic acids are cDNA molecules. In some embodiments, the mutant BTK nucleic acids do not contain genomic DNA. In some embodiments, the mutant BTK nucleic acids are unmethylated. In some embodiments, the mutant BTK nucleic acids are do not contain BTK genomic intron sequences. In some embodiments, the mutant BTK nucleic acids comprise a sequence of nucleotides from two or more exons of the BTK genomic sequence, including nucleic acid comprising the codon sequence encoding position 481 of the BTK polypeptide. In some embodiments, the mutant BTK nucleic acids comprise a sequence of nucleotides that encode serine at a position corresponding to position 481 of the wild-type BTK polypeptide.

In some embodiments, the nucleic acid encoding a modified BTK polypeptide provided herein is a DNA or an RNA molecule. In some embodiments, the nucleic acid encoding a mutant BTK polypeptide comprises a modification where the encoded polypeptide comprises a substitution of the amino acid cysteine at the position corresponding to amino acid position 481 of the wild-type BTK polypeptide set forth in SEQ ID NO: 1. In some embodiments, the nucleic acid comprises the sequence of nucleic acids set forth in SEQ ID NO: 3, wherein the nucleic acid codon encoding amino acid at position 481 is modified, whereby the codon does not encode cysteine, or a variant that has at least or at least about 60%, 70%, 75%, 80%, 85%, 90%, 95%, 96%, 97%, 98%, 99% or more sequence identity with the polypeptide having the sequence set forth in SEQ ID NO: 3, wherein the nucleic acid codon encoding amino acid at position 481 does not encode cysteine.

In some embodiments the nucleic acid modification is a missense mutation or a deletion of one or more codons that encode the BTK polypeptide. In some embodiments, the modification is a missense mutation that changes the nucleic acid codon that encodes cysteine at amino position 481 of the BTK polypeptide. In some embodiments, the nucleic acid codon that encodes cysteine at amino position 481 of the BTK polypeptide is TGC or TGT. In some embodiments, the nucleic acid codon that encodes cysteine at amino position 481 of the BTK polypeptide is TGC. In some embodiments, the nucleic acid codon that encodes cysteine at amino position 481 of the BTK polypeptide is TGT. In some embodiments, the modification changes the nucleic acid codon that encodes cysteine at amino position 481 of the BTK polypeptide from TGC to a nucleic acid codon that encodes serine. In some embodiments, the modification changes the nucleic acid codon that encodes cysteine at amino position 481 of the BTK polypeptide from TGT to a nucleic acid codon that encodes serine. In some embodiments, the nucleic acid codon that encodes serine is selected from among TCT, TCC, TCA, TCG, AGT or AGC.

In some embodiments, the modification is a missense mutation that comprises a substitution of thymine (t) for adenine (a) at nucleic acid position 1634 in the nucleic acid set forth in SEQ ID NO: 3. In some embodiments, the modification changes the nucleic acid codon that encodes cysteine at amino position 481 of the BTK polypeptide from TGC to AGC (Serine). In some embodiments, the nucleic acid encoding the mutant BTK polypeptide comprises a sequence of nucleotides set forth in SEQ ID NO: 7 or 22.

In some embodiments, the modification is a missense mutation that comprises a substitution of guanine (g) for cytosine (g) at nucleic acid position 1635 in the nucleic acid set forth in SEQ ID NO: 3. In some embodiments, the modification changes the nucleic acid codon that encodes cysteine at amino position 481 of the BTK polypeptide from TGC to TCC (Serine). In some embodiments, the nucleic acid encoding the mutant BTK polypeptide comprises a sequence of nucleotides set forth in SEQ ID NO: 8 or 23.

In some embodiments the nucleic acid encoding the mutant BTK polypeptide comprises a nucleic acid having 65%, 70%, 75%, 80%, 85%, 90%, 95%, 96%, 97%, 98%, or 99% nucleotide acid sequence identity to the nucleic acid having the sequence of nucleotides set forth in SEQ ID NO: 7 or 22, where the encoded mutant BTK polypeptide comprises a modification relative to the wild-type BTK polypeptide at a position corresponding to amino acid position 481. In some embodiments the nucleic acid encoding the mutant BTK polypeptide comprises a nucleic acid having 65%, 70%, 75%, 80%, 85%, 90%, 95%, 96%, 97%, 98%, or 99% nucleotide acid sequence identity to the nucleic acid having the sequence of nucleotides set forth in SEQ ID NO: 8 or 23, where the encoded mutant BTK polypeptide comprises a modification relative to the wild-type BTK polypeptide at a position corresponding to amino acid position 481. In some embodiments the nucleic acid encoding the mutant BTK polypeptide comprises a nucleic acid having 65%, 70%, 75%, 80%, 85%, 90%, 95%, 96%, 97%, 98%, or 99% nucleotide acid sequence identity to the nucleic acid having the sequence of nucleotides set forth in SEQ ID NO: 7 or 22, where the encoded mutant BTK polypeptide does not comprise a cysteine at the position corresponding to amino acid position 481. In some embodiments the nucleic acid encoding the mutant BTK polypeptide comprises a nucleic acid having 65%, 70%, 75%, 80%, 85%, 90%, 95%, 96%, 97%, 98%, or 99% nucleotide acid sequence identity to the nucleic acid having the sequence of nucleotides set forth in SEQ ID NO: 8 or 23, where the encoded mutant BTK polypeptide does not comprise a cysteine at the position corresponding to amino acid position 481. In some embodiments the nucleic acid encoding the mutant BTK polypeptide comprises a nucleic acid having 65%, 70%, 75%, 80%, 85%, 90%, 95%, 96%, 97%, 98%, or 99% nucleotide acid sequence identity to the nucleic acid having the sequence of nucleotides set forth in SEQ ID NO: 7 or 22, where the encoded mutant BTK comprises a serine at the position corresponding to amino acid position 481. In some embodiments the nucleic acid encoding the mutant BTK polypeptide comprises a nucleic acid having 65%, 70%, 75%, 80%, 85%, 90%, 95%, 96%, 97%, 98%, or 99% nucleotide acid sequence identity to the nucleic acid having the sequence of nucleotides set forth in SEQ ID NO: 8 or 23, where the encoded mutant BTK comprises a serine at the position corresponding to amino acid position 481.

In some embodiments, the nucleic acid provided herein encoding a mutant BTK polypeptide is an isolated nucleic acid. In some embodiments, the nucleic acid provided herein encoding a mutant BTK polypeptide is a DNA molecule. In some embodiments, the nucleic acid provided herein encoding a mutant BTK polypeptide is a cDNA molecule. In some embodiments, the nucleic acid provided herein encoding a mutant BTK polypeptide is an RNA molecule. In some embodiments, the nucleic acid provided herein encoding a mutant BTK polypeptide is an inhibitory RNA molecule (i.e. RNAi). In some embodiments, the nucleic acid provided herein is a nucleic acid molecule that is complementary, or binds to, an nucleic acid encoding a mutant BTK polypeptide.

In some embodiments, the nucleic acid provided herein encoding a mutant BTK polypeptide encodes a portion of a mutant BTK polypeptide provided herein that comprises amino acid position 481. In some embodiments, the codon encodes an amino acid that is not cysteine. In some embodiments, the codon encodes an amino acid that is serine. In some embodiments, the nucleic acid provided herein encoding a mutant BTK polypeptide encodes one or more domains of a mutant BTK polypeptide provided herein. In some embodiments, the nucleic acid provided herein encoding a mutant BTK polypeptide encodes a kinase domain of a mutant BTK polypeptide provided herein.

In some embodiments, the nucleic acid provided herein encoding a mutant BTK polypeptide or a portion thereof contains nucleic acid encoding an amino acid at position 481 that is not cysteine. In some embodiments, the nucleic acid provided herein encoding a mutant BTK polypeptide or a portion thereof contains nucleic acid encoding serine at amino acid position 481.

In some embodiments, the nucleic acid provide herein is an oligonucleotide that encodes a portion of the mutant BTK polypeptide. In some embodiments the nucleic acid provided herein is an oligonucleotide that encodes a portion of the mutant BTK polypeptide that contains a nucleotide codon encoding the amino acid corresponding to amino acid position 481. In some embodiments, the codon encodes an amino acid that is not cysteine. In some embodiments, the codon encodes an amino acid that is serine.

In some embodiments, the nucleic acid provided herein is a vector that comprises a nucleic acid molecule encoding a modified BTK polypeptide provided herein. In some embodiments, the nucleic acid provided herein is a vector that comprises nucleic acid encoding a mutant BTK polypeptide provided herein is an expression vector. In some embodiments, the nucleic acid encoding a mutant BTK polypeptide provided herein is operably linked to a promoter. In some embodiments, the promoter is a constitutive or an inducible promoter. In some embodiments, provided herein is a host cell, comprising the vector or nucleic acid molecule encoding a modified BTK polypeptide provided herein. In some embodiments, the cell is a prokaryotic cell or a eukaryotic cell. Also provided herein is a mutant BTK polypeptide expressed by the host cell.

In some embodiments, the vector is a viral or plasmid vector. In some embodiments, the viral vector is a DNA or RNA viral vector. Exemplary viral vectors include, but are not limited to, a vaccinia, adenovirus, adeno-associated virus (AAV), retrovirus, or herpesvirus vector.

In some embodiments, provided herein is an array comprising a nucleic acid encoding any of the mutant BTK polypeptides provided herein. In some embodiments, the mutant BTK nucleic acid is bound to a microchip. In some embodiments, the mutant BTK nucleic acid is bound directly to the microchip. In some embodiments, the mutant BTK nucleic acid is bound indirectly to the microchip via a linker. In some embodiments, provided herein is a microchip array comprising a nucleic acid encoding any of the mutant BTK polypeptides provided herein.

Production of Nucleic Acids and Polypeptides

In some embodiments, an isolated nucleic acid molecule encoding a mutant BTK polypeptide provided herein is generated by standard recombinant methods. In some embodiments, an isolated nucleic acid molecule encoding a mutant BTK polypeptide provided herein is generated by amplification of a mutant BTK sequence from genomic DNA. In some embodiments, an isolated nucleic acid molecule encoding a mutant BTK polypeptide provided herein is generated by polymerase chain reaction using BTK sequence specific primers. In some embodiments, an isolated nucleic acid molecule encoding a mutant BTK polypeptide In some embodiments, an isolated nucleic acid molecule encoding a mutant BTK polypeptide provided herein is inserted into an expression vector and expressed in a host cell or a non-cell extract. In some embodiments, an isolated nucleic acid molecule encoding a mutant BTK polypeptide provided herein is operatively linked to a promoter for expression of the encoding polypeptide in a cell or non-cell extract. In some embodiments, the promoter is a constitutive promoter. In some embodiments, the promoter is an inducible promoter.

In some embodiments, the nucleic acid molecule encoding a mutant BTK polypeptide provided herein is "exogenous" to a cell, which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference.

Methods for the expression of a protein in a cell are well known in the art and include, for example, expression in cells, such as animal and plant cells. Exemplary animal cells for the expression of mutant BTK polypeptides provided herein include but are not limited to bacteria, yeast, insect cells, amphibian, and mammalian cells, such as for example, human, primate, rodent, bovine, and ovine cells. In some embodiments, the nucleic acid encoding the mutant BTK is integrated into the genome of the host cell.

In some embodiments, a method for the expression of a mutant BTK polypeptide provided herein comprises culturing a host cell containing an expression vector encoding a mutant BTK polypeptide such that the mutant BTK polypeptide is produced by the cell. In some methods, the nucleic acid encoding as mutant polypeptide is connected to nucleic acid encoding a signal sequence such that the signal sequence is expressed as a fusion peptide with the mutant BTK polypeptide. In some embodiments the signal sequence allows for the secretion of the mutant BTK polypeptide by the host cell.

In some embodiments the mutant BTK polypeptide is isolated from a host cell expressing the mutant polypeptide. In some embodiments an extract is prepared from the host cell and the mutant BTK polypeptide is isolated by purification methods such as but not limited to chromatography or immunoaffinity with an antibody that is specific for BTK polypeptides or specific to the mutant BTK polypeptide in particular.

Antibodies

Provided herein are isolated antibodies that bind to a modified BTK polypeptide having a modification at amino acid position 481, wherein the antibodies do not bind to or bind with lower affinity to a wild-type BTK polypeptide having the sequence of amino acids set forth in SEQ ID NO: 1. In some embodiments, the modification is a substitution of cysteine to serine at amino acid position 481 of the BTK polypeptide.

In some embodiments, mutant BTK polypeptides provided herein are detected using antibodies that specifically recognize the mutant BTK polypeptides, but do not recognize wild-type BTK polypeptides. In some embodiments, mutant BTK polypeptides provided herein are detected using antibodies that specifically recognize a mutant BTK polypeptide having a serine at amino acid position 481, but do not recognize wild-type BTK polypeptides. In some embodiments, antibodies are raised against one or more allelic forms of the mutant BTK polypeptides provided herein. Techniques for using a specific protein or an oligopeptide as an antigen to elicit antibodies that specifically recognize epitopes on the peptide or protein are well known. In one embodiment, the DNA sequence of the desired allelic form of the target gene is cloned by insertion into an appropriate expression vector and translated into protein in a prokaryotic or eukaryotic host cell. The protein is recovered and used as an antigen to elicit the production of specific antibodies. In another embodiment, the DNA of the desired allelic form of the target gene is amplified by PCR technology and is subsequently translated in vitro into protein to be used as the antigen to elicit the production of specific antibodies. In another embodiment, the DNA sequence of the alternative alleles is used as a basis for the generation of synthetic peptides representing the amino acid sequence of the alleles for use as the antigen to elicit the production of specific antibodies.

In some embodiments, antibodies are generated either by standard monoclonal antibody techniques or generated through recombinant based expression systems. See generally, Abbas, Lichtman, and Pober, Cellular and Molecular Immunology, W. B. Saunders Co. (1991). The term "antibodies" is meant to include intact antibody molecules as well as antibody fragments or derivatives, such as Fab and F(ab')2, which are capable of specifically binding to antigen. The antibodies so produced preferentially bind only the mutant protein produced in the allelic form which was used as an antigen to create the antibody. Methods of generating allele-specific antibodies are also described in U.S. Pat. Nos. 6,200,754 and 6,054,273, the entire contents of which are incorporated herein by reference.

In some embodiments, the antibody provided herein is a humanized antibody. A "humanized antibody" refers to a type of engineered antibody having its CDRs derived from a non-human donor immunoglobulin, the remaining immunoglobulin-derived parts of the molecule being derived from one or more human immunoglobulin(s). In some embodiments, framework support residues are altered to preserve binding affinity (see, e.g., Queen et al. Proc. Natl. Acad Sci USA, 86:10029-10032 (1989), Hodgson et al. Bio/Technology, 9:421 (1991)). In some embodiments, a suitable human acceptor antibody is one selected from a conventional database, e.g., the KABAT® database, Los Alamos database, and Swiss Protein database, by homology to the nucleotide and amino acid sequences of the donor antibody. In some embodiments, a human antibody characterized by a homology to the framework regions of the donor antibody (on an amino acid basis) is suitable to provide a heavy chain constant region and/or a heavy chain variable framework region for insertion of the donor CDRs. In some embodiments, a suitable acceptor antibody capable of donating light chain constant or variable framework regions is selected in a similar manner. In some embodiments, the acceptor antibody heavy and light chains originate from the same acceptor antibody. In some embodiments, the acceptor antibody heavy and light chains originate from the different acceptor antibodies. The prior art describes several ways of producing such humanized antibodies—see, for example, EP-A-0239400 and EP-A-054951.

In some embodiments, antibodies specific for mutant BTK polypeptides provided herein are used to detect the presence of a mutant BTK polypeptide provided herein in a sample, e.g., an assay sample, a cell sample, a cell extract, a biological sample, or a patient sample, using techniques known in the art. These techniques include, for example, Western blot, immunohistochemistry, indirect immunofluorescence, and antibody microarray. In some embodiments, an antibody which specifically recognizes a mutant BTK polypeptide is a second-generation BTK inhibitor. In some embodiments, the ability of an antibody which specifically recognizes a mutant BTK polypeptide to inhibit the biological activity of the mutant BTK polypeptide can be determined using the methods described herein for identifying second-generation BTK inhibitors.

Diagnostic Assays for Detecting Mutant BTK Polypeptides and Nucleic Acids Encoding Mutant BTK Polypeptides Provided herein are diagnostic methods that involve the detection of a mutant BTK polypeptide in a subject or a nucleic acid encoding a mutant BTK polypeptide in a subject. In some embodiments, the subject has an BTK-mediated disease or condition. In some embodiments, the subject has an BTK-mediated disease or condition is a B-cell cancer. In some embodiments, the diagnostic methods are employed for the screening subjects having a B-cell cancer that is resistant to therapy with a covalent and/or irreversible BTK inhibitor, identifying subjects for the treatment with a covalent and/or irreversible BTK inhibitor, identifying subjects as likely or unlikely to respond to treatment with a covalent and/or irreversible BTK inhibitor, predicting whether a subject is likely to develop resistance to treatment with a covalent and/or irreversible BTK inhibitor, monitoring the therapy of subjects receiving therapy with a covalent and/or irreversible BTK inhibitor, optimizing the therapy of subjects receiving a covalent and/or irreversible BTK inhibitor therapy, and combinations thereof. In some embodiments, the methods comprises selecting a subject for therapy with a second-generation BTK inhibitor. In some embodiments, the methods further comprise administering to the subject a second-generation BTK inhibitor that inhibits the mutant BTK. In some embodiments, the BTK modification confers resistance of a cancer cell to treatment with a covalent and/or irreversible BTK inhibitor.

In some embodiments, the mutant BTK polypeptide detected comprises a modification at a position corresponding to amino acid position 481 of the wild-type BTK polypeptide set forth in SEQ ID NO: 1. In some embodiments, the mutant BTK polypeptide detected comprises a substitution of the amino acid cysteine to serine at the position corresponding to amino acid position 481 of the wild-type BTK polypeptide set forth in SEQ ID NO: 1. In some embodiments, a subject having a mutant BTK polypeptide comprising a modification at amino acid position 481 is resistant to inhibition with a covalent and/or irreversible BTK inhibitor. In some embodiments, a subject having a mutant BTK polypeptide comprising a modification at amino acid position 481 is resistant to inhibition with a covalent and/or irreversible BTK inhibitor that is ibrutinib. In some embodiments, a subject having a mutant BTK polypeptide comprising a modification at amino acid position 481 is resistant to inhibition with a covalent and/or irreversible BTK inhibitor that covalently binds to cysteine 481 of the wild-type BTK. In some embodiments, a subject having a mutant BTK polypeptide comprising a modification at amino acid position 481 is resistant to inhibition with a covalent and/or irreversible BTK inhibitor that is ibrutinib, PCI-45292, PCI-45466, AVL-101, AVL-291, AVL-292, or ONO-WG-37. In some embodiments, a subject having a mutant BTK polypeptide comprising a modification at amino acid position 481 is resistant to inhibition with a covalent and/or irreversible BTK inhibitor that is ibrutinib.

In some embodiments, provided is a method for determining whether a subject is or likely to become less responsive to therapy with a covalent and/or irreversible BTK inhibitor, comprising: (a) testing a sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1; and (b) characterizing the subject as resistant or likely to become resistant to therapy with a covalent and/or irreversible BTK inhibitor if the subject has the modification. In some embodiments, step (a) is performed ex vivo. In some embodiments, the method further comprises continuing treatment with a BTK inhibitor if the subject does not have the modification. In some embodiments, the method further comprises administering second generation BTK inhibitor that inhibits the modified kinase if the subject has the modification. In some embodiments, the method further comprises administering an inhibitor of LYN, SYK, JAK, PI3K, PLCγ, MAPK, MEK, or NFκB if the subject has the modification. In some embodiments, the method further comprises administering a covalent inhibitor of BTK that does not bind to C481 if the subject has the modification. In some embodiments, the method further comprises administering a reversible inhibitor of BTK if the subject has the modification. In some embodiments of the method, the subject has cancer. In some embodiments, the cancer is a hematologic cancer. In some embodiments, cancer is a B-cell malignancy. Exemplary B-cell malignancies are provided herein. In some embodiments, cancer is selected from among a leukemia, a lymphoma, or a myeloma. In some embodiments, the method further comprises obtaining the sample from the subject.

In some embodiments, provided is a method for characterizing a BTK as resistant to inhibition with a covalent and/or irreversible BTK inhibitor in a subject, comprising: (a) testing a sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1; and (b) characterizing the BTK as resistant to inhibition with a covalent and/or irreversible BTK inhibitor if the subject has the modification. In some embodiments, step (a) is performed ex vivo. In some embodiments, the method further comprises continuing treatment with a BTK inhibitor if the subject does not have the modification. In some embodiments, the method further comprises administering second generation BTK inhibitor that inhibits the modified kinase if the subject has the modification. In some embodiments, the method further comprises administering an inhibitor of LYN, SYK, JAK, PI3K, PLCγ, MAPK, MEK, or NFκB if the subject has the modification. In some embodiments, the method further comprises administering a covalent inhibitor of BTK that does not bind to C481 if the subject has the modification. In some embodiments, the method further comprises administering a reversible inhibitor of BTK if the subject has the modification. In some embodiments of the method, the subject has cancer. In some embodiments, the cancer is a hematologic cancer. In some embodiments, cancer is a B-cell malignancy. Exemplary B-cell malignancies are provided herein. In some embodiments, cancer is selected from among a leukemia, a lymphoma, or a myeloma. In some embodiments, the method further comprises obtaining the sample from the subject.

In some embodiments, provided is a method for monitoring whether a subject receiving a covalent and/or irreversible BTK inhibitor for treatment of a cancer has developed or is likely to develop resistance to the therapy, comprising: (a) testing a sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1; and (b) characterizing the subject as resistant or is likely to become resistant to therapy with a covalent and/or irreversible BTK inhibitor if the subject has the modification. In some embodiments, step (a) is performed ex vivo. In some embodiments, the method further comprises discontinuing treatment with the BTK inhibitor if the subject has the modification. In some embodiments, the method further comprises continuing treatment with a BTK inhibitor if the subject does not have the modification. In some embodiments, the method further comprises administering second generation BTK inhibitor that inhibits the modified kinase if the subject has the modification. In some embodiments, the method further comprises administering an inhibitor of LYN, SYK, JAK, PI3K, PLCγ, MAPK, MEK, or NFκB if the subject has the modification. In some embodiments, the method further comprises administering a covalent inhibitor of BTK that does not bind to C481 if the subject has the modification. In some embodiments, the method further comprises administering a reversible inhibitor of BTK if the subject has the modification. In some embodiments of the method, the subject has cancer. In some embodiments, the cancer is a hematologic cancer. In some embodiments, cancer is a B-cell malignancy. Exemplary B-cell malignancies are provided herein. In some embodiments, cancer is selected from among a leukemia, a lymphoma, or a myeloma. In some embodiments, the method further comprises obtaining the sample from the subject.

In some embodiments, provided is a method for optimizing the therapy of a subject receiving a covalent and/or irreversible BTK inhibitor for treatment of a cancer, comprising: (a) testing a sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1; and (b) discontinuing treatment with the irreversible BTK inhibitor if the subject has the modification or continuing treatment with the irreversible BTK inhibitor if the subject does not have the modification. In some embodiments, the method further comprises administering second-generation BTK inhibitor that inhibits the modified kinase if the subject has the modification. In some embodiments, step (a) is performed ex vivo. In some embodiments, the method further comprises administering an inhibitor of LYN, SYK, JAK, PI3K, PLCγ, MAPK, MEK, or NFκB if the subject has the modification. In some embodiments, the method further comprises administering a covalent inhibitor of BTK that does not bind to C481 if the subject has the modification. In some embodiments, the method further comprises administering a reversible inhibitor of BTK if the subject has the modification. In some embodiments of the method, the subject has cancer. In some embodiments, the cancer is a hematologic cancer. In some embodiments, cancer is a B-cell malignancy. Exemplary B-cell malignancies are provided herein. In some embodiments, cancer is selected from among a leukemia, a lymphoma, or a myeloma. In some embodiments, the method further comprises obtaining the sample from the subject.

In some embodiments, provided is a method for selecting a subject for therapy with a second-generation BTK inhibitor, comprising: (a) testing the sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1; and (b) characterizing the subject as a candidate for therapy with a second generation BTK inhibitor if the subject has the modification. In some embodiments, the method further comprises administering second generation BTK inhibitor that inhibits the modified kinase if the subject has the modification. In some embodiments, step (a) is performed ex vivo. In some embodiments of the method, the subject has cancer. In some embodiments, the cancer is a hematologic cancer. In some embodiments, cancer is a B-cell malignancy. Exemplary B-cell malignancies are provided herein. In some embodiments, cancer is selected from among a leukemia, a lymphoma, or a myeloma. In some embodiments, the method further comprises obtaining the sample from the subject.

In some embodiments, the modification comprises a substitution or a deletion of the amino acid at amino acid position 481 in the BTK polypeptide. In some embodiments, the modification is a substitution of cysteine to an amino acid selected from among leucine, isoleucine, valine, alanine, glycine, methionine, serine, threonine, phenylalanine, tryptophan, lysine, arginine, histidine, proline, tyrosine, asparagine, glutamine, aspartic acid and glutamic acid at amino acid position 481 of the BTK polypeptide. In some embodiments, the modification is a substitution of cysteine to an amino acid selected from among serine, methionine, or threonine at amino acid position 481 of the BTK polypeptide. In some embodiments, the modification is a substitution of cysteine to serine at amino acid position 481 of the BTK polypeptide. In some embodiments, the modification comprises a deletion of nucleic acid encoding amino acid position 481 of the BTK polypeptide.

In some embodiments of the methods, the nucleic acid molecule for use in the assay is RNA or DNA. In some embodiments of the methods, the nucleic acid molecule for use in the assay is genomic DNA. In some embodiments of the methods, the nucleic acid molecule for use in the assay is total RNA. In some embodiments of the methods, the nucleic acid molecule for use in the assay is mRNA. In some embodiments of the methods, the method further comprises isolating mRNA from the RNA sample. In some embodiments of the methods, the nucleic acid molecule for use in the assay is cDNA. In some embodiments of the methods, the method further comprises reverse transcribing an RNA sample into cDNA. In some embodiments of the methods, the method comprises analyzing the cDNA. In some embodiments, the sample is a plasma or serum sample containing circulating tumor DNA (ctDNA), RNA (ctRNA) or microRNA (see e.g. Chan et al. (2007) *Br. J Cancer.* 96(5):681-5).

In some embodiments, the genomic nucleic acid sample is amplified by a nucleic acid amplification method. In some embodiments, the nucleic acid amplification method is polymerase chain reaction (PCR). In some embodiments, the genomic nucleic acid sample is amplified using a set of nucleotide primers specific for the BTK gene. In some embodiments, the set of nucleotide primers flank the nucleic acid sequence encoding amino acid position 481 of the BTK polypeptide. In some embodiments, the amplification product is a nucleic acid encoding amino acid position 481 of the BTK polypeptide. In some embodiments, a sequence specific primer is conjugated to a detectable molecule, such as a fluorescent label, a bioluminescent label, a chemiluminescent label, a radiolabel, an enzyme label, a detectable substrate, or a peptide or molecule that binds to a second detectable molecule.

A variety of methods are available in the art for the detection of single point mutations in nucleic acids encoding mutant BTK polypeptides and amino acid changes in BTK polypeptides in a sample. The following methods for detection of mutations in nucleic acids and mutant polypeptides are meant to be exemplary and are not exclusive.

In some embodiments of the methods, testing the sample comprises performing polymerase chain reaction (PCR) amplification of nucleic acid encoding amino acid position 481 of the BTK polypeptide. In some embodiments, PCR amplification comprises using a pair of oligonucleotide primers that flank the region encoding amino acid position 481 of the BTK polypeptide and amplifying a nucleic acid sequence encoding the BTK polypeptide or portion thereof containing amino acid position 481. In some embodiments, the method comprises sequencing the amplified nucleic acid. In some embodiments, the method comprises sequencing the amplified nucleic acid using a sequence specific primer. In some embodiments, the method comprises ligating the amplified PCR fragment into a vector and then sequencing the nucleic acid encoding the BTK polypeptide or portion thereof containing amino acid position 481. In some embodiments, the method comprises sequencing the amplified nucleic acid in a vector using a vector sequence specific primer.

Exemplary sequencing methods for use in the methods provide herein are well known in the art and include, but are not limited to, dideoxy or chain termination methods, Maxam-Gilbert sequencing, massively parallel signature sequencing (or MPSS), polony sequencing, pyrosequencing, Illumina dye sequencing, SOLiD (or sequencing by ligation) sequencing, ion semiconductor sequencing, DNA nanoball sequencing, heliscope sequencing, and single molecule real time (SMRT) sequencing.

In some embodiments of the methods, testing the sample comprises pyrosequencing. Pyrosequencing is based on sequencing by synthesis. It differs from Sanger sequencing, in that it relies on the detection of pyrophosphate release on nucleotide incorporation, rather than chain termination with dideoxynucleotides. "Sequencing by synthesis" involves taking a single strand of the DNA to be sequenced and then synthesizing its complementary strand enzymatically. The pyrosequencing method is based on detecting the activity of DNA polymerase (a DNA synthesizing enzyme) with another chemiluminescent enzyme. The method allows sequencing of a single strand of DNA by synthesizing the complementary strand along it, one base pair at a time, and detecting which base was actually added at each step. The template DNA is immobile, and solutions of A, C, G, and T nucleotides are sequentially added and removed from the reaction. Light is produced only when the nucleotide solution complements the first unpaired base of the template. The sequence of solutions which produce chemiluminescent signals allows the determination of the sequence of the template. The methods is able measure multi-allelic mutations in mixed populations can detect mutations in a heterogeneous population of leukemic cells.

In some embodiments of the methods, testing the sample comprises contacting the nucleic acid with a sequence specific nucleic acid probe, wherein the sequence specific nucleic acid probe: (a) binds to nucleic acid encoding a modified BTK that is modified at amino acid position 481; and (b) does not bind to nucleic acid encoding the wild-type BTK having cysteine at amino acid position 481. In some embodiments, testing the sample comprises (a) contacting a sample with a mutant BTK nucleic acid sequence specific oligonucleotide probe, whereby if the mutant nucleic acid sequence is present in the sample, a probe-DNA complex is formed, and (b) detecting the probe-DNA complex. In some embodiments, the oligonucleotide probe is specific for nucleic acid encoding serine at a position corresponding to amino acid 481 of a BTK polypeptide. In some embodiments, the sequence specific probe is conjugated to a detectable molecule, such as a fluorescent label, a bioluminescent label, a chemiluminescent label, a radiolabel, an enzyme label, a detectable substrate, or a peptide or molecule that binds to a second detectable molecule.

In some embodiments of the methods, testing comprises using allele specific PCR. In some embodiments, single nucleotide changes are detectable PCR using PCR-based cleaved amplified polymorphic sequences (CAPS) markers which create restriction sites in the mutant sequences (Michaels et al (1998) *Plant J.* 14(3):381-5) or sequence specific hairpin probes attached to detectable moieties, such as, but not limited to, a fluorophore (Mhlanga and Malmberg (2001) *Methods* 25:463-471). In some embodiments, the sequence specific probe is conjugated to a detectable molecule, such as a fluorescent label, a bioluminescent label, a chemiluminescent label, a radiolabel, an enzyme label, a detectable substrate, or a peptide or molecule that binds to a second detectable molecule. In some embodiments, the oligonucleotide probe is specific for nucleic acid encoding serine at a position corresponding to amino acid 481 of a BTK polypeptide.

In some embodiments, the DNA encoding the mutant BTK is assessed by BEAMing (beads, amplification, emulsion, magnetic) PCR sequencing method (see, e.g. Li et al. (2006) *Nat Methods.* 3(2):95-7; Li et al. (2006) *Nat Methods.* 3(7):551-9; and Diehl et al. (2008) *Nat Med.* 14(9): 985-990). BEAMing is a technique in which individual DNA molecules are attached to magnetic beads in water-in-oil emulsions and then subjected to compartmentalized PCR amplification. The mutational status of DNA bound to beads is then determined by hybridization to fluorescent allele-specific probes for mutant or wild-type BTK. Flow cytometry is then used to quantify the level of mutant DNA present in the plasma or serum (see e.g. Higgins et al. (2012) *Clin Cancer Res* 18: 3462-3469).

In some embodiments, testing the sample comprises denaturing high performance liquid chromatography (D-HPLC). D-HPLC relies upon the differential retention kinetics of heteroduplex/homoduplex DNA species within a cartridge matrix designed to separate DNA fragments according to charge density against an electrolyte gradient. (see e.g. Frueh et al (2003) *Clin Chem Lab Med.* 41(4):452-61).

In some embodiments, testing the sample comprises nanofluidics, including using NanoPro to determine the pI differences in a wild-type BTK polypeptide covalently bound to the irreversible BTK inhibitor at amino acid position cysteine 481 and mutant C481S BTK polypeptide that does not covalently bind to the irreversible BTK inhibitor. NanoPro is an instrument that can separate proteins based on small differences in isoelectric points. The covalent modification of cysteine 481 with the irreversible BTK inhibitor compared to the unconjugated mutant BTK will change its isoelectric point, which is used to detect drug binding to BTK.

In some embodiments, testing the sample comprises using a microarray. In some embodiments, the presence of DNA encoding the mutant BTK is assessed using an oligonucleotide array (see e.g. Hastia et al. (1999) *J Med Genet.* 36(10):730-6). In some embodiments, the oligonucleotide array is contained on a microchip. In some embodiments, single nucleotide changes are detectable using microchips.

In some embodiments, nucleic acid encoding a mutant BTK polypeptide provided herein or a portion thereof that contains nucleic acid encoding the amino acid at position 481 that is not cysteine. In some embodiments, nucleic acid encoding a mutant BTK polypeptide provided herein or a portion thereof that contains nucleic acid encoding serine at amino acid position 481.

In some embodiments of the method, the sample for detection of a mutant BTK is a protein sample that contains a BTK polypeptide. In such examples, testing comprises detection of the mutation with an antibody specific for the mutant BTK polypeptide. In some embodiments, the method of detecting a mutant BTK polypeptide comprises providing a sample from a subject, wherein the sample comprises an BTK polypeptide and testing the sample for the presence of a mutant BTK polypeptide by contacting the sample with an antibody that is specific for binding to the mutant BTK polypeptide, and does not bind or binds with decreased affinity for the wild-type BTK polypeptide, wherein the presence of the mutant BTK polypeptide creates an antibody-mutant BTK polypeptide complex. In some embodiments, the method further comprises detecting the antibody-mutant BTK polypeptide complex. In some embodiments, the method further comprises detecting the antibody-mutant BTK polypeptide complex with a detection reagent. In some embodiments, the mutant BTK specific antibody is conjugated to a detectable molecule, such as a fluorescent label, a bioluminescent label, a chemiluminescent label, a radiolabel, an enzyme label, a detectable substrate, or a peptide or molecule that binds to a second detectable protein (e.g. a secondary antibody). In some embodiments, binding of the mutant BTK specific antibody is detected by assaying for the detectable molecule. In some embodiments, binding of the mutant BTK specific antibody is detected by using a secondary (e.g. anti-IgG) antibody.

In some embodiments of the methods, the subject has a BTK-mediated disease or disorder. In some embodiments of the methods, the subject has a B-cell proliferative disorder. In some embodiments of the methods, the subject has cancer. In some embodiments, the cancer is a hematologic cancer. In some embodiments, cancer is a B-cell malignancy. In some embodiments, cancer is selected from among a leukemia, a lymphoma, or a myeloma. In some embodiments, the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the subject has a solid tumor.

In some embodiments, the subject has a solid tumor. In some embodiments, the subject has a sarcoma, carcinoma, a neurofibromatoma or a lymphoma.

In some embodiments, the subject has a cancer of the lung, breast, colon, brain, prostate, liver, pancreas, esophagus, kidney, stomach, thyroid, bladder, uterus, cervix or ovary. In some embodiments, the subject has a metastatic cancer. In some embodiments, the subject has a cancer that is acute lymphoblastic leukemia, acute lymphoblastic leukemia, acute myeloid leukemia, acute promyelocytic leukemia, adenocarcinoma, adenoma, adrenal cancer, adrenocortical carcinoma, AIDS-related cancer, AIDS-related lymphoma, anal cancer, appendix cancer, astrocytoma, basal cell carcinoma, bile duct cancer, bladder cancer, bone cancer, osteosarcoma/malignant fibrous histiocytoma, brainstem glioma, brain cancer, carcinoma, cerebellar astrocytoma, cerebral astrocytoma/malignant glioma, ependymoma, medulloblastoma, supratentorial primitive neuroectodermal tumor, visual pathway or hypothalamic glioma, breast cancer, bronchial adenoma/carcinoid, Burkitt lymphoma, carcinoid tumor, carcinoma, central nervous system lymphoma, cervical cancer, chronic lymphocytic leukemia, chronic myelogenous leukemia, chronic myeloproliferative disorder, colon cancer, cutaneous T-cell lymphoma, desmoplastic small round cell tumor, endometrial cancer, ependymoma. epidermoid carcinoma, esophageal cancer, Ewing's sarcoma, extracranial germ cell tumor, extragonadal germ cell tumor, extrahepatic bile duct cancer, eye cancer/intraocular melanoma, eye cancer/retinoblastoma, gallbladder cancer, gallstone tumor, gastric/stomach cancer, gastrointestinal carcinoid tumor, gastrointestinal stromal tumor, giant cell tumor, glioblastoma multiforme, glioma, hairy-cell tumor, head and neck cancer, heart cancer, hepatocellular/liver cancer, Hodgkin lymphoma, hyperplasia, hyperplastic corneal nerve tumor, in situ carcinoma, hypopharyngeal cancer, intestinal ganglioneuroma, islet cell tumor, Kaposi's sarcoma, kidney/renal cell cancer, laryngeal cancer, leiomyoma tumor, lip and oral cavity cancer, liposarcoma, liver cancer, non-small cell lung cancer, small cell lung cancer, lymphomas, macroglobulinemia, malignant carcinoid, malignant fibrous histiocytoma of bone, malignant hypercalcemia, malignant melanomas, marfanoid habitus tumor, medullary carcinoma, melanoma, merkel cell carcinoma, mesothelioma, metastatic skin carcinoma, metastatic squamous neck cancer, mouth cancer, mucosal neuromas, multiple myeloma, mycosis fungoides, myelodysplastic syndrome, myeloma, myeloproliferative disorder, nasal cavity and paranasal sinus cancer, nasopharyngeal carcinoma, neck cancer, neural tissue cancer, neuroblastoma, oral cancer, oropharyngeal cancer, osteosarcoma, ovarian cancer, ovarian epithelial tumor, ovarian germ cell tumor, pancreatic cancer, parathyroid cancer, penile cancer, pharyngeal cancer, pheochromocytoma, pineal astrocytoma, pineal germinoma, pineoblastoma, pituitary adenoma, pleuropulmonary blastoma, polycythemia vera, primary brain tumor, prostate cancer, rectal cancer, renal cell tumor, reticulum cell sarcoma, retinoblastoma, rhabdomyosarcoma, salivary gland cancer, seminoma, Sezary syndrome, skin cancer, small intestine cancer, soft tissue sarcoma, squamous cell carcinoma, squamous neck carcinoma, stomach cancer, supratentorial primitive neuroectodermal tumor, testicular cancer, throat cancer, thymoma, thyroid cancer, topical skin lesion, trophoblastic tumor, urethral cancer, uterine/endometrial cancer, uterine sarcoma, vaginal cancer, vulvar cancer, Waldenström's macroglobulinemia or Wilm's tumor.

In some embodiments, the subject has a relapsed cancer. In some embodiments, the subject has a refractory cancer. In some embodiments, the subject has a refractory cancer where the cancer is refractory to treatment with a covalent and/or irreversible BTK inhibitor. In some embodiments, the subject has a refractory cancer where the subject exhibits a decrease in sensitivity to treatment with a covalent and/or irreversible BTK inhibitor. In some embodiments, the subject has a refractory cancer where the subject exhibits a decrease in sensitivity to a particular dosage of a covalent and/or irreversible BTK inhibitor. In some embodiments, the subject has a refractory cancer where the subject exhibits a increase in severity or the appearance of one or more symptoms of a cancer (i.e. disease progression). In some embodiments, the subject exhibits a decrease in the regression of a cancer. In some embodiments, the regression of a cancer ceases. In some embodiments, the subject has a relapsed or refractory hematologic cancer. In some embodiments, the subject has a relapsed or refractory B-cell malignancy.

In some embodiments the subject is suspected of having a hematologic cancer or is at high risk of having a hematologic cancer. In some embodiments the subject is suspected of having a B-cell malignancy or is at high risk of having a B-cell malignancy. In some embodiments the subject is suspected of having or is at high risk of having a leukemia, a lymphoma, or a myeloma.

In some embodiments, the subject exhibits one or more symptoms of a hematologic cancer. In some embodiments, the subject exhibits one or more symptoms of a B-cell malignancy. In some embodiments, the subject exhibits one or more symptoms of a leukemia, a lymphoma, or a myeloma. In some embodiments, the subject exhibits one or more symptoms such as, but not limited to, abnormal B-cell function, abnormal B-cell size or shape, abnormal B-cell count, fatigue, fever, night sweats, frequent infection, enlarged lymph nodes, paleness, anemia, easy bleeding or bruising, loss of appetite, weight loss, bone or joint pain, headaches, and petechie.

In some embodiments, the subject is suffering from an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

In other embodiments, the subject is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In some embodiments, the subject has an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In further embodiments, the subject is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In some embodiments, the subject is administered or has been administered one or more therapeutic agents for treatment of a disease or condition. In some embodiments, the subject is administered or has been administered a BTK inhibitor for treatment of a disease or condition. In some embodiments, the subject is administered or has been administered one or more therapeutic agents in addition to a BTK inhibitor for treatment of a disease or condition.

In some embodiments, the subject is administered or has been administered one or more chemotherapeutic agents for treatment of cancer. In some embodiments, the subject is administered or has been administered a BTK inhibitor for treatment of a cancer. In some embodiments, the subject is administered or has been administered one or more chemotherapeutic agents in addition to a BTK inhibitor for treatment of cancer.

In some embodiments, the sample for use in the methods is from any tissue or fluid from an organism. Samples include, but are not limited, to whole blood, dissociated bone marrow, bone marrow aspirate, pleural fluid, peritoneal fluid, central spinal fluid, abdominal fluid, pancreatic fluid, cerebrospinal fluid, brain fluid, ascites, pericardial fluid, urine, saliva, bronchial lavage, sweat, tears, ear flow, sputum, hydrocele fluid, semen, vaginal flow, milk, amniotic fluid, and secretions of respiratory, intestinal or genitourinary tract. In particular embodiments, the sample is a tumor biopsy sample. In particular embodiments, the sample is from a fluid or tissue that is part of, or associated with, the lymphatic system or circulatory system. In some embodiments, the sample is a blood sample that is a venous, arterial, peripheral, tissue, cord blood sample. In particular embodiments, the sample is a blood cell sample containing one or more peripheral blood mononuclear cells (PBMCs). In some embodiments, the sample contains one or more circulating tumor cells (CTCs). In some embodiments, the sample contains one or more disseminated tumor cells (DTC, e.g. in a bone marrow aspirate sample).

Methods for the isolation of nucleic acids and proteins from cells contained in tissue and fluid samples are well-known in the art. In particular embodiments, the sample obtained from the subject is isolated from cells contained in a tumor biopsy from the subject. In particular embodiments, the sample obtained from the subject is isolated from cells in a bone marrow aspirate. In particular embodiments, the sample obtained from the subject is isolated from cells contained a serum sample. In particular embodiments, the sample obtained from the subject is isolated from cells contained in a lymph sample. In particular embodiments, the sample contains circulating tumor nucleic acid not contained in a cell.

In some embodiments, the samples are obtained from the subject by any suitable means of obtaining the sample using well-known and routine clinical methods. Procedures for obtaining fluid samples from a subject are well known. For example, procedures for drawing and processing whole blood and lymph are well-known and can be employed to obtain a sample for use in the methods provided. Typically, for collection of a blood sample, an anti-coagulation agent (e.g. EDTA, or citrate and heparin or CPD (citrate, phosphate, dextrose) or comparable substances) is added to the sample to prevent coagulation of the blood. In some examples, the blood sample is collected in a collection tube that contains an amount of EDTA to prevent coagulation of the blood sample.

In some embodiments, the sample is a tissue biopsy and is obtained, for example, by needle biopsy, CT-guided needle biopsy, aspiration biopsy, endoscopic biopsy, bronchoscopic biopsy, bronchial lavage, incisional biopsy, excisional biopsy, punch biopsy, shave biopsy, skin biopsy, bone marrow biopsy, and the Loop Electrosurgical Excision Procedure (LEEP). Typically, a non-necrotic, sterile biopsy or specimen is obtained that is greater than 100 mg, but which can be smaller, such as less than 100 mg, 50 mg or less, 10 mg or less or 5 mg or less; or larger, such as more than 100 mg, 200 mg or more, or 500 mg or more, 1 gm or more, 2 gm or more, 3 gm or more, 4 gm or more or 5 gm or more. The sample size to be extracted for the assay depends on a number of factors including, but not limited to, the number of assays to be performed, the health of the tissue sample, the type of cancer, and the condition of the patient. In some embodiments, the tissue is placed in a sterile vessel, such as a sterile tube or culture plate, and is optionally immersed in an appropriate media. Typically, the cells are dissociated into cell suspensions by mechanical means and/or enzymatic treatment as is well known in the art. Typically, the cells are collected and then subjected to standard procedures for the isolation of nucleic acid for the assay.

In some embodiments, the collection of a sample from the subject is performed at regular intervals, such as, for example, one day, two days, three days, four days, five days, six days, one week, two weeks, weeks, four weeks, one month, two months, three months, four months, five months, six months, one year, daily, weekly, bimonthly, quarterly, biyearly or yearly.

In some embodiments, the collection of a sample is performed at a predetermined time or at regular intervals relative to treatment with one or more anti-cancer agents. In some embodiments, anticancer agent is administered for the treatment of a leukemia, lymphoma or a myeloma. Exemplary anti-cancer agents for the treatment of a leukemia, lymphoma or a myeloma include but are not limited to adriamycin (doxorubicin), bexxar, bendamustine, bleomycin, blenoxane, bortezomib, dacarbazine, deltasone, cisplatin, cyclophosphamide, cytoxan, DTIC dacarbazine, dasatinib, doxorubicin, etoposide, fludarabine, granisetron, kytril, lenalidomide, matulane, mechlorethamine, mustargen, mustine, natulan, Rituxan (rituximab, anti-CD20 antibody), VCR, neosar, nitrogen mustard, oncovin, ondansetron, orasone, prednisone, procarbazine, thalidomide, VP-16, velban, velbe, velsar, VePesid, vinblastine, vincristine, Zevalin®, zofran, stem cell transplantation, radiation therapy or combination therapies, such as, for example, ABVD (adriamycin, bleomycin, vinblastine and dacarbazine), ChlvPP (chlorambucil, vinblastine, procarbazine and prednisolone), Stanford V (mustine, doxorubicin, vinblastine, vincristine, bleomycin, etoposide and steroids), BEACOPP (bleomycin, etoposide, doxorubicin, cyclophosphamide, vincristine, procarbazine and prednisolone), BEAM (carmustine (BiCNU) etoposide, cytarabine (Ara-C, cytosine arabinoside), and melphalan), CHOP (cyclophosphamide, doxorubicin, vincristine, and prednisone), R-CHOP (rituximab, doxorubicin, cyclophosphamide, vincristine, and prednisone), EPOCH (etoposide, vincristine, doxorubicin, cyclophosphamide, and prednisone), CVP (cyclophosphamide, vincristine, and prednisone), ICE (ifosfamide-carboplatin-etoposide), R-ACVBP (rituximab, doxorubicin, cyclophosphamide, vindesine, bleomycin, and prednisone), DHAP (dexamethasone, high-dose cytarabine, (Ara C), cisplatin), R-DHAP (rituximab, dexamethasone, high-dose cytarabine, (Ara C), cisplatin), ESHAP (etoposide (VP-16), methyl-prednisolone, and high-dose cytarabine (Ara-C), cisplatin), CDE (cyclophosphamide, doxorubicin and etoposide), Velcade® (bortezomib) plus Doxil® (liposomal doxorubicin), Revlimid® (lenalidomide) plus dexamethasone, and bortezomib plus dexamethasone. In some embodiments, anticancer agent is fludarabine. In some embodiments, anticancer agent is bendamustine. In some embodiments, the anticancer agent is Rituxan. In some embodiments, the anticancer agent is dasatinib. In some embodiments, a sample is collected at a predetermined time or at regular intervals prior to, during, or following treatment or between successive treatments with the anti-cancer agent. In particular examples, a sample is obtained from the subject prior to administration of an anti-cancer therapy and then again at regular intervals after treatment has been effected.

In some embodiments, the collection of a sample is performed at a predetermined time or at regular intervals relative to treatment with a covalent and/or irreversible BTK inhibitor. For example, a sample is collected at a predetermined time or at regular intervals prior to, during, or following treatment or between successive treatments. In particular examples, a sample is obtained from the subject prior to administration of a covalent and/or irreversible BTK inhibitor and then again at regular intervals after treatment with the irreversible BTK inhibitor has been effected. In some embodiments, the subject is administered a covalent and/or irreversible BTK inhibitor and one or more additional anti-cancer agents. In some embodiments, the subject is administered a covalent and/or irreversible BTK inhibitor and one or more additional anti-cancer agents that are not irreversible BTK inhibitors. In some embodiments, the subject is administered one or more irreversible BTK inhibitors. In some embodiments, the subject is administered one or more irreversible BTK inhibitors that covalently bind to cysteine 481 of the wild-type BTK. In some embodiments, the irreversible BTK inhibitor is ibrutinib, PCI-45292, PCI-45466, AVL-101, AVL-291, AVL-292, or ONO-WG-37. In some embodiments, the irreversible BTK inhibitor is ibrutinib.

Additional BTK inhibitors for use in any of the methods provided herein can be found, for example, in U.S. Pat. Nos. 7,547,689, 7,960,396 and U.S. Patent Publication Nos. US 2009-0197853 A1 and US 2012-0065201 A1, all of which are incorporated by reference in their entirety. Additional BTK inhibitors for use in any of the methods provided herein also can be found, for example, in US20100029610, WO09051822, WO10123870, WO09158571, WO11034907, WO12021444, WO11029046, WO08110624, WO10080481, WO10144647, WO10056875, WO05047290, WO06053121, WO06099075, WO08033834, WO08033857, WO08033858, WO09137596, WO10056875, WO10068788, WO10068806, WO10068810, WO11140488, WO12030990, WO12031004, WO2010056875, WO05066156, WO10056875, US20120316148, WO09048307, WO09147190, WO11162515, WO11162515, WO06036941, WO10126960, WO07136790, WO12025186, WO2013010380, WO2013010868, WO2013010869, WO2013008095, WO11152351, WO2013060098, WO2013060098, WO07002325, WO07002433, WO07013896, WO09143024, WO10065898, WO2012158764, WO2012158785, WO2012158795, WO2012158810, WO09053269, WO09156284, WO2012020008, WO2012156334, WO2013024078, WO08057252, WO03081210, WO03087051, US20130059847A1, WO06065946, WO07027594, and WO08092199 all of which are incorporated by reference in their entirety.

In some embodiments, the subject is administered a covalent and/or irreversible BTK inhibitor that covalently binds to cysteine 481 of the wild-type BTK in combination with one or more reversible BTK inhibitors. For example, in some embodiments, the subject is administered a covalent and/or irreversible BTK inhibitor that covalently binds to cysteine 481 of the wild-type BTK in combination with one or more reversible BTK inhibitors that are not dependent on cysteine 481 for binding. Reversible BTK inhibitors are known in the art and include, but are not limited to, dasatinib, PC-005, RN486, PCI-29732 or terreic acid. In a particular embodiment, the irreversible BTK inhibitor ibrutinib is administered in combination with the reversible BTK inhibitor dasatinib.

In some embodiments, the sample is obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, 24 months, 26 months, 28 months, 30 months, 32 months, 34 months, 36 months or longer following the first administration of the irreversible BTK inhibitor. In some embodiments, the sample is obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, 24 months, 26 months, 28 months, 30 months, 32 months, 34 months, 36 months or longer following the first administration of the irreversible BTK inhibitor to a subject naïve for exposure to the irreversible BTK inhibitor. In some embodiments, the sample is obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, 24 months, 26 months, 28 months, 30 months, 32 months, 34 months, 36 months or longer following the first administration of the irreversible BTK inhibitor to a subject having a relapsed or refractory cancer. In some embodiments, the sample is obtained 1, 2, 3, 4, 5, 6, 7, 8, 9, 10 times or more over the course of treatment with the irreversible BTK inhibitor. In some embodiments, the subject is responsive the treatment with the irreversible BTK inhibitor when it is first administered.

Maintenance Therapy

Provided herein are methods for maintenance therapy of subject having a B-cell proliferative disorder. In some embodiments, B-cell proliferative disorder is cancer. In some embodiments, the cancer is hematologic cancer. In some embodiments, the methods for maintenance therapy comprise treating a hematologic cancer with a covalent and/or irreversible BTK inhibitor for an initial treatment period, followed by a maintenance therapy regimen. In some embodiments, the methods for maintenance therapy comprise treating a hematologic cancer with a covalent and/or irreversible BTK inhibitor for a period of six months or longer, such as, for example, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 3 years, 4 years, 5 years, 6 years, 7 years, 8 years, 9 years, 10 years or longer. In some embodiments, the irreversible BTK inhibitor covalently binds to cysteine 481 of the wild-type BTK. In some embodiments, the irreversible BTK inhibitor is selected from among ibrutinib, PCI-45292, PCI-45466, AVL-101, AVL-291, AVL-292, or ONO-WG-37. In some embodiments, the irreversible BTK inhibitor is ibrutinib.

In an exemplary method, a subject having a hematologic cancer is treated with an therapeutic effective amount of a covalent and/or irreversible BTK inhibitor and the subject is monitored at predetermined intervals of time to determine whether the subject acquires mutation in an endogenous gene encoding BTK that results in a modification at cysteine 481 of BTK. In some embodiments monitoring comprises testing a sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1. In some embodiments, the modification is C481S. In some embodiments, the sample contains one or more cancer cells or ctDNA. In some embodiments, a sample containing one or more cancer cells or ctDNA is obtained from the subject prior to treatment with the irreversible BTK inhibitor or early in treatment (e.g. after about 1 week to about 2 months) with the irreversible BTK inhibitor to determine whether the subject expresses a wildtype BTK prior to or early in treatment with a covalent and/or irreversible BTK inhibitor.

In some embodiments, provided is method of maintenance therapy in a patient having a hematologic cancer, comprising (a) administering to the patient a maintenance therapy regimen comprising administering a therapeutically effective dose of a covalent and/or irreversible BTK inhibitor; and (b) monitoring the patient at predetermined intervals of time over the course of the maintenance therapy regimen to determine whether the subject has mutation in an endogenous gene encoding BTK that results in a modification at an amino acid position corresponding to amino acid position 481 of the amino acid sequence set forth in SEQ ID NO: 1. In some embodiments monitoring comprises testing a sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1. In some embodiments, the modification is C481S. In some embodiments, the sample contains one or more cancer cells or ctDNA. In some embodiments, a sample containing one or more cancer cells or ctDNA is obtained from the subject prior to treatment with the irreversible BTK inhibitor or early in treatment (e.g. after about 1 week to about 2 months) with the irreversible BTK inhibitor to determine whether the subject expresses a wildtype BTK.

In some embodiments, the method further comprises discontinuing treatment with the BTK inhibitor if the subject has the modification. In some embodiments, the method further comprises continuing treatment with a BTK inhibitor if the subject does not have the modification. In some embodiments, the method further comprises administering second generation BTK inhibitor that inhibits the modified kinase if the subject has the modification. In some embodiments, the method further comprises administering an inhibitor of LYN, SYK, JAK, PI3K, PLCγ, MAPK, MEK, or NFκB if the subject has the modification. In some embodiments, the method further comprises administering a covalent inhibitor of BTK that does not bind to C481 if the subject has the modification. In some embodiments, the method further comprises administering a reversible inhibitor of BTK if the subject has the modification.

In some embodiments, the mutation is a missense mutation in the codon that encodes for cysteine 481 of BTK. In some embodiments, the mutation is a missense mutation results in the substitution of cysteine for another amino acid at amino acid position 481. In some embodiments, the mutation is a missense mutation results in the substitution of cysteine for senile at amino acid position 481. In some embodiments, the mutation is a missense mutation of guanine-1635 to cytosine-1635 resulting the substitution of the Cysteine-481 codon, TGC, to TCC (Serine). In some embodiments, the mutation is a missense mutation of thymine (t)-1634 to adenine (a)-1634 resulting the substitution of the Cysteine-481 codon, TGC, to AGC (Serine).

In some embodiments, the subject is monitored every month, every 2 months, every 3 months, every 4 months, every 5 months, every 6 months, every 7 months, every 8 months, every 9 months, every 10 months, every 11 months, or every year to determine whether the subject acquires mutation in an endogenous gene encoding BTK that results in a modification at cysteine 481 of the BTK polypeptide.

In some embodiments, hematologic cancer is a B-cell malignancy. In some embodiments, cancer is selected from among a leukemia, a lymphoma, or a myeloma. In some embodiments, the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the subject has a solid tumor. In some embodiments, the B-cell malignancy is chronic lymphocytic leukemia (CLL).

In some embodiments, maintenance therapy comprises multiple cycles of administration. In some embodiments, a cycle of administration is one month, 2 months, 3 months, 4 months, 6 months, 6 months, 7 months, 8 months, 9 months, 10 months, 11 months, 12 months or longer. In some embodiments, a cycle of administration comprises administration of a single therapeutic dosage of the irreversible BTK inhibitor over the cycle. In some embodiments, a cycle of administration comprises two or more different dosages of the irreversible BTK inhibitor over the cycle. In some embodiments, the dosage of the irreversible BTK inhibitor differs over consecutive cycles. In some embodiments, the dosage of the irreversible BTK inhibitor increases over consecutive cycles. In some embodiments, the dosage of the irreversible BTK inhibitor is the same over consecutive cycles.

In some embodiments, maintenance therapy comprises administration of a daily dosage of the irreversible BTK inhibitor. In some embodiments, the daily dosage of the irreversible BTK inhibitor administered is at or about 10 mg per day to about 2000 mg per day, such as for example, about 50 mg per day to about 1500 mg per day, such as for example about 100 mg per day to about 1000 mg per day, such as for example about 250 mg per day to about 850 mg per day, such as for example about 300 mg per day to about 600 mg per day. In a particular embodiment, the maintenance dosage of the irreversible BTK inhibitor is about 840 mg per day. In a particular embodiment, where the irreversible inhibitor is ibrutinib, the maintenance dosage is about 840 mg ibrutinib per day. In a particular embodiment, the maintenance dosage of the irreversible BTK inhibitor is about 560 mg per day. In a particular embodiment, where the irreversible inhibitor is ibrutinib, the maintenance dosage is about 560 mg ibrutinib per day. In a particular embodiment, the maintenance dosage is about 420 mg per day. In a particular embodiment, where the irreversible inhibitor is ibrutinib, the maintenance dosage is about 420 mg ibrutinib per day. In a particular embodiment, the maintenance dosage of the irreversible BTK inhibitor is about 140 mg per day. In a particular embodiment, where the irreversible inhibitor is ibrutinib, the maintenance dosage is about 140 mg ibrutinib per day.

In some embodiments, the irreversible BTK inhibitor is administered once per day, two times per day, three times per day or more frequent. In a particular embodiment, the irreversible BTK inhibitor is administered once per day. In some embodiments, the irreversible BTK inhibitor that is ibrutinib is administered once per day, two times per day, three times per day or more frequent. In a particular embodiment, the irreversible BTK inhibitor that is ibrutinib is administered once per day.

In some embodiments, the dosage of the irreversible BTK inhibitor is escalated over time. In some embodiments, the dosage of the irreversible BTK inhibitor that is ibrutinib is escalated over time. In some embodiments, the dosage of the irreversible BTK inhibitor is escalated from at or about 1.25 mg/kg/day to at or about 12.5 mg/kg/day over a predetermined period of time. In some embodiments, the dosage of the irreversible BTK inhibitor that is ibrutinib is escalated from at or about 1.25 mg/kg/day to at or about 12.5 mg/kg/day over a predetermined period of time. In some embodiments the predetermined period of time is over 1 month, over 2 months, over 3 months, over 4 months, over 5 months, over 6 months, over 7 months, over 8 months, over 9 months, over 10 months, over 11 months, over 12 months, over 18 months, over 24 months or longer.

In some embodiments, a cycle of administration comprises administration of the irreversible BTK inhibitor in combination with an additional therapeutic agent. In some embodiments the additional therapeutic is administered simultaneously, sequentially, or intermittently with the irreversible BTK inhibitor. In some embodiments the additional therapeutic agent is an anti-cancer agent. In some embodiments the additional therapeutic agent is an anti-cancer agent for the treatment of a leukemia, lymphoma or a myeloma. Exemplary anti-cancer agents for administration in a combination with a covalent and/or irreversible BTK inhibitor are provided elsewhere herein. In a particular embodiment, the anti-cancer agent is an anti-CD 20 antibody (e.g. Rituxan). In a particular embodiment, the anti-cancer agent bendamustine. In some embodiments, the additional anti-cancer agent is a reversible BTK inhibitor. In some embodiments, the additional anti-cancer agent is a reversible BTK inhibitor that does not depend on cysteine 481 for binding to BTK. In some embodiments, the additional anti-cancer agent is dasatinib.

In some embodiments, provided is a method for monitoring whether a subject receiving maintenance therapy with a covalent and/or irreversible BTK inhibitor for treatment of a hematologic cancer has developed or is likely to develop resistance to the therapy, comprising: (a) testing a sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1; and (b) characterizing the subject as resistant or is likely to become resistant to therapy with a covalent and/or irreversible BTK inhibitor if the subject has the modification. In some embodiments, step (a) is performed ex vivo. In some embodiments, the method further comprises discontinuing treatment with the BTK inhibitor if the subject has the modification. In some embodiments, the method further comprises continuing treatment with a BTK inhibitor if the subject does not have the modification. In some embodiments, the method further comprises administering second generation BTK inhibitor that inhibits the modified kinase if the subject has the modification. In some embodiments, the method further comprises administering an inhibitor of LYN, SYK, JAK, PI3K, PLCγ, MAPK, MEK, or NFκB if the subject has the modification. In some embodiments, the method further comprises administering a covalent inhibitor of BTK that does not bind to C481 if the subject has the modification. In some embodiments, the method further comprises administering a reversible inhibitor of BTK if the subject has the modification. In some embodiments of the method, the subject has cancer. In some embodiments, hematologic cancer is a B-cell malignancy. Exemplary B-cell malignancies are provided herein. In some embodiments, cancer is selected from among a leukemia, a lymphoma, or a myeloma. In some embodiments, the method further comprises obtaining the sample from the subject.

In some embodiments, provided is a method for optimizing the therapy of a subject receiving maintenance therapy with a covalent and/or irreversible BTK inhibitor for treatment of a hematologic cancer, comprising: (a) testing a sample containing a nucleic acid molecule encoding a BTK polypeptide from the subject to determine whether the encoded BTK polypeptide is modified at an amino acid position corresponding to amino acid position 481 of the amino acid sequence set forth in SEQ ID NO: 1; and (b) discontinuing treatment with the covalent and/or irreversible BTK inhibitor if the subject has the modification or continuing treatment with the covalent and/or irreversible BTK inhibitor if the subject does not have the modification. In some embodiments, the method further comprises administering second-generation BTK inhibitor that inhibits the modified kinase if the subject has the modification. In some embodiments, the method further comprises administering an inhibitor of LYN, SYK, JAK, PI3K, PLCγ, MAPK, MEK, or NFκB if the subject has the modification. In some embodiments, the method further comprises administering a covalent inhibitor of BTK that does not bind to C481 if the subject has the modification. In some embodiments, the method further comprises administering a reversible inhibitor of BTK if the subject has the modification. In some embodiments, step (a) is performed ex vivo. In some embodiments, hematologic cancer is a B-cell malignancy. Exemplary B-cell malignancies are provided herein. In some embodiments, cancer is selected from among a leukemia, a lymphoma, or a myeloma. In some embodiments, the method further comprises a step of obtaining the sample from the subject.

Identification of Molecules that Interact with Mutant BTK

Provided herein are methods of using the mutant BTK polypeptides for screening of agents that interact with the mutant BTK polypeptide. In some embodiments, the agents that interact with the mutant BTK polypeptide also inhibit the mutant BTK. Accordingly, provided herein are methods of using the mutant BTK polypeptides for screening of agents that inhibit the mutant BTK (i.e. second-generation BTK inhibitors). In some embodiments, the methods are employed for the identification of second-generation BTK inhibitors for the treatment of a B-cell cancer. In some embodiments, the methods are employed for the identification of second-generation BTK inhibitors for the treatment of resistant cancers, such as a B-cell cancer resistant to treatment with a covalent and/or irreversible BTK inhibitor, such as, for example, ibrutinib. In some embodiments, a second-generation BTK inhibitor identified using the methods provided also inhibits a wild-type BTK polypeptide. Accordingly, in some embodiments, a second-generation BTK inhibitor identified using the methods provided inhibits a mutant BTK polypeptide and a wild-type BTK polypeptide. In some embodiments, the second-generation BTK inhibitor does not inhibit the activity of a wild-type BTK polypeptide.

In some embodiments, a method for identifying second-generation BTK inhibitors comprises (a) providing a modified BTK, wherein the modified BTK is modified at an amino acid position corresponding to amino acid position 481 of the amino acid sequence set forth in SEQ ID NO: 1; (b) contacting the modified BTK with a test compound; and (c) detecting the level of BTK activity, wherein a decrease in activity indicates that the compound inhibits the modified BTK. In some embodiments the cell is contacted with the test compound for about 1 hour, 2, hours, 3 hours, 4 hours, 5 hours, 6 hours, 8 hours, 10 hours, 12 hours, 14 hours, 16 hours, 18 hours, 20 hours, 22 hours, 24 hours or longer prior to detecting the level of BTK activity.

In some embodiments, the modification in BTK is a substitution or deletion of the amino acid at amino acid position 481 of the BTK polypeptide. In some embodiments, the modification is a substitution of cysteine to an amino acid selected from among leucine, isoleucine, valine, alanine, glycine, methionine, serine, threonine, phenylalanine, tryptophan, lysine, arginine, histidine, proline, tyrosine, asparagine, glutamine, aspartic acid and glutamic acid at amino acid position 481 of the BTK polypeptide. In some embodiments, the modification is a substitution of cysteine to an amino acid selected from among serine, methionine and threonine at amino acid position 481 of the BTK polypeptide. In some embodiments, the modification is a substitution of cysteine to serine at amino acid position 481 of the BTK polypeptide. Accordingly, in some embodiments, a second-generation BTK inhibitor identified using the methods provided inhibits a mutant BTK polypeptide having a modification at amino acid position 481 of the BTK polypeptide. In some embodiments, a second-generation BTK inhibitor identified using the methods provided inhibits a mutant BTK polypeptide having a serine at amino acid position 481 of the BTK polypeptide. In some embodiments, a second-generation BTK inhibitor identified using the methods provided also inhibits a wild-type BTK polypeptide.

In some embodiments, detecting the level of BTK activity is assessed by an in vitro kinase assay. In some embodiments, the substrate used in the kinase assay is PLCγ. In some embodiments, the substrate used in the kinase assay is a peptide substrate. In some embodiments, where the modified BTK is resistant to inhibition with a particular irreversible inhibitor, such as ibrutinib, the inhibitor is employed as a control for comparison. In some embodiments, a wild-type BTK polypeptide is employed for comparison.

In some embodiments, detecting the level of BTK activity is assessed by measuring the level of phosphorylation of direct substrates of BTK or phosphorylated targets in the BTK kinase cascade within a cell In some embodiments, the cell is a B lymphocyte, a monocytes, or a macrophage. In some embodiments, the cell is a cancer cell line, such as a lymphoma, leukemia, or myeloma cell line. In some embodiments, the cell line is a MCL, DBCL or a follicular lymphoma cell line. In some embodiments, the cell line is a BTK knockout B lymphoma cell line, such as the DT40 BTK knockout cell line. In some embodiments, phosphor-specific antibodies are used to detect the level of phosphorylation of particular BTK targets, such as PLCγ, ERK1/2 (MAPK), and AKT. in the cell in the presence or absence of the test compound. In some embodiments, the cells are first stimulated to activate BCR signaling pathway prior to, during or following exposure to the test compound. In some embodiments, the cells are first stimulated with anti-IgM or anti-IgG to activate BCR signaling pathway prior to, during or following exposure to the test compound. Methods to detect phosphorylated proteins are known in the art and include, for example, Western blotting or immunohistochemistry.

In some embodiments, the modified BTK polypeptide is purified from a host cell expressing the modified BTK polypeptide. In some embodiments, the modified BTK polypeptide is a recombinant protein. In some embodiments, the purified BTK is used for testing the level of BTK activity. In some embodiments, the modified BTK polypeptide is purified by immunoaffinity or chromatography.

In some embodiments, a host cell line that can be transfected with nucleic acid encoding the modified BTK polypeptide and in which BTK activity can be monitored is used in the method. In some embodiments, the host cell does not express wild-type BTK. In some embodiments, the host cell is deficient for the expression of endogenous wild-type BTK. In some embodiments, the host cell expressing the modified BTK polypeptide stably expresses the modified BTK polypeptide. In some embodiments, the nucleic acid encoding the modified BTK polypeptide is integrated into the genome of the cell.

In some embodiments, the host cell is a chicken DT40 BTK−/− B cell or human BTK−/− B cell. In some embodiments, the cell is a non B-cell. In some embodiments, the cell is a mammalian non-B-cell. In some embodiments, the cell is a CHO cell or a Jurkat T cell. In some embodiments, the cell is a non-mammalian cell. In some embodiments, the cell is an insect cell, a bacterial cell, a yeast cell, or a plant cell.

In some embodiments, the level of BTK activity is assessed using a cell line that is resistant to treatment with a covalent and/or irreversible BTK inhibitor. In some embodiments, the cell line is a resistant MCL (e.g. Mino or Jeko), DLBCL (e.g. OCI-Ly1, OCI-Ly2, OCI-Ly3, OCI-Ly4, OCI-Ly6, OCI-Ly7, OCI-Ly10, OCI-Ly18, OCI-Ly19, U2932, HBL-1, RIVA, or TMD8) or follicular lymphoma (e.g. DoHH2, Granta 519 or HF-1) cell line that has been selected for resistance by long term exposure with a covalent and/or irreversible BTK inhibitor. In some embodiments, selection is performed in vitro. In some embodiments, selection is performed in vivo, in an animal model that has been administered the cancer cells. In some embodiments, the resistant MCL or DLBCL cell line contains a modification of BTK at amino acid position C481. In some embodiments, the modification is C481S.

Cellular functional assays for BTK inhibition include measuring one or more cellular endpoints in response to stimulating a BTK-mediated pathway in a cell line (e.g., BCR activation in Ramos cells) in the absence or presence of a range of concentrations of a candidate BTK inhibitor compound. Useful endpoints for determining a response to BCR activation include, e.g., autophosphorylation of BTK, phosphorylation of a BTK target protein (e.g., PLC-γ), and cytoplasmic calcium flux.

In some embodiments, a downstream transcription target assay is employed to determine BTK activity in the presence or absence of the test compounds. In some embodiments, the downstream transcription target assay is an NF-κB based assay. In some example, a gene encoding a reporter protein is operably linked to an NF-κB responsive promoter that is sensitive to BCR pathway signaling and is inhibited when BTK is inhibited. In some embodiments, the reporter gene encodes a protein selected from among a luciferase, a fluorescent protein, a bioluminescent protein, or an enzyme. In some embodiments, the assay comprises a host cell that contains the reporter and the mutant BTK. Detection of a the level of gene expression in the presence or absence of the test compound indicates whether the test compound inhibits the BCR pathway in the presence of the mutant BTK. In some embodiments, the test compound inhibits the mutant BTK directly.

High throughput assays for many acellular biochemical assays (e.g., kinase assays) and cellular functional assays (e.g., calcium flux) are well known to those of ordinary skill in the art. In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including sample and reagent pipetting, liquid dispensing, timed incubations, and final readings of the microplate in detector(s) appropriate for the assay. Automated systems thereby allow the identification and characterization of a large number of BTK inhibitor compounds without undue effort.

In some embodiments, detecting the level of BTK activity is assessed by an in vivo assay. In some embodiments, detecting the level of BTK activity is assessed in animal model. In some embodiments the animal model is one that is a mouse model of leukemia. Such animal model are known in the art and include, for example, mouse models, of AML and CLL (see, e.g., Zuber, (2009) *Genes and Development* 23(7):877-89 and Pekarsky et al. (2007) *J Cell Biochem.* 100(5):1109-18. In some embodiments the animal model is a transgenic animal that expresses a modified BTK that is modified at Cys 481. In some embodiments, a test compound is administered to a transgenic animal that expresses a modified BTK that is modified at Cys 481 and the activity of BTK is assessed by one or more assays described herein. In some embodiments, the assay is a kinase assay performed with the mutant BTK polypeptide isolated from the transgenic animal administered the test compound and compared to a control. In some embodiments, the level of phosphorylation of one or more BTK targets is assessed in a B-cell sample from the from the transgenic animal administered the test compound and compared to a control. In some embodiments, the control is a sample from an animal not administered the test compound. In some embodiments, the control is a sample from an animal administered a covalent and/or irreversible BTK inhibitor.

Kits and Articles of Manufacture

For use in the diagnostic and therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

In some embodiments, the kits provided herein are for use in detecting nucleic acid encoding a modified BTK polypeptide in a subject or for detecting a modified BTK polypeptide in a subject. In some embodiments, the kits provided herein are for use as a companion diagnostic with one or more covalent and/or irreversible BTK inhibitors. In some embodiments the kits are employed for selecting patients for treatment with a second-generation BTK antagonist, for identifying subjects as resistant or likely to become resistant to a covalent and/or irreversible BTK inhibitor, for monitoring the development of resistance to a covalent and/or irreversible BTK inhibitor, or combinations thereof. The kits provided herein contain one or more reagents for the detection of the nucleic acid encoding a modified BTK polypeptide, for the detection of modified BTK polypeptides, for detection of BTK activity in cells from the subject, for detection of BTK activity in vitro or in vivo or combinations thereof. Exemplary reagents include but are not limited to, oligonucleotide, PCR reagents, buffers, antibodies, BTK substrates for determining kinase activity, substrates for enzymatic staining, chromagens or other materials, such as slides, containers, microtiter plates, and optionally, instructions for performing the methods. Those of skill in the art will recognize many other possible containers and plates and reagents that can be used for contacting the various materials. Kits also can contain control samples, such as for example, nucleic acids or proteins, such as for example a mutant BTK polypeptide provided herein or nucleic acids encoding a modified BTK polypeptide provided herein. In some embodiments, kits contain one or more set of oligonucleotide primers for detection of mutant BTK expression.

In some embodiments, the container(s) can comprise one or more covalent and/or irreversible BTK inhibitors or one or more second-generation BTK inhibitors identified by the methods described herein, optionally in a composition or in combination with another agent as disclosed herein. The container(s) optionally have materials, such as syringes, needles, dosing cups or vials, for administration. Such kits optionally comprise a compound with an identifying description or label or instructions relating to its use in the methods described herein.

In some embodiment, a kit comprises a modified BTK polypeptide or a variant thereof having BTK activity comprising a modification at an amino acid position corresponding to amino acid position 481 of the amino acid sequence set forth in SEQ ID NO: 1. In some embodiments, the modification is a substitution of cysteine to serine at amino acid position 481 of the BTK polypeptide. In some embodiments, a kit comprises a the isolated nucleic acid of any encoding a modified BTK polypeptide provided herein or a vector comprising such nucleic acid. In some embodiments, the modification is a substitution of cysteine to serine at amino acid position 481 of the BTK polypeptide.

In some embodiment, a kit comprises a microchip comprising the modified BTK polypeptide provided herein or the nucleic acid encoding a modified BTK polypeptide provided herein. In some embodiments, the modification is a substitution of cysteine to serine at amino acid position 481 of the BTK polypeptide.

Production of Cell Lines Resistant to Treatment with a Covalent and/or Irreversible BTK Inhibitor Provided herein are methods for producing B-cell cancer cell lines resistant to treatment with a covalent and/or irreversible BTK inhibitor. In some embodiments, the B-cell cancer cell lines are resistant to treatment with a covalent and/or irreversible BTK inhibitor that covalently binds to cysteine 481 of the wild-type BTK. In some embodiments, the B-cell cancer cell lines are resistant to treatment with ibrutinib, PCI-45292, PCI-45466, AVL-101, AVL-291, AVL-292, or ONO-WG-37. In some embodiments, the B-cell cancer cell lines are resistant to treatment with ibrutinib. In some embodiments, the resistant cell lines generated by the method provided express a modified BTK protein. In some embodiments, the BTK protein is modified at an amino acid position corresponding to amino acid position 481 of the amino acid sequence set forth in SEQ ID NO: 1.

In some embodiments, the method comprises contacting a B-cell cancer cell line (i.e. parental cell line) with a covalent and/or irreversible BTK inhibitor and culturing the cells for a predetermined period of time. In some embodiments, the method comprises culturing the cells in increasing concentrations of the irreversible BTK inhibitor for a predetermined period of time. In some embodiments, the concentration of the irreversible BTK inhibitor ranges from about 0.01 µM to about 100 µM, such as, for example, 0.1 µM to about 10 µM. In some embodiments, the cells are cultured at about 0.05 µM, 0.104, 0.5 µM and 1 µM of the irreversible BTK inhibitor. In some embodiments, the concentration of the irreversible BTK inhibitor is increased 2, 3, 4, 5, 6, 7, 8, 9, 10 or more times. In some embodiments, the concentration of the irreversible BTK inhibitor is increased 3 times. In some embodiments, the cells are cultured in the presence of the irreversible BTK inhibitor 1 day, 2 days, 3, days, 4 days, 5 days, 6 days, 1 week, 2 weeks, 3 weeks, 4 weeks, 1 month, 1.5 months, 2 months, 2.5 months, 3 months or more. In some embodiments, the cells are divided and re-plated every 2 days, every 3 days, every 4 days, every 5 days, every 6 days, every week or longer. In some embodiments, the culture media containing the irreversible BTK inhibitor is refreshed every day, every 2 days, every 3 days, every 4 days, every 5 days, every 6 days, every week or longer. In some embodiments, the irreversible BTK inhibitor covalently binds to Cys 481 of a wild-type BTK. In some embodiments, the irreversible BTK inhibitor is ibrutinib, PCI-45292, PCI-45466, AVL-101, AVL-291, AVL-292, or ONO-WG-37. In some embodiments, the irreversible BTK inhibitor is ibrutinib.

In some examples, the parental B-cell cancer cell line is a leukemia, lymphoma or myeloma cell line. In some examples, the parental B-cell cancer cell line is an DLBCL cell line. Exemplary DLBCL cell lines include ABC-DLBCL cell lines including, but not limited to, OCI-LY10, OCI-Ly3, U2932, RIVA, HBL-1, or TMD8 cell lines, and GCB-DLBCL cell lines, including, but not limited to, OCI-Ly19 or OCI-Ly7. In some examples, the parental B-cell cancer cell line is an MCL cell line. Exemplary MCL cell lines include, but are not limited to, Mino and Jeko cell lines.

In some examples, the parental B-cell cancer cell line is an follicular lymphoma cell line. Exemplary follicular lymphoma cell lines include, but are not limited to, DoHH2, Granta 519 and HF-1 cell lines.

In some embodiments, the resistant cell line is identified by an increase in B-cell receptor pathway activation. In some embodiments, an increase in B-cell receptor pathway activation is identified by testing whether downstream targets in the treated cell line exhibit increased phosphorylation in the presence of ibrutinib compared to the parental cell line in the presence of ibrutinib. In some examples, the phosphorylated downstream target is a phosphorylated RAF or a phosphorylated MEK. In some embodiments, the resistant cell line is resistant to treatment with ibrutinib alone, but is sensitive to treatment with a MEK inhibitor with ibrutinib.

Non-BTK Mutations in Ibrutinib Resistant Patients—Detection, Compositions, and Uses Thereof As described herein, in certain instances, mutations in proteins other than BTK lead to resistance of a patient to treatment with a BTK inhibitor, such as, for example, a covalent and/or irreversible inhibitor. In some embodiments, the mutation is in a downstream effector protein in the BTK pathway. In some embodiments, the mutation is a gain of function mutation. In some embodiments, the mutation results in constitutive activation of a downstream effector protein in the BTK pathway.

PLCγ2

In some embodiments, the downstream effector protein is Phospholipase C gamma 2 (PLCγ2). PLC cleaves the phospholipid phosphatidylinositol 4,5-bisphosphate (PIP2) into diacyl glycerol (DAG) and inositol 1,4,5-trisphosphate (IP3). DAG remains bound to the membrane, and IP3 is released as a soluble structure into the cytosol. IP3 then diffuses through the cytosol to bind to IP3 receptors, particular calcium channels in the smooth endoplasmic reticulum (ER). This causes the cytosolic concentration of calcium to increase, causing a cascade of intracellular changes and activity. In addition, calcium and DAG together work to activate protein kinase C, which goes on to phosphorylate other molecules BTK kinase pathway, leading to altered cellular activity. In some embodiments, the mutant PLCγ2 polypeptide are constitutively active (i.e. does not require phosphorylation by BTK).

In some embodiments, a mutation in PLCγ2 results in resistance of a patient to treatment with a BTK inhibitor. In some embodiments, the mutation is a gain of function mutation in PLCγ2. In some embodiments, the mutation results in constitutive activation of PLCγ2. In some embodiments, constitutive activation of PLCγ2 results in mobilization of intracellular calcium, activation of extracellular signal-regulated kinase (ERK) and c-Jun NH2-terminal kinase (JNK) mitogen-activated protein kinase (MAPK) pathways. In some embodiments, the mutation in PLCγ2 results in amino acid substitution in the amino acid corresponding position R665 in PLCγ2. In some embodiments, the mutation the mutation in PLCγ2 results in a substitution of arginine for tryptophan (R665W). In some embodiments, the mutation in PLCγ2 results in amino acid substitution in the amino acid corresponding position S707 in PLCγ2. In some embodiments, the mutation the mutation in PLCγ2 results in a substitution of serine for phenylalanine (S707F).

Any of the methods provided herein for the detection of a modified BTK polypeptide also can be applied to the detection of a PLCγ2 polypeptide. For example, mutant PLCγ2 polypeptides can be detected by PCR methods using mutant specific nucleic acids for detection of somatic mutation in the genome or PLCγ2 mutant specific antibodies for detection of mutant PLCγ2 polypeptides.

In some embodiments, a nucleic acid encoding a mutant PLCγ2 polypeptide is provided. In some embodiments, a nucleic acid vector encoding a mutant PLC-γ2 polypeptide is provided. In some embodiments the vector is a viral vector. In some embodiments, a host cell comprising a nucleic acid encoding a mutant PLCγ2 polypeptide is provided. In some embodiments, a host cell comprising an expressed PLC-γ2 polypeptide is provided.

Any of the methods provided herein and known in the art for the production of modified BTK polypeptides and nucleic acids provided herein, including the use of nucleic acid expression vectors and host cells, also can be applied to the production of mutant PLC-γ2 polypeptides and nucleic acids provide herein.

Provided herein are mutant PLCγ2 polypeptides. In some embodiments, the mutant PLCγ2 polypeptides are recombinant proteins. In some embodiments, the mutant PLCγ2 polypeptides are purified from a host cell.

In some embodiments, the mutant PLCγ2 polypeptides contain one or more amino acid substitutions that confers resistance to inhibition by a BTK inhibitor. In some embodiments, the mutant PLCγ2 polypeptides contain one or more amino acid substitutions that confers resistance to inhibition by a covalent and/or irreversible BTK inhibitor that is ibrutinib, PCI-45292, PCI-45466, AVL-101, AVL-291, AVL-292, or ONO-WG-37. In some embodiments, the mutant PLCγ2 polypeptides contain one or more amino acid substitutions that confers resistance to inhibition by a BTK inhibitor.

Provided herein is an isolated PLCγ2 polypeptide or a variant thereof having PLCγ2 activity comprising a modification at an amino acid position corresponding to amino acid position 665 or 707 of the amino acid sequence set forth in SEQ ID NO: 11.

In some embodiments, the modification comprises a substitution or a deletion of the amino acid at amino acid position 665 or 707 compared to a wild type PLCγ2 set forth in SEQ ID NO: 11. In some embodiments, the modification comprises substitution of the amino acid at position 665 or 707 compared to a wild type PLCγ2 set forth in SEQ ID NO: 11. In some embodiments, the modification is a substitution of arginine at position 665 to an amino acid selected from among leucine, isoleucine, valine, alanine, glycine, methionine, cysteine, threonine, phenylalanine, tryptophan, lysine, serine, histidine, proline, tyrosine, asparagine, glutamine, aspartic acid and glutamic acid at amino acid position 665 of the PLCγ2 polypeptide. In some embodiments, the modification is a substitution of arginine to tryptophan at amino acid position 665 of the PLCγ2 polypeptide. In some embodiments, the substitution is R665W. In some embodiments, the modification is a substitution of arginine at position 707 to an amino acid selected from among leucine, isoleucine, valine, alanine, glycine, methionine, cysteine, threonine, phenylalanine, tryptophan, lysine, arginine, histidine, proline, tyrosine, asparagine, glutamine, aspartic acid and glutamic acid at amino acid position 707 of the PLCγ2 polypeptide. In some embodiments, the modification is a substitution of serine to phenylalanine at amino acid position 707 of the PLCγ2 polypeptide. In some embodiments, the substitution is S707W.

In some embodiments, the mutant PLCγ2 polypeptide comprises a substitution of the amino acid at position 665 or 707 compared to a wild type PLCγ2 set forth in SEQ ID NO: 11 and one or more additional amino acid substitutions. In some embodiments, the mutant PLCγ2 polypeptide comprises a modification at amino acid position 665 or 707 and a modification at one or more additional amino acid positions. In some embodiments, the mutant PLCγ2 polypeptide comprises a modification at amino acid position 665 or 707 and a modification at 1, 2, 3, 4, 5, 6, 7, 8, 9, 10, 11, 12, 13, 14, 15, 16, 17, 18, 19, 20 or more amino acid positions. In some embodiments, the modification at amino acid position 665 is a substitution that is R665W. In some embodiments, the modification at amino acid position 707 is a substitution that is S707F.

In some embodiments, a PLCγ2 polypeptide comprising a modification at amino acid position 665 or 707 of the wild-type PLCγ2 polypeptide set forth in SEQ ID NO: 11 linked to a peptide tag. In some embodiments, the peptide tag is an epitope tag recognized by a tag-specific antibody. In some embodiments the tag is an epitope tag, such as, but not limited to a c-myc, V-5, hemagglutinin (HA), FLAG, tag. In some embodiments the tag is an affinity tag, such as, but not limited to, biotin, strep-tag, chitin binding protein (CBP), maltose binding protein (MBP), glutathione-S-transferase (GST), or a poly(His) tag. In some embodiments, a PLCγ2 polypeptide comprising a modification at amino acid position 665 or 707 of the wild-type PLCγ2 polypeptide set forth in SEQ ID NO: 11 linked to a detectable protein or moiety, such a luminescent, chemiluminescent, bioluminescent, or fluorescent protein or moiety. In some embodiments, the fluorescent protein is a green (GFP), red (RFP), cyan (CFP), yellow (YFP), or blue (BFP) fluorescent protein. In some embodiments, a PLCγ2 polypeptide comprising a modification at amino acid position 665 or 707 of the wild-type PLCγ2 polypeptide set forth in SEQ ID NO: 11 linked to an enzyme for example, a luciferase or a beta-galactosidase.

Provided herein are nucleic acids encoding mutant PLCγ2 polypeptides. Provided herein are nucleic acids encoding any of the mutant PLCγ2 polypeptides described herein. Methods for deducing nucleic acids that encode particular polypeptides are known in the art and involve standard molecular biology techniques. Exemplary nucleic acids encoding mutant PLCγ2 polypeptides provided herein are provided. It is understood that due to the degeneracy of the genetic code multiple variants nucleic acids exist that encode the same polypeptide. Nucleic acids that encode the mutant PLCγ2 polypeptides provided herein encompass such variants.

In some embodiments, the nucleic acid encoding a modified PLCγ2 polypeptide provided herein is a DNA or an RNA molecule. In some embodiments, the nucleic acid encoding a mutant PLCγ2 polypeptide comprises a modification where the encoded polypeptide comprises a substitution of the amino acid arginine at the position corresponding to amino acid position 665 or 707 of the wild-type PLCγ2 polypeptide set forth in SEQ ID NO: 11. In some embodiments, the nucleic acid comprises the sequence of nucleic acids set forth in SEQ ID NO: 12, wherein the nucleic acid codon encoding amino acid at position 665 is modified, whereby the codon does not encode arginine, or a variant that has at least or at least about 60%, 70%, 75%, 80%, 85%, 90%, 95%, 96%, 97%, 98%, 99% or more sequence identity with the polypeptide having the sequence set forth in SEQ ID NO: 12, wherein the nucleic acid codon encoding amino acid at position 665 does not encode arginine or the nucleic acid codon encoding amino acid at position 707 does not encode serine.

In some embodiments the nucleic acid modification is a missense mutation or a deletion of one or more codons that encode the PLCγ2 polypeptide. In some embodiments, the modification is a missense mutation that changes the nucleic acid codon that encodes arginine at amino position 665 of the PLCγ2 polypeptide. In some embodiments, the modification is a missense mutation that changes the nucleic acid codon that encodes serine at amino position 707 of the PLCγ2 polypeptide.

In some embodiments, the nucleic acid codon that encodes Arginine at amino position 665 of the PLCγ2 polypeptide is CGT, CGC, CGA, CGG, AGA or AGG. In some embodiments, the modification changes the nucleic acid codon that encodes Arginine at amino position 665 of the PLCγ2 polypeptide to a nucleic acid codon that encodes Tryptophan. In some embodiments, the nucleic acid codon that encodes Tryptophan is TGG.

In some embodiments, the nucleic acid codon that encodes serine at amino position 707 of the PLCγ2 polypeptide is TCT, TCC, TCA, TCG, AGT, or AGC. In some embodiments, the modification changes the nucleic acid codon that encodes serine at amino position 707 of the PLCγ2 polypeptide to a nucleic acid codon that encodes Phenylalanine. In some embodiments, the nucleic acid codon that encodes Phenylalanine is TTT or TTC.

In some embodiments, methods are provided for determining whether a subject is or likely to become less responsive to therapy with a BTK inhibitor, comprising: (a) testing a sample containing a nucleic acid molecule encoding a PLCγ2 polypeptide from the subject to determine whether the encoded PLCγ2 polypeptide is modified at an amino acid position corresponding to amino acid position 665 or 707 of the amino acid sequence set forth in SEQ ID NO: 11; and (b) characterizing the subject as resistant or likely to become resistant to therapy with a BTK inhibitor if the subject has the modification. In some embodiments, the method further comprises a step of obtaining the sample from the subject. In some embodiments, the modification comprises a R665W or S707F substitution in PLCγ2. In some embodiments, the BTK inhibitor is a covalent or irreversible inhibitor.

Described herein, in certain embodiments are methods for monitoring whether a subject receiving a BTK inhibitor for treatment of a cancer has developed or is likely to develop resistance to the therapy, comprising: (a) testing a sample containing a nucleic acid molecule encoding a PLCγ2 polypeptide from the subject to determine whether the encoded PLCγ2 polypeptide is modified at an amino acid position corresponding to amino acid position 665 or 707 of the amino acid sequence set forth in SEQ ID NO: 11; and (b) characterizing the subject as resistant or is likely to become resistant to therapy with a BTK inhibitor if the subject has the modification. In some embodiments, the method further comprises discontinuing treatment with the BTK inhibitor if the subject has the modification. In some embodiments, the method further comprises continuing treatment with a BTK inhibitor if the subject does not have the modification. In some embodiments, the method further comprises a step of obtaining the sample from the subject. In some embodiments, the method further comprises administering an inhibitor of LYN, SYK, JAK, PI3K, MAPK, MEK, or NFκB if the subject has the modification. In some embodiments, the modification comprises a R665W or S707F substitution in PLCγ2. In some embodiments, the BTK inhibitor is a covalent or irreversible inhibitor.

Described herein, in certain embodiments are methods for optimizing the therapy of a subject receiving an irreversible BTK inhibitor for treatment of a cancer, comprising: (a) testing a sample containing a nucleic acid molecule encoding a PLCγ2 polypeptide from the subject to determine whether the encoded PLCγ2 polypeptide is modified at an amino acid position corresponding to amino acid position 665 of the amino acid sequence set forth in SEQ ID NO: 11; and (b) discontinuing treatment with the irreversible BTK inhibitor if the subject has the modification or continuing treatment with the irreversible BTK inhibitor if the subject does not have the modification. In some embodiments, the method further comprises administering second generation BTK inhibitor that inhibits the modified kinase if the subject has the modification. In some embodiments, the method further comprises a step of obtaining the sample from the subject. In some embodiments, the method further comprises administering an inhibitor of LYN, SYK, JAK, PI3K, MAPK, MEK, or NFκB if the subject has the modification. In some embodiments, the modification comprises a R665W or S707F substitution in PLCγ2. In some embodiments, the BTK inhibitor is a covalent or irreversible inhibitor.

In some embodiments of the methods, the nucleic acid molecule for use in the assay is RNA or DNA. In some embodiments of the methods, the nucleic acid molecule is a cDNA In some embodiments of the methods, the nucleic acid molecule for use in the assay is genomic DNA. In some embodiments of the methods, the nucleic acid molecule for use in the assay is total RNA. In some embodiments of the methods, the nucleic acid molecule for use in the assay is mRNA. In some embodiments of the methods, the method further comprises isolating mRNA from the RNA sample.

In some embodiments of the methods, testing comprises performing polymerase chain reaction (PCR) amplification of nucleic acid encoding amino acid position 665 or 707 of the PLCγ2 polypeptide. In some embodiments, PCR amplification comprises using a pair of oligonucleotide primers that flank the region encoding amino acid position 665 or 707 of the PLCγ2 polypeptide. In some embodiments, the method comprises sequencing the amplified nucleic acid.

In some embodiments of the methods, testing comprises contacting the nucleic acid with a sequence specific nucleic acid probe, wherein the sequence specific nucleic acid probe: (a) binds to nucleic acid encoding a modified PLCγ2 that is modified at amino acid position 665; and (b) does not bind to nucleic acid encoding the wild-type PLCγ2 having Arginine at amino acid position 665 or 707. In some embodiments of the methods, testing comprises PCR amplification using the sequence specific nucleic acid probe.

In some embodiments, the sample for use in the methods contains one or more tumor cells from the subject. In some embodiments, the sample for use in the methods contains circulating tumor DNA (ctDNA).

In some embodiments of the methods, the nucleic acid used in the method is isolated from a tumor cell sample from the subject. In some embodiments, the sample is a tumor biopsy sample, a blood sample, a serum sample, a lymph sample, or a bone marrow aspirate.

In some embodiments, the BTK inhibitor is selected from among ibrutinib (PCI-32765), PCI-45292, PCI-45466, AVL-101, AVL-291, AVL-292, or ONO-WG-37. In some embodiments, the PLCγ2 inhibitor is ibrutinib.

In some embodiments of the methods, the subject has cancer. In some embodiments, the cancer is a hematologic cancer. In some embodiments, cancer is a B-cell malignancy. In some embodiments, cancer is selected from among a leukemia, a lymphoma, or a myeloma. In some embodiments, the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the subject has a solid tumor.

In some embodiments of the methods, the subject is treated with the BTK inhibitor prior to obtaining the sample. In some embodiments, the sample is obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, or 24 months following the first administration of the irreversible BTK inhibitor. In some embodiments, the sample is obtained 1, 2, 3, 4, 5, 6, 7, 8, 9, 10 times over the course of treatment with the BTK inhibitor. In some embodiments, the subject is responsive the treatment with the BTK inhibitor when it is first administered.

Described herein, in certain embodiments, is a kit comprising one or more reagents for the detection of a modified PLCγ2 polypeptide comprising a modification at amino acid position 665. In some embodiments, the kit comprises a microchip comprising a mutant PLCγ2 polypeptide having a modification that is R665W or S707F.

Described herein, in certain embodiments, is a kit comprising one or more reagents for the detection of nucleic acid encoding a mutant PLCγ2 polypeptide comprising a modification at amino acid position 665 or 707. In some embodiments, the kit comprises a microchip comprising nucleic acid encoding a mutant PLCγ2 polypeptide having a modification that is R665W or S707F.

Described herein, in certain embodiments, is a system for detecting a modified PLCγ2 that confers resistance to inhibition with an irreversible BTK inhibitor in a subject, comprising: (a) a sample containing a nucleic acid molecule encoding a PLCγ2 polypeptide from the subject; and (b) a microarray comprising nucleic acid encoding a mutant PLCγ2 polypeptide or a portion thereof that is modified at an amino acid position corresponding to amino acid position 665 or 707 of the amino acid sequence set forth in SEQ ID NO: 11. In some embodiments, the microarray is contained on a microchip.

Described herein, in certain embodiments, is a system for detecting a modified PLCγ2 that that confers resistance to inhibition with a BTK inhibitor in a subject, comprising: (a) a sample containing a nucleic acid molecule encoding a PLCγ2 polypeptide from the subject; and (b) a sequence specific nucleic acid probe, wherein the sequence specific nucleic acid probe: (i) binds to nucleic acid encoding a modified PLCγ2 that is modified at amino acid position 665 or 707; and (ii) does not bind to nucleic acid encoding the wild-type PLCγ2 having Arginine at amino acid position 665 or serine at position 707.

Described herein, in certain embodiments, is a system for detecting a modified PLCγ2 that that confers resistance to inhibition with an BTK inhibitor in a subject, comprising: (a) a sample containing a nucleic acid molecule encoding a PLCγ2 polypeptide from the subject; and (b) a pair oligonucleotide primers that flank the nucleic acid region encoding amino acid 665 or 707 of a PLCγ2 polypeptide.

Described herein, in certain embodiments, is method of maintenance therapy in a patient having a hematologic cancer, comprising: (a) administering to the patient a maintenance therapy regimen comprising administering a therapeutically effective dose of a BTK inhibitor; and (b) monitoring the patient at predetermined intervals of time over the course of the maintenance therapy regimen to determine whether the subject has mutation in an endogenous gene encoding PLCγ2 that results in a modification at an amino acid position corresponding to amino acid position 665 or 707 of the amino acid sequence set forth in SEQ ID NO: 11. In some embodiments, monitoring comprises: (a) testing a sample containing a nucleic acid molecule encoding a PLCγ2 polypeptide from the subject to determine whether the encoded PLCγ2 polypeptide is modified at an amino acid position corresponding to amino acid position 665 or 707 of the amino acid sequence set forth in SEQ ID NO: 11. In some embodiments, the method further comprises discontinuing treatment with the BTK inhibitor if the subject has the mutation. In some embodiments, the method further comprises continuing treatment with a BTK inhibitor if the subject does not have the mutation. In some embodiments, the method further comprises administering an inhibitor of LYN, SYK, JAK, PI3K, MAPK, MEK, or NFκB if the subject has the modification. In some embodiments, the modification in the PLCγ2 polypeptide is R665W or S707F. In some embodiments, the predetermined interval of time is every month, every 2 months, every 3 months, every 4 months, every 5 months, every 6 months, every 7 months, every 8

In some embodiments, the BTK inhibitor is administered at a daily dosage of about 10 mg per day to about 2000 mg per day, about 50 mg per day to about 1500 mg per day, about 100 mg per day to about 1000 mg per day, about 250 mg per day to about 850 mg per day, or about 300 mg per day to about 600 mg per day. In some embodiments, ibrutinib is administered at a daily dosage of about 140 mg per day, 420 mg per day, 560 mg per day or 840 mg per day. In some embodiments, the BTK inhibitor is a covalent and/or irreversible BTK inhibitor. In some embodiments, the BTK inhibitor is selected from among ibrutinib (PCI-32765), PCI-45292, PCI-45466, AVL-101, AVL-291, AVL-292, or ONO-WG-37. In some embodiments, the BTK inhibitor is ibrutinib.

CARD11

In some embodiments, the downstream effector protein is Caspase recruitment domain-containing protein 11(CARD11) also known as CARD-containing MAGUK protein 1 (Carma 1). CARD11 belongs to the MAGUK (membrane-associated guanylate kinase) family that typically function as molecular scaffolds in the assembly of multiprotein complexes. MAGUK family members contain an SH3 domain, a PDZ domain and a GuK domain homologous to guanylate kinase. In addition, CARD11 contains an amino-terminal CARD domain (caspase recruitment domain). This domain plays an important role in forming interactions with a number of proteins containing CARD domains that are involved in regulating apoptosis and NF-κB activation. CARD11 is predominately expressed in lymphocytes and associates with the CARD domain of Bcl10. When overexpressed, CARD11 leads to the phosphorylation of Bcl10 and activation of NF-κB.

In some embodiments, a mutation in CARD11 results in resistance of a patient to treatment with a BTK inhibitor. In some embodiments, the mutation is a gain of function mutation in CARD11. In some embodiments, the mutation results in constitutive activation of the NF-κB mediated transcription. In some embodiments, the mutation in CARD11 results in amino acid insertion at amino acid position 232 in CARD11. In some embodiments, the mutation the mutation in CARD11 results in an insertion of leucine at amino acid position L232. In some embodiments, the modification is L232LL. In some embodiments, the mutation the mutation in CARD11 results in an insertion of isoleucine at amino acid position L232. In some embodiments, the modification is L232IL or L232L1.

Any of the methods provided herein for the detection of a modified BTK polypeptide also can be applied to the detection of a CARD11 polypeptide. For example, mutant CARD11 polypeptides can be detected by PCR methods using mutant specific nucleic acids for detection of somatic mutation in the genome or CARD11 mutant specific antibodies for detection of mutant CARD11 polypeptides.

In some embodiments, a nucleic acid encoding a mutant CARD11 polypeptide is provided. In some embodiments, a nucleic acid vector encoding a mutant CARD11 polypeptide is provided. In some embodiments the vector is a viral vector. In some embodiments, a host cell comprising a nucleic acid encoding a mutant CARD11 polypeptide is provided. In some embodiments, a host cell comprising an expressed CARD11 polypeptide is provided.

Any of the methods provided herein and known in the art for the production of modified BTK polypeptides and nucleic acids provided herein, including the use of nucleic acid expression vectors and host cells, also can be applied to the production of mutant CARD11 polypeptides and nucleic acids provide herein.

Provided herein are mutant CARD11 polypeptides. In some embodiments, the mutant CARD11 polypeptides are recombinant proteins. In some embodiments, the mutant CARD11 polypeptides are purified from a host cell.

In some embodiments, the mutant CARD11 polypeptides contain one or more amino acid substitutions that confers resistance to inhibition by a BTK inhibitor. In some embodiments, the mutant CARD11 polypeptides contain one or more amino acid substitutions that confers resistance to inhibition by a covalent and/or irreversible BTK inhibitor. In some embodiments, the mutant CARD11 polypeptides contain one or more amino acid substitutions that confers resistance to inhibition by a covalent and/or irreversible BTK inhibitor that is ibrutinib, PCI-45292, PCI-45466, AVL-101, AVL-291, AVL-292, or ONO-WG-37. In some embodiments, the mutant CARD11 polypeptides contain one or more amino acid substitutions that confers resistance to inhibition by a BTK inhibitor.

Provided herein is an isolated CARD11 polypeptide or a variant thereof having CARD11 activity comprising a modification at an amino acid position corresponding to amino acid position L232 of the amino acid sequence set forth in SEQ ID NO: 19.

In some embodiments, the modification comprises a substitution or a deletion of the amino acid at amino acid position L232 compared to a wild type CARD11 set forth in SEQ ID NO: 19. In some embodiments, the modification comprises substitution of the amino acid at position L232 compared to a wild type CARD11 set forth in SEQ ID NO: 19. In some embodiments, the modification is an insertion of leucine at amino acid 232 of the CARD11 polypeptide (e.g. L232LL).

In some embodiments, the mutant CARD11 polypeptide comprises an insertion of leucine at amino acid 232 of the CARD11 polypeptide compared to a wild type CARD11 set forth in SEQ ID NO: 19 and one or more additional amino acid substitutions. In some embodiments, the mutant CARD11 polypeptide comprises an insertion of leucine at amino acid 232 and a modification at 1, 2, 3, 4, 5, 6, 7, 8, 9, 10, 11, 12, 13, 14, 15, 16, 17, 18, 19, 20 or more amino acid positions. In some embodiments, the modification at amino acid position 232 is L232LL.

In some embodiments, a CARD11 polypeptide comprising a modification at amino acid position 232 of the wild-type CARD11 polypeptide set forth in SEQ ID NO: 19 linked to a peptide tag. In some embodiments, the peptide tag is an epitope tag recognized by a tag-specific antibody. In some embodiments the tag is an epitope tag, such as, but not limited to a c-myc, V-5, hemagglutinin (HA), FLAG, tag. In some embodiments the tag is an affinity tag, such as, but not limited to, biotin, strep-tag, chitin binding protein (CBP), maltose binding protein (MBP), glutathione-S-transferase (GST), or a poly(His) tag. In some embodiments, a CARD11 polypeptide comprising a modification at amino acid position 232 of the wild-type CARD11 polypeptide set forth in SEQ ID NO: 19 linked to a detectable protein or moiety, such a luminescent, chemiluminescent, bioluminescent, or fluorescent protein or moiety. In some embodiments, the fluorescent protein is a green (GFP), red (RFP), cyan (CFP), yellow (YFP), or blue (BFP) fluorescent protein. In some embodiments, a CARD11 polypeptide comprising a modification at amino acid position 232 of the wild-type CARD11 polypeptide set forth in SEQ ID NO: 19 linked to an enzyme for example, a luciferase or a beta-galactosidase.

Provided herein are nucleic acids encoding mutant CARD11 polypeptides. Provided herein are nucleic acids encoding any of the mutant CARD11 polypeptides described herein. Methods for deducing nucleic acids that encode particular polypeptides are known in the art and involve standard molecular biology techniques. Exemplary nucleic acids encoding mutant CARD11 polypeptides provided herein are provided. It is understood that due to the degeneracy of the genetic code multiple variants nucleic acids exist that encode the same polypeptide. Nucleic acids that encode the mutant CARD11 polypeptides provided herein encompass such variants.

In some embodiments, the nucleic acid encoding a modified CARD11 polypeptide provided herein is a DNA or an RNA molecule. In some embodiments, the nucleic acid encoding a mutant CARD11 polypeptide comprises a modification where the encoded polypeptide comprises an insertion of an amino acid at the position corresponding to amino acid position 232 of the wild-type CARD11 polypeptide set forth in SEQ ID NO: 19. In some embodiments, the nucleic acid comprises the sequence of nucleic acids set forth in SEQ ID NO: 20, or a variant that has at least or at least about 60%, 70%, 75%, 80%, 85%, 90%, 95%, 96%, 97%, 98%, 99% or more sequence identity with the polypeptide having the sequence set forth in SEQ ID NO: 20.

In some embodiments, methods are provided for determining whether a subject is or likely to become less responsive to therapy with a BTK inhibitor, comprising: (a) testing a sample containing a nucleic acid molecule encoding a CARD11 polypeptide from the subject to determine whether the encoded CARD11 polypeptide is modified at an amino acid position corresponding to amino acid position 232 of the amino acid sequence set forth in SEQ ID NO: 19; and (b) characterizing the subject as resistant or likely to become resistant to therapy with a BTK inhibitor if the subject has the modification. In some embodiments, the method further comprises a step of obtaining the sample from the subject. In some embodiments, the modification comprises a L232LL insertion in CARD11. In some embodiments, the BTK inhibitor is a covalent or irreversible inhibitor.

Described herein, in certain embodiments are methods for monitoring whether a subject receiving a BTK inhibitor for treatment of a cancer has developed or is likely to develop resistance to the therapy, comprising: (a) testing a sample containing a nucleic acid molecule encoding a CARD11 polypeptide from the subject to determine whether the encoded CARD11 polypeptide is modified at an amino acid position corresponding to amino acid position 232 of the amino acid sequence set forth in SEQ ID NO: 19; and (b) characterizing the subject as resistant or is likely to become resistant to therapy with a BTK inhibitor if the subject has the modification. In some embodiments, the method further comprises discontinuing treatment with the BTK inhibitor if the subject has the modification. In some embodiments, the method further comprises continuing treatment with a BTK inhibitor if the subject does not have the modification. In some embodiments, the method further comprises a step of obtaining the sample from the subject. In some embodiments, the method further comprises administering an inhibitor of LYN, SYK, JAK, PI3K, MAPK, MEK, or NFκB if the subject has the modification. In some embodiments, the modification comprises a L232LL insertion in CARD11. In some embodiments, the BTK inhibitor is a covalent or irreversible inhibitor.

Described herein, in certain embodiments are methods for optimizing the therapy of a subject receiving an irreversible BTK inhibitor for treatment of a cancer, comprising: (a) testing a sample containing a nucleic acid molecule encoding a CARD11 polypeptide from the subject to determine whether the encoded CARD11 polypeptide is modified at an amino acid position corresponding to amino acid position 232 of the amino acid sequence set forth in SEQ ID NO: 19; and (b) discontinuing treatment with the irreversible BTK inhibitor if the subject has the modification or continuing treatment with the irreversible BTK inhibitor if the subject does not have the modification. In some embodiments, the method further comprises administering second generation BTK inhibitor that inhibits the modified kinase if the subject has the modification. In some embodiments, the method further comprises a step of obtaining the sample from the subject. In some embodiments, the method further comprises administering an inhibitor of LYN, SYK, JAK, PI3K, MAPK, MEK, or NFκB if the subject has the modification. In some embodiments, the modification comprises a L232LL insertion in CARD11. In some embodiments, the BTK inhibitor is a covalent or irreversible inhibitor.

In some embodiments of the methods, the nucleic acid molecule for use in the assay is RNA or DNA. In some embodiments of the methods, the nucleic acid molecule is a cDNA In some embodiments of the methods, the nucleic acid molecule for use in the assay is genomic DNA. In some embodiments of the methods, the nucleic acid molecule for use in the assay is total RNA. In some embodiments of the methods, the nucleic acid molecule for use in the assay is mRNA. In some embodiments of the methods, the method further comprises isolating mRNA from the RNA sample.

In some embodiments of the methods, testing comprises performing polymerase chain reaction (PCR) amplification of nucleic acid encoding amino acid position 232 of the CARD11 polypeptide. In some embodiments, PCR amplification comprises using a pair of oligonucleotide primers that flank the region encoding amino acid position 232 of the CARD11 polypeptide. In some embodiments, the method comprises sequencing the amplified nucleic acid.

In some embodiments of the methods, testing comprises contacting the nucleic acid with a sequence specific nucleic acid probe, wherein the sequence specific nucleic acid probe: (a) binds to nucleic acid encoding a modified CARD11 that is modified at amino acid position 232; and (b) does not bind to nucleic acid encoding the wild-type CARD11. In some embodiments of the methods, testing comprises PCR amplification using the sequence specific nucleic acid probe.

In some embodiments, the sample for use in the methods contains one or more tumor cells from the subject. In some embodiments, the sample for use in the methods contains circulating tumor DNA (ctDNA).

In some embodiments of the methods, the nucleic acid used in the method is isolated from a tumor cell sample from the subject. In some embodiments, the sample is a tumor biopsy sample, a blood sample, a serum sample, a lymph sample, or a bone marrow aspirate.

In some embodiments, the BTK inhibitor is selected from among ibrutinib (PCI-32765), PCI-45292, PCI-45466, AVL-101, AVL-291, AVL-292, or ONO-WG-37. In some embodiments, the CARD11 inhibitor is ibrutinib.

In some embodiments of the methods, the subject has cancer. In some embodiments, the cancer is a hematologic cancer. In some embodiments, cancer is a B-cell malignancy. In some embodiments, cancer is selected from among a leukemia, a lymphoma, or a myeloma. In some embodiments, the B-cell malignancy is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), primary mediastinal B-cell lymphoma (PMBL), non-Hodgkin lymphoma, Burkitt's lymphoma, follicular lymphoma, immunoblastic large cell lymphoma, precursor B-lymphoblastic lymphoma, precursor B-cell acute lymphoblastic leukemia, hairy cell leukemia, mantle cell lymphoma, B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the subject has a solid tumor.

In some embodiments of the methods, the subject is treated with the BTK inhibitor prior to obtaining the sample. In some embodiments, the sample is obtained at 1 week, 2 weeks, 3 weeks, 1 month, 2 months, 3 months, 4 months, 5 months, 6 months, 7 months, 8 months, 9 months, 10 months, 11 months, 12 months, 14 months, 16 months, 18 months, 20 months, 22 months, or 24 months following the first administration of the irreversible BTK inhibitor. In some embodiments, the sample is obtained 1, 2, 3, 4, 5, 6, 7, 8, 9, 10 times over the course of treatment with the BTK inhibitor. In some embodiments, the subject is responsive the treatment with the BTK inhibitor when it is first administered.

Described herein, in certain embodiments, is a kit comprising one or more reagents for the detection of a modified CARD11 polypeptide comprising a modification at amino acid position 232. In some embodiments, the kit comprises a microchip comprising a mutant CARD11 polypeptide having a modification that is L232LL.

Described herein, in certain embodiments, is a kit comprising one or more reagents for the detection of nucleic acid encoding a mutant CARD11 polypeptide comprising a modification at amino acid position 232. In some embodiments, the kit comprises a microchip comprising nucleic acid encoding a mutant CARD11 polypeptide having a modification that is L232LL.

Described herein, in certain embodiments, is a system for detecting a modified CARD11 that confers resistance to inhibition with an irreversible BTK inhibitor in a subject, comprising: (a) a sample containing a nucleic acid molecule encoding a CARD11 polypeptide from the subject; and (b) a microarray comprising nucleic acid encoding a mutant CARD11 polypeptide or a portion thereof that is modified at an amino acid position corresponding to amino acid position 232 of the amino acid sequence set forth in SEQ ID NO: 19. In some embodiments, the microarray is contained on a microchip.

Described herein, in certain embodiments, is a system for detecting a modified CARD11 that that confers resistance to inhibition with a BTK inhibitor in a subject, comprising: (a) a sample containing a nucleic acid molecule encoding a CARD11 polypeptide from the subject; and (b) a sequence specific nucleic acid probe, wherein the sequence specific nucleic acid probe: (i) binds to nucleic acid encoding a modified CARD11 that is modified at amino acid position 232; and (ii) does not bind to nucleic acid encoding the wild-type CARD11.

Described herein, in certain embodiments, is a system for detecting a modified CARD11 that that confers resistance to inhibition with an BTK inhibitor in a subject, comprising: (a) a sample containing a nucleic acid molecule encoding a CARD11 polypeptide from the subject; and (b) a pair oligonucleotide primers that flank the nucleic acid region encoding amino acid 232 of a CARD11 polypeptide.

Described herein, in certain embodiments, is method of maintenance therapy in a patient having a hematologic cancer, comprising: (a) administering to the patient a maintenance therapy regimen comprising administering a therapeutically effective dose of a BTK inhibitor; and (b) monitoring the patient at predetermined intervals of time over the course of the maintenance therapy regimen to determine whether the subject has mutation in an endogenous gene encoding CARD11 that results in a modification at an amino acid position corresponding to amino acid position 232 of the amino acid sequence set forth in SEQ ID NO: 19. In some embodiments, monitoring comprises: (a) testing a sample containing a nucleic acid molecule encoding a CARD11 polypeptide from the subject to determine whether the encoded CARD11 polypeptide is modified at an amino acid position corresponding to amino acid position 232 of the amino acid sequence set forth in SEQ ID NO: 19. In some embodiments, the method further comprises discontinuing treatment with the BTK inhibitor if the subject has the mutation. In some embodiments, the method further comprises continuing treatment with a BTK inhibitor if the subject does not have the mutation. In some embodiments, the method further comprises administering an inhibitor of LYN, SYK, JAK, PI3K, MAPK, MEK, or NFκB if the subject has the modification. In some embodiments, the modification in the CARD11 polypeptide is L232LL. In some embodiments, the predetermined interval of time is every month, every 2 months, every 3 months, every 4 months, every 5 months, every 6 months, every 7 months, every 8

In some embodiments, the BTK inhibitor is administered at a daily dosage of about 10 mg per day to about 2000 mg per day, about 50 mg per day to about 1500 mg per day, about 100 mg per day to about 1000 mg per day, about 250 mg per day to about 850 mg per day, or about 300 mg per day to about 600 mg per day. In some embodiments, ibrutinib is administered at a daily dosage of about 140 mg per day, 420 mg per day, 560 mg per day or 840 mg per day. In some embodiments, the BTK inhibitor is a covalent and/or irreversible BTK inhibitor. In some embodiments, the BTK inhibitor is selected from among ibrutinib (PCI-32765), PCI-45292, PCI-45466, AVL-101, AVL-291, AVL-292, or ONO-WG-37. In some embodiments, the BTK inhibitor is ibrutinib.

EXAMPLES

These examples are provided for illustrative purposes only and not to limit the scope of the claims provided herein.

Example 1

In this example, mutations in Bruton's Tyrosine Kinase (BTK) were identified in leukemia patients receiving therapy with the covalent BTK inhibitor ibrutinib.

Patients suffering from chronic lymphocytic leukemia (CLL) were treated with multiple cycles of ibrutinib therapy at a dosage of 560 mg per day. After approximately 18 months of treatment, one patient exhibited clinical disease progression. Progression was characterized by a rise in absolute lymphocyte count (ALC) and increased lymph node size. The dosage of ibrutinib was then increased from 560 mg to 840 mg per day. The increased dosage, however did not inhibit disease progression. Another patient in a subsequent study was treated with cycles of 420 mg ibrutinib in combination with Bendamustine and Rituxan. This patient also exhibited clinical disease progression after approximately 12 months of treatment.

Whole blood was collected from patients before study, during treatment, and when the patient was considered disease progressed by set IWCLL assessment criteria. Whole blood was collected into BD Vacutainer Cell Preparation Tubes (CPT) with sodium citrate as a coagulant. Collected whole blood was shipped within 48 hrs of blood draw to analysis site where the CPT collection tubes were centrifuged immediately for 20 min in a horizontal rotor centrifuge at 1800 RCF at RT. The peripheral blood mononuclear cell (PBMC) layer under the plasma layer was carefully collected with a pipette after aspiration of the upper plasma component. The collected cells were resuspended in Sigma Red Blood Cell (RBC) Lysing buffer (Cat No. R 7757) for 5 min to remove residual RBC, and subsequently washed twice with PBS to stop the lysis and centrifuged to collect the cell pellet. In some instances, the PBMC pellets were sorted with magnetic beads for enrichment of B cells, T cells or monocytes at this point. For RNA assays described below, the PBMC cell pellets were resuspended in Qiagen RLT Lysis buffer and placed into a −80° C. freezer until analysis. For storage and use in later assays, the cell pellets were frozen as viable cells and resuspended in 90% FBS, and 10% DMSO solution added dropwise to the pellet gently and slowly. These vials were pre-chilled in Mister Frosty containers (Nalgene®) and placed in a −80° C. freezer for 24 hrs before permanently storing in the liquid nitrogen tank.

Total DNA, RNA, and protein were isolated from PBMC using the Qiagen All Prep kit. A first-strand cDNA of the BTK mRNA was synthesized via reverse transcription using a kit purchased from Agilent Technologies (catalog #600184) using the following reverse direction BTK primer (called BTK #2R): 5'-aagtgaaattggggcttgtg-3' (SEQ ID NO.: 9). The manufacturer's directions were followed for the reaction. Template RNA, gene-specific primer, dNTP mixture, and buffer were mixed in a microtube. The mixture was denatured at 65° C. for 5 minutes and primer annealed at 25° C. for 5 minutes. DTT and AccuScript High Fidelity reverse transcriptase were then added and the DNA was extend at 42° C. for 30 to 90 minutes, cooled to 4° C., then held at −20° C.

The mRNA-cDNA hybrid from the reverse transcription reaction was then amplified via polymerase chain reaction (PCR) using PfuUltra II HS polymerase from Agilent Technologies. One to three microliters of the reverse transcription reaction was used in the PCR reaction. The same reverse primer BTK #2R was used with a forward primer: (called BTK #2F) 5'-agtcccaccttccaagtcct-3'(SEQ ID NO.: 10). The following PCR protocol was used for amplification using a thermocycler: Step 1—denature at 95° C. for 2 minutes; Step 2—denature 95° C. for 30 seconds, anneal 55° C. for 30 seconds, extend at 68° C. for 1.25 min; Step 3—repeat step 2 thirty-nine times; Step 4—extend 68° C. for 5 minutes, cool to 4° C., and then hold at −20° C. 10% of the PCR product was analyzed by ethidium bromide agarose gel electrophoresis. The reminder of the sample was then purified using QiaQuick PCR product purification kit.

Sequencing of both strands of the entire BTK open reading frame was performed at Sequetech Corporation (Mountain View, Calif.) using primers designed and synthesized by Sequetech. The wild type mRNA sequence of BTK (accession number NM_000061.2) is set forth in SEQ ID NO.: 3. The DNA sequence of Resistant Patient #1 (200-004/200-007) is set forth in SEQ ID NO.: 7. The DNA sequence of Resistant Patient #2 (350-105) is set forth in SEQ ID NO.: 8. Sequencing revealed that the mRNA sequence in the cells that were collected from two patients prior to receiving Ibrutinib/early in treatment is wild-type, i.e. the RNA encodes a normal Cysteine at position 481 in the amino acid protein sequence of BTK. In cells from the end-of-study (EOS)/later in treatment from resistant patients, the sequence of the mRNA is altered such that the mRNA now codes for Serine instead of Cysteine at position 481 of BTK. Resistant Patient #1 had a missense mutation at thymine (t)—1634 to adenine (a)—1634 (i.e. t1634a). This mutation changes the Cysteine-481 codon, TGC, to AGC (Serine). Resistant Patient #2 had a missense mutation at guanine (g)—1635 to cytosine (c)—1635 (i.e. g1635c). This mutation also changes the Cysteine-481 codon, TGC, to TCC (Serine).

A highly sensitive allele-specific PCR assay (1% analytic sensitivity) further confirmed the unique presence of the mutation in the genomic DNA of relapsed samples suggesting the mutation was acquired during the patient's treatment. For PCR of genomic BTK DNA, the following 4 primers were used: BTKg-F1: TGATGGGCTCCAAATCCCTG (SEQ ID NO: 13); BTKg-R1: AATGATGGCACCAGCAGC (SEQ ID NO: 14); BTKg-F2: AATCCCTGCTTGCTTCCACA (SEQ ID NO: 15); BTKg-R2: TTGATGGGCTCAGCACTGG (SEQ ID NO: 16).

In a separate method for preparation of samples for sequencing, total RNA was isolated from patients' PBMC before treatment and after disease progression using QIAamp RNA Blood Mini Kit. mRNA is first purified using polyA selection, cleared for globin RNA (Expression Analysis) and then chemically fragmented. The mRNA fragments were converted into single-stranded cDNAs using random hexamer primer of reverse transcription. Next, the second strand was generated to create double-stranded cDNA, followed by end repair and the addition of a single-A base at each end of the molecule. Adapters that enable attachment to the flow cell surface was then ligated to each end of the fragments. The adapters contain unique index sequences (Expression Analysis) which allow the libraries to be pooled during multiplexing. PCR was then performed to amplify and enrich ligated material to create the cDNA library, followed by cluster generation and direct Illumina (Illumina HiSeq 2000) sequencing-by-synthesis using the TruSeq SBS kit. Paired-end sequencing was conducted with each sample running in a separate sequencing lane. More than 100 millions reads were yielded with an average of 88× coverage/sample.

Example 2

In this example cell lines are generated that express the BTK C481S mutant. The nucleic acid encoding the BTK C481S mutant is inserted into an expression vector construct, whereby the nucleic acid is operably linked to a promoter for expression of the mutant protein. The BTK C481S constructs are stably transfected into cell lines such as insect cells for recombinant protein production or into cell lines deficient for BTK such as CHO cells or Jurkat T cells or chicken DT40 BTK−/− B cell lines or human BTK knocked out B cell lines.

The cell lines are used for screening second generation compounds or for the production of purified protein for use in in vitro assays, such as a kinase assay.

For in vitro assays, C481S BTK recombinant protein is produced in cells, such as insect cells, purified to homogeneity and evaluated for its tyrosine kinase specific activity towards various substrates, including universal peptides or specific downstream substrates (such as PLCγ) and subjected to in vitro kinase assays (C481S, ATP, cofactors Mg/Mn, peptide substrate). PCi-32765 (ibrutinib) is used as a negative control.

The chicken DT40 BTK−/− or human BTK−/− are stably transfected with either wild type BTK or C481S BTK and used in HTS type functional assays. In one example the cells are stimulated with anti-IgM/G to ligate and activate B cell receptor (BCR) and therefore downstream BTK in these cell lines. Following 18 hrs of stimulation, surface CD69 activation is evaluated in these cells with and without serial diluted compounds. A BTK inhibitor that covalent binds to C481S is expected to inhibit and reduce CD69 following cell washout experiments.

Example 3

Figure 2A:
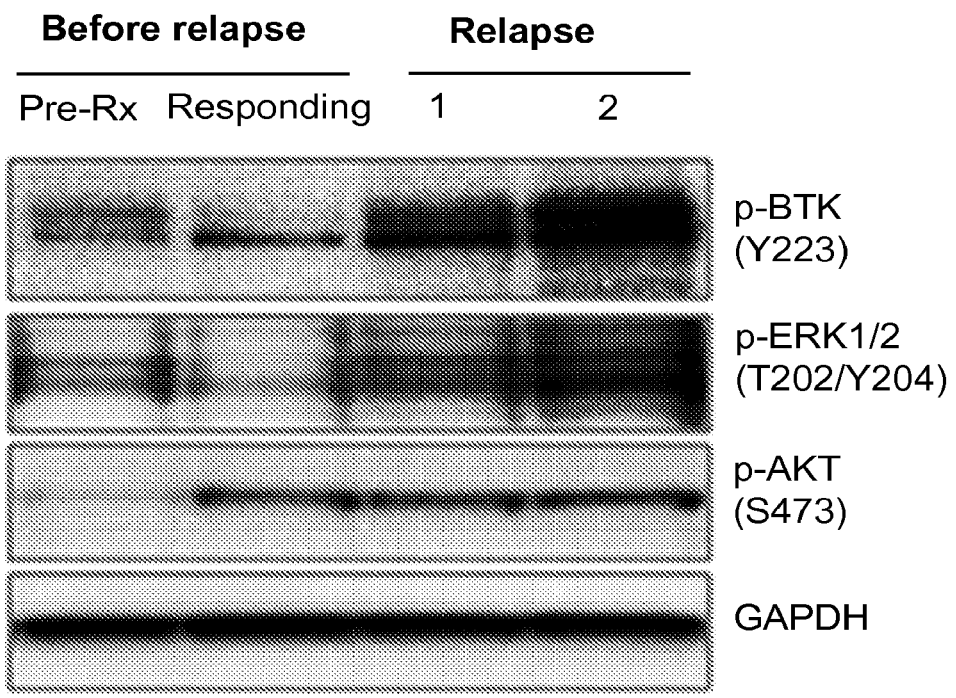

Ibrutinib binds covalently to BTK, an essential component of BCR signaling, via a Michael addition with the sulfhydryl group of C481 in the active site resulting in potent and irreversible inhibition of kinase activity (Honigberg et al, PNAS 107(29): 13075-13080. Structural modeling demonstrates that the C481S mutation would disrupt this covalent binding, but not the ability of ibrutinib to fit into the enzyme's active site (FIG. 1). In response to BCR signaling, LYN and SYK phosphorylate BTK at Y551, inducing BTK autophosophorylation at Y223 leading to kinase activation. Thus, the phosphorylation of Y223 thus reflects BTK enzyme activity. Immunoblot analysis of demonstrates that p-BTK (Y223) was decreased relative to baseline when the patient was responding to ibrutinib, and elevated with disease relapse (FIG. 2A, Lanes 3 and 4). Changes in p-ERK displayed a similar trend as p-BTK, decreasing during the patient's clinical response, and subsequently rising above baseline at the time of disease relapse, increasing further when reassessed four weeks later. On the other hand, p-AKT increased with ibrutinib treatment and did not change depending upon clinical course. Overall, changes in the levels of p-BTK and p-ERK correlated with each other and suggest that the mutation allows BCR signaling in the presence of ibrutinib.

In exemplary methods, BTK phosphorylation at site Y551 and certain related signaling events are also monitored by a flow cytometric assay using cultured cells (e.g. HEK293T cells) that are transfected with a plasmid encoding human BTK. Expression in HEK293T cells results in constitutive phosphorylation of the Y551 site in BTK and this is detectable by flow cytometry using a fluorescently-coupled antibody (BD Biosciences catalog #558134). Expression of BTK in HEK293T cells also results in phosphorylation of Erk at T202/Y204, and this is detectable by flow cytometry using BD Biosciences catalog #612566. Phosphorylation of both Y551 in BTK and T202/Y204 in Erk are dose-dependently inhibited by treatment with Ibrutinib (and dasatinib) and constitutive phosphorylation does not occur when a kinase-inactive mutant of BTK is expressed instead of wild type or C481S BTK, indicating that BTK kinase activity is required for these phosphorylation events to occur. Expression levels of total BTK are monitored by flow cytometry using BD Biosciences catalog #558527.

An exemplary procedure for the preparation of the cells is as follows: HEK293T cells are seeded into 10 cm plates and allowed to adhere overnight. Cells are transfected using the calcium phosphate method with a plasmid containing human wild type or C481S mutant BTK or C481A mutant BTK or K430A mutant BTK (carboxyl-terminal 6His fusions) under the control of the CMV promoter. Approximately 16 hours post-transfection, cells are detached and seeded into multiwell plates. Approximately 24 hours later, the cells are treated with Ibrutinib or other inhibitors and either fixed in situ with paraformaldehyde; or mechanically detached, washed into fresh drug-free medium and incubated for 1.5 hours, and then fixed. Permeabilized cells are stained with the indicated BD Biosciences fluorescently-labeled antibodies and analyzed on a BD CantoII flow cytometer. FlowJo software and fluorescence-minus-one controls are used to gate on positive cell populations and gates are equally applied to each sample. Total positive cell counts are taken as a ratio of BTK-expressing cells.

Example 4

Figure 2B:
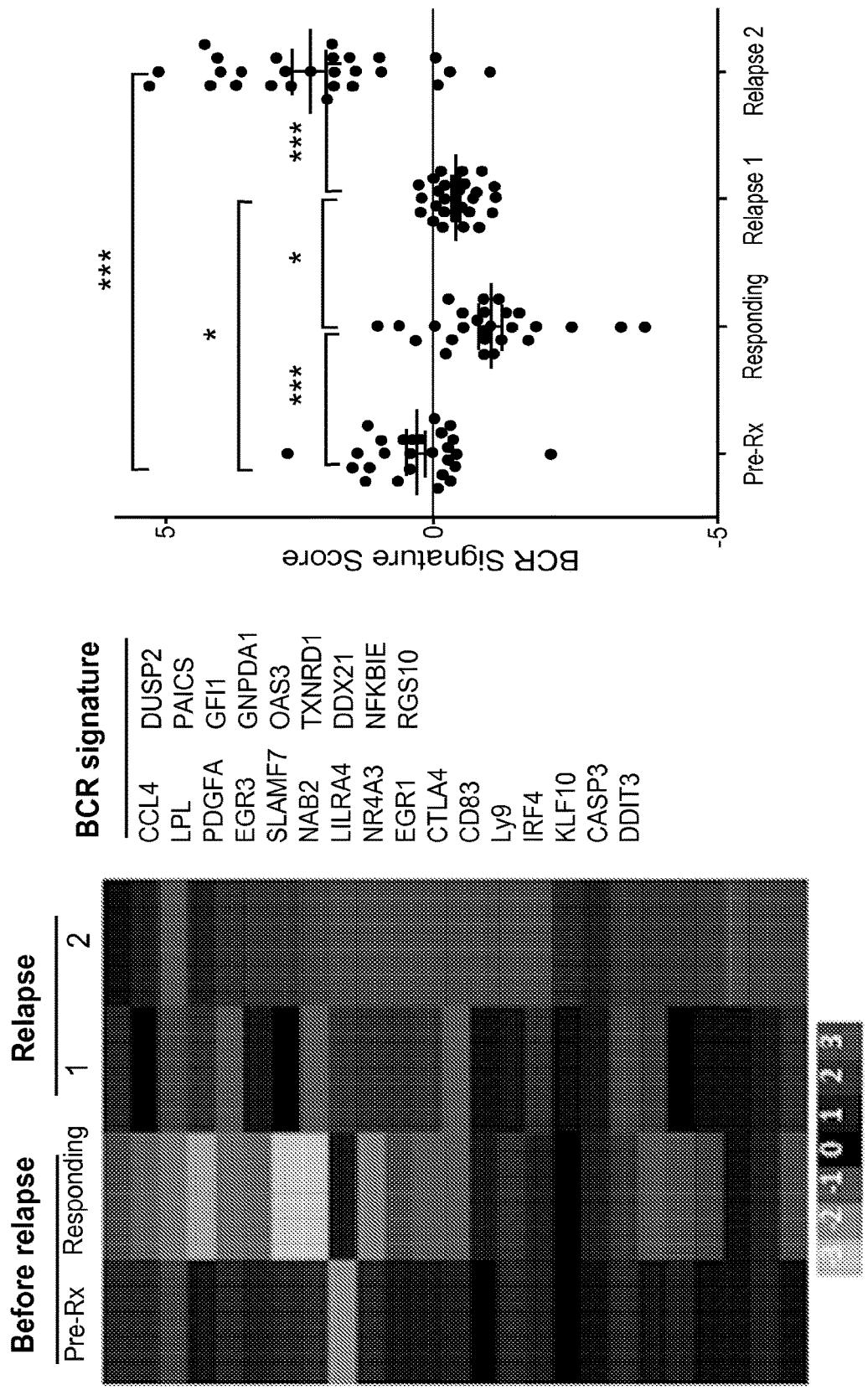

In this example, gene expression data in patients was analyzed. RNA-Seq data for gene expression using an established 27-gene BCR expression signature (Blood. 2011 Jan. 13; 117(2):563-74) demonstrated a responding patient's BCR signature was down-regulated relative to baseline pre-treatment (FIG. 2B). However, the expression of this cluster of genes increased in both relapse stages, initially assessed and four weeks later.

To perform RNA-Seq, total RNA was isolated from patients' PBMC before treatment and after disease progression suing QIAamp RNA Blood Mini Kit. mRNA is first purified using polyA selection, cleared for globin RNA (Expression Analysis) and then chemically fragmented. The mRNA fragments are converted into single-stranded cDNA using random hexamer primer of reverse transcription. Next, the second strand is generated to create double-stranded cDNA, followed by end repair and the addition of a single-A base at each end of the molecule. Adapters that enable attachment to the flow cell surface are then ligated to each end of the fragments. The adapters contain unique index sequences (Expression Analysis) which allow the libraries to be pooled during multiplexing. PCR is then performed to amplify and enrich ligated material to create the cDNA library, followed by cluster generation and direct Illumina (Illumina HiSeq 2000) sequencing-by-synthesis using the TruSeq SBS kit. Paired-end sequencing was conducted with each sample running in a separate sequencing lane. More than 100 millions reads were yielded with an average of 88× coverage/sample. The reads were aligned to the HG19 genome assembly using TopHat package with Bowtie2 aligner. Reads not mapped to the genome or potential PCR duplicates were excluded with samtools. Cufflinks and cuffmerge were used to quantify levels of transcript expression. Reads per kilobase per million mapped reads (RPKM) were computed: the number of reads mapped to each transcript sequence was normalized by the template length in kbs and divided by the number of reads mapping to the whole transcriptome. Hierarchical cluster analysis for BCR signature genes was performed using Cluster 3.0 software, and heat map was generated using TreeView.

Notably, the trend of changes in gene expression was analogous to the trend of changes in p-BTK and p-ERK. Taken together, the data from the mutation analyses, signal transduction and gene expression profiling strongly suggest that 1) gain of BTK C481S mutation allows BCR signaling in CLL cells in the presence of ibrutinib and 2) BCR signaling activity over the treatment course correlates with the status of the patient's disease.

Example 5

Figure 3A:
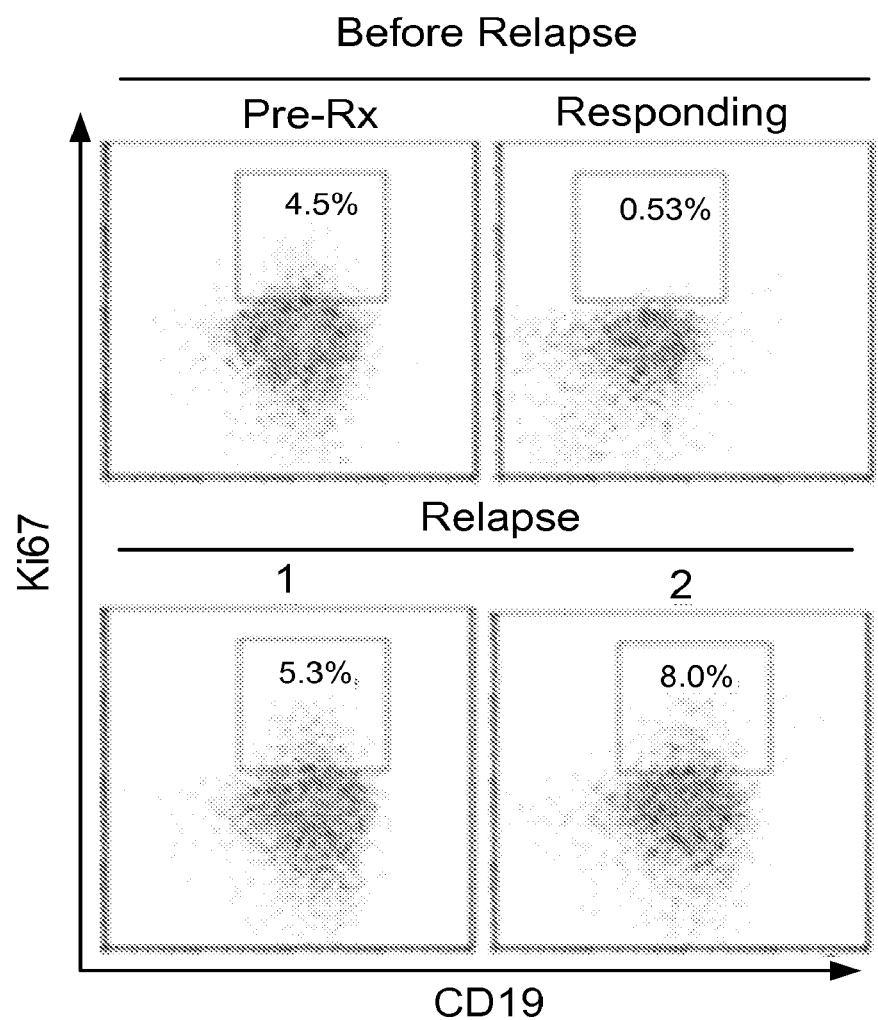
FIG. 3A-C: BTK mutation leads to increased ex vivo cell proliferation that remains sensitive to other BCR inhibitors.
Figure 3B:
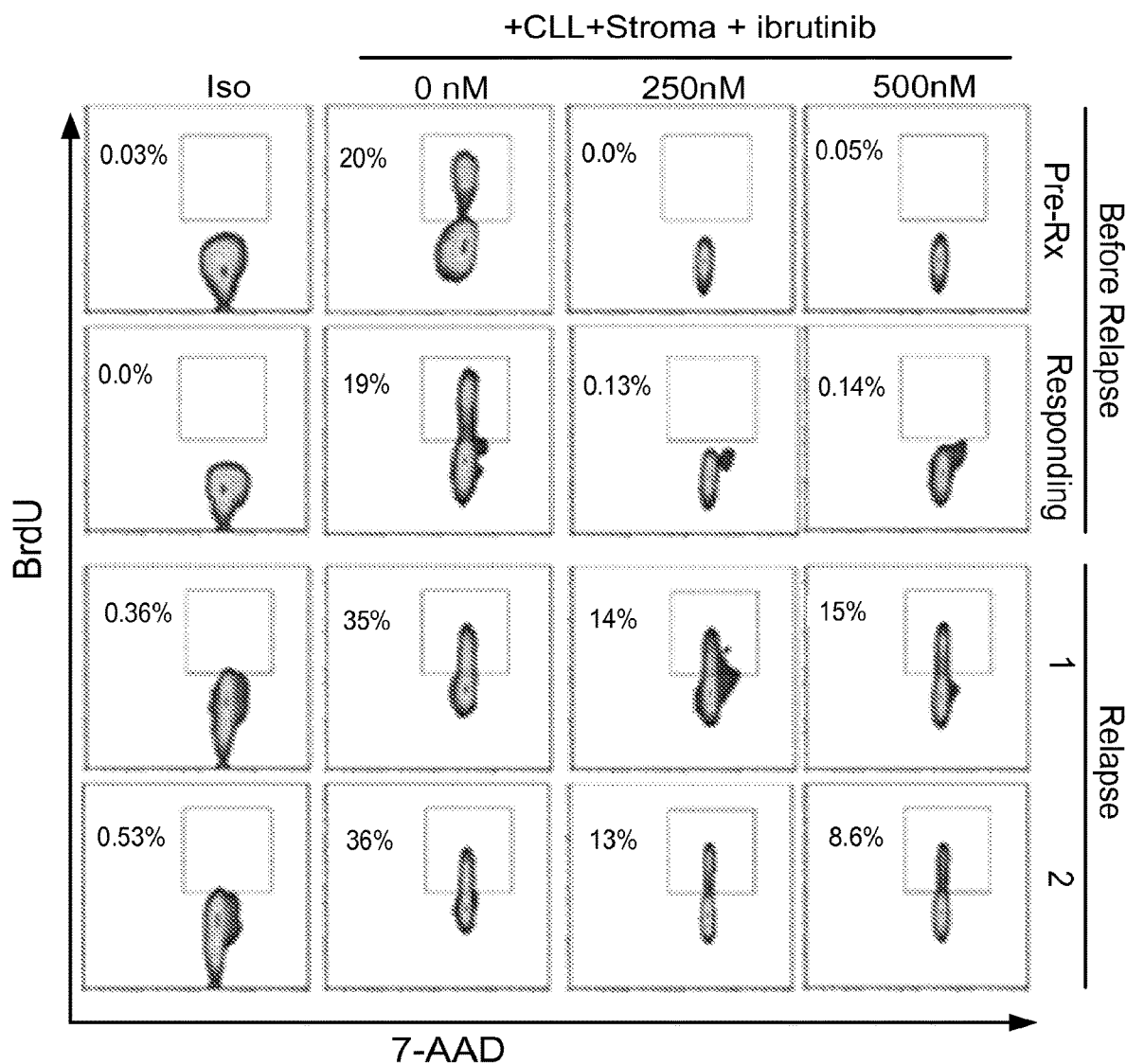
Figure 4:
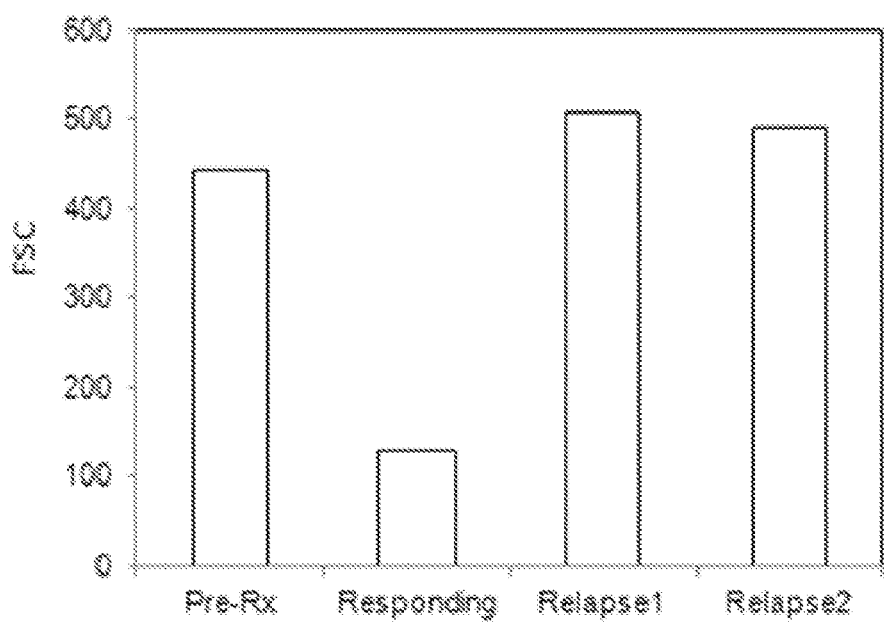
FIG. 4: Changes in cell size reflecting increased proliferation after relapse following treatment with ibrutinib.

This example demonstrates that ibrutinib inhibits proliferation of CLL cells from responding patients' peripheral blood, but not those from patients that have relapsed with the BTK C481S mutation. The number of Ki-67+ cells and cell size decreased over the ibrutinib treatment course in responding patients, but not those relapsed with the mutation. Analysis of serial samples from the current patient also demonstrated a reduction in the percentage of Ki-67+ positive CLL cells from 4.5% to 0.53% during in the Responding sample. In Relapse 1, the number of Ki-67+ cells increased to 5.3%, and then to 8.0% in Relapse 2 (FIG. 3A). As further evidence for ibrutinib's impact upon proliferation, changes in cell size reflecting increased proliferation after relapse were also demonstrated (FIG. 4). In the current study, the size of the proliferative CLL population increased from 19-20% to 35-36% in relapsed samples (FIG. 3B, second column). Treatment of the patient's CLL cells with ibrutinib (250 or 500 nM) completely blocked BrdU incorporation in the pre-Rx and responding samples (FIG. 3B, top two rows, $3^{rd}$ and $4^{th}$ vs $2^{nd}$ columns). However, in both relapsed samples some proliferative CLL cells remained (FIG. 3B, bottom two rows, $2^{nd}$, $3^{rd}$ and $4^{th}$ vs $1^{st}$ columns). Thus, CLL in vitro proliferative response to ibrutinib agrees with the patient's clinical course and acquired resistance to ibrutinib treatment.

Antibodies used in flow cytometry were purchased from BD (San Jose, Calif.) and used according to instructions: CD3-V500, CD19-APCCy7, CD19-APC, CD5-PerCPCy5.5, CD5-FITC, CXCR4-PECy7, CXCR4-PE, CD38-PE, CD62L-PE, CCR7-V450, CXCR3-Alexa488, CXCR5-Alexa647, CD49d-APC, CD29-PE, CD44-V450, CD54-PE, CD11a-APC, CD11c-V450, CD18-FITC, CD40-PECy7, Ki67-Alexa488, Ig k light chain-APC, Ig l light chain-FITC. Antibodies used for Western blots: phospho-p44/42 MAP kinase [T202/Y204] against ERK1 and 2, phospho-AKT [Ser473] against PKB/AKT (New England Biolabs, Ipswich, Mass.), phospho-BTK [Y551] against BTK (BD Biosciences), phospho-BTK [Y223] against BTK (Epitomics, Burlingame, Calif.) and phospho-PLCγ2 [Y759] against PLCγ2 (BD Biosciences); anti-ERK2 (C-14; Santa Cruz Biotechnology, Santa Cruz, Calif.), anti-AKT (H-136; Santa Cruz Biotechnology), anti-BTK (Clone 53; BD Biosciences), goat F(ab)'$_2$ anti-human IgM (LE/AF; Southern Biotech, Birmingham, Ala.), horseradish peroxidase (HRP)-conjugated rabbit anti-mouse and HRP-conjugated goat anti-rabbit (DAKO, Houston, Tex.).

Example 6

Figure 3C:
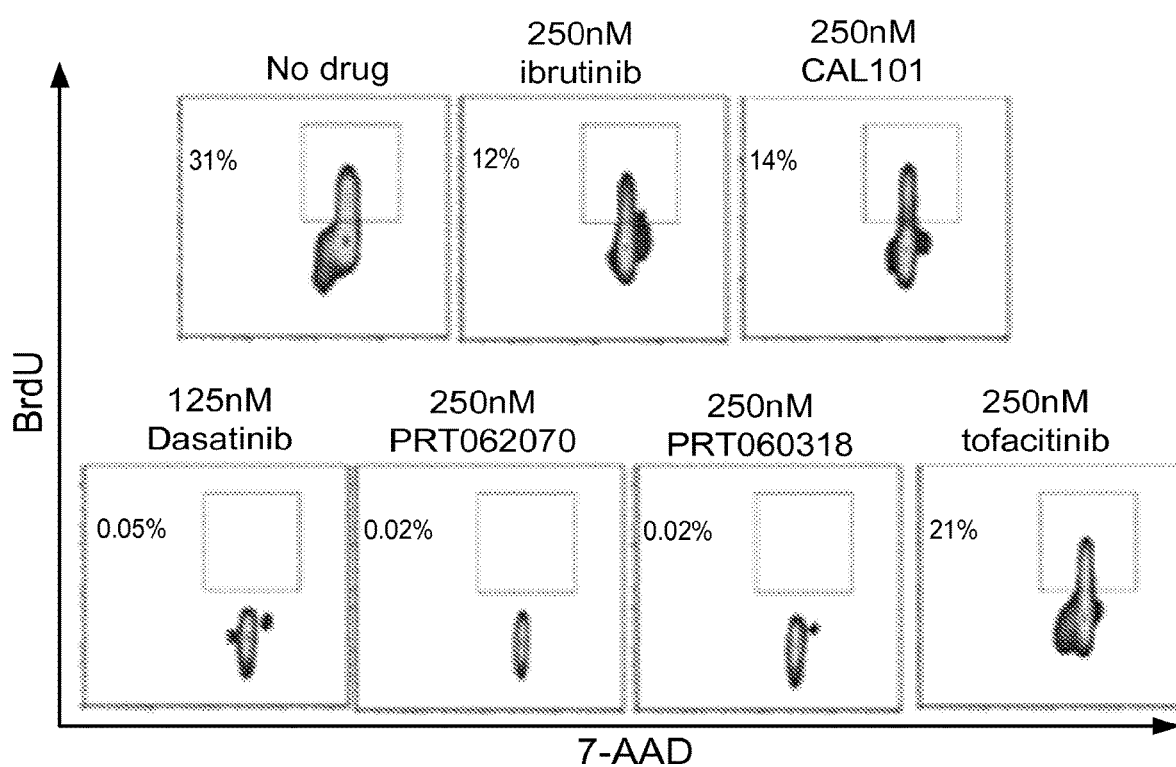

This example demonstrates that other inhibitors of the BCR or alternative pathways can suppress CLL proliferation and override the resistance caused by the C481S mutation. Using the in vitro CLL proliferation model, cells were treated with GS-1101 (CAL-101, a PI3Kdelta inhibitor), dasatinib (downstream BCR targets LYN and BTK), PRT062070 (a SYK/JAK dual inhibitor), PRT060318 (a highly specific SYK inhibitor, ref) and tofacitinib (a JAK inhibitor) in addition to ibrutinib. FIG. 3C demonstrates that ibrutinib and GS-1101 brought proliferation down from 31% to 12 and 14% while tofacitinib decreased the proliferation only to 21%. Dasatinib and the two inhibitors with activity against SYK (PRT062070 and PRT060318) led to complete inhibition of proliferation. These results suggest the BTK-mutated CLL cells remain sensitive to BCR inhibition. Accordingly, additional or alternative inhibitors of LYN, SYK, JAK, PI3K, PLCγ, MAPK, MEK, NFκB other covalent inhibitors of BTK or other reversible inhibitors of BTK are also predicted to be effective in patients with the C481S mutations.

Example 7

Early trials of ibrutinib mono- or combination therapy enrolled 246 CLL patients receiving a median of 14 months of ibrutinib. RNAseq and whole exome sequencing (WES) followed by comparative genome analysis was performed at baseline and after relapse or progressive disease (PD) and confirmed by Sanger sequencing for 3 patients that acquired resistance to ibrutinib. RNAseq and WES data were aligned using TopHat and BWA software.

Single nucleotide variations (SNVs) were identified using SAMtools mpileup. Compared to patients who relapsed from conventional chemotherapy, minimal genomic changes were acquired in ibrutinib resistant patients, reflecting relative genomic stability. SNVs were discovered in 3 patients specific to the relapse sample. 2 out of 3 patients had distinct SNVs that each encode a cysteine-to-serine substitution at position 481 of BTK (C481S). Homologous cysteine residues in BMX, ITK, TEC and BLK were wild-type (WT). Ibrutinib inhibited recombinant C481S 25 fold less potently than WT, and could not covalently bind C481S expressed in cells. The third patient had WT BTK, but acquired a potential gain-of-function mutation, c1993t in exon 19 of PLCγ2, encoding a R665W substitution, a substrate of BTK, consistent with constitutive PLCγ2 activation.

In subsequent studies of patients that initially responded to ibrutinib and later became drug-resistant, two additional mutations were identified. Nucleic acid sequencing revealed that patient blood samples taken at the beginning of treatment were wild-type, while samples collected upon physician-designated disease-progression were mutated at the following sites: 1) One patient was found to have acquired a mutation in PLCγ2. The tutation is an in-frame single-nucleotide point mutation: c2120t (i.e. thymine at position 2120 instead of cytosine of the PLCγ2 coding region. The mutation results in a PLCγ2 protein with substitution of a serine at codon 707 for phenylalanine (S707F). 2) One patient was found to have acquired a mutation in CARD11. The mutation is an insertion of three thymine nucleotides between nucleotide positions 694 and 695 of the CARD11 coding region. The mutation was named 694_695insTTT. The mutation results in a CARD11 protein with insertion of a leucine codon between leucine-232 and lysine-233. The mutant is called L232_K233- or L232LL. (Note that there are alternative start sites for translation of CARD11 mRNA. In some instances, CARD11 mutation at this site is noted as position 225 instead of 232).

The S707F mutation is expected to be a gain-of-function mutation that results in constitutive activity of the PLCγ2 protein. A similar mutation (S707Y) in PLCγ2 was described by Zhou et al. in American Journal of Human Genetics (2012) 91; 713-720, confers constitutive activity to the PLCγ2 protein, and results in an autoinflammatory and immunodeficiency disease. Like the R665W mutation, S707F is in the auto-inhibitory carboxyl-terminal SH2 domain. Given that PLCγ2 is downstream of BTK, the effect of conferring gain-of-function constitutive PLCγ2 activity supports drug resistance to ibrutinib.

The CARD11 L232LL mutant protein is also expected to have constitutive activity. A similar mutation was found in B cell lymphoma patient samples (isoleucine insertion between 232 and 233) as described by Lenz et al. in Science (2008) 319; 1676-1679. As described by Lenz et al., the mutation confers constitutive activity of the downstream NF-kB pathway and enhanced cellular survival. Like PLCγ2, CARD11 is a protein that is activated downstream of Btk. CARD11 is phosphorylated and activated by PKC-beta, which is a downstream effector of Btk and PLCg2. Thus, gain-of-function mutations in CARD11 that confer constitutive activity may bypass Btk and allow cells to activate growth and anti-apoptotic signaling pathways in the presence of Btk inhibitors such as ibrutinib. The L232LL mutation is in the amino-terminal coiled-coil domain, which is important for CARD11 oligomerization and NF-kB activation, and where several different mutations in CARD11 have been found in B cell lymphoma patient specimens.

The examples and embodiments described herein are for illustrative purposes only and various modifications or changes suggested to persons skilled in the art are to be included within the spirit and purview of this application and scope of the appended claims.

What is claimed is:

1. A method for treating a hematological cancer with ibrutinib in a subject in need thereof, the method comprising:
testing a sample containing a nucleic acid molecule encoding a BTK polypeptide from the subject to determine whether the encoded BTK polypeptide has a modification at amino acid position 481 of the amino acid sequence set forth in SEQ ID NO: 1;
detecting the absence of the modification in the sample from the subject; and
administering ibrutinib to the subject at a daily dosage of 420 mg/day or 560 mg/day.

2. The method of claim 1, wherein the modification comprises a substitution or a deletion of the amino acid at amino acid position 481 in the BTK polypeptide.

3. The method of claim 2, wherein the modification is a substitution of cysteine to an amino acid selected from leucine, isoleucine, valine, alanine, glycine, methionine, serine, threonine, phenylalanine, tryptophan, lysine, arginine, histidine, proline, tyrosine, asparagine, glutamine, aspartic acid and glutamic acid at amino acid position 481 of the BTK polypeptide.

4. The method of claim 3, wherein the modification is a substitution of cysteine to serine at amino acid position 481 of the BTK polypeptide.

5. The method of claim 1, wherein the modification comprises a deletion of nucleic acid encoding amino acid position 481 of the BTK polypeptide.

6. The method of claim 4, wherein the nucleic acid encoding the modified BTK polypeptide has a mutation of guanine to cytosine at nucleic acid position corresponding to nucleic acid position 1635 in the sequence of nucleotides set forth in SEQ ID NO: 3 or thymine to adenine at nucleic acid position corresponding to nucleic acid position 1634 in the sequence of nucleotides set forth in SEQ ID NO: 3.

7. The method of claim 1, wherein the cancer is a B-cell malignancy.

8. The method of claim 1, wherein the cancer is selected from a leukemia and a lymphoma.

9. The method of claim 1, wherein prior to the testing step of the method the subject received ibrutinib.

10. The method of claim 7, wherein the B-cell malignancy is chronic lymphocytic leukemia/small lymphocytic lymphoma (CLL/SLL), and wherein the ibrutinib is administered at a dosage of 420 mg/day.

11. The method of claim 10, wherein the CLL/SLL is relapsed or refractory.

12. The method of claim 7, wherein the B-cell malignancy is diffuse large B-cell lymphoma (DLBCL), and wherein the ibrutinib is administered at a dosage of 560 mg/day.

13. The method of claim 12, wherein the DLBCL is relapsed or refractory.

14. The method of claim 7, wherein the B-cell malignancy is activated B-cell diffuse large B-cell lymphoma (ABC-DLBCL), and wherein the ibrutinib is administered at a dosage of 560 mg/day.

15. The method of claim 14, wherein the ABC-DLBCL is relapsed or refractory.

16. The method of claim 7, wherein the B-cell malignancy is follicular lymphoma (FL), and wherein the ibrutinib is administered at a dosage of 560 mg/day.

17. The method of claim 16, wherein the FL is relapsed or refractory.

18. The method of claim 7, wherein the B-cell malignancy is mantle cell lymphoma (MCL), and wherein the ibrutinib is administered at a dosage of 560 mg/day.

19. The method of claim 18, wherein the MCL is relapsed or refractory.

20. The method of claim 7, wherein the B-cell malignancy is Waldenstrom's Macroglobulinemia (WM), and wherein the ibrutinib is administered at a dosage of 420 mg/day.

21. The method of claim 20, wherein the WM is relapsed or refractory.

22. The method of claim 7, wherein the B-cell malignancy is marginal zone lymphoma (MZL), and wherein the ibrutinib is administered at a dosage of 560 mg/day.

23. The method of claim 22, wherein the MZL is relapsed or refractory.

* * * * *

UNITED STATES PATENT AND TRADEMARK OFFICE
CERTIFICATE OF CORRECTION

PATENT NO. : 10,954,567 B2  
APPLICATION NO. : 14/417097  
DATED : March 23, 2021  
INVENTOR(S) : Betty Chang et al.

Page 1 of 1

It is certified that error appears in the above-identified patent and that said Letters Patent is hereby corrected as shown below:

On the Title Page

Item (71):
"Pharmacyclics LLC, Sunnyvale, CA (US)"
Should read:
--Pharmacyclics LLC, Sunnyvale, CA (US); Cornell University, Ithaca, NY (US)--

Item (72):
"Betty Chang, Cupertino, CA (US); Joseph J. Buggy, Mountain View, CA (US); Susanne M. Steggerda, San Francisco, CA (US)"
Should read:
--Betty Chang, Cupertino, CA (US); Joseph J. Buggy, Mountain View, CA (US); Susanne M. Steggerda, San Francisco, CA (US); Y. Lynn Wang, Glen Mills, PA (US); Richard Furman, New York, NY (US); Shuhua Cheng, Brooklyn, NY (US)--

Item (60):
"Provisional application No. 61/675,303, filed on Jul. 24, 2012."
Should read:
--Provisional application No. 61/780,652, filed on Mar. 13, 2013, provisional application No. 61/682,688, filed on Aug. 13, 2012, provisional application No. 61/675,303, filed on Jul. 24, 2012.--

Signed and Sealed this  
Second Day of November, 2021

Drew Hirshfeld  
*Performing the Functions and Duties of the  
Under Secretary of Commerce for Intellectual Property and  
Director of the United States Patent and Trademark Office*